United States Patent
Atton et al.

(10) Patent No.: US 12,258,338 B2
(45) Date of Patent: Mar. 25, 2025

(54) MODULATORS OF THE INTEGRATED STRESS RESPONSE PATHWAY

(71) Applicant: EVOTEC INTERNATIONAL GMBH, Hamburg (DE)

(72) Inventors: Holly Atton, Abingdon (GB); Christopher John Brown, Abingdon (GB); James Lindsay Carr, Abingdon (GB); Serge Convers-Reignier, Abingdon (GB); Michael Corr, Abingdon (GB); Marissa Flower, Abingdon (GB); Christopher Francis Palmer, Abingdon (GB); Irena Reboule, Abingdon (GB); Mohamad Sabbah, Abingdon (GB); Scott Sadler, Abingdon (GB); Jonathan Shine, Abingdon (GB); Daryl Simon Walter, Abingdon (GB)

(73) Assignee: Evotec International GmbH, Hamburg (DE)

( * ) Notice: Subject to any disclaimer, the term of this patent is extended or adjusted under 35 U.S.C. 154(b) by 778 days.

(21) Appl. No.: 17/605,037

(22) PCT Filed: Apr. 22, 2020

(86) PCT No.: PCT/EP2020/061150
§ 371 (c)(1),
(2) Date: Oct. 20, 2021

(87) PCT Pub. No.: WO2020/216766
PCT Pub. Date: Oct. 29, 2020

(65) Prior Publication Data
US 2022/0227747 A1    Jul. 21, 2022

(30) Foreign Application Priority Data
Apr. 23, 2019 (EP) .................................. 19170504
Dec. 17, 2019 (EP) .................................. 19216875

(51) Int. Cl.
*C07D 413/14* (2006.01)
*C07D 413/04* (2006.01)

(52) U.S. Cl.
CPC ......... *C07D 413/14* (2013.01); *C07D 413/04* (2013.01)

(58) Field of Classification Search
CPC ............................ C07D 413/14; C07D 413/04
USPC ........................................................ 514/343
See application file for complete search history.

(56) References Cited

U.S. PATENT DOCUMENTS

| | | | |
|---|---|---|---|
| 10,851,053 B2 | 12/2020 | Axten et al. | |
| 11,547,704 B2 | 1/2023 | Axten et al. | |
| 2018/0237441 A1 | 8/2018 | Axten et al. | |

FOREIGN PATENT DOCUMENTS

| | | |
|---|---|---|
| JP | 2007-532672 A | 11/2007 |
| WO | WO 01/46779 A1 | 6/2001 |
| WO | 01/54507 A1 | 8/2001 |
| WO | WO 2005/105075 A1 | 11/2005 |
| WO | 2014/144952 A2 | 9/2014 |
| WO | WO-2016/001855 A1 | 1/2016 |
| WO | WO-2017/046739 A1 | 3/2017 |
| WO | 2017/193030 A1 | 11/2017 |
| WO | 2017/193034 A1 | 11/2017 |
| WO | 2017/193041 A1 | 11/2017 |
| WO | 2017/193063 A1 | 11/2017 |
| WO | 2017/212423 A1 | 12/2017 |
| WO | 2017/212425 A1 | 12/2017 |
| WO | 2018/225093 A1 | 12/2018 |

(Continued)

OTHER PUBLICATIONS

Young et al., "Upstream open reading frames differentially regulate gene-specific translation in the integrated stress response", The Journal of Biological Chemistry, 291(33): 16927-16935, (2016).
Office Action and Search Report issued in Chinese Patent Application No. 202080045788.1 dated May 25, 2023. [Eng. Translation].
Registry [Online] Columbus, Ohio, US, CPCH2162440P (12 pages).
Wandong Wang, "Expression and Significance of Activating Transcription Factor 4 in Oleic Acid-Induced Hepatocyte Steatosis in Vitro," Journal of Army Medical University, vol. 32, No. 14, pp. 1487-1490 (Jul. 30, 2010). [Eng. Abstract].
Office Action issued in co-pending Japanese Patent Application No. 2021-562988 dated Apr. 2, 2024 (5 pages).
Alelyunas et al., "Experimental solubility profiling of marketed CNS drugs, exploring solubility limit of CNS discovery candidate", Bioorganic & Medicinal Chemistry Letters 20:7312-7316 (2010).
Avivar-Valderas et al., "PERK Integrates Autophagy and Oxidative Stress Response To Promote Survival during Extracellular Matrix Detachment", Molecular and Cellular Biology 31(17):3616-3629 (2011).

(Continued)

*Primary Examiner* — Kahsay Habte
(74) *Attorney, Agent, or Firm* — Foley & Lardner LLP

(57) ABSTRACT

The present invention relates to compounds of formula (I) or pharmaceutically acceptable salts, solvates, hydrates, tautomers or stereoisomers thereof, wherein $R^1$, $R^2$, $R^{2a}$, $R^3$, $R^{a2}$, $R^{a4}$, $R^{a5}$, $R^{a6}$, $R^{a7}$, $X^1$, $X^{1a}$, $A^1$ and $A^2$ have the meaning as indicated in the description and claims. The invention further relates to pharmaceutical compositions comprising said compounds, their use as medicament and in a method for treating and preventing of one or more diseases or disorders associated with integrated stress response.

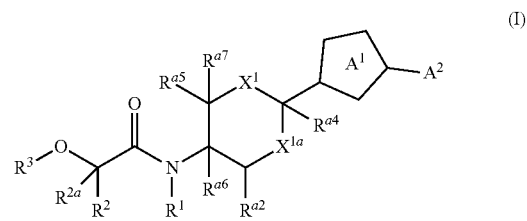

31 Claims, No Drawings

(56) References Cited

FOREIGN PATENT DOCUMENTS

| | | |
|---|---|---|
| WO | 2019/008506 A1 | 1/2019 |
| WO | 2019/008507 A1 | 1/2019 |
| WO | 2019/032743 A1 | 2/2019 |
| WO | 2019/046779 A1 | 3/2019 |
| WO | 2019/090069 A1 | 5/2019 |
| WO | 2019/090074 A1 | 5/2019 |
| WO | 2019/090076 A1 | 5/2019 |
| WO | 2019/090078 A1 | 5/2019 |
| WO | 2019/090081 A1 | 5/2019 |
| WO | 2019/090082 A1 | 5/2019 |
| WO | 2019/090085 A1 | 5/2019 |
| WO | 2019/090088 A1 | 5/2019 |
| WO | 2019/090090 A1 | 5/2019 |
| WO | 2019/118785 A2 | 6/2019 |
| WO | 2019/183589 A1 | 9/2019 |
| WO | 2019/193540 A1 | 10/2019 |
| WO | 2019/193541 A1 | 10/2019 |

OTHER PUBLICATIONS

Bi et al., "ER stress-regulated translation increases tolerance to extreme hypoxia and promotes tumor growth", The EMBO Journal 24:3470-3481 (2005).

Blais et al., "Perk-Dependent Translational Regulation Promotes Tumor Cell Adaptation and Angiogenesis in Response to Hypoxic Stress", Molecular and Cellular Biology 26(24):9517-9532 (2006).

Bobrovnikova-Marjon et al., "PERK promotes cancer cell proliferation and tumor growth by limiting oxidative DNA damage", Oncogene 29:3881-3895 (2010).

Bugiani et al., "Vanishing white matter: a leukodystrophy due to astrocytic dysfunction", Brain Pathology 28: 408-421 (2018).

Donnelly et al., "The eIF2a kinases: their structures and functions", Cellular and Molecular Life Sciences 70:3493-3511 (2013).

Frackenpohl et al., "Synthesis of Enantiopure 3-Quinuclidinone Analogues with Three Stereogenic Centers: (1S,2R,4S)- and (1S,2S,4S)-2-(Hydroxymethyl)-1-azabicyclo[2.2.2]octan-5-one and Stereocontrol of Nucleophilic Addition to the Carbonyl Group", J. Org. Chem 65:3982-3996 (2000).

Halliday et al., "Review: Modulating the unfolded protein response to prevent neurodegeneration and enhance memory", Neuropathology and Applied Neurobiology 41:414-427 (2015).

Halliday et al., "Partial restoration of protein synthesis rates by the small molecule ISRIB prevents neurodegeneration without pancreatic toxicity", Cell Death and Disease 6: e1672 (2015).

Hamilton et al., "Natural History of Vanishing White Matter", Ann Neurol. 84:274-288 (2018).

Hinnebusch et al., "Translational control by 5'-untranslated regions of eukaryotic mRNAs", Science 352(6292): 1413-1416 (2016).

Jackson et al., "The mechanism of eukaryotic translation initiation and principles of its regulation", Nature Reviews: Molecular Cell Biology 10: 113-127 (2010).

Krishnamoorthy et al., "Tight Binding of the Phosphorylated a Subunit of Initiation Factor 2 (eIF2a) to the Regulatory Subunits of Guanine Nucleotide Exchange Factor eIF2B Is Required for Inhibition of Translation Initiation", Molecular and Cellular Biology 21(15): 5018-5030 (2001).

Lin et al., "Divergent Effects of PERK and IRE1 Signaling on Cell Viability", PLoS One 4(1): 1-4 (2009).

Lomakin et al., "The initiation of mammalian protein synthesis and mRNA scanning mechanism", Nature 500: 307-311 (2013).

Moreno et al., "Sustained translational repression by eIF2a-P mediates prion neurodegeneration", Nature 485: 507-511 (2012) and Corrigendum.

Nguyen et al., "Development of a stress response therapy targeting aggressive prostate cancer", Science Translational Medicine 10, eaar2036 (2018).

Pain, "Initiation of protein synthesis in eukaryotic cells", Eur. J. Biochem 236: 747-771 (1996).

Pakos-Zebrucka et al., "The integrated stress response," EMBO Reports 17: 1374-1395 (2016).

Pavitt, "Regulation of translation initiation factor eIF2B at the hub of the integrated stress response", WIREs RNA 9: e1491 (2018).

Redfern et al., "Relationships between preclinical cardiac electrophysiology, clinical QT interval prolongation and torsade de pointes for a broad range of drugs: evidence for a provisional safety margin in drug development", Cardiovascular Research 58: 32-45 (2003).

Remondelli et al., "The Endoplasmic Reticulum Unfolded Protein Response in Neurodegenerative Disorders and Its Potential Therapeutic Significance", Frontiers in Molecular Neuroscience 10(187): 1-16 (2017).

Shore et al., "Signaling cell death from the endoplasmic reticulum stress response", Current Opinion in Cell Biology 23: 143-149 (2011).

Skopkova et al., "EIF2S3 Mutations Associated with Severe X-Linked Intellectual Disability Syndrome MEHMO", Human Mutation 38(4): 409-425 (2017).

Taalab et al., "Mechanisms of disordered neurodegenerative function: concepts and facts about the different roles of the protein kinase RNA-like endoplasmic reticulum kinase (PERK)", Rev. Neurosci. 29(4): 387-415 (2018).

Tabas et al., "Integrating the mechanisms of apoptosis induced by endoplasmic reticulum stress", Nature Cell Biology 13(3): 184-190 (2011).

Waring, "Lipophilicity in drug discovery," Expert Opin. Drug Discov. 5(3): 235-248 (2010).

Wek et al., "Coping with stress: eIF2 kinases and translational control", Biochemical Society Transactions 34(1): 7-11 (2006).

Wong et al., "The small molecule ISRIB rescues the stability and activity of Vanishing White Matter Disease eIF2B mutant complexes", eLIFE 7: e32733 (2018).

International Search Report for International Patent Application No. PCT/EP2020/061150, dated May 29, 2020.

International Preliminary Report on Patentability for International Patent Application No. PCT/EP2020/061150, dated Sep. 28, 2021.

Wong et al., "eIF2B activator prevents neurological defects caused by a chronic integrated stress response", eLIFE (2019).

MODULATORS OF THE INTEGRATED STRESS RESPONSE PATHWAY

The present invention relates to compounds of formula (I)

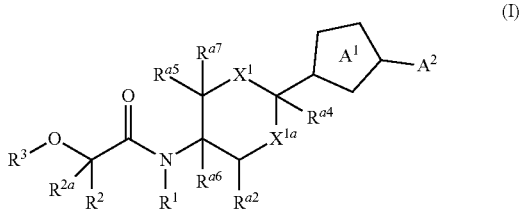

(I)

or pharmaceutically acceptable salts, solvates, hydrates, tautomers or stereoisomers thereof, wherein $R^1$, $R^2$, $R^{2a}$, $R^3$, $R^{a2}$, $R^{a4}$, $R^{a5}$, $R^{a6}$, $R^{a7}$, $X^1$, $X^{1a}$, $A^1$ and $A^2$ have the meaning as indicated in the description and claims. The invention further relates to pharmaceutical compositions comprising said compounds, their use as medicament and in a method for treating and preventing of one or more diseases or disorders associated with integrated stress response.

The Integrated Stress Response (ISR) is a cellular stress response common to all eukaryotes (1). Dysregulation of ISR signaling has important pathological consequences linked inter alia to inflammation, viral infection, diabetes, cancer and neurodegenerative diseases.

ISR is a common denominator of different types of cellular stresses resulting in phosphorylation of the alpha subunit of eukaryotic translation initiation factor 2 (eIF2alpha) on serine 51 leading to the suppression of normal protein synthesis and expression of stress response genes (2). In mammalian cells the phosphorylation is carried out by a family of four eIF2alpha kinases, namely: PKR-like ER kinase (PERK), double-stranded RNA-dependent protein kinase (PKR), heme-regulated eIF2alpha kinase (HRI), and general control non-derepressible 2 (GCN2), each responding to distinct environmental and physiological stresses (3).

eIF2alpha together with eIF2beta and eIF2gamma form the eIF2 complex, a key player of the initiation of normal mRNA translation (4). The eIF2 complex binds GTP and Met-tRNA; forming a ternary complex (eIF2-GTP-Met-tRNA$_i$), which is recruited by ribosomes for translation initiation (5, 6).

eIF2B is a heterodecameric complex consisting of 5 subunits (alpha, beta, gamma, delta, epsilon) which in duplicate form a GEF-active decamer (7).

In response to ISR activation, phosphorylated eIF2alpha inhibits the eIF2B-mediated exchange of GDP for GTP, resulting in reduced ternary complex formation and hence in the inhibition of translation of normal mRNAs characterized by ribosomes binding to the 5' AUG start codon (8). Under these conditions of reduced ternary complex abundance the translation of several specific mRNAs including the mRNA coding for the transcription factor ATF4 is activated via a mechanism involving altered translation of upstream ORFs (uORFs) (7, 9, 10). These mRNAs typically contain one or more uORFs that normally function in unstressed cells to limit the flow of ribosomes to the main coding ORF. For example, during normal conditions, uORFs in the 5' UTR of ATF occupy the ribosomes and prevent translation of the coding sequence of ATF4. However, during stress conditions, i.e. under conditions of reduced ternary complex formation, the probability for ribosomes to scan past these upstream ORFs and initiate translation at the ATF4 coding ORF is increased. ATF4 and other stress response factors expressed in this way subsequently govern the expression of an array of further stress response genes. The acute phase consists in expression of proteins that aim to restore homeostasis, while the chronic phase leads to expression of pro-apoptotic factors (1, 11, 12, 13).

Upregulation of markers of ISR signaling has been demonstrated in a variety of conditions, among these cancer and neurodegenerative diseases. In cancer, ER stress-regulated translation increases tolerance to hypoxic conditions and promotes tumor growth (14, 15, 16), and deletion of PERK by gene targeting has been shown to slow growth of tumours derived from transformed PERK mouse embryonic fibroblasts (14, 17). Further, a recent report has provided proof of concept using patient derived xenograft modeling in mice for activators of eIF2B to be effective in treating a form of aggressive metastatic prostate cancer (28). Taken together, prevention of cytoprotective ISR signaling may represent an effective anti-proliferation strategy for the treatment of at least some forms of cancer.

Further, modulation of ISR signaling could prove effective in preserving synaptic function and reducing neuronal decline, also in neurodegenerative diseases that are characterized by misfolded proteins and activation of the unfolded protein response (UPR), such as amyotrophic lateral sclerosis (ALS), frontotemporal dementia (FTD), Alzheimer's disease (AD), Parkinson's disease (PD) and Jakob Creutzfeld (prion) diseases (18, 19, 20). With prion disease an example of a neurodegenerative disease exists where it has been shown that pharmacological as well as genetic inhibition of ISR signaling can normalize protein translation levels, rescue synaptic function and prevent neuronal loss (21). Specifically, reduction of levels of phosphorylated eIF2alpha by overexpression of the phosphatase controlling phosphorylated eIF2alpha levels increased survival of prion-infected mice whereas sustained eIF2alpha phosphorylation decreased survival (22).

Further, direct evidence for the importance of control of protein expression levels for proper brain function exists in the form of rare genetic diseases affecting functions of eIF2 and eIF2B. A mutation in eIF2gamma that disrupts complex integrity of eIF2 and hence results in reduced normal protein expression levels is linked to intellectual disability syndrome (ID) (23). Partial loss of function mutations in subunits of eIF2B have been shown to be causal for the rare leukodystrophy Vanishing White Matter Disease (VWMD) (24, 25). Specifically, stabilization of eIF2B partial loss of function in a VWMD mouse model by a small molecule related to ISRIB has been shown to reduce ISR markers and improve functional as well as pathological end points (26, 27).

Modulators of the eIF2 alpha pathway are described in WO 2014/144952 A2. WO 2017/193030 A1, WO 2017/193034 A1, WO 2017/193041 A1 and WO 2017/193063 A1 describe modulators of the integrated stress pathway. WO 2017/212423 A1, WO 2017/212425 A1, WO 2018/225093 A1, WO 2019/008506 A1 and WO 2019/008507 A1 describe inhibitors of the ATF4 pathway. WO 2019/032743 A1 and WO 2019/046779 A1 relate to eukaryotic initiation factor 2B modulators.

Further documents describing modulators of the integrated stress pathway are WO 2019/090069 A1, WO 2019/090074 A1, WO 2019/090076 A1, WO 2019/090078 A1, WO 2019/090081 A1, WO 2019/090082 A1, WO 2019/090085 A1, WO 2019/090088 A1, WO 2019/090090 A1. Modulators of eukaryotic initiation factors are described in WO 2019/183589 A1. WO 2019/118785 A2 describes inhibitors of the integrated stress response pathway. Heteroaryl derivatives as ATF4 inhibitors are described in WO 2019/193540 A1. Bicyclic aromatic ring derivatives as ATF4 inhibitors are described in WO 2019/193541 A1.

However, there is a continuing need for new compounds useful as modulators of the integrated stress response pathway with good pharmacokinetic properties.

Thus, an object of the present invention is to provide a new class of compounds as modulators of the integrated stress response pathway, which may be effective in the treatment of integrated stress response pathway related diseases and which may show improved pharmaceutically relevant properties including activity, solubility, selectivity, ADMET properties and/or reduced side effects.

Accordingly, the present invention provides a compound of formula (I)

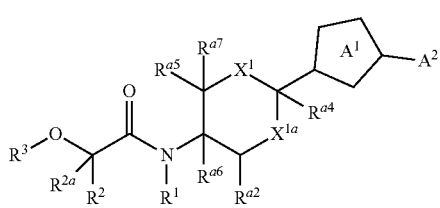

(I)

or a pharmaceutically acceptable salt, solvate, hydrate, tautomer or stereoisomer thereof for use as a medicament, wherein $X^1$ is $N(R^{a1})$;

$X^{1a}$ is a covalent single bond, $CH(R^{a3})$, or $CH(R^{a3})CH_2$;

$R^{a1}$ is H, $C(O)OC_{1-4}$ alkyl, or $C_{1-4}$ alkyl, wherein $C(O)OC_{1-4}$ alkyl and $C_{1-4}$ alkyl are optionally substituted with one or more substituents selected from the group consisting of halogen, OH, and O—$C_{1-3}$ alkyl, wherein the substituents are the same or different;

$R^{a2}$, $R^{a3}$ are independently selected from the group consisting of H; OH; $OC_{1-4}$ alkyl; halogen; $C_{1-4}$ alkyl; and $A^{2a}$; and $R^{a4}$, $R^{a5}$, $R^{a6}$, $R^{a7}$ are independently selected from the group consisting of H; halogen; $C_{1-4}$ alkyl; and $A^{2a}$, provided that only one of $R^{a2}$, $R^{a3}$, $R^{a4}$, $R^{a5}$, $R^{ab}$, $R^{a7}$ is $A^{2a}$.

or $R^{a1}$ and one of $R^{a2}$ and $R^{a3}$ form a methylene or ethylene group;

or $R^{a1}$ and $R^{a6}$ form an ethylene group;

or $R^{a2}$ and $R^{a5}$ form a covalent single bond;

or $R^{a5}$, $R^{a7}$ are joined to form an oxo group;

$A^1$ is $C_5$ cycloalkylene, $C_5$ cycloalkenylene, or a nitrogen ring atom containing 5-membered heterocyclene, wherein $A^1$ is optionally substituted with one or more $R^4$, which are the same or different;

each $R^4$ is independently oxo (=O) where the ring is at least partially saturated, thiooxo (=S) where the ring is at least partially saturated, halogen, CN, $OR^5$, or $C_{1-6}$ alkyl, wherein $C_{1-6}$ alkyl is optionally substituted with one or more halogen, which are the same or different;

$R^5$ is H or $C_{1-6}$ alkyl, wherein $C_{1-6}$ alkyl is optionally substituted with one or more halogen, which are the same or different;

$A^2$ is $R^{6a}$ or $A^{2a}$;

$R^{6a}$ is $OR^{6a1}$, $SR^{6a1}$, $N(R^{6a1}R^{6a2})$; $C_{1-6}$ alkyl, $C_{2-6}$ alkenyl or $C_{2-6}$ alkynyl, wherein $C_{1-6}$ alkyl, $C_{2-6}$ alkenyl, and $C_{2-6}$ alkynyl are optionally substituted with one or more substituents selected from the group consisting of halogen; CN; $OR^{6a3}$; and $A^{2a}$, wherein the substituents are the same or different;

$R^{6a1}$, $R^{6a2}$ are independently selected from the group consisting of H; $C_{1-6}$ alkyl; $C_{2-6}$ alkenyl; $C_{2-6}$ alkynyl; and $A^{2a}$, wherein $C_{1-6}$ alkyl; $C_{2-6}$ alkenyl; and $C_{2-6}$ alkynyl are optionally substituted with one or more substituents selected from the group consisting of halogen; CN; $OR^{6a3}$; $OA^{2a}$ and $A^{2a}$, wherein the substituents are the same or different;

$R^{6a3}$ is H; or $C_{1-4}$ alkyl, wherein $C_{1-4}$ alkyl is optionally substituted with one or more halogen, which are the same or different;

$A^{2a}$ is phenyl; $C_{3-7}$ cycloalkyl; $C_{4-12}$ bicycloalkyl; or 3- to 7-membered heterocyclyl, wherein $A^{2a}$ is optionally substituted with one or more $R^6$, which are the same or different;

each $R^6$ is independently $R^{6b}$; OH; $OR^{6b}$; halogen; or CN, wherein $R^{6b}$ is cyclopropyl, $C_{1-6}$ alkyl; $C_{2-6}$ alkenyl; or $C_{2-6}$ alkynyl, wherein $R^{6b}$ is optionally substituted with one or more halogen, which are the same or different; or two $R^6$ are joined to form together with the atoms to which they are attached a ring $A^{2b}$;

$A^{2b}$ is phenyl; $C_{3-7}$ cycloalkyl; or 3 to 7 membered heterocyclyl, wherein A2b is optionally substituted with one or more $R^7$, which are the same or different;

each $R^7$ is independently $C_{1-6}$ alkyl, $C_{2-6}$ alkenyl or $C_{2-6}$ alkynyl, wherein $C_{1-6}$ alkyl, $C_{2-6}$ alkenyl, and $C_{2-6}$ alkynyl are optionally substituted with one or more halogen, which are the same or different;

$R^1$ is H or $C_{1-4}$ alkyl, preferably H, wherein $C_{1-4}$ alkyl is optionally substituted with one or more halogen, which are the same or different;

$R^2$ is H; F; or $C_{1-4}$ alkyl, wherein $C_{1-4}$ alkyl is optionally substituted with one or more halogen, which are the same or different; and $R^3$ is $A^3$, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more $R^8$, which are the same or different; or $R^2$ and $R^3$ are joined to form together with the oxygen atom and carbon atom to which they are attached a ring $A^{3a}$, wherein $A^{3a}$ is a 7 to 12 membered heterobicyclyl, wherein 7 to 12 membered heterobicyclyl is optionally substituted with one or more $R^{10}$, which are the same or different;

$R^{2a}$ is H or F, preferably H;

each $R^8$ is independently halogen; CN, $C(O)OR^9$, $OR^9$, $C(O)R^9$, $C(O)N(R^9R^{9a})$ $S(O)_2N(R^9R^{9a})$, $S(O)N(R^9R^{9a})$, $S(O)_2R^9$, $S(O)R^9$, $N(R^9)S(O)_2N(R^{9a}R^{9b})$, $SR^9$, $N(R^9R^{9a})$, $NO_2$, $OC(O)R^9$, $N(R^9)C(O)R^{9a}$, $N(R^9)SO_2R^{9a}$, $N(R^9)S(O)R^{9a}$, $N(R^9)C(O)N(R^{9a}R^{9b})$, $N(R^9)C(O)OR^{9a}$, $OC(O)N(R^9R^{9a})$, or $A^3$;

$R^9$, $R^{9a}$, $R^{9b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different, or one OH, or one $OC_{1-4}$ alkyl, or one $A^3$;

each $A^3$ is independently phenyl, naphthyl, $C_{3-7}$ cycloalkyl, 3 to 7 membered heterocyclyl, or 7 to 12 membered heterobicyclyl, wherein $A^3$ is optionally substituted with one or more $R^{10}$, which are the same or different;

each $R^{10}$ is independently halogen, CN, $C(O)OR^{11}$, $OR^{11}$, $C(O)R^{11}$, $C(O)N(R^{11}R^{11a})$, $S(O)_2N(R^{11}R^{11a})$, $S(O)N ($R^{11}R^{11a}$), $S(O)_2R^{11}$, $S(O)R^{11}$, $N(R^{11})S(O)_2N$
($R^{11a}R^{11b}$), $SR^{11}$, $N(R^{11}R^{11a})$, $NO_2$, $OC(O)R^{11}$, $N(R^{11})$
$C(O)R^{11a}$, $N(R^{11})S(O)_2R^{11a}$, $N(R^{11})S(O)R^{11a}$, $N(R^{11})$
$C(O)OR^{11a}$, $N(R^{11})C(O)N(R^{11a}R^{11b})$, $OC(O)N$
($R^{11}R^{11a}$), oxo (=O) where the ring is at least partially saturated, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more $R^{12}$, which are the same or different;

$R^{11}$, $R^{11a}$, $R^{11b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different;

each $R^{12}$ is independently halogen, CN, $C(O)OR^{13}$, $OR^{13}$, $C(O)R^{13}$, $C(O)N(R^{13}R^{13a})$, $S(O)_2N(R^{13}R^{13a})$, $S(O)N$ ($R^{13}R^{13a}$), $S(O)_2R^{13}$, $S(O)R^{13}$, $N(R^{13})S(O)_2N$ ($R^{13a}R^{13b}$), $SR^{13}$, $N(R^{13}R^{13a})$, $NO_2$, $OC(O)R^{13}$, $N(R^{13})C(O)R^{13a}$, $N(R^{13})SO_2R^{13a}$, $N(R^{13})S(O)R^{13a}$, $N(R^{13})C(O)N(R^{13a}R^{13b})$, $N(R^{13})C(O)OR^{13a}$, or $OC(O)N(R^{13}R^{13a})$;

$R^{13}$, $R^{13a}$, $R^{13b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different.

A compound not restricted to the use as a medicament as defined above with preferences as defined below and a pharmaceutically acceptable salt, solvate, hydrate, tautomer or stereoisomer thereof, is also within the scope of the present invention provided that the following compounds or a pharmaceutically acceptable salt, solvate, hydrate, tautomer or stereoisomer thereof are excluded:

CAS 1396491-78-3

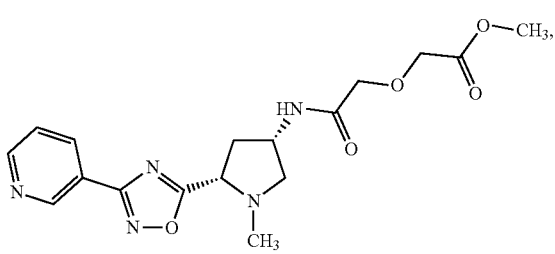

CAS 1212733-42-0

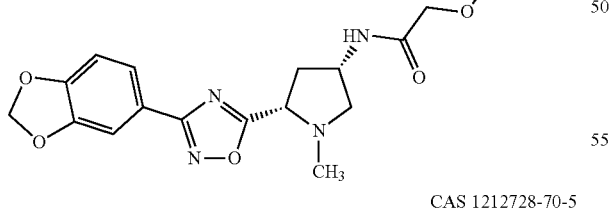

CAS 1212728-70-5

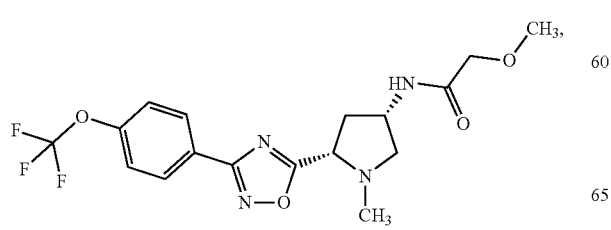

-continued

CAS 1212723-70-0

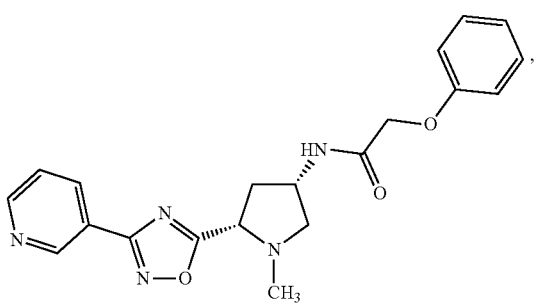

CAS 1212688-74-8

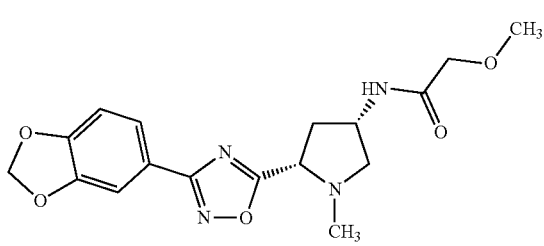

CAS 1212685-85-2

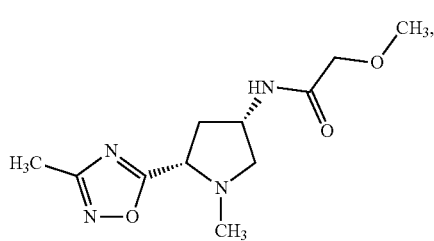

CAS 1212683-11-8

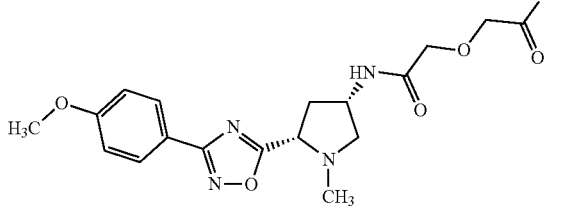

CAS 1212664-04-4

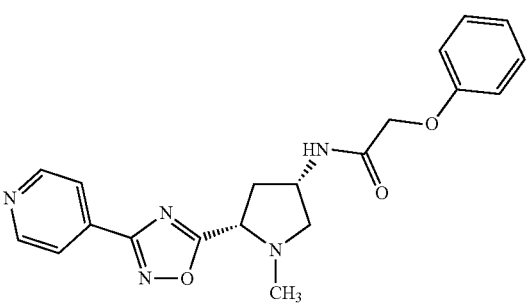

CAS 1212658-99-5

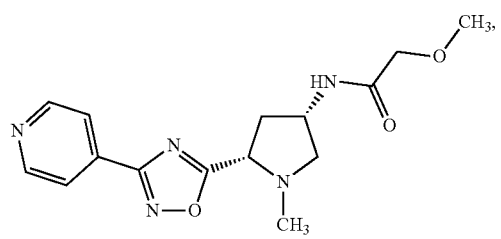

CAS 1212634-69-9

CAS 1212633-89-0

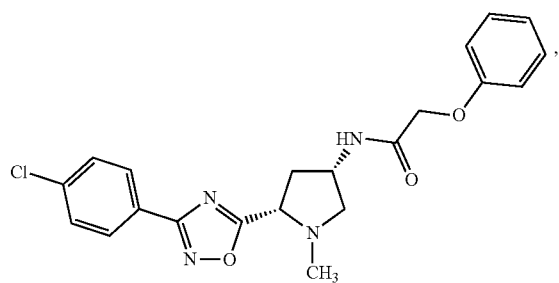

CAS 1212628-07-3

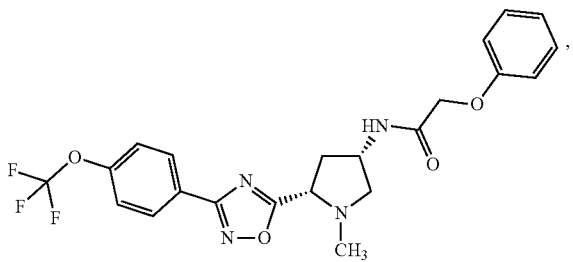

CAS 1212619-73-2

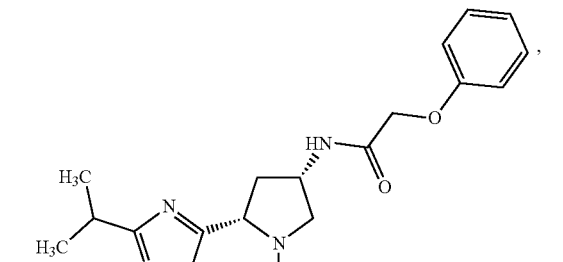

CAS 1212618-04-6

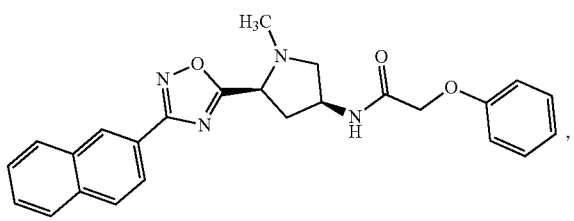

CAS 1212567-76-4

CAS 1212561-17-5

CAS 1212554-50-1

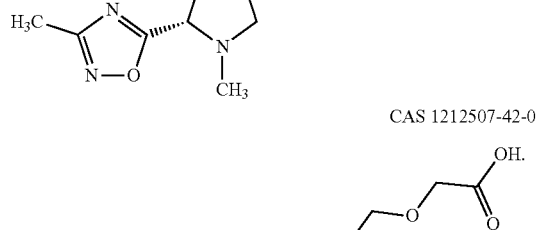

CAS 1212507-42-0

The excluded compounds represent commercial compounds without indication of the use.

The present invention also provides preferred compounds of formula (I) or a pharmaceutically acceptable salt, solvate, hydrate, tautomer or stereoisomer thereof for use as a medicament, wherein $X^1$ is $N(R^{a1})$;

$X^{1a}$ is a covalent single bond, $CH(R^{a3})$, or $CH(R^{a3})CH_2$;

$R^{a1}$ is H, C(O)OC$_{1-4}$ alkyl, or C$_{1-4}$ alkyl, wherein C(O)OC$_{1-4}$ alkyl and C$_{1-4}$ alkyl are optionally substituted with one or more substituents selected from the group consisting of halogen, OH, and O—C$_{1-3}$ alkyl, wherein the substituents are the same or different;

$R^{a2}$, $R^{a3}$ are independently selected from the group consisting of H; OH; OC$_{1-4}$ alkyl; halogen; C$_{1-4}$ alkyl; and $A^{2a}$; and $R^{a4}$, $R^{a5}$, $R^{a6}$, $R^{a7}$ are independently selected from the group consisting of H; halogen; C$_{1-4}$ alkyl; and $A^{2a}$, provided that only one of $R^{a2}$, $R^{a3}$, $R^{a4}$, $R^{a5}$, $R^{a6}$, $R^{a7}$ is $A^{2a}$;

or $R^{a1}$ and one of $R^{a2}$ and $R^{a3}$ form a methylene or ethylene group;

or $R^{a1}$ and $R^{a6}$ form an ethylene group;

or $R^{a2}$ and $R^{a5}$ form a covalent single bond;

or $R^{a5}$, $R^{a7}$ are joined to form an oxo group;

$A^1$ is C$_5$ cycloalkylene, C$_5$ cycloalkenylene, or a nitrogen ring atom containing 5-membered heterocyclene, wherein $A^1$ is optionally substituted with one or more $R^4$, which are the same or different;

each $R^4$ is independently oxo (=O) where the ring is at least partially saturated, thiooxo (=S) where the ring is at least partially saturated, halogen, CN, OR$^5$, or C$_{1-6}$ alkyl, wherein C$_{1-6}$ alkyl is optionally substituted with one or more halogen, which are the same or different;

$R^5$ is H or C$_{1-6}$ alkyl, wherein C$_{1-6}$ alkyl is optionally substituted with one or more halogen, which are the same or different;

$A^2$ is $R^{6a}$ or $A^{2a}$;

$R^{6a}$ is OR$^{6a1}$, SR$^{6a1}$, N(R$^{6a1}$R$^{6a2}$); C$_{1-6}$ alkyl, C$_{2-6}$ alkenyl or C$_{2-6}$ alkynyl, wherein C$_{1-6}$ alkyl, C$_{2-6}$ alkenyl, and C$_{2-6}$ alkynyl are optionally substituted with one or more substituents selected from the group consisting of halogen; CN; OR$^{6a3}$; and $A^{2a}$, wherein the substituents are the same or different;

$R^{6a1}$, $R^{6a2}$ are independently selected from the group consisting of H; C$_{1-6}$ alkyl; C$_{2-6}$ alkenyl; C$_{2-6}$ alkynyl; and $A^{2a}$, wherein C$_{1-6}$ alkyl; C$_{2-6}$ alkenyl; and C$_{2-6}$ alkynyl are optionally substituted with one or more substituents selected from the group consisting of halogen; CN; OR$^{6a3}$; and $A^{2a}$, wherein the substituents are the same or different;

$R^{6a3}$ is H; or C$_{1-4}$ alkyl, wherein C$_{1-4}$ alkyl is optionally substituted with one or more halogen, which are the same or different;

$A^{2a}$ is phenyl; C$_{3-7}$ cycloalkyl; C$_{4-12}$ bicycloalkyl; or 3- to 7-membered heterocyclyl, wherein $A^{2a}$ is optionally substituted with one or more $R^6$, which are the same or different;

each $R^6$ is independently $R^{6b}$; OH; OR$^{6b}$; halogen; or CN, wherein $R^{6b}$ is cyclopropyl, C$_{1-6}$ alkyl; C$_{2-6}$ alkenyl; or C$_{2-6}$ alkynyl, wherein $R^{6b}$ is optionally substituted with one or more halogen, which are the same or different; or two $R^6$ are joined to form together with the atoms to which they are attached a ring $A^{2b}$;

$A^{2b}$ is phenyl; C$_{3-7}$ cycloalkyl; or 3 to 7 membered heterocyclyl, wherein $A^{2b}$ is optionally substituted with one or more $R^7$, which are the same or different;

each $R^7$ is independently C$_{1-6}$ alkyl, C$_{2-6}$ alkenyl or C$_{2-6}$ alkynyl, wherein C$_{1-6}$ alkyl, C$_{2-6}$ alkenyl, and C$_{2-6}$ alkynyl are optionally substituted with one or more halogen, which are the same or different;

$R^1$ is H or C$_{1-4}$ alkyl, preferably H, wherein C$_{1-4}$ alkyl is optionally substituted with one or more halogen, which are the same or different;

$R^2$ is H; F; or C$_{1-4}$ alkyl, wherein C$_{1-4}$ alkyl is optionally substituted with one or more halogen, which are the same or different; and $R^3$ is $A^3$, C$_{1-6}$ alkyl, C$_{2-6}$ alkenyl, or C$_{2-6}$ alkynyl, wherein C$_{1-6}$ alkyl, C$_{2-6}$ alkenyl, and C$_{2-6}$ alkynyl are optionally substituted with one or more $R^8$, which are the same or different; or $R^2$ and $R^3$ are joined to form together with the oxygen atom and carbon atom to which they are attached a ring $A^{3a}$, wherein $A^{3a}$ is a 7 to 12 membered heterobicyclyl, wherein 7 to 12 membered heterobicyclyl is optionally substituted with one or more $R^{10}$, which are the same or different;

$R^{2a}$ is H or F, preferably H;

each $R^8$ is independently halogen; CN, C(O)OR$^9$, OR$^9$, C(O)R$^9$, C(O)N(R$^9$R$^{9a}$) S(O)$_2$N(R$^9$R$^{9a}$), S(O)N(R$^9$R$^{9a}$), S(O)$_2$R$^9$, S(O)R$^9$, N(R$^9$)S(O)$_2$N(R$^{9a}$R$^{9b}$), SR$^9$, N(R$^9$R$^{9a}$), NO$_2$, OC(O)R$^9$, N(R$^9$)C(O)R$^{9a}$, N(R$^9$)SO$_2$R$^{9a}$, N(R$^9$)S(O)R$^{9a}$, N(R$^9$)C(O)N(R$^{9a}$R$^{9b}$), N(R$^9$)C(O)OR$^{9a}$, OC(O)N(R$^9$R$^{9a}$), or $A^3$;

$R^9$, $R^{9a}$, $R^{9b}$ are independently selected from the group consisting of H, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are optionally substituted with one or more halogen, which are the same or different, or one OH, or one OC$_{1-4}$ alkyl, or one $A^3$;

each $A^3$ is independently phenyl, naphthyl, C$_{3-7}$ cycloalkyl, 3 to 7 membered heterocyclyl, or 7 to 12 membered heterobicyclyl, wherein $A^3$ is optionally substituted with one or more $R^{10}$, which are the same or different;

each $R^{10}$ is independently halogen, CN, C(O)OR$^{11}$, OR$^{11}$, C(O)R$^{11}$, C(O)N(R$^{11}$R$^{11a}$) S(O)$_2$N(R$^{11}$R$^{11a}$), S(O)N(R$^{11}$R$^{11a}$), S(O)$_2$R$^{11}$, S(O)R$^{11}$, N(R$^{11}$)S(O)$_2$N(R$^{11a}$R$^{11b}$), SR$^{11}$, N(R$^{11}$R$^{11a}$), NO$_2$, OC(O)R$^{11}$, N(R$^{11}$)C(O)R$^{11a}$, N(R$^{11}$)S(O)$_2$R$^{11a}$, N(R$^{11}$)S(O)R$^{11a}$, N(R$^{11}$)C(O)OR$^{11a}$, N(R$^{11}$)C(O)N(R$^{11a}$R$^{11b}$), OC(O)N(R$^{11}$R$^{11a}$), oxo (=O) where the ring is at least partially saturated, C$_{1-6}$ alkyl, C$_{2-6}$ alkenyl, or C$_{2-6}$ alkynyl, wherein C$_{1-6}$ alkyl, C$_{2-6}$ alkenyl, and C$_{2-6}$ alkynyl are optionally substituted with one or more $R^2$, which are the same or different;

$R^{11}$, $R^{11a}$, $R^{11b}$ are independently selected from the group consisting of H, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are optionally substituted with one or more halogen, which are the same or different;

each $R^{12}$ is independently halogen, CN, C(O)OR$^{13}$, OR$^{13}$, C(O)R$^{13}$, C(O)N(R$^{13}$R$^{13a}$) S(O)$_2$N(R$^{13}$R$^{13a}$), S(O)N(R$^{13}$R$^{13a}$), S(O)$_2$R$^{13}$, S(O)R$^{13}$, N(R$^{13}$)S(O)$_2$N(R$^{13a}$R$^{13b}$), SR$^{13}$, N(R$^{13}$R$^{13a}$), NO$_2$, OC(O)R$^{13}$, N(R$^{13}$)C(O)R$^{13a}$, N(R$^{13}$)SO$_2$R$^{13a}$, N(R$^{13}$)S(O)R$^{13a}$, N(R$^{13}$)C(O)N(R$^{13a}$R$^{13b}$), N(R$^{13}$)C(O)OR$^{13a}$, or OC(O)N(R$^{13}$R$^{13a}$);

$R^{13}$, $R^{13a}$, $R^{13b}$ are independently selected from the group consisting of H, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are optionally substituted with one or more halogen, which are the same or different.

The present invention also provides preferred compounds of formula (I), wherein $X^{1a}$ is CH(R$^{a3}$), $R^{a7}$ and $R^{2a}$ are H and thus having formula (I-1)

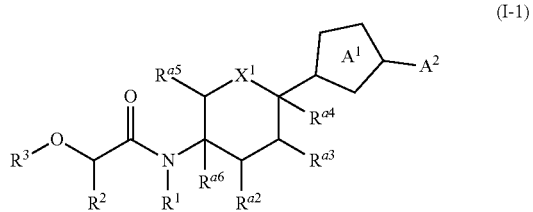

(I-1)

or a pharmaceutically acceptable salt, solvate, hydrate, tautomer or stereoisomer thereof, wherein $X^1$ is N(Ra);

$R^{a1}$ is H, or $C_{1-4}$ alkyl, wherein $C_{1-4}$ alkyl is optionally substituted with one or more substituents selected from the group consisting of halogen, OH, and O—$C_{1-3}$ alkyl, wherein the substituents are the same or different, preferably $R^{a1}$ is H; and $R^{a2}$, $R^{a3}$, $R^{a4}$, $R^{a5}$, $R^{a6}$ are H;

or $R^{a1}$ and one of $R^{a2}$ and $R^{a3}$ form a methylene or ethylene group;

or $R^{a1}$ and $R^{a6}$ form an ethylene group;

$A^1$ is $C_5$ cycloalkylene, $C_5$ cycloalkenylene, or a nitrogen ring atom containing 5-membered heterocyclene, wherein $A^1$ is optionally substituted with one or more $R^4$, which are the same or different;

each $R^4$ is independently halogen, CN, $OR^5$, oxo (=O) where the ring is at least partially saturated or $C_{1-6}$ alkyl, wherein $C_{1-6}$ alkyl is optionally substituted with one or more halogen, which are the same or different;

$R^5$ is H or $C_{1-6}$ alkyl, wherein $C_{1-6}$ alkyl is optionally substituted with one or more halogen, which are the same or different;

$A^2$ is phenyl or 5- to 6-membered aromatic heterocyclyl, wherein $A^2$ is optionally substituted with one or more $R^6$, which are the same or different;

each $R^6$ is independently OH, O($C_{1-6}$ alkyl), halogen, CN, cyclopropyl, $C_{1-6}$ alkyl, $C_{2-6}$ alkenyl, or $C_{2-6}$ alkynyl, wherein cyclopropyl, $C_{1-6}$ alkyl, $C_{2-6}$ alkenyl, and $C_{2-6}$ alkynyl are optionally substituted with one or more halogen, which are the same or different; or two $R^6$ are joined to form together with atoms to which they are attached a ring $A^{2b}$;

$A^{2b}$ is phenyl; $C_{3-7}$ cycloalkyl; or 3 to 7 membered heterocyclyl, wherein $A^{2b}$ is optionally substituted with one or more $R^7$, which are the same or different;

each $R^7$ is independently $C_{1-6}$ alkyl, $C_{2-6}$ alkenyl or $C_{2-6}$ alkynyl, wherein $C_{1-6}$ alkyl, $C_{2-6}$ alkenyl, and $C_{2-6}$ alkynyl are optionally substituted with one or more halogen, which are the same or different;

$R^1$ is H or $C_{1-4}$ alkyl, preferably H, wherein $C_{1-4}$ alkyl is optionally substituted with one or more halogen, which are the same or different;

$R^2$ is H or $C_{1-4}$ alkyl, wherein $C_{1-4}$ alkyl is optionally substituted with one or more halogen, which are the same or different; and $R^3$ is $A^3$, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more $R^8$, which are the same or different; or $R^2$ and $R^3$ are joined to form a 7 to 12 membered heterobicyclyl, wherein 7 to 12 membered heterobicyclyl is optionally substituted with one or more $R^{10}$, which are the same or different;

each $R^8$ is independently halogen; CN, C(O)$OR^9$, $OR^9$, C(O)$R^9$, C(O)N($R^9R^{9a}$) S(O)$_2$N($R^9R^{9a}$), S(O)N($R^9R^{9a}$), S(O)$_2R^9$, S(O)$R^9$, N($R^9$)S(O)$_2$N($R^{9a}R^{9b}$), S$R^9$, N($R^9R^{9a}$), NO$_2$, OC(O)$R^9$, N($R^9$)C(O)$R^{9a}$, N($R^9$)SO$_2R^{9a}$, N($R^9$)S(O)$R^{9a}$, N($R^9$)C(O)N($R^{9a}R^{9b}$), N($R^9$)C(O)O$R^{9a}$, OC(O)N($R^9R^{9a}$), or $A^3$;

$R^9$, $R^{9a}$, $R^{9b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different;

each $A^3$ is independently phenyl, naphthyl, $C_{3-7}$ cycloalkyl, 3 to 7 membered heterocyclyl, or 7 to 12 membered heterobicyclyl, wherein $A^3$ is optionally substituted with one or more $R^{10}$, which are the same or different;

each $R^{10}$ is independently halogen, CN, C(O)$OR^{11}$, $OR^{11}$, C(O)$R^{11}$, C(O)N($R^{11}R^{11a}$), S(O)$_2$N($R^{11}R^{11a}$), S(O)N($R^{11}R^{11a}$), S(O)$_2R^{11}$, S(O)$R^{11}$, N($R^1$)S(O)$_2$N($R^{11a}R^{11b}$), S$R^{11}$, N($R^{11}R^{11a}$), NO$_2$, OC(O)$R^{11}$, N($R^{11}$)C(O)$R^{11a}$, N($R^{11}$)S(O)$_2R^{11a}$, N($R^{11}$)S(O)$R^{11a}$, N($R^{11}$)C(O)O$R^{11a}$, N($R^{11}$)C(O)N($R^{11a}R^{11b}$), OC(O)N($R^{11}R^{11a}$), oxo (=O) where the ring is at least partially saturated, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more $R^{12}$, which are the same or different;

$R^{11}$, $R^{11a}$, $R^{11b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different;

each $R^{12}$ is independently halogen, CN, C(O)$OR^{13}$, $OR^{13}$, C(O)$R^{13}$, C(O)N($R^{13}R^{13a}$) S(O)$_2$N($R^{13}R^{13a}$), S(O)N($R^{13}R^{13a}$), S(O)$_2R^{13}$, S(O)$R^{13}$, N($R^{13}$)S(O)$_2$N($R^{13a}R^{13b}$), S$R^{13}$, N($R^{13}R^{13a}$), NO$_2$, OC(O)$R^{13}$, N($R^{13}$)C(O)$R^{13a}$, N($R^{13}$)SO$_2R^{13a}$, N($R^{13}$)S(O)$R^{13a}$ N($R^{13}$)C(O)N($R^{13a}R^{13b}$), N($R^{13}$)C(O)O$R^{13a}$, or OC(O)N($R^{13}R^{13a}$);

$R^{13}$, $R^{13a}$, $R^{13b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different.

Surprisingly, the disclosed example compounds according to the present invention have favourable physico-chemical properties and/or selectivity, which combine to help to achieve beneficial therapeutic efficacy whilst limiting unintended liabilities.

In case a variable or substituent can be selected from a group of different variants and such variable or substituent occurs more than once the respective variants can be the same or different.

Within the meaning of the present invention the terms are used as follows:

The term "optionally substituted" means unsubstituted or substituted. Generally—but not limited to—, "one or more substituents" means one, two or three, preferably one or two substituents and more preferably one substituent. Generally these substituents can be the same or different. The term "one or more substituents" also means by way of example one, two, three, four or five, preferably by way of example one, two, three or four.

"Alkyl" means a straight-chain or branched hydrocarbon chain. Each hydrogen of an alkyl carbon may be replaced by a substituent as further specified.

"Alkenyl" means a straight-chain or branched hydrocarbon chain that contains at least one carbon-carbon double bond. Each hydrogen of an alkenyl carbon may be replaced by a substituent as further specified.

"Alkynyl" means a straight-chain or branched hydrocarbon chain that contains at least one carbon-carbon triple bond. Each hydrogen of an alkynyl carbon may be replaced by a substituent as further specified.

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl, tert-butyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-4}$ alkyl carbon may be replaced by a substituent as further specified. The term "$C_{1-3}$ alkyl" is defined accordingly.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl, tert-butyl, n-pentyl, n-hexyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-6}$ alkyl carbon may be replaced by a substituent as further specified.

"$C_{2-6}$ alkenyl" means an alkenyl chain having 2 to 6 carbon atoms, e.g. if present at the end of a molecule: —CH=$CH_2$, —CH=CH—$CH_3$, —$CH_2$—CH=$CH_2$, —CH=CH—$CH_2$—$CH_3$, —CH=CH—CH=$CH_2$, or e.g. —CH=CH—, when two moieties of a molecule are linked by the alkenyl group. Each hydrogen of a $C_{2-6}$ alkenyl carbon may be replaced by a substituent as further specified.

"$C_{2-6}$ alkynyl" means an alkynyl chain having 2 to 6 carbon atoms, e.g. if present at the end of a molecule: —C≡$CH_2$, —$CH_2$—C≡CH, $CH_2$—$CH_2$—C≡CH, $CH_2$—C≡C—$CH_3$, or e.g. —C≡C— when two moieties of a molecule are linked by the alkynyl group. Each hydrogen of a $C_{2-6}$ alkynyl carbon may be replaced by a substituent as further specified.

"$C_{3-7}$ cycloalkyl" or "$C_{3-7}$ cycloalkyl ring" means a cyclic alkyl chain having 3-7 carbon atoms, e.g. cyclopropyl, cyclobutyl, cyclopentyl, cyclohexyl, cyclohexenyl, cycloheptyl. Preferably, cycloalkyl refers to cyclopropyl, cyclobutyl, cyclopentyl, cyclohexyl, or cycloheptyl. Each hydrogen of a cycloalkyl carbon may be replaced by a substituent as further specified herein. The term "$C_{3-5}$ cycloalkyl" or "$C_{3-5}$ cycloalkyl ring" is defined accordingly.

"$C_5$ cycloalkylene" refers to a bivalent cycloalkyl with five carbon atoms, i.e. a bivalent cyclopentyl ring.

"$C_5$ cycloalkenylene" refers to a bivalent cycloalkenylene, i.e. a bivalent cyclopentene or cyclopentadiene.

"$C_{4-12}$ bicycloalkyl" or "$C_{4-12}$ bicycloalkyl ring" means a bicyclic fused, bridged or spiro alkyl chain having 4 to 12 carbon atoms, e.g. hexahydroindane, Octahydropentalen, bicycle[2.2.1]heptane or spiro(3.2)hexane. Each hydrogen of a bicycloalkyl carbon may be replaced by a substituent as further specified herein.

"Halogen" means fluoro, chloro, bromo or iodo. It is generally preferred that halogen is fluoro or chloro.

"3 to 7 membered heterocyclyl" or "3 to 7 membered heterocycle" means a ring with 3, 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 3 to 7 membered heterocycle are aziridine, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. The term "5 to 6 membered heterocyclyl" or "5 to 6 membered heterocycle" is defined accordingly and and includes 5 to 6 membered aromatic heterocyclyl or heterocycle. The term "5 membered heterocyclyl" or "5 membered heterocycle" is defined accordingly and includes 5 membered aromatic heterocyclyl or heterocycle.

The term "nitrogen ring atom containing 5-membered heterocyclene" refers to a bivalent 5-membered heterocycle, wherein at least one of the five ring atoms is a nitrogen atom and wherein the ring is linked to the rest of the molecule via a carbon or nitrogen atom.

"Saturated 4 to 7 membered heterocyclyl" or "saturated 4 to 7 membered heterocycle" means fully saturated "4 to 7 membered heterocyclyl" or "4 to 7 membered heterocycle".

"4 to 7 membered at least partly saturated heterocyclyl" or "4 to 7 membered at least partly saturated heterocycle" means an at least partly saturated "4 to 7 membered heterocyclyl" or "4 to 7 membered heterocycle".

"5 to 6 membered aromatic heterocyclyl" or "5 to 6 membered aromatic heterocycle" means a heterocycle derived from cyclopentadienyl or benzene, where at least one carbon atom is replaced by a heteroatom selected from the group consisting of sulfur (including —S(O)—, —S(O)$_2$—), oxygen and nitrogen (including =N(O)—). Examples for such heterocycles are furan, thiophene, pyrrole, imidazole, pyrazole, oxazole, isoxazole, thiazole, isothiazole, thiadiazole, triazole, tetrazole, pyridine, pyrimidine, pyridazine, pyrazine, triazine.

"5 membered aromatic heterocyclyl" or "5 membered aromatic heterocycle" means a heterocycle derived from cyclopentadienyl, where at least one carbon atom is replaced by a heteroatom selected from the group consisting of sulfur (including —S(O)—, —S(O)$_2$—), oxygen and nitrogen (including =N(O)—). Examples for such heterocycles are furan, thiophene, pyrrole, imidazole, pyrazole, oxazole, isoxazole, thiazole, isothiazole, thiadiazole, triazole, tetrazole.

"7 to 12 membered heterobicyclyl" or "7 to 12 membered heterobicycle" means a heterocyclic system of two rings with 7 to 12 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 7 to 12 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 7 to 12 membered heterobicycle also includes spiro structures of two rings like 6-oxa-2-azaspiro[3,4]octane, 2-oxa-6-azaspiro[3.3]heptan-6-yl or 2,6-diazaspiro[3.3]heptan-6-yl or bridged heterocycles like 8-aza-bicyclo[3.2.1]octane or 2,5-diazabicyclo[2.2.2]octan-2-yl or 3,8-diazabicyclo[3.2.1]octane.

"Saturated 7 to 12 membered heterobicyclyl" or "saturated 7 to 12 membered heterobicycle" means fully saturated "7 to 12 membered heterobicyclyl" or "7 to 12 membered heterobicycle".

"7 to 12 membered at least partly saturated heterobicyclyl" or "7 to 12 membered at least partly saturated heterobicycle" means an at least partly saturated "7 to 12 membered heterobicyclyl" or "7 to 12 membered heterobicycle".

"9 to 11 membered aromatic heterobicyclyl" or "9 to 11 membered aromatic heterobicycle" means a heterocyclic system of two rings, wherein at least one ring is aromatic and wherein the heterocyclic ring system has 9 to 11 ring atoms, where two ring atoms are shared by both rings and that may contain up to the maximum number of double bonds (fully or partially aromatic) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for an 9 to 11 membered aromatic heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, dihydroquinoline, tetrahydroquinoline, isoquinoline, tetrahydroisoquinoline, dihydroisoquinoline, benzazepine, purine or pteridine. The terms "9 to 10 membered aromatic heterobicyclyl" or "9 to 10 membered aromatic heterobicycle" are defined accordingly.

Preferred compounds of formula (I) are those compounds in which one or more of the residues contained therein have the meanings given above or below, with all combinations of preferred substituent definitions being a subject of the present invention. With respect to all preferred compounds of the formula (I) the present invention also includes all tautomeric and stereoisomeric forms and mixtures thereof in all ratios, and their pharmaceutically acceptable salts.

In preferred embodiments of the present invention, the substituents mentioned below independently have the following meaning. Hence, one or more of these substituents can have the preferred or more preferred meanings given below.

Preferably, $X^1$ is NH or N—$C_{1-4}$ alkyl, wherein $C_{1-4}$ alkyl is optionally substituted with one or more substituents selected from the group consisting of halogen, OH, and O—$C_{1-3}$ alkyl, wherein the substituents are the same or different; more preferably $X^1$ is NH, N(CH$_3$), N(CH$_2$CH$_3$), or N(CH$_2$CH$_2$OCH$_3$); even more preferably NH or N(CH$_3$); even more preferably NH.

Preferably, $X^{1a}$ is CH($R^{a3}$) or CH($R^{a3}$)CH$_2$, even more preferably CH($R^{a3}$).

Preferably, $R^{a2}$, $R^{a3}$ are independently selected from the group consisting of H; OH; OC$_{1-4}$ alkyl; halogen; C$_{1-4}$ alkyl; and $A^{2a}$; and $R^{a4}$, $R^{a5}$, $R^{a6}$, $R^{a7}$ are independently selected from the group consisting of H; halogen; C$_{1-4}$ alkyl; and $A^{2a}$, provided that only one of $R^{a2}$, $R^{a3}$, $R^{a4}$, $R^{a5}$, $R^{a6}$, $R^{a7}$ is $A^{2a}$;

or $R^{a5}$, $R^{a7}$ are joined to form an oxo group.

Preferably, $R^{a2}$, $R^{a3}$, $R^{a4}$, $R^{a5}$, $R^{a6}$, $R^{a7}$ are independently selected from the group consisting of H; halogen; C$_{1-4}$ alkyl; and $A^{2a}$, provided that only one of $R^{a2}$, $R^{a3}$, $R^{a4}$, $R^{a5}$, $R^{a6}$, $R^{a7}$ is $A^{2a}$. More preferably, $R^{a2}$, $R^{a3}$, $R^{a4}$, $R^{a5}$, $R^{a6}$, $R^{a7}$ are H or $R^{a2}$, $R^{a3}$, $R^{a4}$, $R^{a6}$ are H and $R^{a5}$, $R^{a7}$ are joined to form an oxo group. Even more preferably $R^{a2}$, $R^{a3}$, $R^{a4}$, $R^{a5}$, $R^{a6}$, $R^{a7}$ are H.

Preferably, $A^1$ is a nitrogen ring atom containing 5-membered heterocyclene and wherein $A^1$ is optionally substituted with one or more $R^4$, which are the same or different.

More preferably, $A^1$ is a nitrogen ring atom containing 5-membered heterocyclene selected from the group of bivalent heterocycles consisting of oxadiazole, imidazole, imidazolidine, pyrazole and triazole, preferably oxadiazole, and wherein $A^1$ is optionally substituted with one or more $R^4$, which are the same or different.

Preferably, $A^1$ is unsubstituted or substituted with one or two $R^4$, which are the same or different, preferably $A^1$ is unsubstituted.

Preferably, $R^4$ is independently oxo (=O) where the ring is at least partially saturated, halogen, CN, OR$^5$ or C$_{1-6}$ alkyl, wherein C$_{1-6}$ alkyl is optionally substituted with one or more halogen, which are the same or different.

Preferably, $R^4$ is oxo, where the ring is at least partly saturated.

Preferably, $A^1$ is

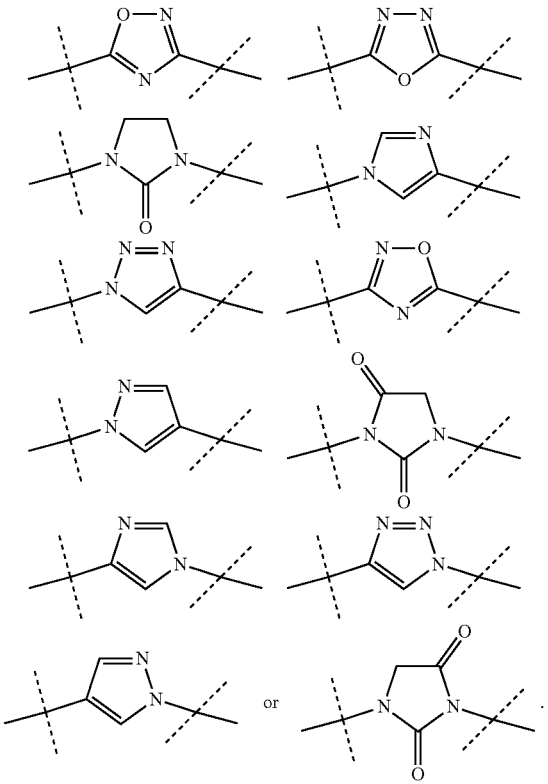

More preferably, $A^1$ is

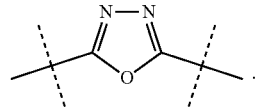

In one embodiment $A^2$ is $R^{6a}$.
Preferably, $R^{6a}$ is OR$^{6a1}$.

In an embodiment, $R^{6a1}$, $R^{6a2}$ are independently selected from the group consisting of H; $C_{1-6}$ alkyl; $C_{2-6}$ alkenyl; $C_{2-6}$ alkynyl; and $A^{2a}$, wherein $C_{1-6}$ alkyl; $C_{2-6}$ alkenyl; and $C_{2-6}$ alkynyl are optionally substituted with one or more substituents selected from the group consisting of halogen; CN; $OR^{6a3}$; and $A^{2a}$, wherein the substituents are the same or different.

$R^{6a1}$ is preferably $A^{2a}$ or $C_{1-6}$ alkyl, optionally substituted with one or more halogen and/or one $A^{2a}$ and/or one $OR^{6a3}$. More preferably, $R^{6a1}$ is $C_{1-6}$ alkyl, optionally substituted with one or more F and/or one $OR^{6a3}$.

Preferably, $R^{6a}$ is $C_{1-6}$ alkyl, optionally substituted with one or more halogen and/or one $A^{2a}$ and/or one $OR^{6a3}$. More preferably, $R^{6a}$ is $C_{1-6}$ alkyl, optionally substituted with one or more halogen and/or one $OR^{6a3}$.

In one preferred embodiment $R^{6a1}$ is unsubstituted $C_{4-6}$ alkyl; more preferably 3-methylbut-1yl or n-butyl. In another preferred embodiment $R^{6a1}$ is $C_{2-6}$ alkyl, substituted with one or more halogen, which are the same or different, preferably one or more fluoro; more preferably $R^{6a1}$ is 3,3,3-trifluoropropyl, 2-methyl-3,3,3-trifluoropropyl, 4,4,4-trifluorobut-2-yl, 2,2,3,3,3-pentafluoropropyl, 3,3-difluorobutyl or 3,3,3-trifluorobutyl. In another preferred embodiment $R^{6a1}$ is $A^{2a}$, $CH_2A^{2a}$, $CH_2CH_2A^{2a}$, wherein $A^{2a}$ is unsubstituted or substituted with one or more halogen, which are the same or different, preferably one or more fluoro; more preferably $R^{6a1}$ is cyclobutyl, cyclopentyl, $CH_2$-cyclopropyl, $CH_2$-cyclobutyl, $CH_2CH_2$-cyclopropyl, wherein $R^{6a1}$ is substituted with one or more F.

In a particularly preferred embodiment $A^2$ is $R^{6a}$, $R^{6a}$ is $OR^{6a1}$ and $R^{6a1}$ is $CH_2CH_2CF_3$ or $CH_2CH_2OCF_3$, preferably $CH_2CH_2OCF_3$.

Preferably, $R^{6a2}$ is H.

Preferably, $R^{6a}$ is $OC_{1-4}$ alkyl; $OC_{1-4}$ alkyl-$OC_{1-4}$ alkyl, wherein each $C_{1-4}$ alkyl is optionally substituted with one to three F; or $OCH_2A^{2a}$.

In another embodiment $A^2$ is $A^{2a}$.

Preferably, $A^{2a}$ is phenyl; $C_{3-7}$ cycloalkyl; or 3- to 7-membered heterocyclyl, wherein $A^{2a}$ is optionally substituted with one or more $R^6$, which are the same or different.

Preferably, $A^{2a}$ is phenyl; cyclobutyl; azetidinyl; pyrrolidinyl; or 5- to 6-membered aromatic heterocyclyl, preferably pyridyl, pyrazinyl, pyridazinyl, pyrazolyl or 1,2,4-oxadiazolyl, wherein $A^{2a}$ is optionally substituted with one or more $R^6$, which are the same or different.

More preferably, $A^{2a}$ is phenyl, or 5- to 6-membered aromatic heterocyclyl, preferably pyridyl, pyrazinyl, pyridazinyl, pyrazolyl or 1,2,4-oxadiazolyl, wherein $A^{2a}$ is optionally substituted with one or more $R^6$, which are the same or different.

Even more preferably, $A^{2a}$ is phenyl; cyclobutyl; pyridyl; azetidinyl; pyrazolyl; or pyrrolidinyl, wherein $A^{2a}$ is optionally substituted with one or more $R^6$, which are the same or different.

Preferably, $A^{2a}$ is $C_{3-7}$ cycloalkyl, more preferably cyclobutyl, wherein $A^{2a}$ is optionally substituted with one or more $R^6$, which are the same or different.

Preferably, $A^{2a}$ is substituted with one or two $R^6$, which are the same or different.

Preferably, $R^6$ is independently F, Cl, $CF_3$, $OCH_3$, $OCF_3$, $OCHF_2$, $CH_3$, $CH_2CH_3$, $CH_2CF_3$, O-cyclopropyl, or cyclopropyl. More preferably, $R^6$ is independently F, Cl, $CF_3$, $OCH_3$, $OCF_3$, $CH_3$, $CH_2CH_3$, or cyclopropyl, preferably F, Cl, $CF_3$, $OCH_3$, $CH_3$, $CH_2CH_3$, or cyclopropyl.

Preferably, $R^2$ is $CH_3$; F; or H, more preferably H.

Preferably, $R^9$, $R^{9a}$, $R^{9b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different, or one OH, or one $OC_{1-4}$ alkyl, or one $A^3$.

Preferably, $R^3$ is $A^3$.

Preferably, $A^3$ is phenyl, pyridyl, pyrazinyl, pyrimidazyl, cyclopropyl, cyclobutyl or cyclohexyl, wherein $A^3$ is optionally substituted with one or more $R^{10}$, which are the same or different. More preferably, $A^3$ is phenyl, wherein $A^3$ is optionally substituted with one or more $R^{10}$, which are the same or different.

Preferably, $A^3$ is substituted with one, two or three, preferably one or two, (more preferably two) $R^{10}$, which are the same or different.

Preferably, $R^2$ and $R^3$ are joined together with the oxygen and carbon atom to which they are attached to form a dihydrobenzopyran ring, wherein the ring is optionally substituted with one or more $R^{10}$, which are the same or different, preferably the ring is substituted with one or two $R^{10}$.

Preferably, $R^{10}$ is independently F, Cl, Br, CN, $CHF_2$, $CF_3$, $OCH_3$, $OCF_3$, CH=O, $CH_2OH$ or $CH_3$; preferably, F, Cl, Br, $CF_3$, $OCF_3$, CH=O, $CH_2OH$ or $CH_3$; more preferably F, Cl, $CF_3$, CH=O, $CH_2OH$ or $CH_3$. More preferably, $R^{10}$ is independently F or Cl.

Preferably, $R^{a1}$ is H, or $C_{1-4}$ alkyl, wherein $C_{1-4}$ alkyl is optionally substituted with one or more substituents selected from the group consisting of halogen, OH, and O—$C_{1-3}$ alkyl, wherein the substituents are the same or different; preferably $R^{a1}$ is H; $CH_3$ or $CH_2CH_3$; more preferably $R^{a1}$ is H.

Compounds of the formula (I) in which some or all of the above-mentioned groups have the preferred or more preferred meanings are also an object of the present invention.

Preferred specific compounds of the present invention are selected from the group consisting of tert-butyl (2R,5S)-5-[2-(4-chloro-3-fluorophenoxy)acetamido]-2-{5-[4-(trifluoromethyl)phenyl]-1,3,4-oxadiazol-2-yl}piperidine-1-carboxylate 2-(4-chloro-3-fluorophenoxy)-N-[(3S,6R)-6-{5-[4-(trifluoromethyl)phenyl]-1,3,4-oxadiazol-2-yl}piperidin-3-yl]acetamide tert-butyl (2R,5S)-5-[2-(4-chlorophenoxy)propanamido]-2-{5-[4-(trifluoromethyl)phenyl]-1,3,4-oxadiazol-2-yl}piperidine-1-carboxylate 2-(4-chlorophenoxy)-N-[(3S,6R)-6-{5-[4-(trifluoromethyl)phenyl]-1,3,4-oxadiazol-2-yl}piperidin-3-yl]propanamide N-[(3R,6S)-6-[5-(4-chlorophenyl)-1,3,4-oxadiazol-2-yl]piperidin-3-yl]-2-[(1s,3s)-3-(trifluoromethoxy)cyclobutoxy]acetamide tert-butyl (2R,5S)-5-{2-[(6-chloro-5-fluoropyridin-3-yl)oxy]acetamido}-2-[5-(4-chlorophenyl)-1,3,4-oxadiazol-2-yl]piperidine-1-carboxylate 2-[(6-chloro-5-fluoropyridin-3-yl)oxy]-N-[(3S,6R)-6-[5-(4-chlorophenyl)-1,3,4-oxadiazol-2-yl]piperidin-3-yl]acetamide tert-butyl (2R,5S)-5-[2-(3,4-dichlorophenoxy)acetamido]-2-{5-[(1s,3s)-3-(trifluoromethoxy)cyclobutyl]-1,3,4-oxadiazol-2-yl}piperidine-1-carboxylate 2-(3,4-dichlorophenoxy)-N-[(3S,6R)-6-{5-[(1s,3s)-3-(trifluoromethoxy)cyclobutyl]-1,3,4-oxadiazol-2-yl}piperidin-3-yl]acetamide 2-[3-chloro-4-(trifluoromethyl)phenoxy]-N-[(3S,6R)-6-{5-[(1s,3s)-3-(trifluoromethoxy)cyclobutyl]-1,3,4-oxadiazol-2-yl}piperidin-3-yl]acetamide 2-[4-chloro-3-(difluoromethyl)phenoxy]-N-[(3S,6R)-6-{5-[2-(trifluoromethoxy)ethoxy]-1,3,4-oxadiazol-2-yl}piperidin-3-yl]acetamide 2-(4-chloro-3-methylphenoxy)-N-[(3S,6R)-6-{5-[2-(trifluoromethoxy)ethoxy]-1,3,4-oxadiazol-2-yl}piperidin-3-yl]acetamide 2-(3,4-dimethylphenoxy)-N-[(3S,6R)-6-{5-[2-(trifluoromethoxy)ethoxy]-1,3,4-oxadiazol-2-yl}piperidin-3-yl]acetamide N-[(3S,6R)-6-{5-[2-(trifluoromethoxy)ethoxy]-1,3,4-oxadiazol-2-yl}piperidin-3-yl]-2-{[6-(trifluoromethyl)pyridin-3-yl]oxy}acetamide 2-[3-methoxy-4-(trifluoromethyl)phenoxy]-N-[(3S,6R)-6-{5-[2-(trifluoromethoxy)ethoxy]-1,3,4-oxadiazol-2-yl}piperidin-3-yl]acetamide tert-butyl (2R,5S)-5-[2-(4-chloro-2-fluorophenoxy)acetamido]-2-[5-(3,3,3-trifluoropropoxy)-1,3,4-oxadiazol-2-yl]piperidine-1-carboxylate 2-(4-chloro-2-fluorophenoxy)-N-[(3S,6R)-6-[5-(3,3,3-trifluoropropoxy)-1,3,4-oxadiazol-2-yl]piperidin-3-yl]acetamide 2-(3-chloro-4-fluorophenoxy)-N-[(3S,6R)-6-[5-(3,3,3-trifluoropropoxy)-1,3,4-oxadiazol-2-yl]piperidin-3-yl]acetamide 2-[4-(trifluoromethyl)phenoxy]-N-[(3S,6R)-6-[5-(3,3,3-trifluoropropoxy)-1,3,4-oxadiazol-2-yl]piperidin-3-yl]acetamide 2-(3,4-dichlorophenoxy)-N-[(3S,6R)-6-[5-(3,3,3-trifluoropropoxy)-1,3,4-oxadiazol-2-yl]piperidin-3-yl]acetamide 2-(4-chloro-2,3-difluorophenoxy)-N-[(3S,6R)-6-[5-(3,3,3-trifluoropropoxy)-1,3,4-oxadiazol-2-yl]piperidin-3-yl]acetamide 2-(4-chloro-3,5-difluorophenoxy)-N-[(3S,6R)-6-[5-(3,3,3-trifluoropropoxy)-1,3,4-oxadiazol-2-yl]piperidin-3-yl]acetamide 2-[3-fluoro-4-(trifluoromethyl)phenoxy]-N-[(3S,6R)-6-[5-(3,3,3-trifluoropropoxy)-1,3,4-oxadiazol-2-yl]piperidin-3-yl]acetamide 2-(4-chloro-3-fluorophenoxy)-2,2-difluoro-N-[(3S,6R)-6-[5-(3,3,3-trifluoropropoxy)-1,3,4-oxadiazol-2-yl]piperidin-3-yl]acetamide 2-[3-chloro-4-(trifluoromethyl)phenoxy]-N-[(3S,6R)-6-[5-(3,3,3-trifluoropropoxy)-1,3,4-oxadiazol-2-yl]piperidin-3-yl]acetamide 2-(3,4,5-trichlorophenoxy)-N-[(3S,6R)-6-[5-(3,3,3-trifluoropropoxy)-1,3,4-oxadiazol-2-yl]piperidin-3-yl]acetamide 2-(4-bromophenoxy)-N-[(3S,6R)-6-[5-(3,3,3-trifluoropropoxy)-1,3,4-oxadiazol-2-yl]piperidin-3-yl]acetamide 2-[3-(trifluoromethyl)phenoxy]-N-[(3S,6R)-6-[5-(3,3,3-trifluoropropoxy)-1,3,4-oxadiazol-2-yl]piperidin-3-yl]acetamide 2-(4-chloro-3-cyanophenoxy)-N-[(3S,6R)-6-{5-[2-(trifluoromethoxy)ethoxy]-1,3,4-oxadiazol-2-yl}piperidin-3-yl]acetamide tert-butyl (2R,4S)-4-[2-(4-chloro-3-fluorophenoxy)acetamido]-2-[5-(4-chlorophenyl)-1,3,4-oxadiazol-2-yl]pyrrolidine-1-carboxylate 2-(4-chloro-3-fluorophenoxy)-N-[(3S,5R)-5-[5-(4-chlorophenyl)-1,3,4-oxadiazol-2-yl]pyrrolidin-3-yl]acetamide tert-butyl (2R,5S)-5-[2-(4-chloro-3-fluorophenoxy)acetamido]-2-[5-(3,3,3-trifluoropropoxy)-1,3,4-oxadiazol-2-yl]piperidine-1-carboxylate 2-(4-chloro-3-fluorophenoxy)-N-[(3S,6R)-6-[5-(3,3,3-trifluoropropoxy)-1,3,4-oxadiazol-2-yl]piperidin-3-yl]acetamide 2-(4-chloro-3-fluorophenoxy)-N-[(3S,6R)-6-[5-(6-methylpyridin-3-yl)-1,3,4-oxadiazol-2-yl]piperidin-3-yl]acetamide 2-(4-chloro-3-fluorophenoxy)-N-[(3R,6S)-6-[5-(4-chlorophenyl)-1,3,4-oxadiazol-2-yl]piperidin-3-yl]acetamide 2-(4-chloro-3-fluorophenoxy)-N-[(3R,6R)-6-[5-(4-chlorophenyl)-1,3,4-oxadiazol-2-yl]piperidin-3-yl]acetamide rac-2-(4-chloro-3-fluorophenoxy)-N-[(3R,6S)-6-[5-(4-chlorophenyl)-1,3,4-oxadiazol-2-yl]-2-oxopiperidin-3-yl]acetamide rac-2-(4-chloro-3-fluorophenoxy)-N-[(3R,6R)-2-oxo-6-{5-[(1s,3s)-3-(trifluoromethoxy)cyclobutyl]-1,3,4-oxadiazol-2-yl}piperidin-3-yl]acetamide tert-butyl (2R,5S)-5-[2-(4-chloro-3-fluorophenoxy)acetamido]-2-[5-(4-chlorophenyl)-1,3,4-oxadiazol-2-yl]piperidine-1-carboxylate 2-(4-chloro-3-fluorophenoxy)-N-[(3S,6R)-6-[5-(4-chlorophenyl)-1,3,4-oxadiazol-2-yl]piperidin-3-yl]acetamide tert-butyl (2S,5R)-5-[2-(4-chloro-3-fluorophenoxy)acetamido]-2-[5-(3,3,3-trifluoropropoxy)-1,3,4-oxadiazol-2-yl]piperidine-1-carboxylate 2-(4-chloro-3-fluorophenoxy)-N-[(3R,6S)-6-[5-(3,3,3-trifluoropropoxy)-1,3,4-oxadiazol-2-yl]piperidin-3-yl]acetamide 2-(4-chloro-3-fluorophenoxy)-N-[(3R,6S)-6-{5-[3-(trifluoromethoxy)azetidin-1-yl]-1,3,4-oxadiazol-2-yl}piperidin-3-yl]acetamide 2-(4-chloro-3-fluorophenoxy)-N-[(3R,6S)-6-[5-(4-chlorophenyl)-1,3,4-oxadiazol-2-yl]-1-methylpiperidin-3-yl]acetamide 2-(4-chloro-3-fluorophenoxy)-N-[(3S,6R)-6-[5-(4-chlorophenyl)-1,3,4-oxadiazol-2-yl]-1-methylpiperidin-3-yl]acetamide 2-(4-chloro-3-fluorophenoxy)-N-[(3S,6R)-6-[5-(4-chlorophenyl)-1,3,4-oxadiazol-2-yl]-1-ethylpiperidin-3-yl]acetamide 2-(4-chloro-3-fluorophenoxy)-N-[(3R,6S)-6-[5-(4-chlorophenyl)-1,3,4-oxadiazol-2-yl]-1-ethylpiperidin-3-yl]acetamide 2-(4-chloro-3-fluorophenoxy)-N-[(3R,6S)-6-[5-(4-chlorophenyl)-1,3,4-oxadiazol-2-yl]-1-(2-methoxyethyl)piperidin-3-yl]acetamide tert-butyl (2R,5S)-5-[2-(4-chloro-3-fluorophenoxy)acetamido]-2-{5-[(1s,3s)-3-(trifluoromethoxy)cyclobutyl]-1,3,4-oxadiazol-2-yl}piperidine-1-carboxylate 2-(4-chloro-3-fluorophenoxy)-N-[(3S,6R)-6-{5-[(1s,3s)-3-(trifluoromethoxy)cyclobutyl]-1,3,4-oxadiazol-2-yl}piperidin-3-yl]acetamide N-[(3S,6R)-6-[5-(5-chloro-1-methyl-1H-pyrazol-3-yl)-1,3,4-oxadiazol-2-yl]piperidin-3-yl]-2-(4-chloro-3-fluorophenoxy)acetamide 2-(4-chloro-3-fluorophenoxy)-N-[(3S,6R)-6-{5-[6-(trifluoromethyl)pyridin-3-yl]-1,3,4-oxadiazol-2-yl}piperidin-3-yl]acetamide 2-(4-chloro-3-fluorophenoxy)-N-[(3S,6R)-6-[5-(5-chloropyridin-2-yl)-1,3,4-oxadiazol-2-yl]piperidin-3-yl]acetamide 2-(4-chloro-3-fluorophenoxy)-N-[(3S,6R)-6-[5-(4-chloro-3-fluorophenyl)-1,3,4-oxadiazol-2-yl]piperidin-3-yl]acetamide 2-(4-chloro-3-fluorophenoxy)-N-[(3S,6R)-6-{5-[3-(trifluoromethoxy)propyl]-1,3,4-oxadiazol-2-yl}piperidin-3-yl]acetamide tert-butyl (2R,5S)-5-[2-(4-chloro-3-fluorophenoxy)acetamido]-2-{5-[1-(2,2,2-trifluoroethyl)azetidin-3-yl]-1,3,4-oxadiazol-2-yl}piperidine-1-carboxylate 2-(4-chloro-3-fluorophenoxy)-N-[(3S,6R)-6-{5-[1-(2,2,2-trifluoroethyl)azetidin-3-yl]-1,3,4-oxadiazol-2-yl}piperidin-3-yl]acetamide tert-butyl (2R,5S)-5-[2-(4-chloro-3-fluorophenoxy)acetamido]-2-[5-(3-cyclopropoxycyclobutyl)-1,3,4-oxadiazol-2-yl]piperidine-1-carboxylate 2-(4-chloro-3-fluorophenoxy)-N-[(3S,6R)-6-[5-(3-cyclopropoxycyclobutyl)-1,3,4-oxadiazol-2-yl]piperidin-3-yl]acetamide 2-(3,4-dichlorophenoxy)-N-[(3S,6R)-6-{5-[(1s,3s)-3-(difluoromethoxy)cyclobutyl]-1,3,4-oxadiazol-2-yl}piperidin-3-yl]acetamide 2-(4-chloro-3-fluorophenoxy)-N-[(3S,6R)-6-{5-[(trifluoromethoxy)methyl]-1,3,4-oxadiazol-2-yl}piperidin-3-yl]acetamide tert-butyl (2R,5S)-5-[2-(4-chloro-3-fluorophenoxy)acetamido]-2-[5-(3,3,3-trifluoro-2-methylpropoxy)-1,3,4-oxadiazol-2-yl]piperidine-1-carboxylate 2-(4-chloro-3-fluorophenoxy)-N-[(3S,6R)-6-[5-(3,3,3-trifluoro-2-methylpropoxy)-1,3,4-oxadiazol-2-yl]piperidin-3-yl]acetamide 2-(4-chloro-3-fluorophenoxy)-N-[(3S,6R)-6-{5-[(4,4,4-trifluorobutan-2-yl)oxy]-1,3,4-oxadiazol-2-yl}piperidin-3-yl]acetamide 2-(4-chloro-3-fluorophenoxy)-N-[(3S,6R)-6-[5-(3,3-difluorobutoxy)-1,3,4-oxadiazol-2-yl]piperidin-3-yl]acetamide 2-(4-chloro-3-fluorophenoxy)-N-[(3S,6R)-6-{5-[(2,2-difluorocyclopropyl)methoxy]-1,3,4-oxadiazol-2-yl}piperidin-3-yl]acetamide N-[(3S,6R)-6-(5-butoxy-1,3,4-oxadiazol-2-yl)piperidin-3-yl]-2-(4-chloro-3-fluorophenoxy)acetamide 2-(4-chloro-3-fluorophenoxy)-N-[(3S,6R)-6-{5-[(3,3-difluorocyclopentyl)oxy]-1,3,4-oxadiazol-2-yl}piperidin-3-yl]acetamide 2-(4-chloro-3-fluorophenoxy)-N-[(3S,6R)-6-[5-(2-cyclopropylethoxy)-1,3,4-oxadiazol-2-yl]piperidin-3-yl]acetamide 2-(4-chloro-3-fluorophenoxy)-N-[(3S,6R)-6-[5-(3-methylbutoxy)-1,3,4-oxadiazol-2-yl]piperidin-3-yl]acetamide 2-(4-chloro-3-fluorophenoxy)-N-[(3S,6R)-6-{5-[(2,2-difluorocyclobutyl)methoxy]-1,3,4-oxadiazol-2-yl}piperidin-3-yl]acetamide 2-(4-chloro-3-fluorophenoxy)-N-[(3S,6R)-6-[5-(3,3-difluorocyclobutoxy)-1,3,4-oxadiazol-2-yl]piperidin-3-yl]acetamide 2-(4-chloro-3-fluorophenoxy)-N-[(3S,6R)-6-[5-(2,2,3,3,3-pentafluoropropoxy)-1,3,4-oxadiazol-2-yl]piperidin-3-yl]acetamide 2-(4-chloro-3-fluorophenoxy)-N-[(3S,6R)-6-[5-(4,4,4-trifluorobutoxy)-1,3,4-oxadiazol-2-yl]piperidin-3-yl]acetamide 2-(4-chloro-3-fluorophenoxy)-N-[(3S,6R)-6-{5-[2-(difluoromethoxy)ethoxy]-1,3,4-oxadiazol-2-yl}piperidin-3-yl]acetamide tert-butyl (2R,5S)-5-[2-(4-chloro-3-fluorophenoxy)acetamido]-2-{5-[2-(trifluoromethoxy)ethoxy]-1,3,4-oxadiazol-2-yl}piperidine-1-carboxylate 2-(4-chloro-3-fluorophenoxy)-N-[(3S,6R)-6-{5-[2-(trifluoromethoxy)ethoxy]-1,3,4-oxadiazol-2-yl}piperidin-3-yl]acetamide 2-(4-chloro-3-fluorophenoxy)-N-[(3S,6R)-6-[5-(pentyloxy)-1,3,4-oxadiazol-2-yl]piperidin-3-yl]acetamide 2-(4-chloro-3-fluorophenoxy)-N-[(3S,6R)-6-[5-(3-methoxypropoxy)-1,3,4-oxadiazol-2-yl]piperidin-3-yl]acetamide 2-(4-chloro-3-fluorophenoxy)-N-[(3S,6R)-6-[5-(2-cyclopropoxyethoxy)-1,3,4-oxadiazol-2-yl]piperidin-3-yl]acetamide 2-(4-chloro-3-fluorophenoxy)-N-[(3S,6R)-6-[5-(2-ethoxyethoxy)-1,3,4-oxadiazol-2-yl]piperidin-3-yl]acetamide 2-(4-chloro-3-fluorophenoxy)-N-[(3S,6R)-6-[5-(2-cyclobutoxyethoxy)-1,3,4-oxadiazol-2-yl]piperidin-3-yl]acetamide 2-(4-chloro-3-fluorophenoxy)-N-[(3R,6S)-6-{5-[2-(trifluoromethoxy)ethoxy]-1,3,4-oxadiazol-2-yl}piperidin-3-yl]acetamide 2-(4-chloro-3-fluorophenoxy)-N-[(3S,6R)-6-{5-[(4,4-difluoropentyl)oxy]-1,3,4-oxadiazol-2-yl}piperidin-3-yl]acetamide 2-(3,4-dichlorophenoxy)-N-[(3S,6R)-6-{5-[2-(trifluoromethoxy)ethoxy]-1,3,4-oxadiazol-2-yl}piperidin-3-yl]acetamide N-[(3S,6R)-6-[5-(2-cyclopropoxyethoxy)-1,3,4-oxadiazol-2-yl]piperidin-3-yl]-2-(3,4-dichlorophenoxy)acetamide 2-(4-chloro-3-fluorophenoxy)-N-[(3S,6R)-6-{5-[2-(2,2-difluorocyclopropoxy)ethoxy]-1,3,4-oxadiazol-2-yl}piperidin-3-yl]acetamide 2-(4-chloro-3-fluorophenoxy)-N-[(3S,6R)-6-(5-{[2-(trifluoromethyl)cyclopropyl]methoxy}-1,3,4-oxadiazol-2-yl)piperidin-3-yl]acetamide tert-butyl (2R,5S)-5-[2-(4-chloro-3-fluorophenoxy)acetamido]-2-{5-[3-(trifluoromethyl)azetidin-1-yl]-1,3,4-oxadiazol-2-yl}piperidine-1-carboxylate 2-(4-chloro-3-fluorophenoxy)-N-[(3S,6R)-6-{5-[3-(trifluoromethyl)azetidin-1-yl]-1,3,4-oxadiazol-2-yl}piperidin-3-yl]acetamide 2-(4-chloro-3-fluorophenoxy)-N-[(3S,6R)-6-{5-[3-(trifluoromethoxy)azetidin-1-yl]-1,3,4-oxadiazol-2-yl}piperidin-3-yl]acetamide 2-(4-chloro-3-fluorophenoxy)-N-[(3S,6R)-6-{5-[3-(2,2,2-trifluoroethyl)azetidin-1-yl]-1,3,4-oxadiazol-2-yl}piperidin-3-yl]acetamide 2-(4-chloro-3-fluorophenoxy)-N-[(3S,6R)-6-{5-[3-methyl-3-(trifluoromethoxy)azetidin-1-yl]-1,3,4-oxadiazol-2-yl}piperidin-3-yl]acetamide 2-(4-chloro-3-fluorophenoxy)-N-[(3S,6R)-6-(5-{methyl[2-(trifluoromethoxy)ethyl]amino}-1,3,4-oxadiazol-2-yl)piperidin-3-yl]acetamide 2-(4-chloro-3-fluorophenoxy)-N-[(3S,6R)-6-[5-(3-cyclopropoxyazetidin-1-yl)-1,3,4-oxadiazol-2-yl]piperidin-3-yl]acetamide 2-(4-chloro-3-fluorophenoxy)-N-[(3S,6R)-6-{5-[3-(trifluoromethoxy)pyrrolidin-1-yl]-1,3,4-oxadiazol-2-yl}piperidin-3-yl]acetamide tert-butyl (2R,5S)-5-[2-(4-chloro-3-fluorophenoxy)acetamido]-2-{5-[(1s,3s)-3-(trifluoromethoxy)cyclobutyl]-1,2,4-oxadiazol-3-yl}piperidine-1-carboxylate 2-(4-chloro-3-fluorophenoxy)-N-[(3S,6R)-6-{5-[(1s,3s)-3-(trifluoromethoxy)cyclobutyl]-1,2,4-oxadiazol-3-yl}piperidin-3-yl]acetamide tert-butyl (2R,5S)-5-{2-[(6-chloro-5-fluoropyridin-3-yl)oxy]acetamido}-2-[5-(3,4-dichlorophenyl)-1,3,4-oxadiazol-2-yl]piperidine-1-carboxylate 2-[(6-chloro-5-fluoropyridin-3-yl)oxy]-N-[(3S,6R)-6-[5-(3,4-dichlorophenyl)-1,3,4-oxadiazol-2-yl]piperidin-3-yl]acetamide 2-(4-chloro-3-fluorophenoxy)-N-[(3S,6R)-1-methyl-6-{5-[2-(trifluoromethoxy)ethoxy]-1,3,4-oxadiazol-2-yl}piperidin-3-yl]acetamide 2-(4-chloro-3-fluorophenoxy)-N-[(3S,6R)-6-(5-{2-[(1R)-2,2-difluorocyclopropoxy]ethoxy}-1,3,4-oxadiazol-2-yl)piperidin-3-yl]acetamide 2-(4-chloro-3-fluorophenoxy)-N-[(3S,6R)-6-(5-{2-[(1S)-2,2-difluorocyclopropoxy]ethoxy}-1,3,4-oxadiazol-2-yl)piperidin-3-yl]acetamide 2-(4-chloro-3-fluorophenoxy)-N-[(3S,6R)-6-{5-[(1r,3r)-3-cyclopropoxycyclobutyl]-1,3,4-oxadiazol-2-yl}piperidin-3-yl]acetamide 2-(4-chloro-3-fluorophenoxy)-N-[(3S,6R)-6-{5-[(1s,3s)-3-cyclopropoxycyclobutyl]-1,3,4-oxadiazol-2-yl}piperidin-3-yl]acetamide (2R)-2-(4-chlorophenoxy)-N-[(3S,6R)-6-{5-[4-(trifluoromethyl)phenyl]-1,3,4-oxadiazol-2-yl}piperidin-3-yl]propanamide (2S)-2-(4-chlorophenoxy)-N-[(3S,6R)-6-{5-[4-(trifluoromethyl)phenyl]-1,3,4-oxadiazol-2-yl}piperidin-3-yl]propanamide 2-(4-chloro-3-fluorophenoxy)-N-[(3S,6R)-6-[5-(4-chlorophenyl)-1,3,4-oxadiazol-2-yl]-2-oxopiperidin-3-yl]acetamide 2-(4-chloro-3-fluorophenoxy)-N-[(3R,6S)-6-[5-(4-chlorophenyl)-1,3,4-oxadiazol-2-yl]-2-oxopiperidin-3-yl]acetamide 2-(4-chloro-3-fluorophenoxy)-N-[(3S,6R)-6-{5-[(3S)-3-(trifluoromethoxy)pyrrolidin-1-yl]-1,3,4-oxadiazol-2-yl}piperidin-3-yl]acetamide 2-(4-chloro-3-fluorophenoxy)-N-[(3S,6R)-6-{5-[(3R)-3-(trifluoromethoxy)pyrrolidin-1-yl]-1,3,4-oxadiazol-2-yl}piperidin-3-yl]acetamide N-[(3S,6R)-6-{5-[2-(trifluoromethoxy)ethoxy]-1,3,4-oxadiazol-2-yl}piperidin-3-yl]-2-[4-(trifluoromethyl)phenoxy]acetamide 2-[3-chloro-4-(difluoromethyl)phenoxy]-N-[(3S,6R)-6-{5-[2-(trifluoromethoxy)ethoxy]-1,3,4-oxadiazol-2-yl}piperidin-3-yl]acetamide and 2-[3-fluoro-4-(trifluoromethyl)phenoxy]-N-[(3S,6R)-6-{5-[2-(trifluoromethoxy)ethoxy]-1,3,4-oxadiazol-2-yl}piperidin-3-yl]acetamide.

Where tautomerism, like e.g. keto-enol tautomerism, of compounds of formula (I) may occur, the individual forms, like e.g. the keto and enol form, are comprised separately and together as mixtures in any ratio. Same applies to stereoisomers, like e.g. enantiomers, cis/trans isomers, conformers and the like.

Especially, when enantiomeric or diastereomeric forms are given in a compound according to formula (I) each pure form separately and any mixture of at least two of the pure forms in any ratio is comprised by formula (I) and is a subject of the present invention.

A preferred compound is a compound or a pharmaceutically acceptable salt, solvate, hydrate, tautomer or stereoisomer thereof of formula (I) with a relative configuration as shown in formula (Ia)

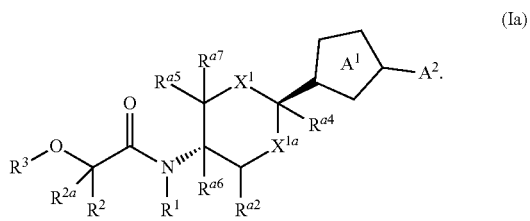

(Ia)

Isotopic labeled compounds of formula (I) are also within the scope of the present invention. Methods for isotope labeling are known in the art. Preferred isotopes are those of the elements H, C, N, O and S. Solvates and hydrates of compounds of formula (I) are also within the scope of the present invention.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of formula (I) may be obtained from stereoselective synthesis using optically pure starting materials, reagents and/or catalysts.

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

As shown below compounds of the present invention are believed to be suitable for modulating the integrated stress response pathway.

The Integrated Stress Response (ISR) is a cellular stress response common to all eukaryotes (1). Dysregulation of ISR signaling has important pathological consequences linked inter alia to inflammation, viral infection, diabetes, cancer and neurodegenerative diseases.

ISR is a common denominator of different types of cellular stresses resulting in phosphorylation of the alpha subunit of eukaryotic translation initiation factor 2 (eIF2alpha) on serine 51 leading to the suppression of normal protein synthesis and expression of stress response genes (2). In mammalian cells the phosphorylation is carried out by a family of four eIF2alpha kinases, namely: PKR-like ER kinase (PERK), double-stranded RNA-dependent protein kinase (PKR), heme-regulated eIF2alpha kinase (HRI), and general control non-derepressible 2 (GCN2), each responding to distinct environmental and physiological stresses (3).

eIF2alpha together with eIF2beta and eIF2gamma form the eIF2 complex, a key player of the initiation of normal mRNA translation (4). The eIF2 complex binds GTP and Met-tRNA$_i$ forming a ternary complex (eIF2-GTP-Met-tRNA$_i$), which is recruited by ribosomes for translation initiation (5, 6).

eIF2B is a heterodecameric complex consisting of 5 subunits (alpha, beta, gamma, delta, epsilon) which in duplicate form a GEF-active decamer (7).

In response to ISR activation, phosphorylated eIF2alpha inhibits the eIF2B-mediated exchange of GDP for GTP, resulting in reduced ternary complex formation and hence in the inhibition of translation of normal mRNAs characterized by ribosomes binding to the 5' AUG start codon (8). Under these conditions of reduced ternary complex abundance the translation of several specific mRNAs including the mRNA coding for the transcription factor ATF4 is activated via a mechanism involving altered translation of upstream ORFs (uORFs) (7, 9, 10). These mRNAs typically contain one or more uORFs that normally function in unstressed cells to limit the flow of ribosomes to the main coding ORF. For example, during normal conditions, uORFs in the 5' UTR of ATF occupy the ribosomes and prevent translation of the coding sequence of ATF4. However, during stress conditions, i.e. under conditions of reduced ternary complex formation, the probability for ribosomes to scan past these upstream ORFs and initiate translation at the ATF4 coding ORF is increased. ATF4 and other stress response factors expressed in this way subsequently govern the expression of an array of further stress response genes. The acute phase consists in expression of proteins that aim to restore homeostasis, while the chronic phase leads to expression of pro-apoptotic factors (1, 11, 12, 13).

Upregulation of markers of ISR signaling has been demonstrated in a variety of conditions, among these cancer and neurodegenerative diseases. In cancer, ER stress-regulated translation increases tolerance to hypoxic conditions and promotes tumor growth (14, 15, 16), and deletion of PERK by gene targeting has been shown to slow growth of tumours derived from transformed PERK mouse embryonic fibroblasts (14, 17). Further, a recent report has provided proof of concept using patient derived xenograft modeling in mice for activators of eIF2B to be effective in treating a form of aggressive metastatic prostate cancer (28). Taken together, prevention of cytoprotective ISR signaling may represent an effective anti-proliferation strategy for the treatment of at least some forms of cancer.

Further, modulation of ISR signaling could prove effective in preserving synaptic function and reducing neuronal decline, also in neurodegenerative diseases that are characterized by misfolded proteins and activation of the unfolded protein response (UPR), such as amyotrophic lateral sclerosis (ALS), frontotemporal dementia (FTD), Alzheimer's disease (AD), Parkinson's disease (PD) and Jakob Creutzfeld (prion) diseases (18, 19, 20). With prion disease an example of a neurodegenerative disease exists where it has been shown that pharmacological as well as genetic inhibition of ISR signaling can normalize protein translation levels, rescue synaptic function and prevent neuronal loss (21). Specifically, reduction of levels of phosphorylated eIF2alpha by overexpression of the phosphatase controlling phosphorylated eIF2alpha levels increased survival of prion-infected mice whereas sustained eIF2alpha phosphorylation decreased survival (22).

Further, direct evidence for the importance of control of protein expression levels for proper brain function exists in the form of rare genetic diseases affecting functions of eIF2 and eIF2B. A mutation in eIF2gamma that disrupts complex integrity of eIF2 and hence results in reduced normal protein expression levels is linked to intellectual disability syndrome (ID) (23). Partial loss of function mutations in subunits of eIF2B have been shown to be causal for the rare leukodystrophy Vanishing White Matter Disease (VWMD) (24, 25). Specifically, stabilization of eIF2B partial loss of function in a VWMD mouse model by a small molecule related to ISRIB has been shown to reduce ISR markers and improve functional as well as pathological end points (26, 27).

The present invention provides compounds of the present invention in free or pharmaceutically acceptable salt form or in the form of solvates, hydrates, tautomers or stereoisomers to be used in the treatment of diseases or disorders mentioned herein. The same applies to a pharmaceutical composition of the present invention.

Thus an aspect of the present invention is a compound or a pharmaceutically acceptable salt, solvate, hydrate, tautomer or stereoisomer thereof of the present invention for use as a medicament as mentioned above. The same applies to a pharmaceutical composition of the present invention.

The therapeutic method described may be applied to mammals such as dogs, cats, cows, horses, rabbits, monkeys and humans. Preferably, the mammalian patient is a human patient.

Accordingly, the present invention provides a compound or a pharmaceutically acceptable salt, solvate, hydrate, tautomer or stereoisomer thereof or a pharmaceutical composition of the present invention to be used in the treatment or prevention of one or more diseases or disorders associated with integrated stress response.

A further aspect of the present invention is a compound or a pharmaceutically acceptable salt, solvate, hydrate, tautomer or stereoisomer thereof or a pharmaceutical composition of the present invention for use in a method of treating or preventing one or more disorders or diseases associated with integrated stress response.

A further aspect of the present invention is the use of a compound or a pharmaceutically acceptable salt, solvate, hydrate, tautomer or stereoisomer thereof or a pharmaceutical composition of the present invention for the manufacture of a medicament for the treatment or prophylaxis of one or more disorders or diseases associated with integrated stress response.

Yet another aspect of the present invention is a method for treating, controlling, delaying or preventing in a mammalian patient in need of the treatment of one or more diseases or disorders associated with integrated stress response, wherein the method comprises administering to said patient a therapeutically effective amount of a compound or a pharmaceutically acceptable salt, solvate, hydrate, tautomer or stereoisomer thereof or a pharmaceutical composition of the present invention.

The present invention provides a compound or a pharmaceutically acceptable salt, solvate, hydrate, tautomer or stereoisomer thereof or a pharmaceutical composition of the present invention to be used in the treatment or prevention of one or more diseases or disorders mentioned below.

A further aspect of the present invention is a compound or a pharmaceutically acceptable salt, solvate, hydrate, tautomer or stereoisomer thereof or a pharmaceutical composition of the present invention for use in a method of treating or preventing one or more disorders or diseases mentioned below.

A further aspect of the present invention is the use of a compound or a pharmaceutically acceptable salt, solvate, hydrate, tautomer or stereoisomer thereof or a pharmaceutical composition of the present invention for the manufacture of a medicament for the treatment or prophylaxis of one or more disorders or diseases mentioned below.

Yet another aspect of the present invention is a method for treating, controlling, delaying or preventing in a mammalian patient in need of the treatment of one or more diseases or disorders mentioned below, wherein the method comprises administering to said patient a therapeutically effective amount of a compound or a pharmaceutically acceptable salt, solvate, hydrate, tautomer or stereoisomer thereof or a pharmaceutical composition of the present invention.

Diseases or disorders include but are not limited to leukodystrophies, intellectual disability syndrome, neurodegenerative diseases and disorders, neoplastic diseases, infectious diseases, inflammatory diseases, musculoskeletal diseases, metabolic diseases, ocular diseases as well as diseases selected from the group consisting of organ fibrosis, chronic and acute diseases of the liver, chronic and acute diseases of the lung, chronic and acute diseases of the kidney, myocardial infarction, cardiovascular disease, arrhythmias, atherosclerosis, spinal cord injury, ischemic stroke, and neuropathic pain.

Leukodystrophies

Examples of leukodystrophies include, but are not limited to, Vanishing White Matter Disease (VWMD) and childhood ataxia with CNS hypo-myelination (e.g. associated with impaired function of eIF2 or components in a signal transduction or signaling pathway including eIF2).

Intellectual Disability Syndrome

Intellectual disability in particular refers to a condition in which a person has certain limitations in intellectual functions like communicating, taking care of him- or herself, and/or has impaired social skills. Intellectual disability syndromes include, but are not limited to, intellectual disability conditions associated with impaired function of eIF2 or components in a signal transduction or signaling pathway including eIF2.

Neurodegenerative Diseases/Disorders

Examples of neurodegenerative diseases and disorders include, but are not limited to, Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, Kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Progressive supranuclear palsy, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes dorsalis, and tauopathies.

In particular, the neurodegenerative disease or and disorder is selected from the group consisting of Alzheimer's disease, Parkinson's disease and amyotrophic lateral sclerosis.

Neoplastic Diseases

A neoplastic disease may be understood in the broadest sense as any tissue resulting from miss-controlled cell growth. In many cases a neoplasm leads to at least bulky tissue mass optionally innervated by blood vessels. It may or may not comprise the formation of one or more metastasis/metastases. A neoplastic disease of the present invention may be any neoplasm as classified by the International Statistical Classification of Diseases and Related Health Problems 10th Revision (ICD-10) classes C00-D48.

Exemplarily, a neoplastic disease according to the present invention may be the presence of one or more malignant neoplasm(s) (tumors) (ICD-10 classes C00-C97), may be the presence of one or more in situ neoplasm(s) (ICD-10 classes D00-D09), may be the presence of one or more benign neoplasm(s) (ICD-10 classes D10-D36), or may be the presence of one or more neoplasm(s) of uncertain or unknown behavior (ICD-10 classes D37-D48). Preferably, a neoplastic disease according to the present invention refers to the presence of one or more malignant neoplasm(s), i.e., is malignant neoplasia (ICD-10 classes C00-C97).

In a more preferred embodiment, the neoplastic disease is cancer.

Cancer may be understood in the broadest sense as any malignant neoplastic disease, i.e., the presence of one or more malignant neoplasm(s) in the patient. Cancer may be solid or hematologic malignancy. Contemplated herein are without limitation leukemia, lymphoma, carcinomas and sarcomas.

In particular, neoplastic diseases, such as cancers, characterized by upregulated ISR markers are included herein.

Exemplary cancers include, but are not limited to, thyroid cancer, cancers of the endocrine system, pancreatic cancer, brain cancer (e.g. glioblastoma multiforme, glioma), breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), cervix cancer, ovarian cancer, uterus cancer, colon cancer, head & neck cancer, liver cancer (e.g. hepatocellular carcinoma), kidney cancer, lung cancer (e.g. non-small cell lung carcinoma, squamous cell lung carcinoma, adenocarcinoma, large cell lung carcinoma, small cell lung carcinoma, carcinoid, sarcoma), colon cancer, esophageal cancer, stomach cancer, bladder cancer, bone cancer, gastric cancer, prostate cancer and skin cancer (e.g. melanoma).

Further examples include, but are not limited to, myeloma, leukemia, mesothelioma, and sarcoma.

Additional examples include, but are not limited to, Medulloblastoma, Hodgkin's Disease, Non-Hodgkin's Lymphoma, multiple myeloma, neuroblastoma, glioma, glioblastoma multiforme, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, and cancer of the hepatic stellate cells.

Exemplary leukemias include, but are not limited to, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

Exemplary sarcomas include, but are not limited to, chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Exemplary melanomas include, but are not limited to, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

Exemplary carcinomas include, but are not limited to, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, and carcinoma villosum.

Infectious Diseases

Examples include, but are not limited to, infections caused by viruses (such as infections by HIV-1: human immunodeficiency virus type 1; IAV: influenza A virus; HCV: hepatitis C virus; DENV: dengue virus; ASFV: African swine fever virus; EBV: Epstein-Barr virus; HSV1: herpes simplex virus 1; CHIKV: chikungunya virus; HCMV: human cytomegalovirus; SARS-CoV: severe acute respiratory syndrome coronavirus; SARS-CoV-2: severe acute respiratory syndrome coronavirus 2) and infections caused by bacteria (such as infections by *Legionella, Brucella, Simkania, Chlamydia, Helicobacter* and *Campylobacter*).

Inflammatory Diseases

Examples of inflammatory diseases include, but are not limited to, postoperative cognitive dysfunction (decline in cognitive function after surgery), traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

Musculoskeletal Diseases

Examples of musculoskeletal diseases include, but are not limited to, muscular dystrophy, multiple sclerosis, Freidrich's ataxia, a muscle wasting disorder (e.g., muscle atrophy, sarcopenia, cachexia), inclusion body myopathy, progressive muscular atrophy, motor neuron disease, carpal tunnel syndrome, epicondylitis, tendinitis, back pain, muscle pain, muscle soreness, repetitive strain disorders, and paralysis.

Metabolic Diseases

Examples of metabolic diseases include, but are not limited to, diabetes (in particular diabetes Type II), non-alcoholic steatohepatitis (NASH), non-alcoholic fatty liver disease (NAFLD), Niemann-Pick disease, liver fibrosis, obesity, heart disease, atherosclerosis, arthritis, cystinosis, phenylketonuria, proliferative retinopathy, and Kearns-Sayre disease.

Ocular Diseases

Examples of ocular diseases include, but are not limited to, edema or neovascularization for any occlusive or inflammatory retinal vascular disease, such as rubeosis irides, neovascular glaucoma, pterygium, vascularized glaucoma filtering blebs, conjunctival papilloma; choroidal neovascularization, such as neovascular age-related macular degeneration (AMD), myopia, prior uveitis, trauma, or idiopathic; macular edema, such as post surgical macular edema, macular edema secondary to uveitis including retinal and/or choroidal inflammation, macular edema secondary to diabetes, and macular edema secondary to retinovascular occlusive disease (i.e. branch and central retinal vein occlusion); retinal neovascularization due to diabetes, such as retinal vein occlusion, uveitis, ocular ischemic syndrome from carotid artery disease, ophthalmic or retinal artery occlusion, sickle cell retinopathy, other ischemic or occlusive neovascular retinopathies, retinopathy of prematurity, or Eale's Disease; and genetic disorders, such as VonHippel-Lindau syndrome.

Further Diseases

Further diseases include, but are not limited to, organ fibrosis (such as liver fibrosis, lung fibrosis, or kidney fibrosis), chronic and acute diseases of the liver (such as fatty liver disease, or liver steatosis), chronic and acute diseases of the lung, chronic and acute diseases of the kidney, myocardial infarction, cardiovascular disease, arrhythmias, atherosclerosis, spinal cord injury, ischemic stroke, and neuropathic pain.

Yet another aspect of the present invention is a pharmaceutical composition comprising at least one compound or a pharmaceutically acceptable salt, solvate, hydrate, tautomer or stereoisomer thereof of the present invention together with a pharmaceutically acceptable carrier, optionally in combination with one or more other bioactive compounds or pharmaceutical compositions.

Preferably, the one or more bioactive compounds are modulators of the integrated stress response pathway other than compounds of formula (I).

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may comprise one or more additional compounds as active ingredients like a mixture of compounds of formula (I) in the composition or other modulators of the integrated stress response pathway.

The active ingredients may be comprised in one or more different pharmaceutical compositions (combination of pharmaceutical compositions).

The term "pharmaceutically acceptable salts" refers to salts prepared from pharmaceutically acceptable non-toxic bases or acids, including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula (I) can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally, for example, as liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula (I) may also be administered parenterally. Solutions or suspensions of these active compounds can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of formula (I) are administered orally.

The effective dosage of active ingredient employed may vary depending on the particular compound employed, the mode of administration, the condition being treated and the severity of the condition being treated. Such dosage may be ascertained readily by a person skilled in the art.

Starting materials for the synthesis of preferred embodiments of the invention may be purchased from commercially available sources such as Array, Sigma Aldrich, Acros, Fisher, Fluka, ABCR or can be synthesized using known methods by one skilled in the art.

In general, several methods are applicable to prepare compounds of the present invention. In some cases various strategies can be combined. Sequential or convergent routes may be used. Exemplary synthetic routes are described below.

EXAMPLES

I Chemical Synthesis

Experimental Procedures:
The following Abbreviations and Acronyms are used:
aq aqueous
ACN acetonitrile
AgOTf silver trifluoromethanesulfonate
BrCN cyanogen bromide
Brine saturated solution of NaCl in water
BnONH$_2$·HCl O-benzylhydroxylamine hydrochloride
Boc tert-butoxycarbonyl
Boc$_2$O di-tert-butyl dicarbonate
$^t$BuOK potassium tert-butoxide
CSA (7,7-dimethyl-2-oxobicyclo[2.2.1]heptan-1-yl)methanesulfonic acid
CV column volume
DAST N,N-diethylaminosulfur trifluoride
DCM dichloromethane
DCE dichloroethane
DMSO dimethylsulfoxide
DMSO-d$_6$ deuterated dimethylsulfoxide
DIPEA diisopropylethylamine
DMF dimethyl formamide
DMAP N,N-dimethylpyridin-4-amine
ESI$^+$ positive ionisation mode
ESI$^-$ negative ionisation mode
EtOAc ethyl acetate
EtOH ethanol
Et$_2$O diethyl ether
H$_2$SO$_4$ sulfuric acid
HATU 1-[bis(dimethylamino)methylidene]-1H-[1,2,3]triazolo[4,5-b]pyridin-1-ium 3-oxide hexafluorophosphate
HCl hydrochloric acid
HPLC high-performance liquid chromatography
h hour(s)
IPA isopropyl alcohol
KHCO$_3$ potassium bicarbonate
LiOH lithium hydroxide
LiOH·H$_2$O lithium hydroxide hydrate
m multiplet
m-CPBA 3-chlorobenzenecarboperoxoic acid
MeOH methanol
MgSO$_4$ magnesium sulphate
min minutes
MsOH methanesulfonic acid
mL millilitre (s)
N$_2$ nitrogen atmosphere
Na$_2$SO$_3$ sodium sulfite
Na$_2$SO$_4$ sodium sulphate
NaBH$_4$ sodium borohydride
NaHCO$_3$ sodium bicarbonate
NH$_2$—NH$_2$—H$_2$O hydrazine hydrate
NH$_4$Cl ammonium chloride
NiCl$_2$·6H$_2$O nickel (II) chloride hexahydrate
NMM 4-methylmorpholine
NMR Nuclear Magnetic Resonance
prep. preparative
r.t. room temperature
Rochelle salt sodium potassium L(+)-tartrate tetrahydrate
RT retention time
satd saturated
SOCl$_2$ thionyl chloride
STAB sodium triacetoxyborohydride
T3P propanephosphonic acid anhydride
TsCl 4-methylbenzenesulfonyl chloride
TCDI 1,1'-thiocarbonyldiimidazole
THF tetrahydrofuran
TFA 2,2,2-trifluoroacetic acid
TFAA trifluoroacetic anhydride
TMS-CF$_3$ trimethyl(trifluoromethyl)silane
TMSOI trimethylsulfoxonium iodide
ZnBr$_2$ zinc dibromide
Analytical LCMS Conditions are as Follows:
System 1 (S1): Acidic IPC Method (MS18 and MS19)
Analytical (MET/CR/1410) HPLC-MS were performed on a Shimadzu LCMS systems using a Kinetex Core shell C18 column (2.1 mm×50 mm, 5 µm; temperature: 40° C.) and a gradient of 5-100% B (A=0.1% formic acid in H$_2$O; B=0.1% formic acid in ACN) over 1.2 min then 100% B for 0.1 min. A second gradient of 100-5% B was then applied over 0.01 min with an injection volume of 3 µL at a flow rate of 1.2 mL/min. UV spectra were recorded at 215 nm using a SPD-M20A photo diode array detector spectrum range: 200-400 nm. Mass spectra were obtained using a 2010EV detector. Data were integrated and reported using Shimadzu LCMS-Solutions and PsiPort software.
System 2 (S2): Acidic IPC Method (MSQ2 and MSQ4):
Analytical (MET/uPLC/1704) uHPLC-MS were performed on a Waters Acquity uPLC system using a Waters UPLC® BEH™ C18 column (2.1 mm×50 mm, 1.7 µm; temperature 40° C.) and a gradient of 5-100% B (A=0.1% formic acid in H$_2$O:B=0.1% formic acid in ACN) over 1.1 min then 100% B for 0.25 min. A second gradient of 100-5% B was then applied over 0.05 min and held for 0.1 min with an injection volume of 1 µL at a flow rate of 0.9 mL/min. UV spectra were recorded at 215 nm on a Waters Acquity PDA with a spectrum range of 200-400 nm. Mass spectra were obtained using a Waters QDa. Data were integrated and reported using Waters MassLynx and OpenLynx software.
System 3 (S3): Basic IPC Method (MS16):

Analytical (MET/CR/1602) uHPLC-MS were performed on a Waters Acquity uPLC system using Waters UPLC® BEH™ C18 column (2.1 mm×30 mm, 1.7 µm; temperature 40° C.) and a gradient of 5-100% B (A: 2 mM ammonium bicarbonate, buffered to pH 10, B: ACN) over 0.75 min, then 100% B for 0.1 min. A second gradient of 100-5% B was then applied over 0.05 min and held for 0.1 min with an injection volume of 1 µL at a flow rate of 1 mL/min. UV spectra were recorded at 215 nm on a Waters Acquity PDA with a spectrum range of 200-400 nm. Mass spectra were obtained using a Waters Quattro Premier XE. Data were integrated and reported using Waters MassLynx and OpenLynx software.
System 4 (S4): Acidic Final Method (MSQ1 and MSQ2):

Analytical (MET/uPLC/AB101) uHPLC-MS were performed on a Waters Acquity uPLC system using a Phenomenex Kinetex-XB C18 column (2.1 mm×100 mm, 1.7 µM; temperature: 40° C.) and a gradient of 5-100% B (A=0.1% formic acid in $H_2O$; B=0.1% formic acid in ACN) over 5.3 min then 100% B for 0.5 min. A second gradient of 100-5% B was then applied over 0.02 min and held for 1.18 min with an injection volume of 1 µL at flow rate of 0.6 mL/min. UV spectra were recorded at 215 nm using a Waters Acquity PDA detector spectrum range: 200-400 nm. Mass spectra were obtained using a Waters SQD (MSQ1) or Waters Acquity QDA (MSQ2). Data were integrated and reported using Waters MassLynx and OpenLynx software.
System 5 (S5): Acidic Final Method (MS18, MS19)

Analytical (MET/CR/1416) HPLC-MS were performed on Shimadzu LCMS systems using a Waters Atlantis dC18 column (2.1 mm×100 mm, 3 µm; temperature: 40° C.) and a gradient of 5-100% B (A=0.1% formic acid in $H_2O$; B=0.1% formic acid in ACN) over 5 min then 100% B for 0.4 min. A second gradient of 100-5% B was then applied over 0.02 min and held for 1.58 min with an injection volume of 3 µL at flow rate of 0.6 mL/min. UV spectra were recorded at 215 nm using a SPD-M20A photo diode array detector spectrum range: 200-400 nm. Mass spectra were obtained using a 2010EV detector. Data were integrated and reported using Shimadzu LCMS-Solutions and PsiPort software.
System 6 (S6): Basic Final Method (MS16)

Analytical (MET/uHPLC/AB105) uPLC-MS were performed on a Waters Acquity uPLC system using a Waters UPLC® BEH™ C18 column (2.1 mm×100 mm, 1.7 µm column; temperature: 40° C.) and a gradient of 5-100% (A=2 mM ammonium bicarbonate, buffered to pH 10; B=ACN) over 5.3 min then 100% B for 0.5 min. A second gradient of 100-5% B was then applied over 0.02 min and held for 1.18 min with an injection volume of 1 µL and at flow rate of 0.6 mL/min. UV spectra were recorded at 215 nm using a Waters Acquity photo diode array detector Spectrum range: 200-400 nm. Mass spectra were obtained using a Waters Quattro Premier XE mass detector. Data were integrated and reported using Waters MassLynx and OpenLynx software.
Purification Methods are as Follows:
Method 1: Acidic Early Method Purifications (P1) LC were performed on a Gilson LC system using a Waters Sunfire C18 column (30 mm×100 mm, 10 µM; temperature: r.t.) and a gradient of 10-95% B (A=0.1% formic acid in $H_2O$; B=0.1% formic acid in ACN) over 14.44 min then 95% B for 2.11 min. A second gradient of 95-10% B was then applied over 0.2 min with an injection volume of 1500 µL at flow rate of 40 mL/min. UV spectra were recorded at 215 nm using a Gilson detector.
Method 2: Acidic Standard Method Purifications (P2) LC were performed on a Gilson LC system using a Waters Sunfire C18 column (30 mm×10 mm, 10 µM; temperature: r.t.) and a gradient of 30-95% B (A=0.1% formic acid in water; B=0.1% formic acid in ACN) over 11.00 min then 95% B for 2.10 min. A second gradient of 95-30% B was then applied over 0.2 min with an injection volume of 1500 µL at flow rate of 40 mL/min. UV spectra were recorded at 215 nm using a Gilson detector.
Method 3: Basic Early Method Purifications (P3) LC were performed on a Gilson LC system using a Waters X-Bridge C18 column (30 mm×100 mm, 10 µM; temperature: r.t.) and a gradient of 10-95% B (A=0.2% $NH_4OH$ in $H_2O$; B=0.2% $NH_4OH$ in ACN) over 14.44 min then 95% B for 2.11 min. A second gradient of 95-10% B was then applied over 0.2 min with an injection volume of 1500 µL at flow rate of 40 mL/min. UV spectra were recorded at 215 nm using a Gilson detector.
Method 4: Basic Standard Method Purifications (P4) LC were performed on a Gilson LC system using a Waters X-Bridge C18 column (30 mm×10 mm, 10 µM; temperature: r.t.) and a gradient of 30-95% B (A=0.2% $NH_4OH$ in water; B=0.2% $NH_4OH$ in ACN) over 11.00 min then 95% B for 2.10 min. A second gradient of 95-30% B was then applied over 0.21 min with an injection volume of 1500 µL at flow rate of 40 mL/min. UV spectra were recorded at 215 nm using a Gilson detector.
Method 5: Reverse Phase Chromatography Using Acidic pH, Standard Elution Method Purifications by FCC on reverse phase silica (acidic pH, standard elution method) were performed on Biotage Isolera systems using the appropriate SNAP C18 cartridge and a gradient of 10% B (A=0.1% formic acid in $H_2O$; B=0.1% formic acid in ACN) over 1.7 CV then 10-100% B over 19.5 CV and 100% B for 2 CV.
Method 6: Reverse Phase Chromatography Using Basic pH, Standard Elution Method Purifications by FCC on reverse phase silica (basic pH, standard elution method) were performed on Biotage Isolera systems using the appropriate SNAP C18 cartridge and a gradient of 10% B (A=0.1% $NH_3$ in $H_2O$; B=0.1% $NH_3$ in ACN) over 1.7 CV then 10-100% B over 19.5 CV and 100% B for 2 CV.
Method 7: Reverse Phase Chromatography Using Acidic pH, Standard Elution Method Purifications by FCC on reverse phase silica (acidic pH, standard elution method) were performed on Biotage Isolera systems using the appropriate SNAP C18 cartridge and a gradient of 10% B (A=0.1% TFA in $H_2O$; B=0.1% TFA in ACN) over 1.7 CV then 10-100% B over 19.5 CV and 100% B for 2 CV.
Chiral Separation Methods:
Method C1

Purification method=15% IPA: 85% heptane; Chiralcel OD-H, 20×250 mm, 5 µm at 18 mL/min. Sample diluent: MeOH, ACN.
Method C2

Purification method=EtOH with Cellulose-4; 21.2×250 mm, 5 µm column at 9 mL/min. Sample diluent: EtOH, MeOH.
Method C3

Purification method=15% IPA+0.2% diethylamine: 85% $CO_2$; Chiralpak AD-H, 10×250 mm, 5 µm at 15 mL/min. Sample diluent: IPA, MeOH, ACN.
Method C4

Purification method=MeOH+0.2% diethylamine; Chiralpak AD-H, 20×250 mm, 5 µm at 7 mL/min. Sample diluent: MeOH.
Method C5

Purification method=75:25 $CO_2$:MeOH; Chiralpak AD-H, 10×250 mm, 5 µm at 15 mL/min. Sample diluent: MeOH.

Method C6

Purification method=15% MeOH, 85% CO₂; Chiralcel OJ-H, 10×250 mm, 5 μm at 15 mL/min. Sample diluent: MeOH, IPA, ACN.

Method C7

Purification method=80:20 heptane:EtOH; Chiralpak AD-H, 20×250 mm, 5 μm at 18 mL/min. Sample diluent: Methanol, IPA.

NMR Conditions

Unless otherwise stated, ¹H NMR spectra were recorded at 500 MHz, 400 MHz or 250 MHz on either a Bruker Avance III HD 500 MHz, Bruker Avance III HD 400 MHz spectrometer or Bruker Avance III HD 250 MHz spectrometer respectively. Chemical shifts, δ, are quoted in parts per million (ppm) and are referenced to the residual solvent peak. The following abbreviations are used to denote the multiplicities and general assignments: s (singlet), d (doublet), t (triplet), q (quartet), dd (doublet of doublets), ddd (doublet of doublet of doublets), dt (doublet of triplets), dq (doublet of quartets), hep (heptet), m (multiplet), pent (pentet), td (triplet of doublets), qd (quartet of doublets), app. (apparent) and br. (broad). Coupling constants, J, are quoted to the nearest 0.1 Hz.

General Synthesis

All the compounds have been synthesised with a purity >95% unless otherwise specified. Chemical names are generated by Marvin Sketch, version 19.19.0, from ChemAxon Ltd.

Step 1.a: ethyl (2R)-5-[(benzyloxy)imino]-2-{[(tert-butoxy)carbonyl]amino}-6-chlorohexanoate

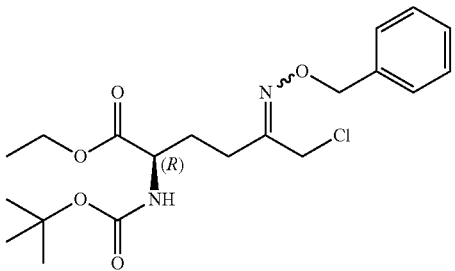

DMSO (75 mL) was added to a solution of TMSOI (12.89 g, 58.3 mmol) and ᵗBuOK (6.27 g, 55.9 mmol) in anhydrous THF (60 mL) and the mixture was stirred at r.t. for 1 h. The reaction mixture was cooled to −12° C. and a solution of ethyl Boc-D-Pyroglutamate (12.5 g, 48.6 mmol) in anhydrous THF (38 mL) was added and stirred at r.t. for 16 h. The reaction mixture was diluted with satd aq NH₄Cl solution (80 mL), H₂O (15 mL) and EtOAc (200 mL), and the organic layer was isolated, washed with brine, and concentrated in vacuo to approximately 100 mL. A solution of BnONH₂·HCl (8.14 g, 51.0 mmol) in EtOAc (62 mL), was added and the mixture was stirred at reflux for 2 h. The reaction mixture was cooled to r.t., washed with H₂O and brine, and the organic layer was concentrated in vacuo to Scheme for route 1

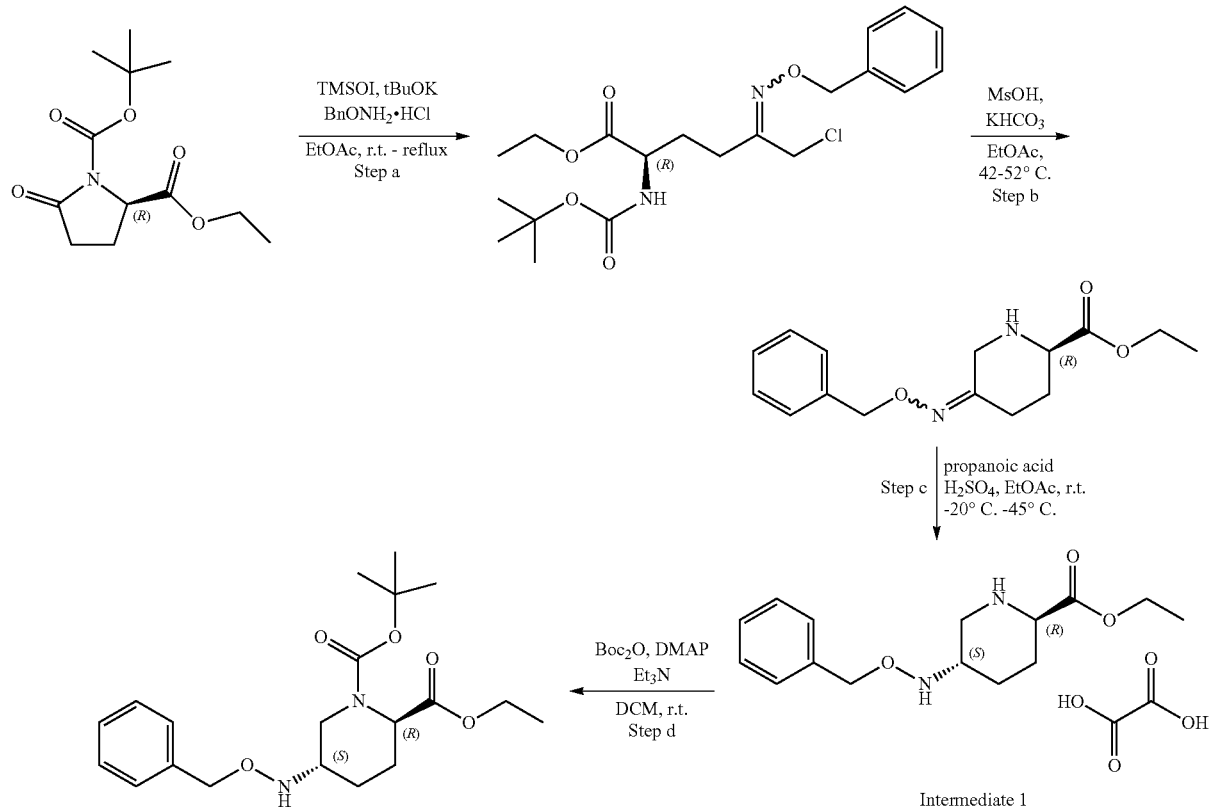

Intermediate 1 afford the title compound (85% purity, 19.5 g, 40.1 mmol, 83% yield) as a colourless oil; ¹H NMR (400 MHz, chloroform-d) δ 7.16-7.33 (m, 5H), 5.01-5.06 (m, 2H), 3.95-4.30 (m, 5H), 2.32-2.50 (m, 2H), 1.98-2.13 (m, 1H), 1.75-1.92 (m, 1H), 1.30-1.40 (m, 9H), 1.12-1.24 (m, 3H), Step 1.b: ethyl (2R)-5-[(benzyloxy)imino]piperidine-2-carboxylate

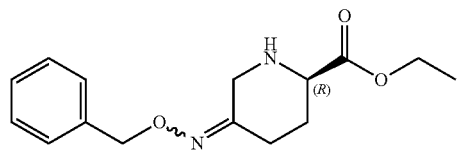

To a solution of ethyl (2R)-5-[(benzyloxy)imino]-2-{[(tert-butoxy)carbonyl]amino}-6-chlorohexanoate (85% purity, 19.5 g, 40.1 mmol) in EtOAc (157 mL) was added MsOH (7.8 mL, 0.12 mol) and the mixture was stirred at 42° C. for 2 h. The resultant mixture was added to a solution of KHCO₃ (20.1 g, 0.201 mol) in H₂O (100 mL) and stirred at 52° C. for 2 h. The reaction mixture was cooled to r.t. and the organic layer was isolated, washed with brine, dried over Na₂SO₄, and concentrated in vacuo to afford the title compound (85% purity, 13.0 g, 40.0 mmol) in quantitative yield as a dark orange oil; ¹H NMR (400 MHz, chloroform-d) δ 7.20-7.34 (m, 5H), 4.99 (d, J=4.8 Hz, 2H), 4.13 (q, J=7.1 Hz, 2H), 3.45-3.56 (m, 1H), 3.25 (dd, J=14.9, 9.8 Hz, 1H), 3.08 (dt, J=14.5, 4.3 Hz, 1H), 2.01-2.32 (m, 3H), 1.55-1.80 (m, 1H), 1.21 (t, J=7.1 Hz, 3H).

Intermediate 1 (Step 1.c): ethyl (2R,5S)-5-[(benzyloxy)amino]piperidine-2-carboxylate oxalic acid Intermediate 1

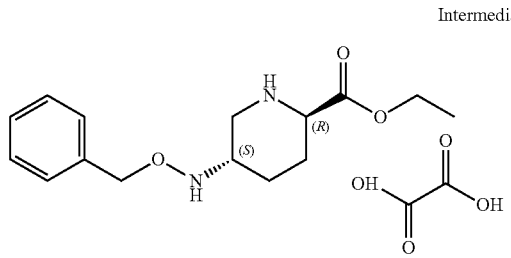

Propanoic acid (23 mL, 0.240 mol) was added to a suspension of NaBH₄ (3.03 g, 80.0 mmol) in EtOAc (95 mL) and the mixture was stirred at r.t. for 1 h. The resultant mixture was added to a solution of ethyl (2R)-5-[(benzyloxy)imino]piperidine-2-carboxylate (85% purity, 13.0 g, 40.0 mmol) in EtOAc (95 mL) and H₂SO₄ (11 mL, 0.20 mol) at −20° C. and stirred at r.t. for 60 h. The reaction mixture was diluted with H₂O (75 mL) and neutralised with aq NH₄OH solution. The organic layer was isolated, washed with brine, dried over Na₂SO₄, and concentrated in vacuo to ~75 mL volume. The solution was warmed to 45° C., and MeOH (30 mL), followed by a solution of oxalic acid (3.60 g, 40.0 mmol) in MeOH (15 mL) was added. The mixture was cooled to 0° C., and the resultant precipitate was isolated via vacuum filtration, washing with MeOH:EtOH (1:4) and EtOAc to afford the title compound (7.17 g, 19.1 mmol, 48% yield); ¹H NMR (500 MHz, DMSO-d₆) δ 7.25-7.42 (m, 5H), 4.59 (s, 2H), 4.17-4.24 (m, 2H), 3.92 (dd, J=12.3, 3.2 Hz, 1H), 3.34-3.40 (m, 1H), 3.10 (ddd, J=15.1, 7.6, 3.9 Hz, 1H), 2.64 (t, J=11.5 Hz, 1H), 2.13 (dt, J=10.2, 3.4 Hz, 1H), 1.87 (dd, J=9.0, 3.8 Hz, 1H), 1.65 (qd, J=13.2, 3.6 Hz, 1H), 1.40 (qd, J=12.8, 3.9 Hz, 1H), 1.23 (t, J=7.1 Hz, 3H); M/Z: 279, [M+H]⁺, ESI⁺, RT=0.81 (S1).

Intermediate 2 (Step 1.d): 1-tert-butyl 2-ethyl (2R, 5S)-5-[(benzyloxy)amino]piperidine-1,2-dicarboxylate Intermediate 2

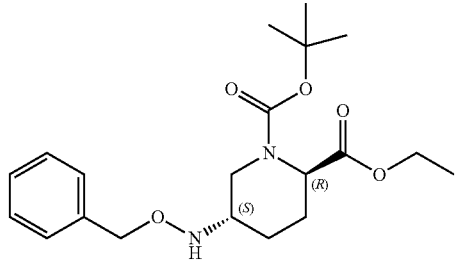

To a solution of ethyl (2R,5S)-5-[(benzyloxy)amino]piperidine-2-carboxylate oxalic acid (2.22 g, 6.03 mmol, Intermediate 1) in anhydrous DCM (30 mL) at 0° C. was added Et₃N (3.6 mL, 25.8 mmol), DMAP (76 mg, 0.622 mmol) and Boc₂O (4.2 mL, 18.3 mmol) and the mixture was stirred at r.t. for 17 h. The reaction mixture was diluted with satd aq NH₄Cl solution and DCM, and the organic layer was isolated, washed with H₂O and brine, dried over Na₂SO₄, and concentrated in vacuo. The residue was purified by chromatography on silica gel (0-20% EtOAc in heptane) to afford the title compound (86% purity, 1.40 g, 3.18 mmol, 53% yield) as a colourless oil; ¹H NMR (500 MHz, chloroform-d) δ 7.40-7.26 (m, 5H), 5.51-5.41 (m, 1H), 4.92-4.80 (m, 1H), 4.79-4.62 (m, 2H), 4.19 (q, J=7.0 Hz, 3H), 3.11 (d, J=45.4 Hz, 2H), 1.96 (s, 2H), 1.73-1.60 (m, 1H), 1.55-1.49 (m, 1H), 1.46 (s, 9H), 1.27 (t, J=7.1 Hz, 3H); M/Z: 379, [M+H]⁺, ESI⁺, RT=1.09 (S2).

Scheme for route 2

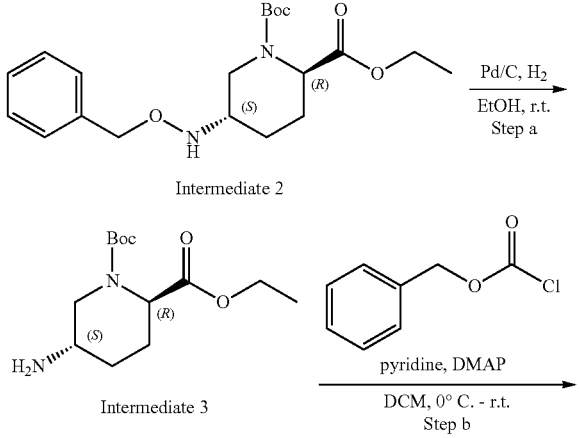

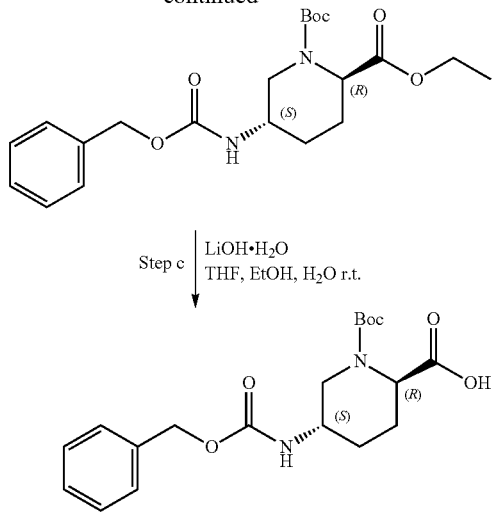

Step c | LiOH·H₂O
THF, EtOH, H₂O r.t.

Intermediate 4

Intermediate 3 (Step 2.a): 1-tert-butyl 2-ethyl (2R,5S)-5-aminopiperidine-1,2-dicarboxylate Intermediate 3

To a solution of 1-tert-butyl 2-ethyl (2R,5S)-5-[(benzyloxy)amino]piperidine-1,2-dicarboxylate (82% purity, 24.9 g, 54.0 mmol, Intermediate 2) in anhydrous EtOH (1 L) was added 10% Pd/C (2.87 g, 2.70 mmol) and the mixture was stirred at r.t. under H₂ for 24 h. The reaction mixture was filtered through a pad of Celite and concentrated in vacuo. The residue was dissolved in Et₂O and washed with 2 M aq HCl solution. The organic layer was discarded, and the aqueous layer was basified using solid NaHCO₃ and then extracted with IPA:DCM (2:8). The organic extracts were washed with brine, dried over MgSO₄, and concentrated in vacuo to afford the title compound (11.5 g, 42.2 mmol, 78% yield) as a pale yellow oil; ¹H NMR (400 MHz, chloroform-d) 1.29 (t, J=7.1 Hz, 3H), 1.48 (s, 9H), 1.51-1.70 (m, 4H), 1.93-2.22 (m, 2H), 3.06-3.38 (m, 2H), 3.66-3.97 (m, 1H), 4.21 (q, J=7.1 Hz, 2H), 4.56-5.01 (m, 1H).

Step 2.b: 1-tert-butyl 2-ethyl (2R,5S)-5-{[(benzyloxy)carbonyl]amino}piperidine-1,2-dicarboxylate To a solution of 1-tert-butyl 2-ethyl (2R,5S)-5-aminopiperidine-1,2-dicarboxylate (2.50 g, 9.18 mmol), DMAP (90 mg, 0.739 mmol) and pyridine (1.49 mL, 18.4 mmol) in DCM (45 mL) at 0° C. was added benzyl carbonochloridate (1.99 mL, 13.9 mmol) and the reaction mixture was stirred at r.t. for 20 h. Further portions of pyridine (700 μL, 8.6 mmol), DMAP (42 mg, 0.34 mmol) and benzyl carbonochloridate (930 μL, 6.5 mmol) were added at 0° C. and the mixture was stirred at r.t. for 1 h. The reaction mixture was diluted with H₂O (20 mL) and extracted with DCM (2×50 mL). The combined organic extracts were dried using a phase separator, concentrated in vacuo and purified by chromatography on silica gel (0-100% EtOAc in heptane) to afford the title compound (84% purity, 3.18 g, 6.57 mmol, 72% yield) as a colourless oil; ¹H NMR (400 MHz, chloroform-d) δ 7.36-7.21 (m, 5H), 5.16-4.92 (m, 3H), 4.87-4.50 (m, 1H), 4.13 (q, J=6.7 Hz, 2H), 3.98-3.72 (m, 2H), 3.21-2.94 (m, 1H), 2.13-1.99 (m, 1H), 1.93-1.67 (m, 2H), 1.37 (s, 9H), 1.19 (d, J=7.1 Hz, 3H), NH proton not observed; M/Z: 307 [M-Boc+H]⁺, ESI⁺, RT=1.08 (S1).

Intermediate 4 (Step 2.c): (2R,5S)-5-{[(benzyloxy)carbonyl]amino}-1-[(tert-butoxy)carbonyl]piperidine-2-carboxylic acid Intermediate 4

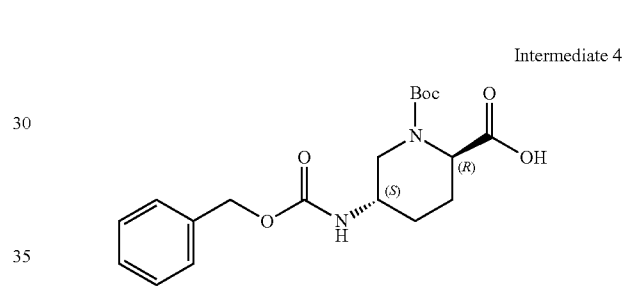

A mixture of 1-tert-butyl 2-ethyl (2R,5S)-5-{[(benzyloxy)carbonyl]amino}piperidine-1,2-dicarboxylate (84% purity, 3.18 g, 6.57 mmol) and LiOH·H₂O (311 mg, 7.23 mmol) in EtOH (25 mL):THF (25 mL):Water (25 mL) was stirred at r.t. for 24 h. The reaction mixture was partitioned between H₂O (30 mL) and EtOAc (30 mL), and the organic layer was discarded. The aqueous layer was then acidified using 1 M aq HCl solution and extracted with EtOAc (2×50 mL). The combined organic extracts were washed with brine (20 mL), dried over MgSO₄ and concentrated in vacuo to afford the title compound (86% purity, 2.04 g, 4.64 mmol, 71% yield) as a colorless solid; M/Z: 377 [M-H]⁻, ESI⁻, RT=0.90 (S2).

Scheme for route 3

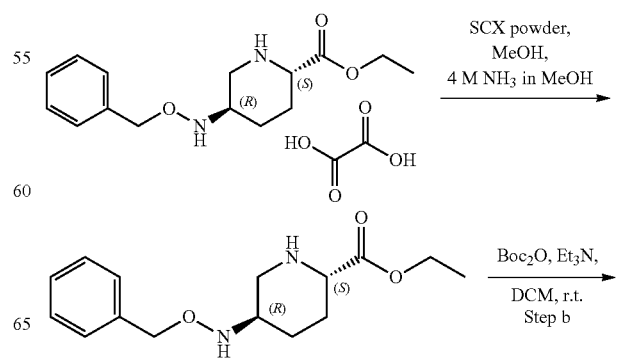

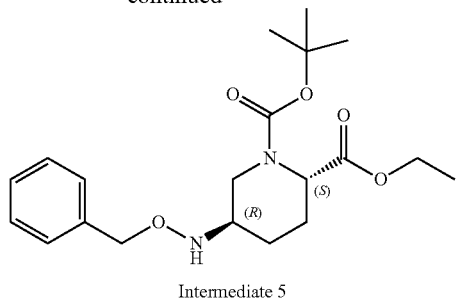

Intermediate 5

Step 3.a: ethyl (2S,5R)-5-[(benzyloxy)amino]piperidine-2-carboxylate

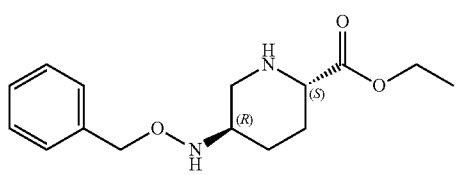

To a solution of ethyl (2S,5R)-5-[(benzyloxy)amino]piperidine-2-carboxylate; oxalic acid (10 g, 27.1 mmol) in MeOH (100 mL) was added SCX powder (50 g) and the mixture was stirred at r.t. for 10 min. The reaction mixture was filtered under vacuum, washing with 4 M $NH_3$ in MeOH, and concentrated in vacuo to afford the title compound (6.22 g, 22.3 mmol, 82% yield) as a viscous, yellow oil; $^1$H NMR (400 MHz, DMSO-$d_6$) δ 7.40-7.21 (m, 5H), 6.46 (s, 1H), 4.57 (s, 2H), 4.07 (q, J=7.1 Hz, 2H), 3.19-3.08 (m, 3H), 2.84-2.70 (m, 1H), 2.23 (dd, J=11.7, 9.9 Hz, 1H), 1.92-1.75 (m, 2H), 1.44-1.25 (m, 1H), 1.23-1.08 (m, 4H); M/Z: 279 [M+H]$^+$, ESI$^+$, RT=0.50 (S2).

Intermediate 5 (Step 3.b): 1-tert-butyl 2-ethyl (2S,5R)-5-[(benzyloxy)amino]piperidine-1,2-dicarboxylate

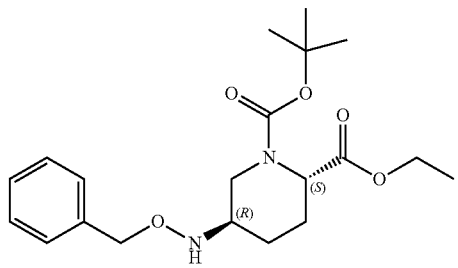

Intermediate 5

$Boc_2O$ (7.32 g, 33.5 mmol) was added to a solution of ethyl (2S,5R)-5-[(benzyloxy)amino]piperidine-2-carboxylate (6.22 g, 22.3 mmol) and $Et_3N$ (12 mL, 89.4 mmol) in anhydrous DCM (110 mL) and the mixture was stirred at r.t. for 2.5 h. The reaction mixture was washed with satd aq $NH_4Cl$ solution (100 mL) and brine (100 mL), dried over $Na_2SO_4$ and concentrated in vacuo. The resultant residue was purified by chromatography on silica gel (5-50% EtOAc in heptane) to afford the title compound (94% purity, 6.82 g, 16.9 mmol, 76% yield) as a colourless oil; $^1$H NMR (500 MHz, chloroform-d) δ 7.44-7.27 (m, 5H), 5.48 (s, 1H), 4.87 (d, J=9.9 Hz, 1H), 4.79-4.58 (m, 2H), 4.20 (q, J=7.0 Hz, 3H), 3.12 (d, J=44.6 Hz, 2H), 1.97 (s, 2H), 1.77-1.62 (m, 2H), 1.58-1.50 (m, 1H), 1.46 (s, 9H), 1.28 (t, J=7.1 Hz, 3H); M/Z: 324 [M-$^t$Butyl+H]$^+$, ESI$^+$, RT=1.34 (S1).

Scheme for route 4

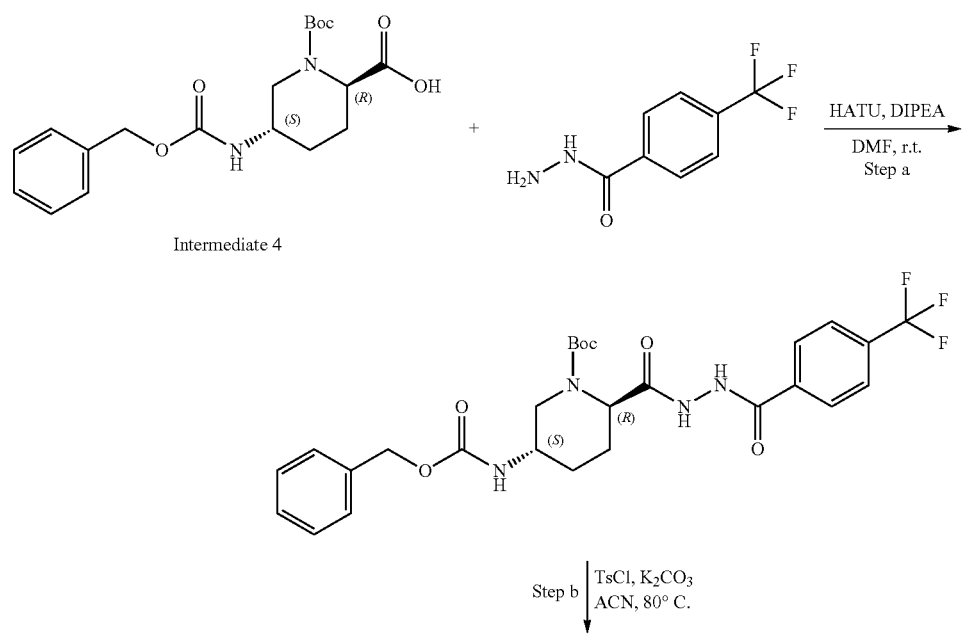

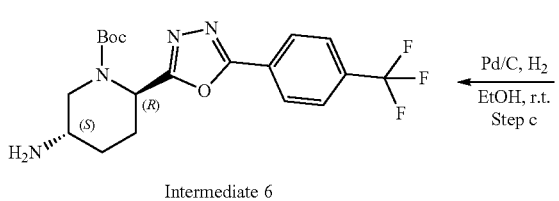

Intermediate 6

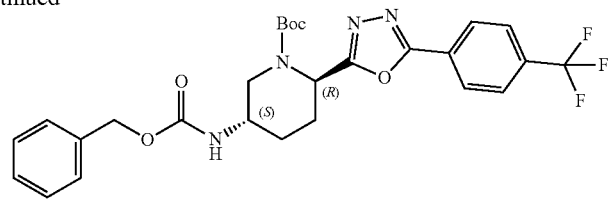

Step 4.a: tert-butyl (2R,5S)-5-{[(benzyloxy)carbonyl]amino}-2-({[4-(trifluoromethyl)phenyl]formohydrazido}carbonyl)piperidine-1-carboxylate

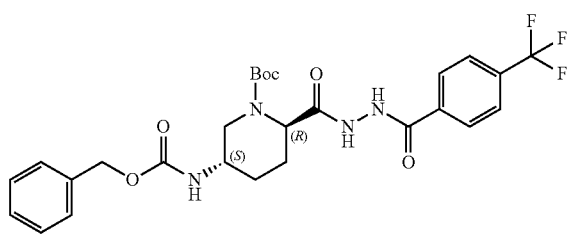

To a solution of (2R,5S)-5-{[(benzyloxy)carbonyl]amino}-1-[(tert-butoxy)carbonyl]piperidine-2-carboxylic acid (90% purity, 2.04 g, 4.85 mmol, Intermediate 4), 4-(trifluoromethyl)benzohydrazide (1.29 g, 6.31 mmol) and HATU (2.21 g, 5.82 mmol) in anhydrous DMF (24 mL) was added DIPEA (1.7 mL, 9.70 mmol) and the mixture was stirred at r.t. for 16 h. The reaction mixture was partitioned between EtOAc (100 mL) and 1 M aq HCl solution (50 mL). The organic layer was isolated, washed with brine (5×50 mL), dried over MgSO$_4$, and concentrated in vacuo. The residue was purified by chromatography on silica gel (0-100% EtOAc in heptane) to afford the title compound (70% purity, 3.80 g, 4.71 mmol, 97% yield) as an off-white solid; $^1$H NMR (400 MHz, DMSO-d$_6$) δ 10.59 (s, 1H), 10.01 (s, 1H), 8.07 (d, J=8.2 Hz, 2H), 7.90 (d, J=8.3 Hz, 2H), 7.46-7.27 (m, 6H), 5.05 (s, 2H), 4.84-4.52 (m, 2H), 4.12-3.92 (m, 1H), 3.74-3.46 (m, 2H), 2.23-2.03 (m, 1H), 1.78-1.62 (m, 1H), 1.63-1.49 (m, 1H), 1.38 (s, 9H); M/Z: 465 [M-Boc+H]$^+$, ESI$^+$, RT=1.01 (S2).

Step 4.b: tert-butyl (2R,5S)-5-{[(benzyloxy)carbonyl]amino}-2-{5-[4-(trifluoromethyl)phenyl]-1,3,4-oxadiazol-2-yl}piperidine-1-carboxylate

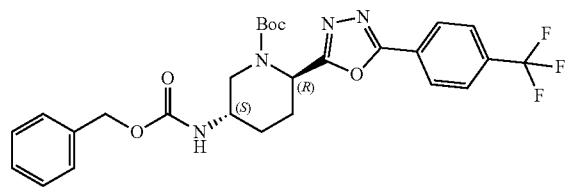

A suspension of tert-butyl (2R,5S)-5-{[(benzyloxy)carbonyl]amino}-2-({[4-(trifluoromethyl)phenyl]formohydrazido}carbonyl)piperidine-1-carboxylate (70% purity, 3.80 g, 4.71 mmol), TsCl (2.70 g, 14.1 mmol) and K$_2$CO$_3$ (1.95 g, 14.1 mmol) in ACN (100 mL) was stirred at 80° C. for 3 h. The reaction mixture was partitioned between EtOAc (100 mL) and H$_2$O (100 mL). The organic layer was isolated, washed with brine (50 mL), dried over MgSO$_4$, and concentrated in vacuo. The residue was purified by chromatography on silica gel (0-100% EtOAc in heptane). The resultant residue was triturated with Et$_2$O, the solid discarded, and the filtrate concentrated in vacuo and purified by prep. HPLC (Method 5) to afford the title compound (75% purity, 2.90 g, 3.98 mmol, 84% yield) as a pale yellow oil; $^1$H NMR (400 MHz, chloroform-d) δ 8.08 (d, J=8.1 Hz, 2H), 7.71 (d, J=8.3 Hz, 2H), 7.34-7.21 (m, 5H), 5.78-5.41 (m, 1H), 5.17-4.95 (m, 3H), 4.73 (s, 1H), 3.86 (s, 1H), 3.11 (s, 1H), 2.24-2.02 (m, 2H), 1.84 (d, J=22.6 Hz, 2H), 1.41 (s, 9H); M/Z: 447 [M-Boc+H]$^+$, ESI$^+$, RT=1.22 (S2).

Intermediate 6 (Step 4.c): tert-butyl (2R,5S)-5-amino-2-{5-[4-(trifluoromethyl)phenyl]-1,3,4-oxadiazol-2-yl}piperidine-1-carboxylate Intermediate 6

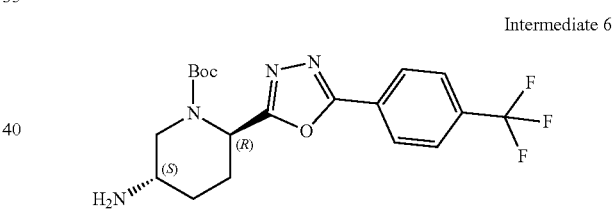

To a solution of tert-butyl (2R,5S)-5-{[(benzyloxy)carbonyl]amino}-2-{5-[4-(trifluoromethyl)phenyl]-1,3,4-oxadiazol-2-yl}piperidine-1-carboxylate (75% purity, 2.90 g, 3.98 mmol) in anhydrous EtOH (80 mL) was added Pd/C (10%, 0.21 g, 0.199 mmol) and the mixture was stirred under H$_2$ at r.t. for 24 h. The reaction mixture was filtered through a pad of Celite and the filtrate concentrated in vacuo. The residue was partitioned between EtOAc and 2 M aq HCl solution. The organic layer was isolated and after 20 min precipitation was observed. The suspension was filtered under vacuum, washing with H$_2$O, to afford the title compound as an HCl salt (0.76 g, 1.68 mmol, 42% yield) as a white solid; $^1$H NMR (400 MHz, chloroform-d) δ 8.74 (s, 3H), 8.08 (d, J=8.2 Hz, 2H), 7.73 (d, J=8.3 Hz, 2H), 5.67 (s, 1H), 4.51-4.36 (m, 1H), 3.63 (s, 1H), 3.19 (s, 2H), 2.61-2.47 (m, 1H), 2.31-2.14 (m, 2H), 1.47 (s, 9H); M/Z: 413 [M+H]$^+$, ESI$^+$, RT=1.08 (S2).

Scheme for route 5

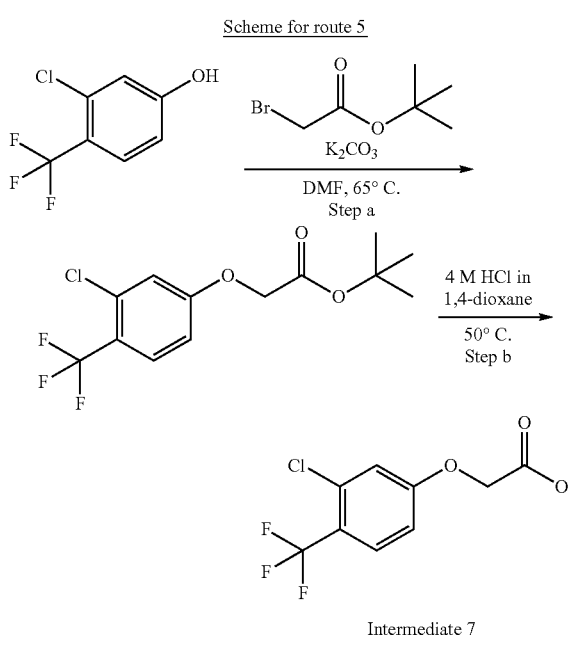

Step 5.a: tert-butyl 2-[3-chloro-4-(trifluoromethyl)phenoxy]acetate

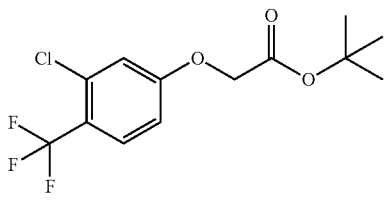 [SMILES: CC(C)(C)OC(=O)COc1ccc(C(F)(F)F)c(Cl)c1]

A mixture of 3-chloro-4-(trifluoromethyl)phenol (1.00 g, 5.09 mmol), tert-butyl 2-bromoacetate (0.83 mL, 5.60 mmol) and $K_2CO_3$ (1.41 g, 10.2 mmol) in anhydrous DMF (5 mL) was stirred at 65° C. for 2.5 h. The reaction mixture was cooled to r.t., diluted with $H_2O$ (30 mL) and extracted with EtOAc (2×30 mL). The combined organic extracts were washed with brine (40 mL), dried over $Na_2SO_4$ and concentrated in vacuo. The residue was purified by chromatography on silica gel (5-50% EtOAc in heptane) to afford the title compound (1.35 g, 4.35 mmol, 85% yield) as a colourless oil; $^1H$ NMR (500 MHz, chloroform-d) δ 7.61 (d, J=8.8 Hz, 1H), 7.02 (d, J=2.5 Hz, 1H), 6.88-6.79 (m, 1H), 4.56 (s, 2H), 1.50 (s, 9H); M/Z: not observed, $ESI^+$, RT=1.16 (S2).

Intermediate 7 (Step 5.b): 2-[3-chloro-4-(trifluoromethyl)phenoxy]acetic acid

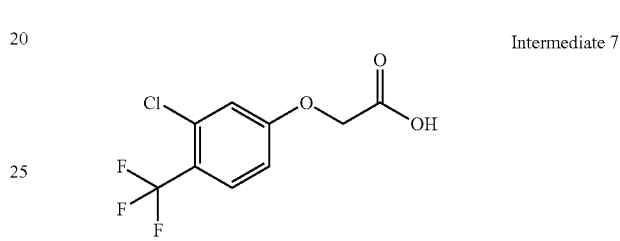

Intermediate 7

A solution of tert-butyl 2-[3-chloro-4-(trifluoromethyl)phenoxy]acetate (1.35 g, 4.35 mmol) in 4 M HCl in 1,4-dioxane (10 mL) was stirred at 50° C. for 6 h. The reaction mixture was concentrated in vacuo to afford the title compound (1.09 g, 4.28 mmol, 99% yield) as a white solid; $^1H$ NMR (400 MHz, DMSO-$d_6$) δ 13.19 (s, 1H), 7.76 (d, J=8.9 Hz, 1H), 7.31 (d, J=2.5 Hz, 1H), 7.07 (dd, J=8.7, 2.4 Hz, 1H), 4.86 (s, 2H); $^{19}F$ NMR (376 MHz, DMSO-$d_6$) δ −59.84 (2F, s).

The intermediates in Table 1 were synthesised according to general route 5 as exemplified by Intermediate 7 using the corresponding starting materials.

TABLE 1

| Intermediate | Structure | Name | Starting material | LCMS data | NMR data |
|---|---|---|---|---|---|
| 8 | ![structure] | 2-[3-fluoro-4-(trifluoromethyl)phenoxy] acetic acid | 3-fluoro-4-(trifluoromethyl)phenol | | $^1H$ NMR (400 MHz, DMSO-$d_6$) δ 13.24 (s, 1H), 7.74 (t, J = 8.8 Hz, 1H), 7.20 (dd, J = 13.1, 2.1 Hz, 1H), 7.00 (dd, J = 8.8, 2.0 Hz, 1H), 4.90 (s, 2H); $^{19}F$ NMR (376 MHz, DMSO-$d_6$) δ −58.87 (3F, d, J = 12.0 Hz), −113.67 (1F, q, J = 12.0 Hz). |
| 9 | ![structure] | 2-(3,4,5-trichlorophenoxy)acetic acid | 3,4,5-trichlorophenol | | $^1H$ NMR (400 MHz, DMSO-$d_6$) δ 13.15 (s, 1H), 7.31 (s, 2H), 4.81 (s, 2H). |

TABLE 1-continued

| Intermediate | Structure | Name | Starting material | LCMS data | NMR data |
|---|---|---|---|---|---|
| 10 | (4-chloro-2,3-difluorophenoxy structure) | 2-(4-chloro-2,3-difluoro-phenoxy)acetic acid | 4-chloro-2,3-difluorophenol | | $^1$H NMR (400 MHz, DMSO-$d_6$) δ 13.21 (s, 1H), 7.42-7.27 (m, 1H), 7.02 (td, J = 9.4, 2.1 Hz, 1H), 4.86 (s, 2H); $^{19}$F NMR (376 MHz, DMSO-$d_6$) δ −138.49 (1F, d, J = 20.6 Hz), −155.58 (1F, d, J = 20.7 Hz). |
| 11 | (4-chloro-3,5-difluorophenoxy structure) | 2-(4-chloro-3,5-difluoro-phenoxy)acetic acid | 4-chloro-3,5-difluorophenol | | $^1$H NMR (400 MHz, DMSO-$d_6$) δ 13.16 (s, 1H), 7.09-6.94 (m, 2H), 4.77 (s, 2H); $^{19}$F NMR (376 MHz, DMSO-$d_6$) δ −113.48 (2F, s). |
| 12 | (6-chloro-5-fluoropyridin-3-yloxy structure) | 2-[(6-chloro-5-fluoropyridin-3-yl)oxy]acetic acid | 6-chloro-5-fluoropyridin-3-ol | M/Z: 206, 208 [M + H]$^+$, ESI$^+$, RT = 0.60 (S2) | $^1$H NMR (500 MHz, DMSO-$d_6$) δ 13.22 (s, 1H), 8.07 (d, J = 2.6 Hz, 1H), 7.76 (dd, J = 10.4, 2.6 Hz, 1H), 4.85 (s, 2H). |
| 13 | (6-trifluoromethylpyridin-3-yloxy structure) | 2-{[6-(trifluoro-methyl)pyridin-3-yl]oxy}acetic acid | 6-(trifluoro-methyl)pyridin-3-ol | M/Z: 222 [M + H]$^+$, ESI$^+$, RT = 0.74 (S2) | $^1$H NMR (400 MHz. DMSO-$d_6$) δ 13.27 (s, 1H), 8.46 (d, J = 2.9 Hz, 1H), 7.85 (d, J = 8.7 Hz, 1H), 7.59 (dd, J = 8.8, 2.9 Hz, 1H), 4.92 (s, 2H). |
| 14 | (4-chloro-3-methylphenoxy structure) | 2-(4-chloro-3-methylphenoxy)acetic acid | 4-chloro-3-methylphenol | M/Z: 199, 201 [M + H]$^+$, ESI$^+$, RT = 0.78 (S2). | $^1$H NMR (500 MHz, DMSO-$d_6$) δ 7.29 (d, J = 8.8 Hz, 1H). 6.93 (d, J = 3.0 Hz, 1H), 6.76 (dd, J = 8.8, 3.1 Hz, 1H), 4.66 (s, 2H), 2.28 (s, 3H). |
| 15 | (3-methoxy-4-trifluoromethylphenoxy structure) | 2-[3-methoxy-4-(trifluoromethyl)phenoxy]acetic acid | 3-methoxy-4-(trifluoro-methyl)phenol | M/Z: 249 [M − H]$^−$, ESI$^−$, RT = 0.78 (S2). | $^1$H NMR (400 MHz, DMSO-$d_6$) δ 13.11 (s, 1H), 7.51 (d, J = 8.8 Hz, 1H), 6.78 (d, J = 2.0 Hz. 1H), 6.60 (dd, J = 8.7, 2.2 Hz, 1H), 4.80 (s, 2H), 3.87 (s, 3H). |

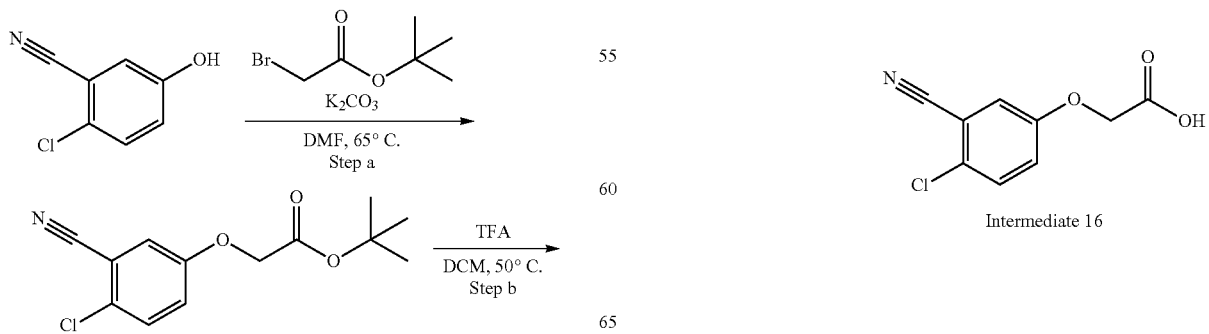

Intermediate 16

51

Step 6.a: tert-butyl 2-(4-chloro-3-cyanophenoxy)acetate

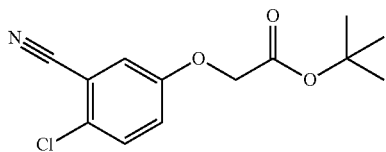 [SMILES: CC(C)(C)OC(=O)COc1ccc(Cl)c(C#N)c1]

A mixture of tert-butyl 2-bromoacetate (1.1 mL, 7.16 mmol), 2-chloro-5-hydroxybenzonitrile (1.00 g, 6.51 mmol) and $K_2CO_3$ (1.80 g, 13.0 mmol) in DMF (6 mL) was stirred at 65° C. for 2 h. The reaction mixture was diluted with $H_2O$ (30 mL) and extracted with EtOAc (2×50 mL). The combined organic extracts were washed with brine (30 mL), dried over $Na_2SO_4$, and concentrated in vacuo to afford the title compound (84% purity, 2.10 g, 6.59 mmol) in quantitative yield as an orange oil; $^1$H NMR (400 MHz, DMSO-$d_6$) δ 7.65 (d, J=9.0 Hz, 1H), 7.61 (d, J=3.1 Hz, 1H), 7.32 (dd, J=9.0, 3.1 Hz, 1H), 4.79 (s, 2H), 1.43 (s, 9H); M/Z: 269, 271 [M+H]$^+$, ESI$^+$, RT=1.11 (S2).

52

Intermediate 16 (Step 6.b): 2-(4-chloro-3-cyanophenoxy)acetic acid

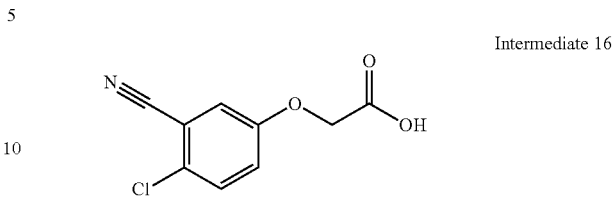

Intermediate 16

To a solution of tert-butyl 2-(4-chloro-3-cyano-phenoxy) acetate (84% purity, 2.50 g, 7.84 mmol) in DCM (5 mL) was added TFA (3.0 mL, 39.2 mmol) and the mixture was stirred at 50° C. for 2.5 h. The reaction mixture was concentrated in vacuo, and the residue was suspended in $H_2O$ and stirred at r.t. for 15 min. The resultant precipitate was filtered under vacuum, washing with $H_2O$, to afford the title compound (94% purity, 1.03 g, 4.58 mmol, 58% yield) as an off white solid; $^1$H NMR (400 MHz, DMSO-$d_6$) δ 13.13 (s, 1H), 7.69-7.56 (m, 2H), 7.32 (dd, J=9.0, 3.1 Hz, 1H), 4.81 (s, 2H); M/Z: 210, 212 [M−H]$^−$, ESI$^−$, RT=0.76 (S2).

Scheme for route 7

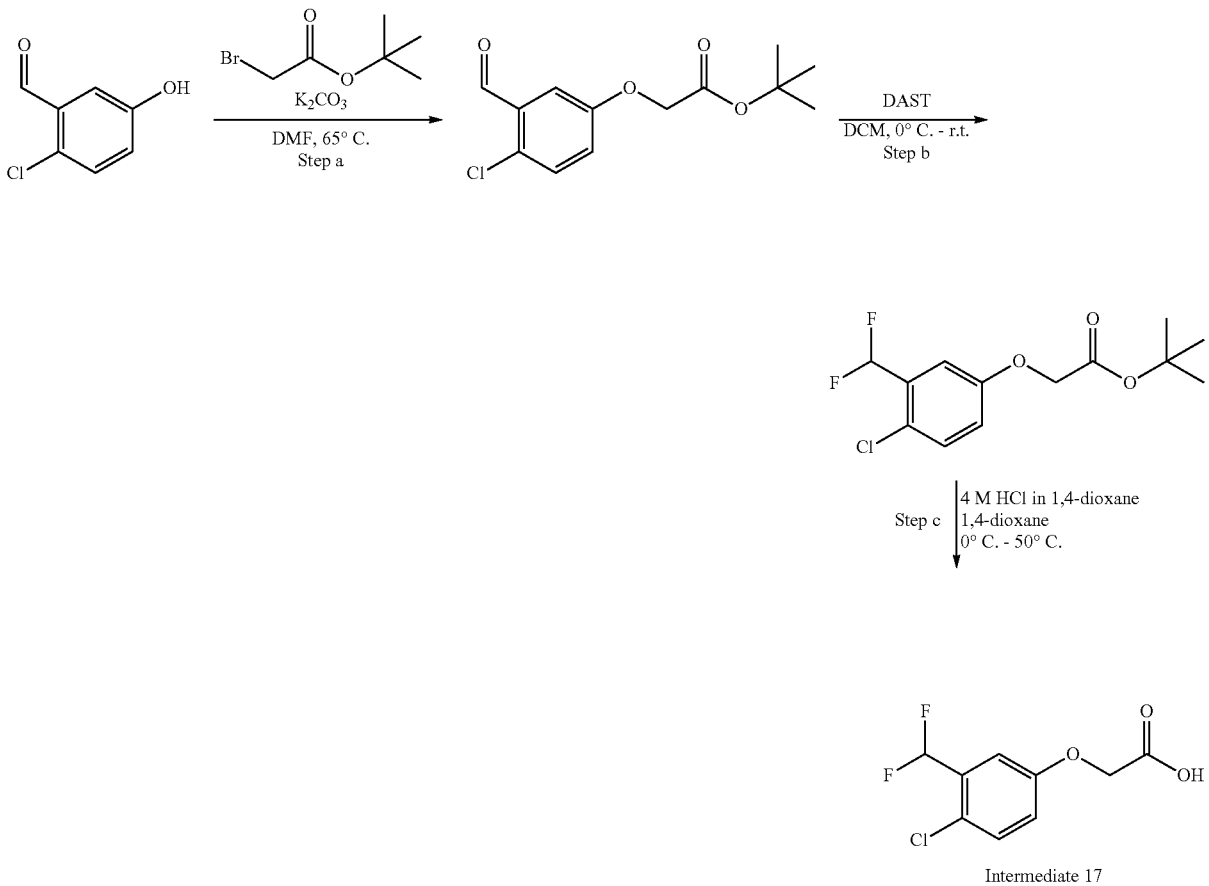

Intermediate 17

Step 7.a: tert-butyl 2-(4-chloro-3-formylphenoxy)acetate

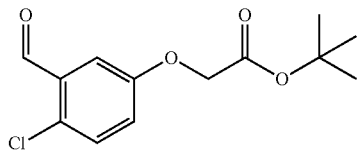 [SMILES: CC(C)(C)OC(=O)COc1ccc(Cl)c(C=O)c1]

To a solution of 2-chloro-5-hydroxybenzaldehyde (1.0 g, 6.39 mmol) in anhydrous DMF (10 mL) was added $K_2CO_3$ (1.77 g, 12.8 mmol) followed by tert-butyl bromoacetate (1.0 mL, 7.03 mmol) and the mixture was stirred at 65° C. for 1 h. The reaction mixture was cooled to r.t., poured onto $H_2O$ (100 mL) and extracted with EtOAc (2×70 mL). The combined organic extracts were washed with brine (100 mL), dried over $Na_2SO_4$, and concentrated in vacuo. The residue was purified by chromatography on silica gel (10-80% EtOAc in heptane) to afford the title compound (1.70 mg, 6.23 mmol, 98% yield) as a white solid; $^1$H NMR (500 MHz, $CDCl_3$) δ 10.42 (s, 1H), 7.40-7.30 (m, 2H), 7.15 (dd, J=8.8, 3.2 Hz, 1H), 4.55 (s, 2H), 1.49 (s, 9H); M/Z: no mass ion observed $[M+H]^+$, $ESI^+$, RT=1.01 (S2).

Step 7.b: tert-butyl 2-[4-chloro-3-(difluoromethyl)phenoxy]acetate

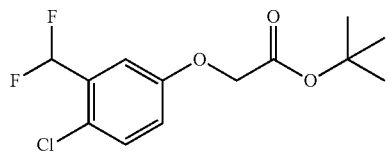 [SMILES: CC(C)(C)OC(=O)COc1ccc(Cl)c(C(F)F)c1]

To a solution of tert-butyl 2-(4-chloro-3-formylphenoxy) acetate (1.0 g, 3.66 mmol) in anhydrous DCM (10 mL) at 0° C. was added DAST (0.72 mL, 5.49 mmol) dropwise and the mixture was stirred at r.t. for 20 h. The reaction mixture was poured onto satd aq $NaHCO_3$ solution (30 mL) and extracted with DCM (2×30 mL). The combined organic extracts were dried over $Na_2SO_4$, concentrated in vacuo, and purified by chromatography on silica gel (10-40% EtOAc in heptane) to afford the title compound (809 mg, 2.74 mmol, 75% yield) as a colourless oil; $^1$H NMR (500 MHz, chloroform-d) δ 7.32 (d, J=8.8 Hz, 1H), 7.14 (d, J=3.0 Hz, 1H), 7.02-6.76 (m, 2H), 4.53 (s, 2H), 1.49 (s, 9H); $^{19}$F NMR (376 MHz, chloroform-d) δ -115.44; M/Z: 316, 318 $[M+Na]^+$, $ESI^+$, RT=1.08 (S2).

Intermediate 17 (Step 7.c): 2-[4-chloro-3-(difluoromethyl)phenoxy]acetic acid

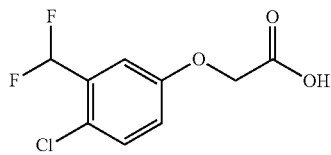

Intermediate17

To a solution of tert-butyl 2-[4-chloro-3-(difluoromethyl)phenoxy]acetate (809 mg, 2.74 mmol) in 1,4-dioxane (10 mL) at 0° C. was added 4 M HCl in 1,4-dioxane (3.4 mL, 13.7 mmol) and the mixture was stirred under $N_2$ at r.t. for 20 h. A further portion of 4 M HCl in 1,4-dioxane (3.4 mL, 13.7 mmol) was added and the mixture was stirred at 50° C. for 7 h. A further portion of 4 M HCl in 1,4-dioxane (3.4 mL, 13.7 mmol) was added and the mixture was stirred at r.t. for 20 h. The reaction mixture was concentrated in vacuo, triturated using $H_2O$ and dried under vacuum filtration for 1 h to afford the title compound (574 mg, 2.35 mmol, 86% yield) as a white powder; $^1$H NMR (400 MHz, DMSO-$d_6$) δ 7.50 (d, J=8.8 Hz, 1H), 7.30-6.97 (m, 3H), 4.78 (s, 2H); M/Z: 235, 237 $[M-H]^-$, $ESI^-$, RT=1.07 (S2).

The intermediate in Table 2 was synthesised according to general route 7 as exemplified by Intermediate 17 using the corresponding starting materials.

TABLE 2

| Intermediate | Structure | Name | Starting material | LCMS data | $^1$H NMR data |
|---|---|---|---|---|---|
| 56 | (structure shown) | 2-[3-chloro-4-(difluoromethyl)phenoxy]acetic acid | 2-chloro-4-hydroxy-benzaldehyde | M/Z: 235, 237 [M − H]$^-$, ESI$^-$ RT = 0.75 (S2) | $^1$H NMR (500 MHz, DMSO-$d_6$) δ 13.16 (s, 1H), 7.62-7.57 (m, 1H), 7.25-6.99 (m, 3H), 4.81 (s, 2H). |

Scheme for route 8

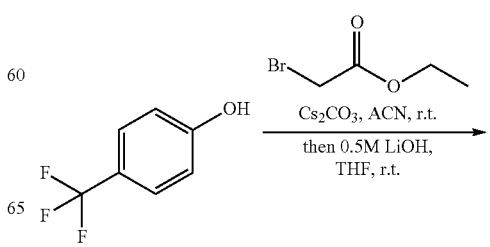

DMSO-d$_6$) δ 13.16 (s, 1H), 7.65 (d, J=8.6 Hz, 2H), 7.10 (d, J=8.6 Hz, 2H), 4.79 (s, 2H); M/Z: 219 [M–H]$^-$, ESI$^-$, RT=1.03 (S1).

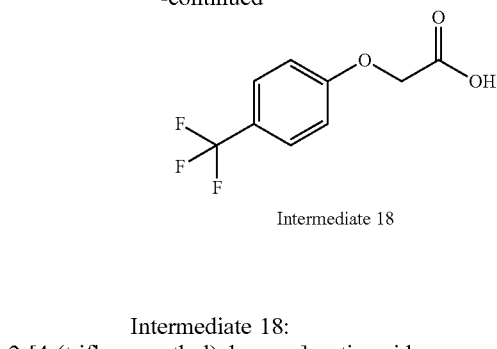

Intermediate 18

Intermediate 18: 2-[4-(trifluoromethyl)phenoxy]acetic acid

To a suspension of 4-(trifluoromethyl)phenol (2.00 g, 12.3 mmol) and ethyl 2-bromoacetate (1.4 mL, 12.6 mmol) in anhydrous ACN (50 mL) was added Cs$_2$CO$_3$ (6.00 g, 18.4 mmol) and the mixture was stirred at r.t. for 17 h. The reaction mixture was diluted with EtOAc (20 mL), washed with H$_2$O (2×20 mL) and brine (20 mL), dried using a phase separator, and concentrated in vacuo. The residue was dissolved in THF (50 mL) and a solution of 0.5 M aq LiOH solution (49 mL, 24.7 mmol) was added, and the mixture was stirred at r.t. for 1.5 h. The reaction mixture was diluted with H$_2$O (20 mL), extracted with EtOAc (2×20 mL), and the organic extracts discarded. The aqueous solution was then acidified to pH 1-2 using 1 M aq HCl solution and extracted with DCM (3×20 mL). The combined organic extracts were dried using a phase separator and concentrated in vacuo to afford the title compound (2.90 g, 12.9 mmol) in quantitative yield as a white solid; $^1$H NMR (500 MHz, Scheme for route 9

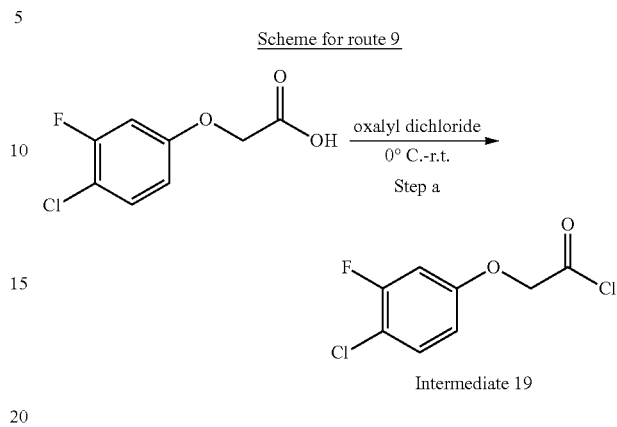

Intermediate 19: 2-(4-chloro-3-fluorophenoxy)acetyl chloride

To a solution of 2-(4-chloro-3-fluorophenoxy)acetic acid (5.16 g, 22.7 mmol) in DCM (45 mL) at 0° C. was added oxalyl dichloride (10 mL, 0.115 mol) followed by DMF (81 μL, 1.11 mmol) and the mixture was stirred at r.t. for 17 h. The reaction mixture was concentrated in vacuo to afford the title compound (90% purity, 5.30 g, 21.4 mmol, 94% yield) as a orange oil; $^1$H NMR (400 MHz, chloroform-d) δ 7.31 (t, J=8.6 Hz, 1H), 6.75 (dt, J=10.2, 2.9 Hz, 1H), 6.66 (ddd, J=8.9, 2.9, 1.2 Hz, 1H), 4.96 (s, 2H).

The intermediates in Table 3 were synthesised according to the general route 9 as exemplified by Intermediate 19 using the corresponding starting materials.

TABLE 3

| Intermediate | Structure | Name | Starting material | LCMS data | $^1$H NMR |
|---|---|---|---|---|---|
| 20 | 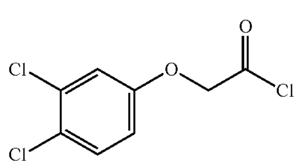 [SMILES: O=C(Cl)COc1ccc(Cl)c(Cl)c1] | 2-(3,4-dichlorophenoxy)acetyl chloride | 2-(3,4-dichlorophenoxy)acetic acid | | $^1$H NMR (500 MHz, DMSO-d$_6$) δ 7.53 (d, J = 8.9 Hz, 1H), 7.24 (d, J = 2.9 Hz, 1H), 6.96 (dd, J = 8.9, 3.0 Hz, 1H), 4.76 (s, 2H). |
| 21 | 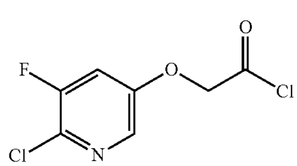 [SMILES: O=C(Cl)COc1cnc(Cl)c(F)c1] | 2-[(6-chloro-5-fluoropyridin-3-yl)oxy]acetyl chloride | 2-[(6-chloro-5-fluoropyridin-3-yl)oxy]acetic acid (Intermediate 12) | | Used crude |

Scheme for route 10

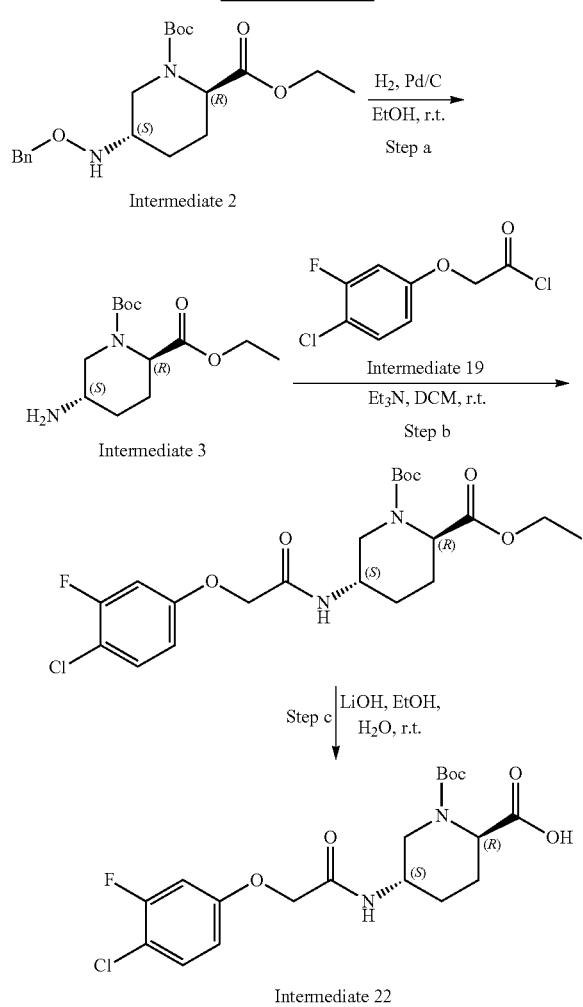

Intermediate 3 (Step 10.a): 1-tert-butyl 2-ethyl (2R,5S)-5-aminopiperidine-1,2-dicarboxylate

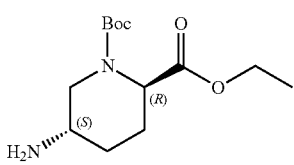

To a solution of 1-tert-butyl 2-ethyl (2R,5S)-5-[(benzyloxy)amino]piperidine-1,2-dicarboxylate (93% purity, 8.7 g, 21.3 mmol, Intermediate 2) in anhydrous EtOH (200 mL) under N₂ was added Pd/C (10%, 2.28 g, 2.14 mmol) and the mixture was stirred under H₂ at r.t. for 17 h. The reaction mixture was filtered through a pad of Celite and the filtrate concentrated in vacuo. The residue was purified using an SCX-2 cartridge, first flushing with MeOH and second eluting with 3 M NH₃ in MeOH to afford the title compound (4.88 g, 17.0 mmol, 80% yield) as a pale yellow oil; ¹H NMR (400 MHz, chloroform-d) δ 4.98-4.57 (m, 1H), 4.18 (q, J=7.1 Hz, 2H), 3.87-3.64 (m, 1H), 3.35-2.99 (m, 2H), 2.14-1.92 (m, 2H), 1.64-1.52 (m, 2H), 1.45 (s, 11H), 1.26 (t, J=7.1 Hz, 3H).

Step 10.b: 1-tert-butyl 2-ethyl (2R,5S)-5-[2-(4-chloro-3-fluorophenoxy)acetamido]piperidine-1,2-dicarboxylate

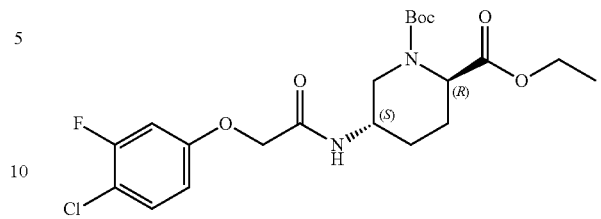

To a mixture of 1-tert-butyl 2-ethyl (2R,5S)-5-aminopiperidine-1,2-dicarboxylate (4.89 g, 17.1 mmol) and Et₃N (14 mL, 0.103 mol) in DCM (170 mL) at 0° C. was added dropwise a solution of 2-(4-chloro-3-fluoro-phenoxy)acetyl chloride (4.19 g, 18.8 mmol, Intermediate 19) in DCM (10 mL) and stirred at r.t. for 48 h. The reaction mixture was diluted with DCM (250 mL) and washed with satd aq NaHCO₃ solution (2×100 mL) and brine (100 mL), dried over Na₂SO₄ and concentrated in vacuo. The residue was purified by chromatography on silica gel (0-50% EtOAc in heptane) to afford the title compound (7.14 g, 15.6 mmol, 91% yield) as a colourless oil; ¹H NMR (400 MHz, chloroform-d) δ 7.32 (t, J=8.6 Hz, 1H), 6.86-6.72 (m, 2H), 6.69-6.63 (m, 1H), 4.98-4.66 (m, 1H), 4.45 (s, 2H), 4.29-4.13 (m, 3H), 4.09-3.87 (m, 1H), 3.33-3.10 (m, 1H), 2.23-2.02 (m, 1H), 2.00-1.71 (m, 2H), 1.56 (s, 1H), 1.44 (s, 9H), 1.28 (t, J=7.2 Hz, 3H); M/Z: 459, 461 [M+H]⁺, ESI⁺, RT=3.83 (S4).

Intermediate 22 (Step 10.c): (2R,5S)-1-[(tert-butoxy)carbonyl]-5-[2-(4-chloro-3-fluorophenoxy)acetamido]piperidine-2-carboxylic acid

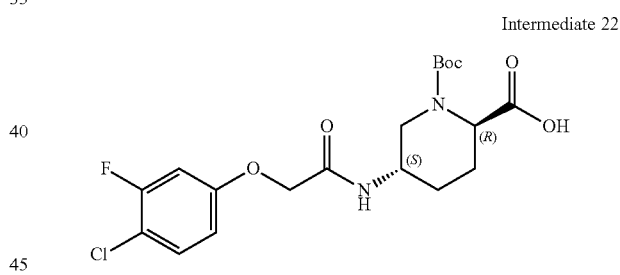

LiOH (0.78 g, 31.1 mmol) was added to a solution of 1-tert-butyl 2-ethyl (2R,5S)-5-[2-(4-chloro-3-fluorophenoxy)acetamido]piperidine-1,2-dicarboxylate (7.1 g, 15.6 mmol) in EtOH (80 mL) and H₂O (20 mL) and the mixture was stirred at r.t. for 3 h. The reaction mixture was concentrated in vacuo, redissolved in H₂O (50 mL), and extracted with DCM (2×100 mL). The aqueous layer was then acidified to pH 2 using 2 M aq HCl solution and extracted with EtOAc (3×100 mL). The combined organic extracts were washed with brine (100 mL), dried over anhydrous Na₂SO₄, and concentrated in vacuo to afford the title compound (87% purity, 5.60 g, 11.3 mmol, 73% yield) as a white solid; ¹H NMR (400 MHz, DMSO-d₆) δ 8.02 (d, J=7.3 Hz, 1H), 7.47 (t, J=8.9 Hz, 1H), 7.03 (dd, J=11.4, 2.8 Hz, 1H), 6.83-6.75 (m, 1H), 4.59-4.54 (m, 2H), 3.93 (s, 1H), 3.73 (d, J=54.2 Hz, 1H), 3.13-2.94 (m, 1H), 2.06-1.87 (m, 2H), 1.61 (d, J=12.2 Hz, 1H), 1.56-1.43 (m, 1H), 1.37 (s, 10H); M/Z: 429, 431 [M+H], ESI⁺, RT=0.91 min (S1).

The intermediates in Table 4 were synthesised according to general route 10 as exemplified by Intermediate 22 using the corresponding starting materials.

TABLE 4

| Intermediate | Structure | Name | Starting material | LCMS data | ¹H NMR data |
|---|---|---|---|---|---|
| 23 | (structure: Boc-piperidine with 4-chloro-3-fluorophenoxy acetamide, carboxylic acid, (R)) | (5R)-1-[{tert-butoxy)carbonyl]-5-[2-(4-chloro-3-fluorophenoxy)acetamido]piperidine-2-carboxylic acid | tert-butyl-ethyl (5R)-5-(benzyloxyamino)piperidine-1,2-dicarboxylate following steps 10.a-10.c | M/Z: 375, 377 [M − Boc + H]⁺, ESI⁺, RT = 0.91 (S2) | ¹H NMR (500 MHz, DMSO-$d_6$) δ 12.86 (s, 1H), 8.03 (d, J = 7.3 Hz, 1H), 7.47 (t, J = 8.9 Hz, 1H), 7.03 (dd, J = 11.4, 2.8 Hz, 1H), 6.81 (d, J = 8.7 Hz, 1H), 4.70-4.45 (m, 3H), 4.00-3.70 (m, 2H), 3.06 (d, J = 32.9 Hz, 1H), 2.07-1.83 (m, 2H), 1.73-1.42 (m, 2H), 1.37 (s, 9H). |
| 24 | (structure: Boc-piperidine (2R,5S) with 3,4-dichlorophenoxy acetamide) | (2R,5S)-1-[(tert-butoxy)carbonyl]-5-[2-(3,4-dichlorophenoxy)acetamido]piperidine-2-carboxylic acid | 2-(3,4-dichlorophenoxy)acetyl chloride (Intermediate 20) following steps 10 10.c.b and | M/Z: 374, 377, 351 [M − Boc + H]⁺, ESI⁺, RT = 0.99 (S2) | ¹H NMR (500 MHz, DMSO-$d_6$) δ 12.83 (s, 1H), 8.04 (d, J = 7.3 Hz, 1H), 7.53 (d, J = 8.9 Hz, 1H), 7.22 (d, J = 2.8 Hz, 1H), 6.98-6.91 (m, 1H), 4.68-4.50 (m, 3H), 4.02-3.88 (m, 1H), 3.86-3.75 (m, 1H), 3.14-3.00 (m, 1H), 2.06-1.87 (m, 2H), 1.73-1.59 (m, 1H), 1.53-1.43 (m, 1H), 1.37 (s, 9H). |
| 25 | (structure: Boc-piperidine (2S,5R) with 4-chloro-3-fluorophenoxy acetamide) | (2S,5R)-1-[(tert-butoxy)carbonyl]-5-[2-(4-chloro-3-fluorophenoxy)acetamido]piperidine-2-carboxylic acid | 1-tert-butyl 2-ethyl (2S,5R)-5-aminopiperidine-1,2-dicarboxylate following steps 01.b and 10.c | M/Z: 375, 377 [M − ᵗButyl + H]⁺, ESI⁺, RT = 0.91 (S2) | ¹H NMR (500 MHz, DMSO-$d_6$) δ 12.86 (s, 1H), 8.03 (d, J = 7.3 Hz, 1H), 7.47 (t, J = 8.9 Hz, 1H), 7.03 (dd, J = 11.4, 2.8 Hz, 1H), 6.81 (d, J = 8.7 Hz, 1H), 4.70-4.45 (m, 3H), 4.00-3.70 (m, 2H), 3.06 (d, J = 32.9 Hz, 1H), 2.07-1.83 (m, 2H), 1.73-1.42 (m, 2H), 1.37 (s, 9H). |

Scheme for route 11

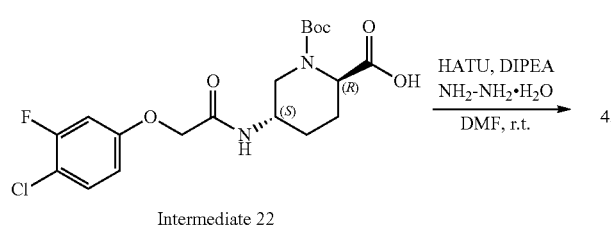

Intermediate 22

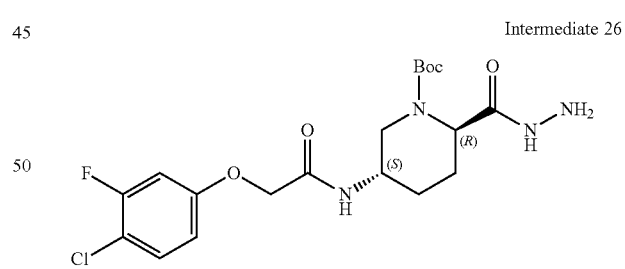

Intermediate 26

Intermediate 26: tert-butyl (2R,5S)-5-[2-(4-chloro-3-fluorophenoxy)acetamido]-2-(hydrazinecarbonyl)piperidine-1-carboxylate To a solution of (2R,5S)-1-[(tert-butoxy)carbonyl]-5-[2-(4-chloro-3-fluorophenoxy)acetamido]piperidine-2-carboxylic acid (8.43 g, 19.2 mmol, Intermediate 22) and HATU (8.75 g, 23.0 mmol) in DMF (80 mL) was added DIPEA (4.0 mL, 23.0 mmol) and stirred at r.t under $N_2$ for 30 min. The resultant solution was added dropwise via a cannula to a solution of $NH_2$—$NH_2 \cdot H_2O$ (1.9 mL, 38.3 mmol) in DMF (40 mL) and stirred at r.t. for 30 min. The reaction mixture was diluted with EtOAc (150 mL) and washed with $H_2O$ (4×100 mL). The combined organic extracts were dried over MgSO₄, concentrated in vacuo, and purified by chromatography on silica gel (0-10% MeOH in DCM) to afford the title compound (4.57 g, 10.3 mmol, 54% yield) as a white solid; ¹H NMR (400 MHz, chloroform-d) δ 7.35-7.27 (m, 2H), 6.88-6.58 (m, 3H), 4.75 (s, 1H), 4.45 (d, J=3.8 Hz, 2H), 4.12 (s, 2H), 3.88 (s, 2H), 3.09 (d, J=13.2 Hz, 1H), 2.21-2.12 (m, 1H), 1.86 (s, 2H), 1.69 (ddt, J=17.8, 14.0, 6.1 Hz, 1H), 1.44 (s, 9H); M/Z: 345, 347 [M-Boc+H]⁺, ESI⁺, RT=0.82 (S2).

The intermediates in Table 5 were synthesised according to general route 11 as exemplified by Intermediate 26 using the corresponding starting materials.

TABLE 5

| Intermediate | Structure | Name | Starting material | LCMS data | ¹H NMR data |
|---|---|---|---|---|---|
| 27 | 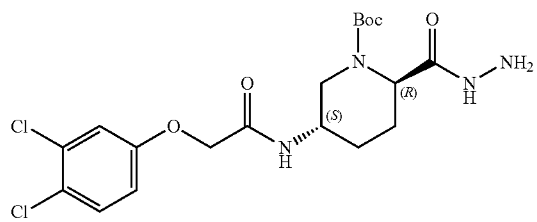 | tert-butyl (2R,5S)-5-[2-(3,4-dichlorophenoxy)acetamido]-2-(hydrazinecarbonyl)piperidine-1-carboxylate | (2R,5S)-1-[(tert-butoxy)carbonyl]-5-[2-(3,4-dichlorophenoxy)acetamido]piperidine-2-carboxylic acid (Intermediate 24) | M/Z: 361, 363, 365 [M − Boc + H]⁺, ESI⁺, RT = 0.92 (S2) | ¹H NMR (400 MHz, DMSO-d₆) δ 9.23 (s, 1H), 7.97 (d, J = 7.3 Hz, 1H), 7.53 (d, J = 8.8 Hz, 1H), 7.23 (d, J = 2.9 Hz, 1H), 6.96 (dd, J = 9.0, 2.9 Hz, 1H), 4.65-4.45 (m, 3H), 3.99-3.88 (m, 1H), 3.88-3.76 (m, 1H), 2.03-1.90 (m, 1H), 1.87-1.74 (m, 1H), 1.66-1.50 (m, 2H), 1.36 (s, 9H), 1.29-1.24 (m, 1H). |
| 28 | 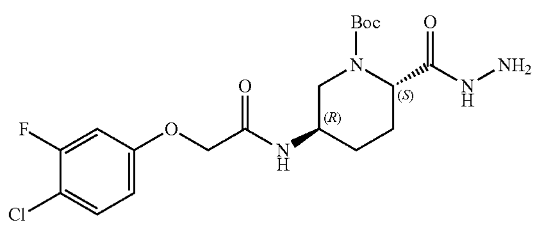 | tert-butyl (2S,5R)-5-[2-(4-chloro-3-fluorophenoxy)acetamido]-2-(hydrazinecarbonyl)piperidine-1-carboxylate | (2S,5R)-1-[(tert-butoxy)carbonyl]-5-[2-(4-chloro-3-fluorophenoxy)acetamido]piperidine-2-carboxylic acid (Intermediate 25) | M/Z: 345, 347 [M − Boc + H]⁺, ESI⁺, RT = 0.86 (S2) | ¹H NMR (400 MHz, DMSO-d₆) δ 9.07 (s, 1H), 7.96 (d, J = 7.0 Hz, 1H), 7.48 (t, J = 8.9 Hz, 1H), 7.05 (dd, J = 11.4, 2.8 Hz, 1H), 6.82 (ddd, J = 9.0, 2.8, 1.1 Hz, 1H), 4.63-4.41 (m, 3H), 4.20 (d, J = 3.7 Hz, 2H), 3.98-3.87 (m, 1H), 3.87-3.77 (m, 1H), 2.08-1.88 (m, 1H), 1.88-1.73 (m, 1H), 1.69-1.46 (m, 2H), 1.36 (s, 9H). |
| 29 | 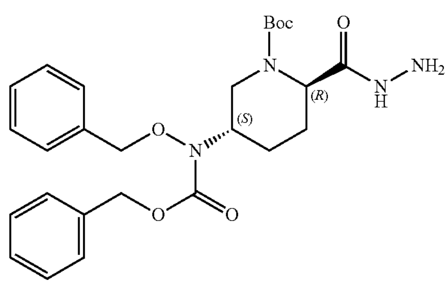 | tert-butyl (2R,5S)-5-[(benzyloxy)[(benzyloxy)carbonyl]amino]-2-(hydrazinecarbonyl)piperidine-1-carboxylate | (2R,5S)-5-[(benzyloxy)[(benzyloxy)carbonyl]amino]-1-[(tert-butoxy)carbonyl]piperidine-2-carboxylic acid (Intermediate 44) | M/Z: 499 [M + H]⁺, ESI⁺, RT = 1.00 (S2) | ¹H NMR (500 MHz, DMSO-d₆) δ 7.46-7.24 (m, 10H), 5.20 (s, 2H), 4.93-4.76 (m, 2H), 4.35-4.13 (m, 3H), 3.98-3.87 (m, 1H), 3.68-3.46 (m, 2H), 3.29-3.04 (m, 1H), 2.07-1.90 (m, 1H), 1.87-1.59 (m, 3H), 1.28 (s, 9H). |
| 30 | 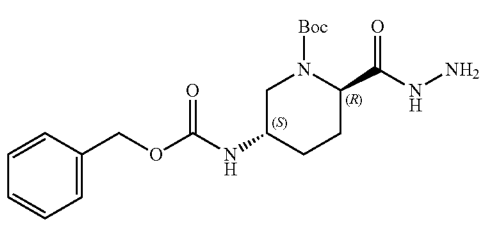 | tert-butyl (2R,5S)-5-{[(benzyloxy)carbonyl]amino}-2-(hydrazinecarbonyl)piperidine-1-carboxylate | (2R,5S)-5-{[(benzyloxy)carbonyl]amino}-1-[(tert-butoxy)carbonyl]piperidine-2-carboxylic acid (Intermediate 4) | M/Z: 293 [M − Boc + H]⁺, ESI⁺, RT = 0.79 (S2). | ¹H NMR (400 MHz, DMSO-d₆) δ 9.04 (s, 1H), 7.46-7.24 (m, 5H), 5.03 (s, 2H), 4.62-4.37 (m, 1H), 4.20 (s, 2H), 4.06-3.82 (m, 1H), 3.76-3.48 (m, 1H), 3.26-3.13 (m, 1H), 2.12-1.93 (m, 1H), 1.80-1.54 (m, 2H), 1.54-1.44 (m, 1H), 1.42-1.20 (m, 10H) |

Scheme for route 12

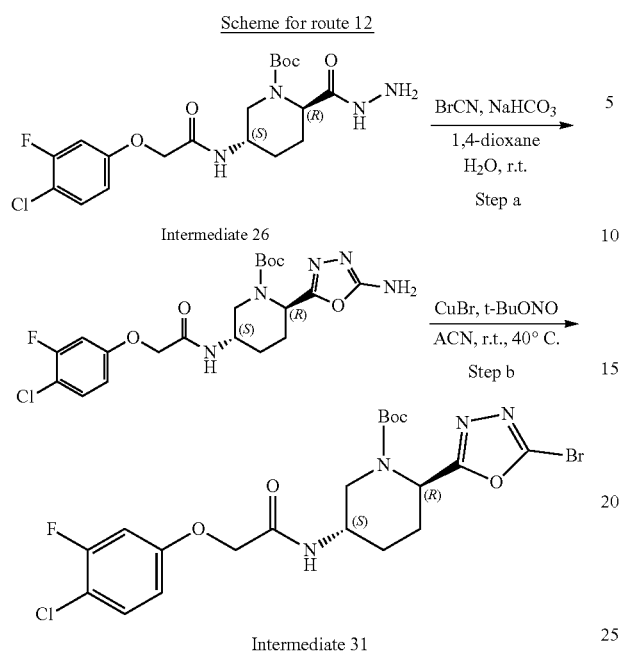

Intermediate 26

Intermediate 31

Step 12.a: tert-butyl (2R,5S)-2-(5-amino-1,3,4-oxa-diazol-2-yl)-5-[[2-(4-chloro-3-fluoro-phenoxy)acetyl]amino]piperidine-1-carboxylate

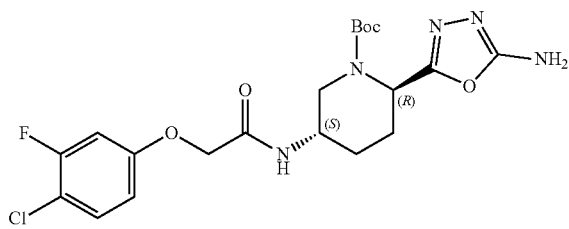

To a solution of tert-butyl (2R,5S)-5-[2-(4-chloro-3-fluorophenoxy)acetamido]-2-(hydrazinecarbonyl)piperidine-1-carboxylate (3.50 g, 7.87 mmol, Intermediate 26) and NaHCO₃ (991 mg, 11.8 mmol) in H₂O (10 mL) and 1,4-dioxane (40 mL) was added BrCN (833 mg, 7.87 mmol) and the mixture was stirred at r.t. for 12 h. The reaction mixture was diluted with H₂O (60 mL) and extracted with EtOAc (3×60 mL). The combined organic extracts were dried over MgSO₄ and concentrated in vacuo to afford the title compound (2.30 g, 4.65 mmol, 59% yield) as a white solid; ¹H NMR (400 MHz, chloroform-d) δ 7.33 (t, J=8.6 Hz, 1H), 6.88-6.64 (m, 3H), 5.48 (s, 1H), 4.95 (s, 2H), 4.53-4.40 (m, 2H), 4.22-4.01 (m, 2H), 3.15 (s, 1H), 2.23-1.83 (m, 4H), 1.46 (s, 9H); M/Z: 470, 472 [M+H]⁺, ESI⁺, RT=0.87 (S2).

Intermediate 31 (Step 12.b): tert-butyl (2R,5S)-2-(5-bromo-1,3,4-oxadiazol-2-yl)-5-[[2-(4-chloro-3-fluoro-phenoxy)acetyl]amino]piperidine-1-carboxylate To a solution of tert-butyl (2R,5S)-2-(5-amino-1,3,4-oxa-diazol-2-yl)-5-[[2-(4-chloro-3-fluoro-phenoxy)acetyl] amino]piperidine-1-carboxylate (2.30 g, 4.65 mmol) in anhydrous ACN (35 mL) was added CuBr (3.16 g, 14.0 mmol) and the mixture was stirred at r.t. for 5 min. Tert-butyl nitrite (1.9 mL, 14.0 mmol) was added and the mixture was stirred at r.t. for 16 h then at 40° C. for 12 h. The reaction mixture was concentrated in vacuo and the residue was diluted with Rochelle salt (150 mL) and extracted with EtOAc (3×150 mL). The combined organic extracts were dried over MgSO₄, concentrated in vacuo, and purified by chromatography on silica gel (12-100% EtOAc in heptane) to afford the title compound (1.10 g, 2.03 mmol, 4300 yield) as a pale yellow solid; ¹H NMR (500 MHz, chloroform-d) δ 7.33 (t, J=8.6 Hz, 1H), 6.87-6.71 (m, 2H), 6.67 (ddd, J=8.9, 2.8, 1.1 Hz, 1H), 5.77-5.37 (m, 1H), 4.57-4.41 (m, 2H), 4.27-3.98 (m, 2H), 3.35-2.95 (m, 1H), 2.29-2.12 (m, 1H), 2.07-1.79 (m, 3H), 1.46 (s, 9H); M/Z: 433, 435 [M-Boc+H]⁺, ESI⁺, RT=1.05 (S2).

The intermediates in Table 6 were synthesised according to general route 12 as exemplified by Intermediate 31 using the corresponding starting materials.

TABLE 6

| Intermediate | Structure | Name | Starting material | LCMS data | ¹H NMR Data |
|---|---|---|---|---|---|
| 32 | 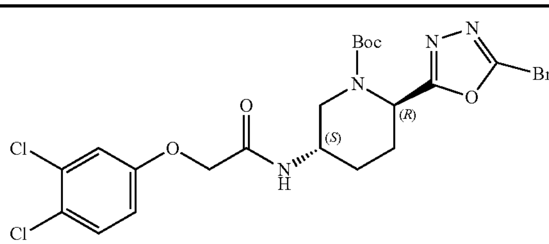 | tert-butyl (2R,5S)-2-(5-bromo-1,3,4-oxadiazol-2-yl)-5-[2-(3,4-dichlorophenoxy)acetamido]piperidine-1- | tert-butyl (2R,5S)-5-[2-(3,4-dichlorophenoxy)acetamido]-2-(hydrazinecarbonyl)piperidine-1-carboxylate | M/Z: 451, 453, 455 [M − Boc + H]⁺, ESI⁺, RT = 1.03 (S2) | ¹H NMR (400 MHz, DMSO-d₆) δ 8.10 (d, J = 7.0 Hz, 1H), 7.54 (d, J = 8.9 Hz, 1H), 7.24 (d, J = 2.9 Hz, 1H), 6.97 (dd, J = 9.0, 2.9 Hz, 1H), 5.58-5.46 (m, 1H), 4.65-4.55 (m, 2H), 3.91 (s, 2H), 3.00 (d, J = 12.3 Hz, 1H), 2.29-2.21 (m, 1H), 2.07-2.01 (m, 1H), 1.83-1.74 (m, 1H), 1.68- |

TABLE 6-continued

| Intermediate | Structure | Name | Starting material | LCMS data | ¹H NMR Data |
|---|---|---|---|---|---|
| | | carboxylate | (Intermediate 27) | | 1.61 (m, 1H), 1.39 (s, 9H). |
| 33 | 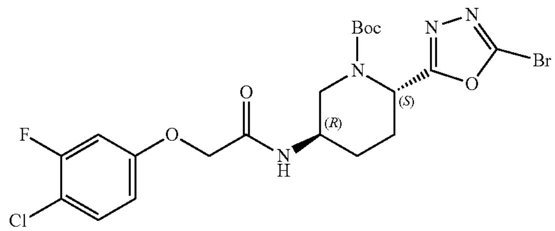 | tert-butyl (2S,5R)-2-(5-bromo-1,3,4-oxadiazol-2-yl)-5-[2-(4-chloro-3-fluorophenoxy)acetamido]piperidine-1-carboxylate | tert-butyl (2S,5S)-5-[2-(4-chloro-3-fluorophenoxy)acetamido]-2-(hydrazinecarbonyl)piperidine-1-carboxylate (Intermediate 28) | M/Z: 435, 437 [M − Boc + H]⁺, ESI⁺, RT = 1.17 (S2) | ¹H NMR (400 MHz, DMSO-d₆) δ 8.11 (d, J = 7.0 Hz, 1H), 7.49 (t, J = 8.9 Hz, 1H), 7.05 (dd, J = 11.4, 2.8 Hz, 1H), 6.89-6.77 (m, 1H), 5.51 (s, 1H), 4.65-4.48 (m, 2H), 3.96-3.81 (m, 2H), 3.06-2.93 (m, 1H), 2.31-2.16 (m, 1H), 2.10-2.00 (m, 1H), 1.85-1.71 (m, 1H), 1.70-1.59 (m, 1H), 1.39 (s, 9H). |

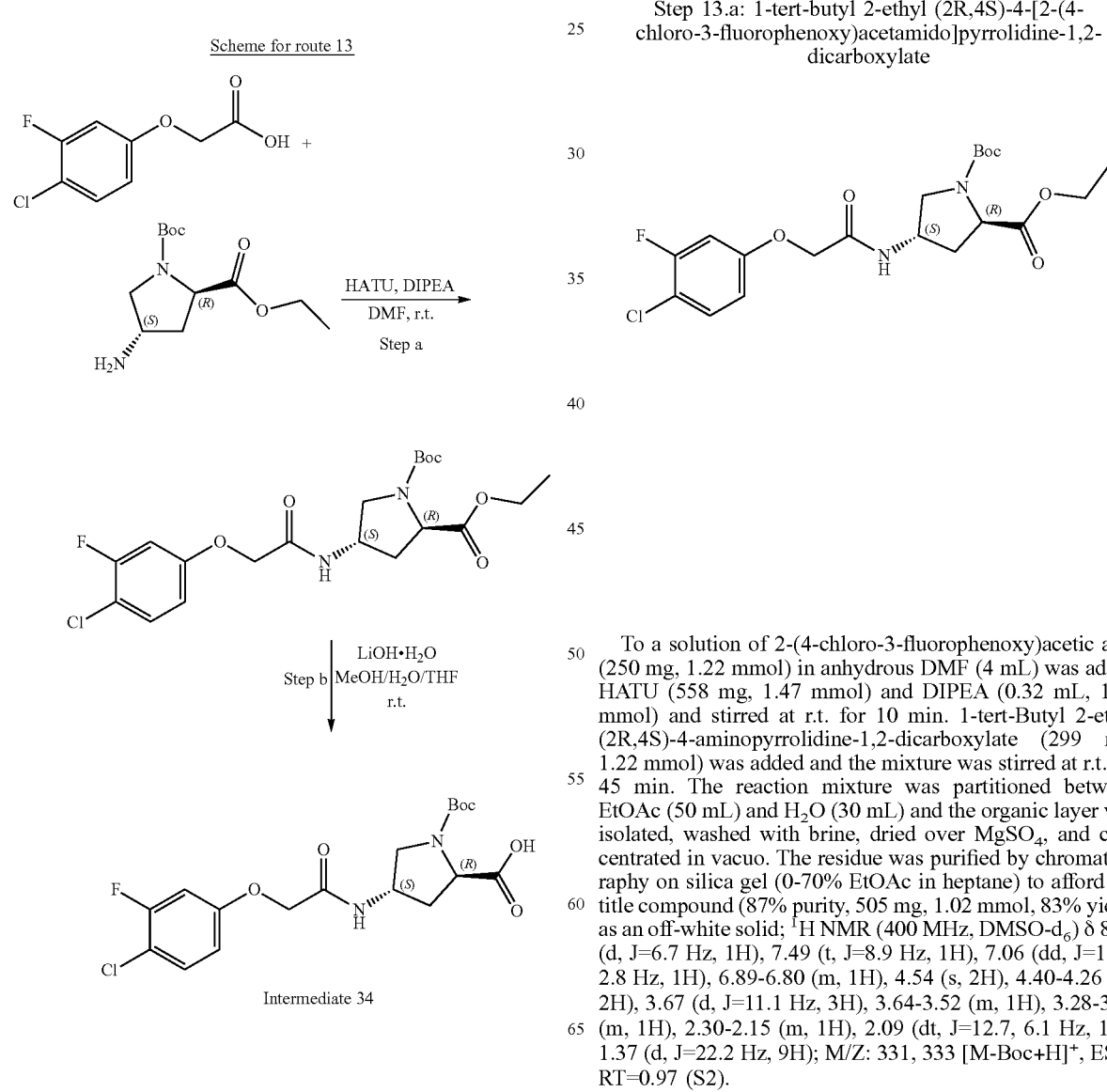

Step 13.a: 1-tert-butyl 2-ethyl (2R,4S)-4-[2-(4-chloro-3-fluorophenoxy)acetamido]pyrrolidine-1,2-dicarboxylate To a solution of 2-(4-chloro-3-fluorophenoxy)acetic acid (250 mg, 1.22 mmol) in anhydrous DMF (4 mL) was added HATU (558 mg, 1.47 mmol) and DIPEA (0.32 mL, 1.83 mmol) and stirred at r.t. for 10 min. 1-tert-Butyl 2-ethyl (2R,4S)-4-aminopyrrolidine-1,2-dicarboxylate (299 mg, 1.22 mmol) was added and the mixture was stirred at r.t. for 45 min. The reaction mixture was partitioned between EtOAc (50 mL) and H₂O (30 mL) and the organic layer was isolated, washed with brine, dried over MgSO₄, and concentrated in vacuo. The residue was purified by chromatography on silica gel (0-70% EtOAc in heptane) to afford the title compound (87% purity, 505 mg, 1.02 mmol, 83% yield) as an off-white solid; ¹H NMR (400 MHz, DMSO-d₆) δ 8.38 (d, J=6.7 Hz, 1H), 7.49 (t, J=8.9 Hz, 1H), 7.06 (dd, J=11.4, 2.8 Hz, 1H), 6.89-6.80 (m, 1H), 4.54 (s, 2H), 4.40-4.26 (m, 2H), 3.67 (d, J=11.1 Hz, 3H), 3.64-3.52 (m, 1H), 3.28-3.16 (m, 1H), 2.30-2.15 (m, 1H), 2.09 (dt, J=12.7, 6.1 Hz, 1H), 1.37 (d, J=22.2 Hz, 9H); M/Z: 331, 333 [M-Boc+H]⁺, ESI⁺, RT=0.97 (S2).

Intermediate 34 (Step 13.b): (2R,4S)-1-[(tert-butoxy)carbonyl]-4-[2-(4-chloro-3-fluorophenoxy)acetamido]pyrrolidine-2-carboxylic acid

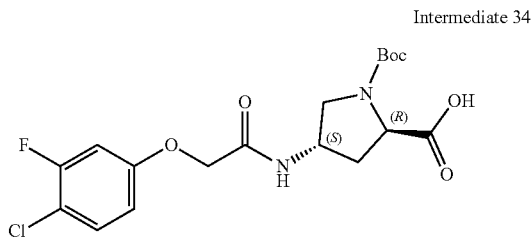

Intermediate 34

To a solution of 1-tert-butyl 2-ethyl (2R,4S)-4-[2-(4-chloro-3-fluorophenoxy)acetamido]pyrrolidine-1,2-dicarboxylate (87% purity, 505 mg, 1.02 mmol) in MeOH (2 mL):THF (2 mL):H₂O (2 mL) was added LiOH·H₂O (53 mg, 1.22 mmol) and the mixture was stirred at r.t. for 17 h. The reaction mixture was partitioned between EtOAc (30 mL) and 1 M aq HCl solution (10 mL). The organic layer was isolated, washed with brine, dried over MgSO₄, and concentrated in vacuo to afford the title compound (80% purity, 401 mg, 0.770 mmol, 76% yield) as a colourless oil; $^1$H NMR (400 MHz, DMSO-d$_6$) δ 8.37 (d, J=6.9 Hz, 1H), 7.54-7.45 (m, 1H), 7.06 (dd, J=11.4, 2.8 Hz, 1H), 6.84 (dt, J=9.0, 1.4 Hz, 1H), 4.54 (s, 2H), 4.35 (dq, J=12.1, 6.5 Hz, 1H), 4.26-4.15 (m, 1H), 3.64-3.52 (m, 1H), 3.20 (dq, J=15.0, 5.9, 5.5 Hz, 1H), 2.28-2.12 (m, 1H), 2.12-2.01 (m, 1H), 1.37 (d, J=15.9 Hz, 9H); M/Z: 317, 319 [M-Boc+H]⁺, ESI⁺, RT=0.86 (S2).

Scheme for route 14

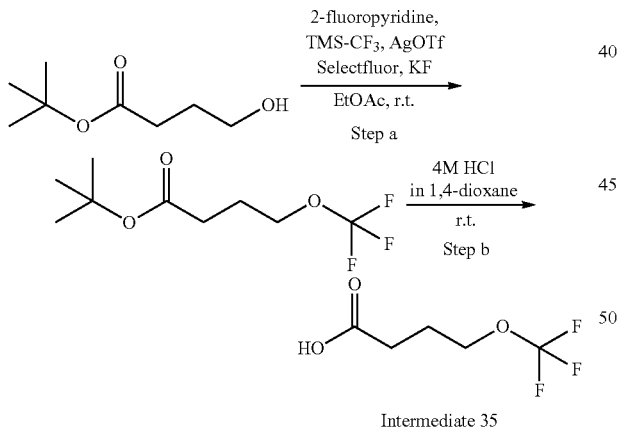

Step 14.a: tert-butyl 4-(trifluoromethoxy)butanoate

2-Fluoropyridine (1.6 mL, 18.2 mmol) and TMS-CF₃ (2.7 mL, 18.2 mmol) were successively added dropwise to a solution of tert-butyl 4-hydroxybutanoate (1.0 g, 6.05 mmol), AgOTf (4.69 g, 18.2 mmol), Selectfluor (3.22 g, 9.08 mmol) and KF (1.41 g, 24.2 mmol) in EtOAc (50 mL) under N₂ in a foil-covered flask and the mixture was stirred at r.t. for 24 h. The reaction mixture was filtered through Celite, washing with EtOAc (30 mL), and concentrated in vacuo. The residue was purified by chromatography on silica gel (5-30% EtOAc in heptane) to afford the title compound (90% purity, 330 mg, 1.30 mmol, 21% yield) as a colourless oil; $^1$H NMR (400 MHz, chloroform-d) δ 4.02 (t, J=6.2 Hz, 2H), 2.37 (t, J=7.2 Hz, 2H), 1.98 (p, J=6.7 Hz, 2H), 1.46 (s, 9H); $^{19}$F NMR (376 MHz, chloroform-d) δ -60.81 (3F, s).

Intermediate 35 (Step 14.b): 4-(trifluoromethoxy)butanoic acid

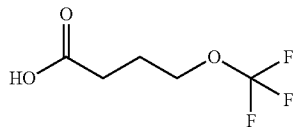

Intermediate 35

A solution of tert-butyl 4-(trifluoromethoxy)butanoate (330 mg, 1.45 mmol) in 4 M HCl in 1,4-dioxane (5 mL) was stirred at r.t. for 2 h. The reaction mixture was concentrated in vacuo to afford the title compound (83% purity, 73 mg, 0.352 mmol, 24% yield) as a yellow oil; $^1$H NMR (400 MHz, DMSO-d$_6$) δ 12.20 (s, 1H), 4.32 (td, J=6.4, 4.2 Hz, 1H), 4.09 (t, J=6.5 Hz, 2H), 2.32 (td, J=7.2, 2.8 Hz, 3H), 1.95-1.80 (m, 3H), 1.40 (s, 1H); $^{19}$F NMR (376 MHz, DMSO-d$_6$) δ -58.82 (3F, s).

Scheme for route 15

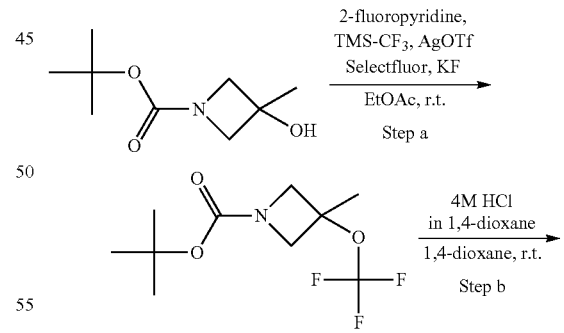

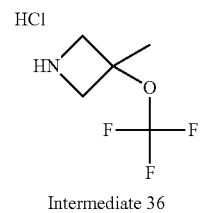

Intermediate 36

Step 15.a: tert-butyl 3-methyl-3-(trifluoromethoxy)azetidine-1-carboxylate

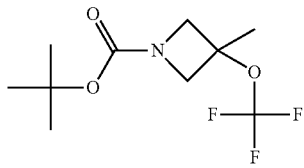 [SMILES: CC(C)(C)OC(=O)N1CC(C)(OC(F)(F)F)C1]

To a solution of tert-butyl 3-hydroxy-3-methylazetidine-1-carboxylate (1.00 g, 5.34 mmol) in EtOAc (30 mL) at r.t. under $N_2$ in a foil-covered flask was added AgOTf (4.13 g, 16.0 mmol), KF (1.24 g, 21.4 mmol) and Selectfluor (2.84 g, 8.01 mmol) and stirred at r.t. for 5 min. 2-Fluoropyridine (1.4 mL, 16.0 mmol) and TMS-CF$_3$ (2.4 mL, 16.0 mmol) were then added and the mixture was stirred at r.t. for 3 h. The reaction mixture was filtered through Celite, washing with EtOAc (100 mL), and the filtrate was concentrated in vacuo. The residue was purified by chromatography on silica gel (0-50% EtOAc in heptane) to afford the title compound (163 mg, 0.639 mmol, 12% yield) as a colourless oil; $^1$H NMR (400 MHz, DMSO-d$_6$) δ 4.02 (d, J=9.5 Hz, 2H), 3.91 (d, J=9.6 Hz, 2H), 1.67 (s, 3H), 1.39 (s, 9H).

Intermediate 36 (Step 15.b):
3-methyl-3-(trifluoromethoxy)azetidine hydrochloride Intermediate 36

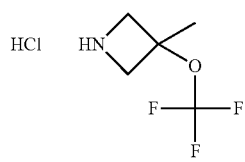

To a solution of tert-butyl 3-methyl-3-(trifluoromethoxy)azetidine-1-carboxylate (160 mg, 0.627 mmol) in anhydrous 1,4-dioxane (3 mL) was added 4 M HCl in 1,4-dioxane (1.0 mL, 4.00 mmol) and the mixture was stirred at r.t. for 20 h. The reaction mixture was concentrated in vacuo to afford the title compound (116 mg, 0.605 mmol, 97% yield) as a white powder; $^1$H NMR (400 MHz, DMSO-d$_6$) δ 9.18 (s, 2H), 4.22 (d, J=12.2 Hz, 2H), 4.07 (d, J=12.5 Hz, 2H), 1.74 (s, 3H); M/Z: 156 [M+H]$^+$, ESI$^+$, RT=0.37 (S2).

Scheme for route 16

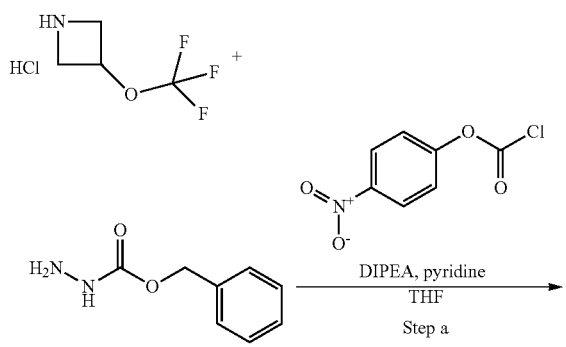

Step 16.a: ({[(benzyloxy)carbonyl]amino}amino)[3-(trifluoromethoxy)azetidin-1-yl]methanone To a solution of benzyl hydrazinecarboxylate (406 μL, 2.52 mmol) and pyridine (407 μL, 5.03 mmol) in anhydrous THF (5 mL) was added a solution of 4-nitrophenyl carbonochloridate (558 mg, 2.77 mmol) in anhydrous THF (3 mL) and the mixture was stirred under $N_2$ at r.t. for 1 h. The mixture was then added slowly to a solution of 3-(trifluoromethoxy)azetidine hydrochloride (469 mg, 2.64 mmol) and DIPEA (1.3 mL, 7.55 mmol) in anhydrous THF (5 mL) and stirred at r.t. under $N_2$ for 30 min. The reaction mixture was quenched with satd aq NaHCO$_3$ solution (10 mL) and extracted with EtOAc (3×10 mL). The combined organic extracts were washed with H$_2$O (30 mL) and brine (30 mL), dried over MgSO$_4$, and concentrated in vacuo. The residue was dissolved in EtOAc (10 mL) and washed with satd aq K$_2$CO$_3$ solution (3×10 mL). The organic layer was dried over MgSO$_4$ and concentrated in vacuo to afford the title compound (92% purity, 770 mg, 2.13 mmol, 85% yield) as an off-white powder; $^1$H NMR (500 MHz, DMSO-d$_6$) δ 9.00 (s, 1H), 8.51 (s, 1H), 7.41-7.26 (m, 5H), 5.21-5.11 (m, 1H), 5.07 (s, 2H), 4.27-4.17 (m, 2H), 3.92-3.83 (m, 2H); M/Z: 334 [M+H]$^+$, ESI$^+$, RT=0.74 (S2).

Intermediate 37 (Step 16.b):
3-(trifluoromethoxy)azetidine-1-carbohydrazide

Intermediate 37

To a solution of ({[(benzyloxy)carbonyl]amino}amino)[3-(trifluoromethoxy)azetidin-1-yl]methanone (92% purity, 767 mg, 2.12 mmol) in anhydrous EtOH (21 mL) under N₂ was added 10% Pd/C (226 mg, 0.212 mmol) and the mixture was stirred under H₂ at r.t. for 4 h. The reaction mixture was filtered through a pad of Celite, washing with warm EtOH (3×15 mL) and concentrated in vacuo to afford the title compound (88% purity, 269 mg, 1.19 mmol, 56% yield) as a brown solid; ¹H NMR (500 MHz, DMSO-d₆) δ 7.65 (s, 1H), 5.18-5.07 (m, 1H), 4.23-4.11 (m, 2H), 3.88 (s, 2H), 3.86-3.76 (m, 2H).

diluted with IPA (30 mL) and H₂O (50 mL), and the organic layer was isolated and washed successively with satd aq NaHCO₃ solution (50 mL) and brine (50 mL). The organic layer was dried over MgSO₄ and concentrated in vacuo to afford the title compound (90% purity, 4.09 g, 21.4 mmol, 54% yield) as a pale yellow oil; ¹H NMR (500 MHz, chloroform-d) δ 2.28-2.57 (m, 2H), 3.69 (s, 2H), 4.19-4.36 (m, 2H), 5.99 (s, 1H).

Scheme for route 17

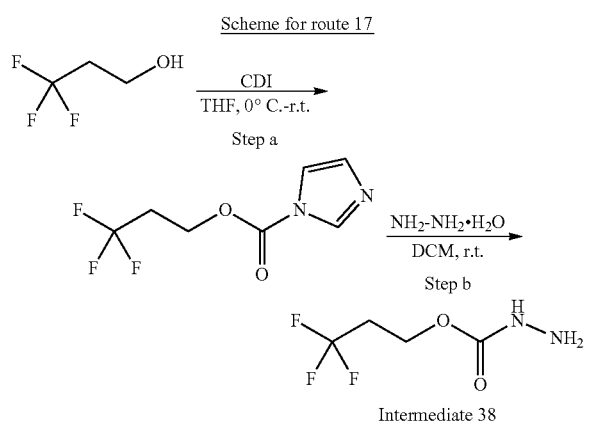

Scheme for route 18

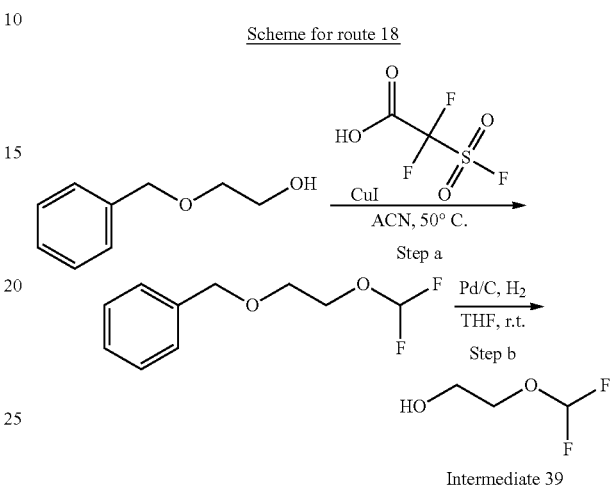

Step 17.a: 3,3,3-trifluoropropyl imidazole-1-carboxylate

Step 18.a: {[2-(difluoromethoxy)ethoxy]methyl}benzene 3,3,3-trifluoropropan-1-ol (1.00 g, 8.77 mmol) in DCM (20 mL) was added to a solution of CDI (2.13 g, 13.1 mmol) in THF (50 mL) at 0° C. under N₂ and the mixture was stirred at r.t. for 2 h. The reaction mixture was concentrated in vacuo and the residue was purified by chromatography on silica gel (12-100% EtOAc in heptane) to afford the title compound (92% purity, 827 mg, 3.89 mmol, 44% yield) as a colourless oil; ¹H NMR (500 MHz, DMSO-d₆) δ 8.25 (s, 1H), 7.58 (s, 1H), 7.12-7.08 (m, 1H), 4.64-4.58 (m, 2H), 2.87 (tp, J=11.3, 5.8 Hz, 2H).

Intermediate 38 (Step 17.b): (3,3,3-trifluoropropoxy)carbohydrazide

Intermdiate 38

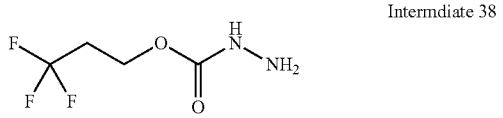 [SMILES: NNC(=O)OCCC(F)(F)F]

A solution of 3,3,3-trifluoropropyl imidazole-1-carboxylate (92% purity, 8.95 g, 39.6 mmol) in DCM (140 mL) was treated with NH₂NH₂—H₂O (7.8 mL, 0.158 mol) and the mixture was stirred at r.t. for 1 h. The reaction mixture was To a solution of 2-(benzyloxy)ethanol (1.50 g, 9.86 mmol) in anhydrous ACN (20 mL) was added CuI (469 mg, 2.46 mmol) and the mixture was stirred at 50° C. for 5 min. A solution of 2,2-difluoro-2-(fluorosulfonyl)acetic acid (2.63 g, 14.8 mmol) in anhydrous ACN (10 mL) was added dropwise over 25 min and the resultant mixture was stirred at 50° C. for 1 h. The reaction mixture was concentrated in vacuo and the residue was dissolved in EtOAc. The resultant precipitate was filtered under vacuum, and the filtrate was isolated and concentrated in vacuo. The residue was purified by chromatography on silica gel (10-100% EtOAc in heptane) to afford the title compound (90% purity, 620 mg, 2.76 mmol, 28% yield) as a colourless oil; ¹H NMR (400 MHz, chloroform-d) δ 7.40-7.27 (m, 5H), 6.28 (t, J=74.8 Hz, 1H), 4.58 (s, 2H), 4.04-3.97 (m, 2H), 3.71-3.62 (m, 2H); 19F NMR (376 MHz, chloroform-d) δ −84.27.

Intermediate 39 (Step 18.b): 2-(difluoromethoxy)ethan-1-ol

Intermediate 39

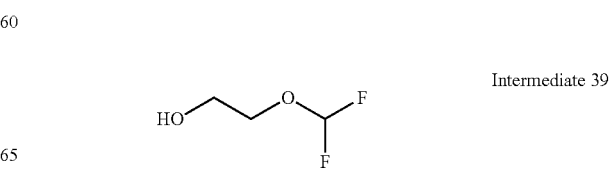

A suspension of {[2-(difluoromethoxy)ethoxy]methyl}benzene (90% purity, 620 mg, 2.76 mmol) and 10% Pd/C (587 mg, 0.552 mmol) in THF (7.5 mL) was stirred under H$_2$ for 18 h. The reaction mixture was filtered through Celite and washed with THF. The filtrate was recharged with 10% Pd/C (1.47 g, 1.38 mmol) and the mixture was stirred under H$_2$ for 18 h. The reaction mixture was filtered through Celite, washing with THF, to afford a crude solution estimated to be 2.23% of the title compound in THF/toluene (2.23:95.9:1.83, ~10 mL); $^1$H NMR (400 MHz, chloroform-d) δ 6.20 (t, J=74.9 Hz, 1H), 3.89-3.81 (m, 2H), 3.76-3.56 (m, 2H).

Scheme for route 19

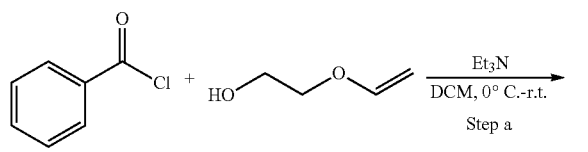

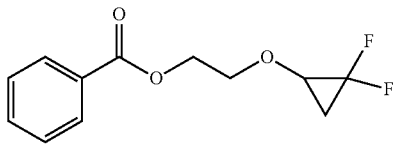 [SMILES: O=C(OCCOC1CC1(F)F)c1ccccc1]

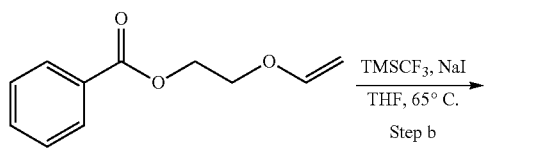

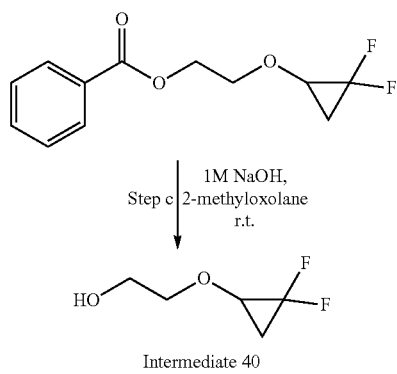

Intermediate 40

Step 19.a: 2-(ethenyloxy)ethyl benzoate

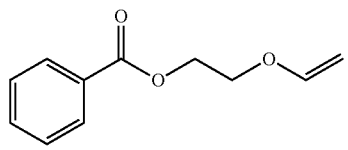

To a solution of 2-(ethenyloxy)ethan-1-ol (1.00 g, 11.3 mmol) in DCM (40 mL) at 0° C. was added Et$_3$N (4.0 mL, 28.4 mmol) followed dropwise by benzoyl chloride (2.0 mL, 17.0 mmol) and the mixture was stirred at r.t. for 6 h. The reaction mixture was cooled to 0° C. and quenched with 1 M aq HCl solution (10 mL). The aqueous solution was extracted with DCM (3×20 mL) and the combined organic extracts were washed sequentially with satd aq NaHCO$_3$ solution (15 mL) and brine (15 mL), dried over Na$_2$SO$_4$, and concentrated in vacuo. The residue was purified by chromatography on silica gel (0-80% EtOAc in heptane) to afford the title compound (760 mg, 3.95 mmol, 35% yield) as a clear oil; $^1$H NMR (400 MHz, DMSO-d$_6$) δ 8.00-7.93 (m, 2H), 7.70-7.61 (m, 1H), 7.58-7.49 (m, 2H), 6.55 (dd, J=14.3, 6.8 Hz, 1H), 4.51-4.45 (m, 2H), 4.26 (dd, J=14.3, 1.9 Hz, 1H), 4.05-3.99 (m, 3H).

Step 19.b: 2-(2,2-difluorocyclopropoxy)ethyl benzoate

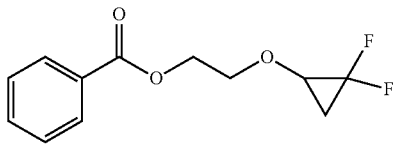 [SMILES: O=C(OCCOC1CC1(F)F)c1ccccc1]

To a solution of 2-(ethenyloxy)ethyl benzoate (50 mg, 0.260 mmol) in THF (2 mL) was added TMSCF$_3$ (77 μL, 0.520 mmol) and NaI (86 mg, 0.572 mmol) and the mixture was stirred under N$_2$ at 65° C. for 4 h. The reaction mixture was cooled to r.t., diluted with H$_2$O (5 mL) and extracted with EtOAc (3×5 mL). The combined organic extracts were washed with brine (5 mL), dried over Na$_2$SO$_4$ and concentrated in vacuo. The residue was purified by chromatography on silica gel (0-80% EtOAc in heptane) to afford the title compound (62 mg, 0.246 mmol, 94% yield) as a clear oil; $^1$H NMR (500 MHz, DMSO-d$_6$) δ 8.02-7.91 (m, 2H), 7.71-7.62 (m, 1H), 7.59-7.48 (m, 2H), 4.49-4.37 (m, 2H), 4.02-3.93 (m, 1H), 3.95-3.84 (m, 2H), 1.76-1.65 (m, 1H), 1.60-1.50 (m, 1H); M/Z: 243 [M+H]$^+$, ESI$^+$, RT=1.22 (S1).

Intermediate 40 (Step 19.c): 2-(2,2-difluorocyclopropoxy)ethan-1-ol

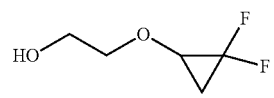

Intermediate 40

To a solution of 2-(2,2-difluorocyclopropoxy)ethyl benzoate (60 mg, 0.248 mmol) in 2-methyloxolane (1 mL) was added 1 M aq NaOH solution (0.99 mL, 0.991 mmol) and the mixture was stirred at r.t. for 24 h. The reaction mixture was diluted with H$_2$O (3 mL) and extracted with Et$_2$O (3×3 mL). The combined organic extracts were dried over MgSO$_4$, and concentrated in vacuo at r.t. to afford the title compound (17 mg, 0.123 mmol, 50% yield) as a clear oil; $^1$H NMR (500 MHz, DMSO-d$_6$) δ 4.72 (t, J=5.3 Hz, 1H), 3.91-3.84 (m, 1H), 3.59-3.49 (m, 4H), 1.71-1.59 (m, 1H), 1.54-1.43 (m, 1H).

Scheme for route 20

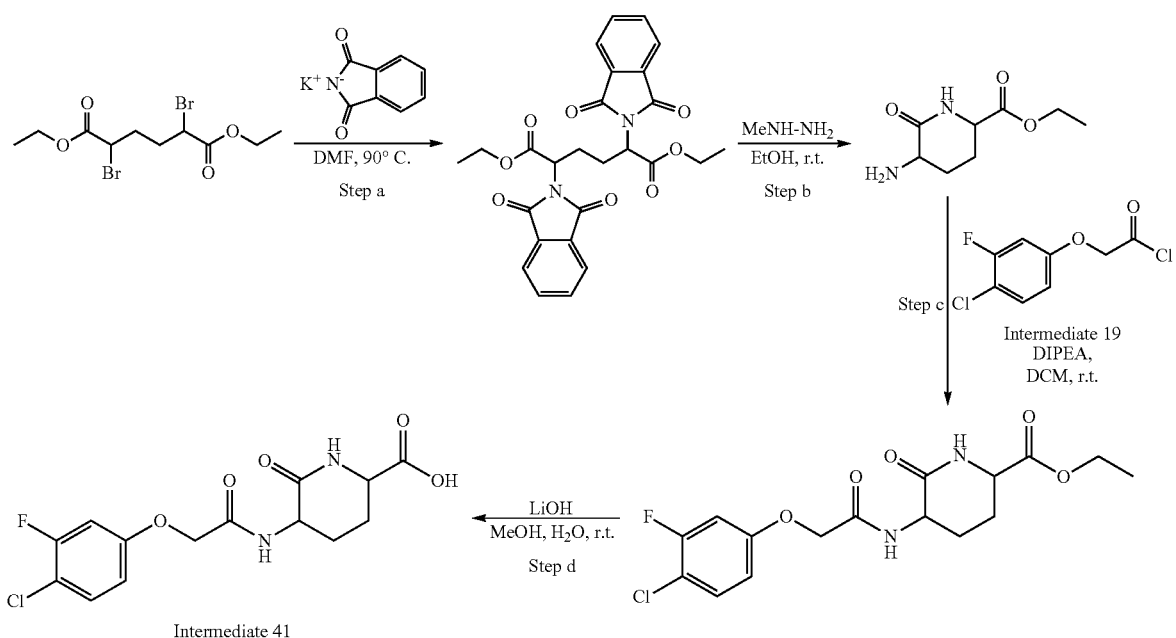

Step 20.a: 1,6-diethyl 2,5-bis(1,3-dioxo-2,3-dihydro-1H-isoindol-2-yl)hexanedioate

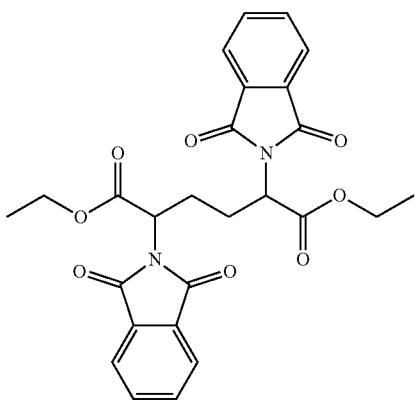 [SMILES: CCOC(=O)C(CCC(C(=O)OCC)N1C(=O)c2ccccc2C1=O)N1C(=O)c2ccccc2C1=O]

A mixture of (1,3-dioxoisoindolin-2-yl)potassium (4.55 g, 24.4 mmol) and diethyl 2,5-dibromohexanedioate (4.0 g, 11.1 mmol) in DMF (40 mL) was stirred at 90° C. for 4 h and then allowed to cool to r.t. The reaction mixture was concentrated in vacuo, and the residue was diluted with H$_2$O (150 mL) and extracted with EtOAc (2×100 mL). The combined organic extracts were dried over Na$_2$SO$_4$, concentrated in vacuo, and purified by prep. HPLC (Method 5) to afford the title compound (91% purity, 2.51 g, 4.64 mmol, 42% yield) as a yellow oil; $^1$H NMR (500 MHz, chloroform-d) δ 7.92-7.80 (m, 4H), 7.79-7.70 (m, 4H), 4.95-4.89 (m, 1H), 4.82-4.74 (m, 1H), 4.23-4.07 (m, 4H), 2.38-2.21 (m, 4H), 1.20-1.13 (m, 6H); M/Z: 493 [M+H]$^+$, ESI$^+$, RT=1.02 (S1).

Step 20.b: ethyl 5-amino-6-oxopiperidine-2-carboxylate

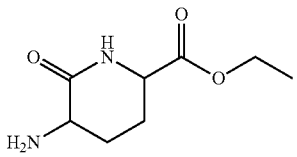

Methylhydrazine (0.73 mL, 13.72 mmol) was added to a suspension of 1,6-diethyl 2,5-bis(1,3-dioxo-2,3-dihydro-1H-isoindol-2-yl)hexanedioate (2.40 g, 4.64 mmol) in EtOH (25 mL) and the mixture was stirred at reflux for 6 h. The reaction mixture was concentrated by half and cooled to 0° C. The solid was filtered under vacuum and the filtrate concentrated in vacuo. The residue was dissolved in EtOH (5 mL) and purified using an SCX-2 cartridge, first flushing with EtOH (2×20 mL) and second eluting with 7 M NH$_3$ in MeOH to afford the title compound (835 mg, 4.48 mmol, 97% yield) as a tan oil; M/Z: 187 [M+H]$^+$, ESI$^+$, RT=0.16 (S1).

Step 20.c: ethyl 5-[2-(4-chloro-3-fluorophenoxy)acetamido]-6-oxopiperidine-2-carboxylate

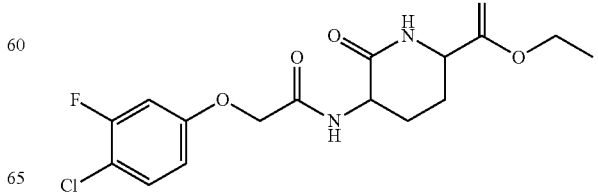

To a stirred solution of ethyl 5-amino-6-oxo-piperidine-2-carboxylate (700 mg, 3.76 mmol) and DIPEA (1.3 mL, 7.52 mmol) in DCM (8 mL) at 0° C. was added a solution of 2-(4-chloro-3-fluoro-phenoxy)acetyl chloride (838 mg, 3.76 mmol) in DCM (2 mL) and stirred at r.t. for 2 h. The mixture was diluted with DCM (20 mL), and washed with 1 M aq HCl solution (20 mL). The organic extracts were dried over $Na_2SO_4$, concentrated in vacuo, and purified by prep. HPLC (Method 5) to afford the title compound (72% purity, 433 mg, 0.836 mmol, 22% yield) as a white solid; $^1$H NMR (400 MHz, chloroform-d) δ 7.41-7.28 (m, 2H), 6.80-6.74 (m, 1H), 6.73-6.66 (m, 1H), 6.33-6.25 (m, 1H), 4.51-4.46 (m, 2H), 4.35-4.22 (m, 2H), 4.20-4.11 (m, 1H), 2.71-2.49 (m, 1H), 2.47-2.13 (m, 2H), 2.01-1.88 (m, 1H), 1.80-1.67 (m, 1H), 1.64-1.50 (m, 1H), 1.35-1.26 (m, 2H), (contains 25% methyl ester impurity); M/Z: 373, 375 [M+Na]$^+$, ESI$^+$, RT=0.80 (S2).

Intermediate 41 (Step 20.d): 5-[2-(4-chloro-3-fluorophenoxy)acetamido]-6-oxopiperidine-2-carboxylic acid

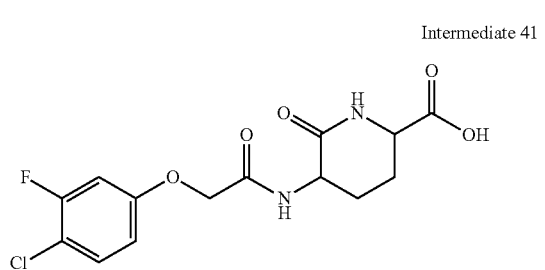 [SMILES: O=C(COc1ccc(Cl)c(F)c1)NC1CCC(C(=O)O)NC1=O]

Intermediate 41

To a solution of ethyl 5-[2-(4-chloro-3-fluorophenoxy)acetamido]-6-oxopiperidine-2-carboxylate (72% purity, 330 mg, 0.637 mmol) in $H_2O$ (3 mL) and MeOH (5 mL) was added dropwise 2 M aq LiOH solution (0.38 mL, 0.765 mmol) and the mixture was stirred at r.t. for 5 h. The reaction mixture was acidified to pH 5 using 1 M aq HCl solution (0.6 mL), and then concentrated in vacuo to afford the title compound (55% purity, 397 mg, 0.633 mmol, 99% yield) as an off-white solid; M/Z: 345, 347, [M+H]$^+$, ESI$^+$, RT=0.66, 0.68 (S2).

Scheme for route 21

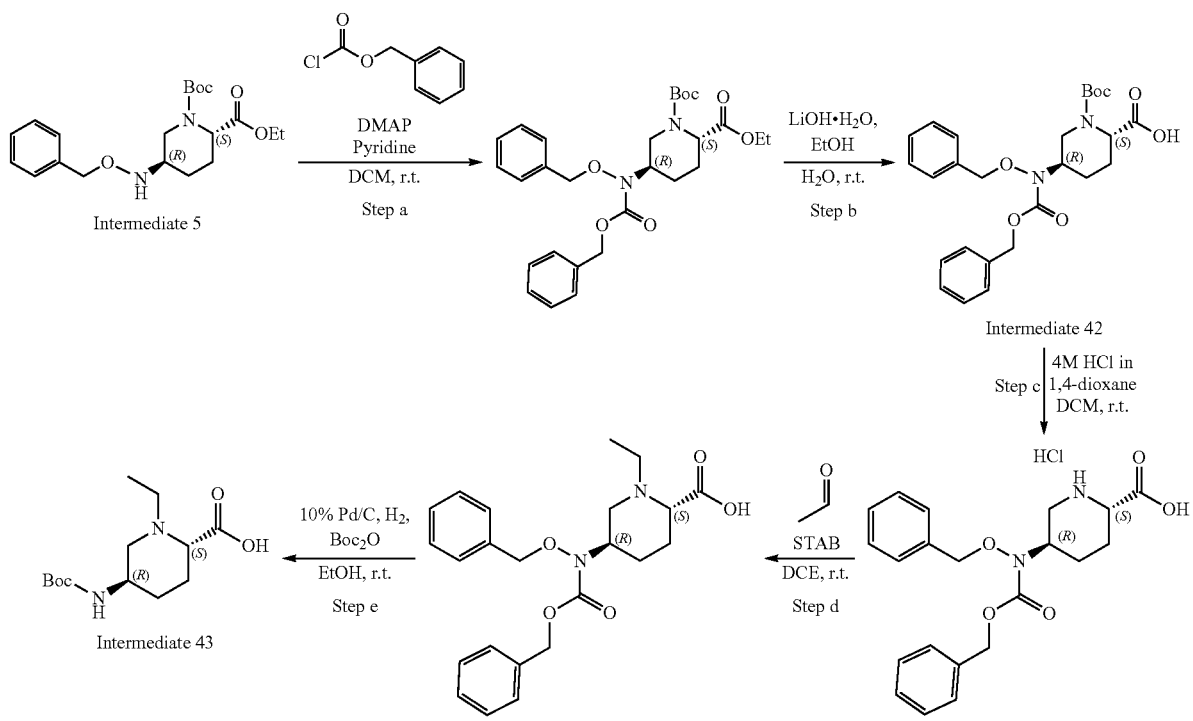

Step 21.a: 1-tert-butyl 2-ethyl (2S,5R)-5-[(benzyloxy)[(benzyloxy)carbonyl]amino]piperidine-1,2-dicarboxylate

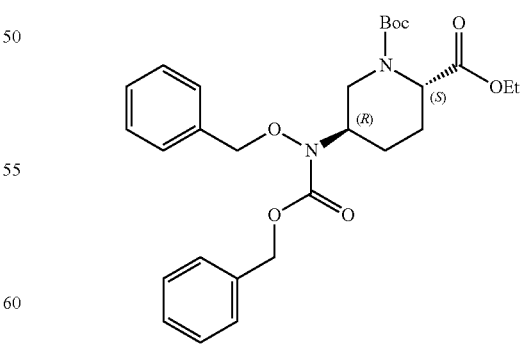

To a mixture of 1-tert-butyl 2-ethyl (2S,5R)-5-[(benzyloxy)amino]piperidine-1,2-dicarboxylate (2.30 g, 6.08 mmol, Intermediate 5), DMAP (74 mg, 0.608 mmol) and pyridine (0.98 mL, 12.2 mmol) in DCM (23 mL) at 0° C.

was added benzyl carbonochloridate (1.3 mL, 9.12 mmol) and the mixture was stirred at r.t. for 4 h. The reaction mixture was poured onto brine and extracted with DCM. The combined organic extracts were dried over $Na_2SO_4$, and concentrated in vacuo. The residue was purified by chromatography on silica gel (0-50% EtOAc in heptane) to afford the title compound (91% purity, 2.97 g, 5.27 mmol, 87% yield) as a colorless oil; $^1$H NMR (400 MHz, chloroform-d) δ 7.45-7.27 (m, 10H), 5.28-5.17 (m, 2H), 4.92-4.84 (m, 2H), 4.56 (s, 1H), 4.28 (s, 1H), 4.19 (q, J=7.1 Hz, 2H), 3.51 (dd, J=14.2, 5.0 Hz, 1H), 2.27-2.18 (m, 1H), 1.94-1.85 (m, 2H), 1.77-1.68 (m, 1H), 1.40 (s, 9H), 1.26 (td, J=7.1, 3.0 Hz, 3H); M/Z: 535 [M+Na]$^+$, ESI$^+$, RT=1.44 (S1).

Intermediate 42 (Step 21.b): (2S,5R)-5-[(benzyloxy)[(benzyloxy)carbonyl]amino]-1-[(tert-butoxy)carbonyl]piperidine-2-carboxylic acid Intermediate 42

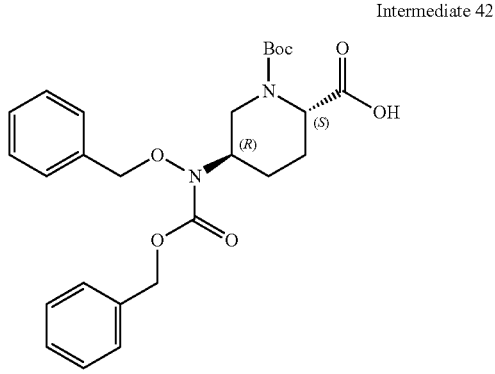

To a solution of 1-tert-butyl 2-ethyl (2S,5R)-5-[(benzyloxy)[(benzyloxy)carbonyl]amino]piperidine-1,2-dicarboxylate (91% purity, 2.97 g, 5.27 mmol) in THF (10 mL) and EtOH (10 mL) was added a solution of LiOH·H$_2$O (249 mg, 5.80 mmol) in H$_2$O (10 mL) and stirred at r.t. for 16 h. The reaction mixture was acidified to ~pH 4 using 1 M aq HCl solution and extracted with EtOAc (2×100 mL). The combined organic extracts were dried over Na$_2$SO$_4$, concentrated in vacuo, and purified by chromatography on silica gel (25-100% EtOAc in heptane) to afford the title compound (77% purity, 2.01 g, 3.19 mmol, 61% yield) as a clear oil; $^1$H NMR (400 MHz, DMSO-d$_6$) δ 7.45-7.17 (m, 10H), 5.22-5.17 (m, 2H), 4.88-4.77 (m, 2H), 4.66-4.54 (m, 1H), 4.52-4.47 (m, 1H), 4.43-4.32 (m, 1H), 4.26-4.12 (m, 1H), 3.97-3.88 (m, 1H), 2.16-2.02 (m, 1H), 1.83-1.66 (m, 3H), 1.30 (s, 9H); M/Z: 507 [M+H]$^+$, ESI$^+$, RT=1.28 (S1).

Step 21.c: (2S,5R)-5-[(benzyloxy)[(benzyloxy)carbonyl]amino]piperidine-2-carboxylic acid hydrochloride

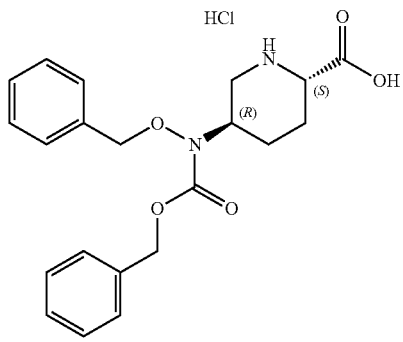

To a stirred solution of (2S,5R)-5-[(benzyloxy)[(benzyloxy)carbonyl]amino]-1-[(tert-butoxy)carbonyl]piperidine-2-carboxylic acid (77% purity, 200 mg, 0.318 mmol, Intermediate 42) in DCM (2 mL) at 0° C. was added 4 M HCl in 1,4-dioxane (0.50 mL, 2.0 mmol) and the mixture was stirred at r.t for 2 h. The reaction mixture was concentrated in vacuo to afford the title compound (58% purity, 180 mg, 0.248 mmol, 78% yield) as a white solid; M/Z: 385 [M+H]$^+$, ESI$^+$, RT=0.97 (S1).

Step 21.d: (2S,5R)-5-[(benzyloxy)[(benzyloxy)carbonyl]amino]-1-ethylpiperidine-2-carboxylic acid

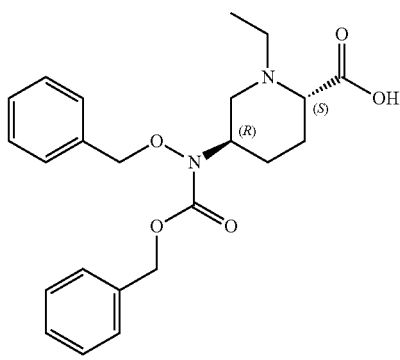

To a suspension of (2S,5R)-5-[(benzyloxy)(benzyloxy)carbonyl]amino]piperidine-2-carboxylic acid hydrochloride (58% purity, 169 mg, 0.233 mmol) in DCE (5 mL) was added acetaldehyde (36 mg, 0.806 mmol) and stirred at r.t. for 10 min. STAB (198 mg, 0.93 mmol) was added and the mixture was stirred at r.t. for 16 h. The reaction mixture was concentrated in vacuo and purified by prep. HPLC (Method 5) to afford the title compound (78 mg, 0.183 mmol, 59% yield) as a beige solid; M/Z: 413 [M+H]$^+$, ESI$^+$, RT=1.00 (S1).

Intermediate 43 (Step 21.e): (2S,5R)-5-{[(tert-butoxy)carbonyl]amino}-1-ethylpiperidine-2-carboxylic acid Intermediate 43

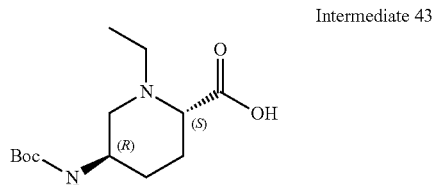

To a solution of (2S,5R)-5-[(benzyloxy)[(benzyloxy)carbonyl]amino]-1-ethylpiperidine-2-carboxylic acid (78 mg, 0.183 mmol) and Boc$_2$O (52 mg, 0.238 mmol) in EtOH (10 mL) was added 10% Pd/C (10 mg, 0.0940 mmol) and the mixture stirred under H$_2$ at r.t. for 6 h. The reaction mixture was filtered through Celite and the filtrate concentrated in vacuo to afford the title compound (35% purity, 130 mg, 0.167 mmol, 91% yield) as a colourless gum; M/Z: 273 [M+H]$^+$, ESI$^+$, RT=0.76 (S1).

The intermediate in Table 7 was synthesised according to general route 21 as exemplified by Intermediate 42 using the corresponding starting material.

TABLE 7

| Intermediate | Structure | Name | Starting material | LCMS data | ¹H NMR |
|---|---|---|---|---|---|
| 44 | 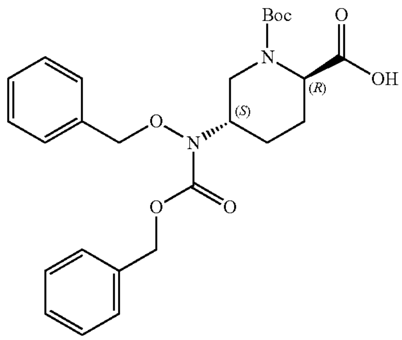 | (2R,5S)-5-[(benzyloxy)[(benzyloxy)carbonyl]amino]-1-[(tert-butoxy)carbonyl]piperidine-2-carboxylic acid | 1-tert-butyl 2-ethyl (2R,5S)-5-[(benzyloxy)amino]piperidine-1,2-dicarboxylate (Intemediate 2) following steps 21.a and 21.b | M/Z: 483 [M − H]⁻, ESI⁻, RT = 1.31 (S1) | ¹H NMR (400 MHz, chloroform-d) δ 7.43-7.13 (m, 10H), 5.28-5.17 (m, 2H), 4.92-4.83 (m, 2H), 4.66-4.53 (m, 1H), 4.37-4.21 (m, 1H), 4.18-3.89 (m, 2H), 3.51 (dd, J = 14.2, 4.9 Hz, 1H), 2.31-2.18 (m, 1H), 2.01-1.86 (m, 2H), 1.86-1.72 (m, 1H), 1.40 (s, 9H). |

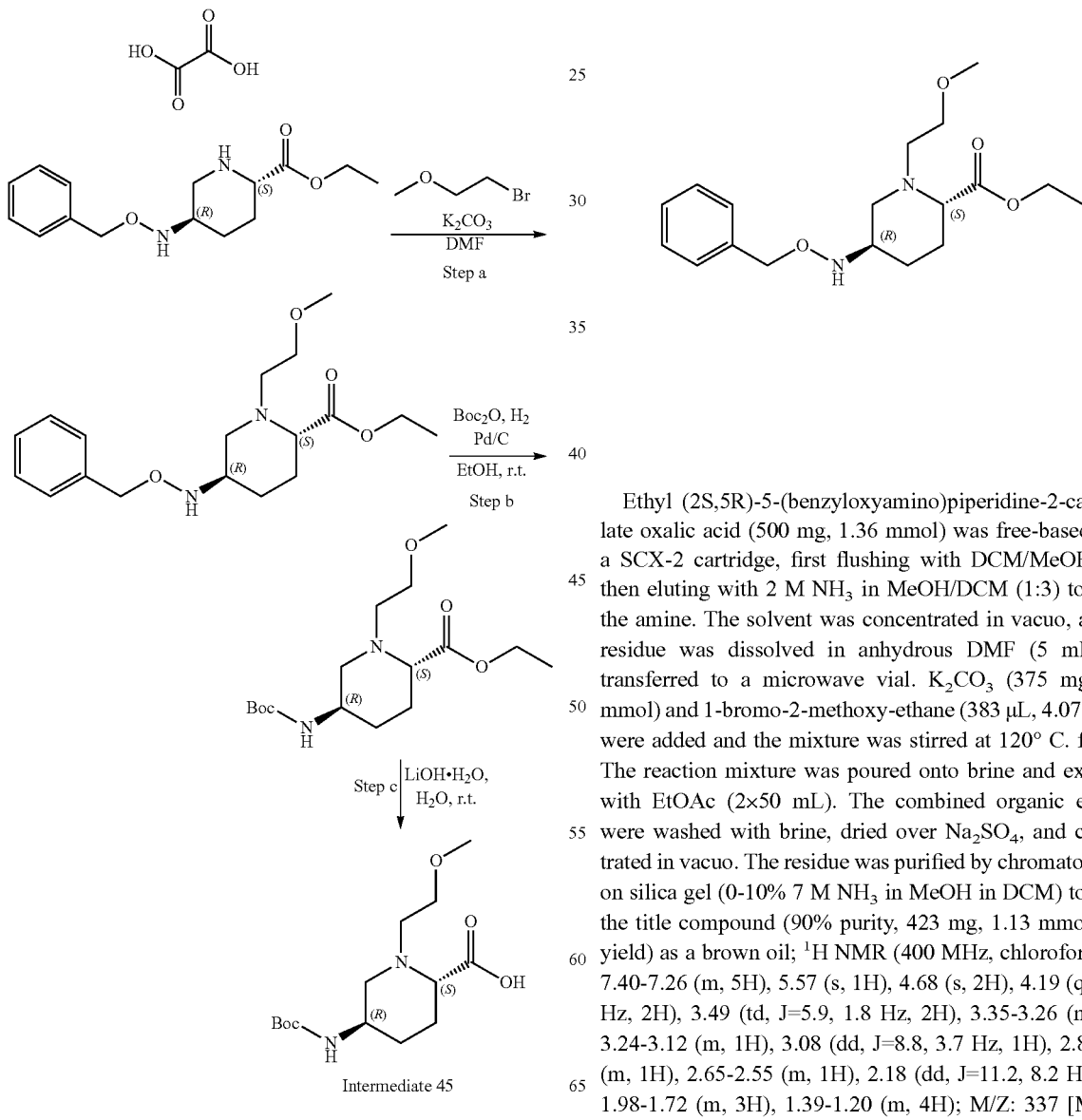

Step 22.a: ethyl (2S,5R)-5-[(benzyloxy)amino]-1-(2-methoxyethyl)piperidine-2-carboxylate Ethyl (2S,5R)-5-(benzyloxyamino)piperidine-2-carboxylate oxalic acid (500 mg, 1.36 mmol) was free-based using a SCX-2 cartridge, first flushing with DCM/MeOH (3:1) then eluting with 2 M $NH_3$ in MeOH/DCM (1:3) to afford the amine. The solvent was concentrated in vacuo, and the residue was dissolved in anhydrous DMF (5 mL) and transferred to a microwave vial. $K_2CO_3$ (375 mg, 2.71 mmol) and 1-bromo-2-methoxy-ethane (383 μL, 4.07 mmol) were added and the mixture was stirred at 120° C. for 1 h. The reaction mixture was poured onto brine and extracted with EtOAc (2×50 mL). The combined organic extracts were washed with brine, dried over $Na_2SO_4$, and concentrated in vacuo. The residue was purified by chromatography on silica gel (0-10% 7 M $NH_3$ in MeOH in DCM) to afford the title compound (90% purity, 423 mg, 1.13 mmol, 83% yield) as a brown oil; ¹H NMR (400 MHz, chloroform-d) δ 7.40-7.26 (m, 5H), 5.57 (s, 1H), 4.68 (s, 2H), 4.19 (q, J=7.1 Hz, 2H), 3.49 (td, J=5.9, 1.8 Hz, 2H), 3.35-3.26 (m, 4H), 3.24-3.12 (m, 1H), 3.08 (dd, J=8.8, 3.7 Hz, 1H), 2.83-2.72 (m, 1H), 2.65-2.55 (m, 1H), 2.18 (dd, J=11.2, 8.2 Hz, 1H), 1.98-1.72 (m, 3H), 1.39-1.20 (m, 4H); M/Z: 337 [M+H]⁺, ESI⁺, RT=0.86 (S1).

83

Step 22.b: ethyl (2S,5R)-5-{[(tert-butoxy)carbonyl]amino}-1-(2-methoxyethyl)piperidine-2-carboxylate

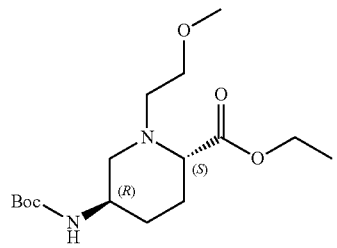

A solution of ethyl (2S,5R)-5-[(benzyloxy)amino]-1-(2-methoxyethyl)piperidine-2-carboxylate (90% purity, 423 mg, 1.13 mmol), Boc$_2$O (321 mg, 1.47 mmol) and 10% Pd/C (120 mg, 0.113 mmol) in EtOH (10 mL) was stirred under H$_2$ at r.t. for 16 h. The reaction mixture was filtered through a pad of Celite, washing with EtOAc, and the filtrate was concentrated in vacuo to afford the title compound (50% purity, 627 mg, 0.949 mmol, 84% yield) as a colourless oil; M/Z: 331 [M+H]$^+$, ESI$^+$, RT=0.78 (S1).

84

Intermediate 45 (Step 22.c): (2S,5R)-5-{[(tert-butoxy)carbonyl]amino}-1-(2-methoxyethyl)piperidine-2-carboxylic acid

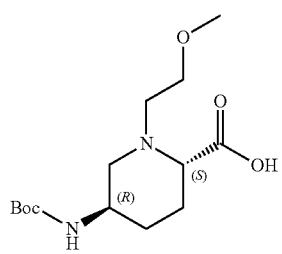

Intermediate 45

A solution of ethyl (2S,5R)-5-{[(tert-butoxy)carbonyl]amino}-1-(2-methoxyethyl)piperidine-2-carboxylate (50% purity, 627 mg, 0.949 mmol) in THF (10 mL) was treated with a solution of LiOH·H$_2$O (408 mg, 9.48 mmol) in H$_2$O (10 mL) at r.t. for 16 h. 1 M aq HCl H$_2$O solution (7.6 mL, 7.59 mmol) was added dropwise, the organic solvent was extracted and evaporated to afford the title compound (286 mg, 0.95 mmol, 99% yield) as a white solid; M/Z: 303 [M+H]$^+$, ESI$^+$, RT=0.79 (S1).

Scheme for route 23

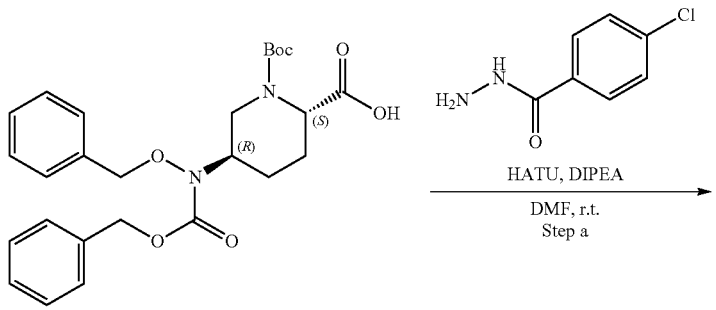

Intermediate 42

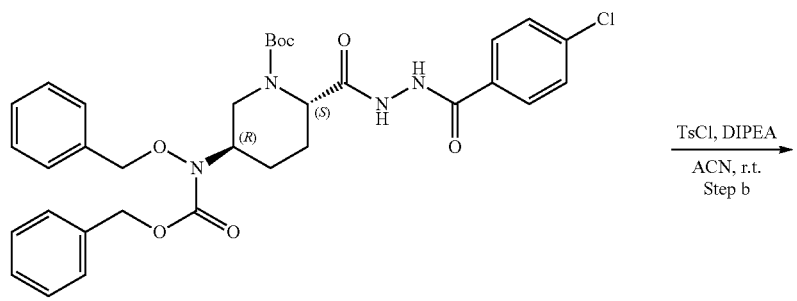

-continued

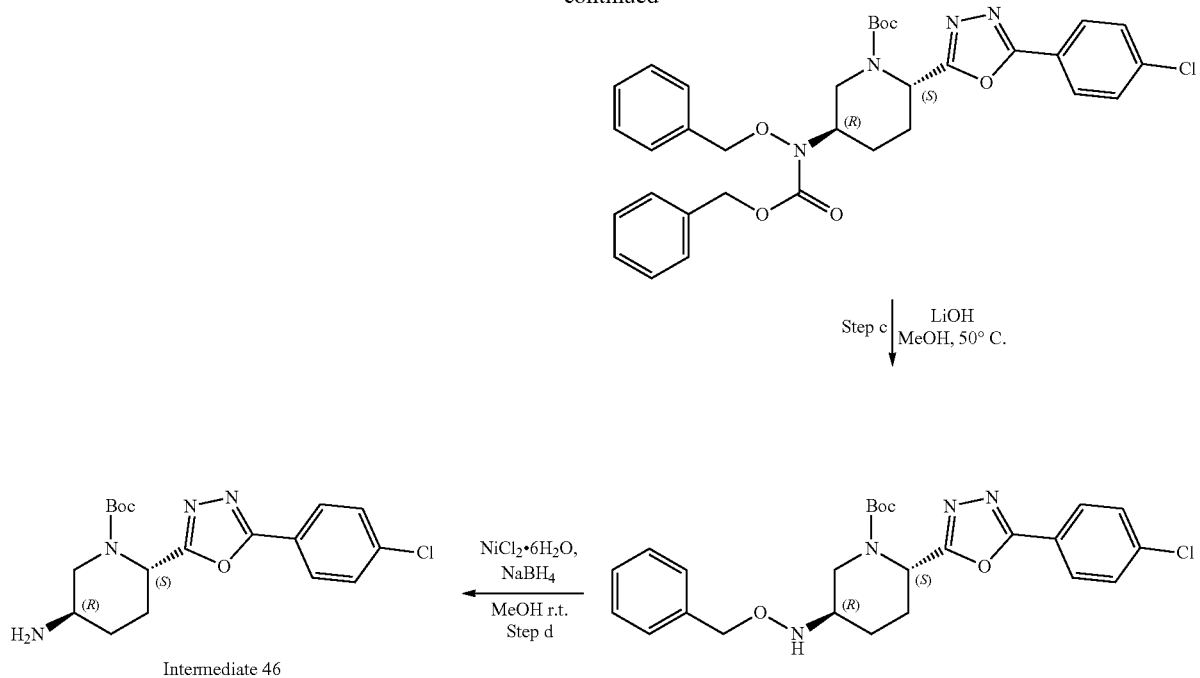

Step c | LiOH
MeOH, 50° C.

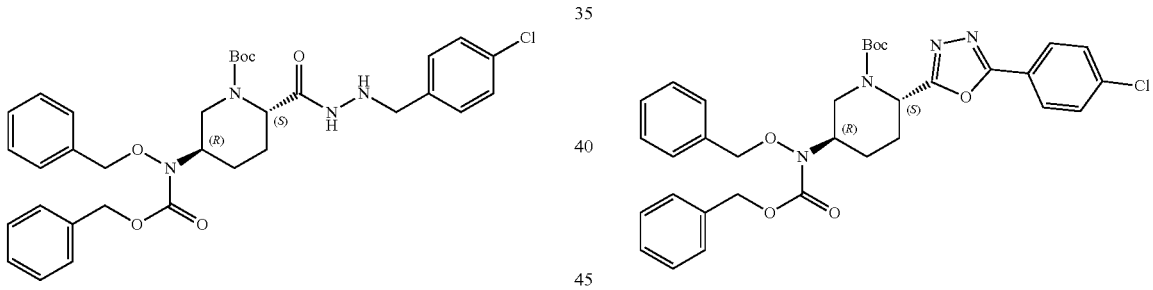

Step 23.a: tert-butyl (2S,5R)-5-[(benzyloxy)[(benzyloxy)carbonyl]amino]-2-{[(4-chlorophenyl)formohydrazido]carbonyl}piperidine-1-carboxylate To a solution of (2S,5R)-5-[(benzyloxy)[(benzyloxy)carbonyl]amino]-1-[(tert-butoxy)carbonyl]piperidine-2-carboxylic acid (77% purity, 1.0 g, 1.59 mmol, Intermediate 42) in anhydrous DMF (10 mL) at 0° C. was added HATU (725 mg, 1.91 mmol) followed by DIPEA (0.56 mL, 3.18 mmol) and stirred at r.t for 10 min. 4-Chlorobenzohydrazide (271 mg, 1.59 mmol) was then added and the mixture was stirred at r.t. for 2 h. The reaction mixture was diluted with H$_2$O (80 mL), stirred at r.t. for 20 min, and the resultant suspension was filtered under vacuum, washing with H$_2$O (50 mL). The residue was purified by chromatography on silica gel (5-80% EtOAc in heptane) to afford the title compound (91% purity, 640 mg, 0.91 mmol, 57% yield) as a white solid; M/Z: 537, 539 [M-Boc+H]$^+$, ESI$^+$, RT=1.33 (S1).

Step 23.b: tert-butyl (2S,5R)-5-[(benzyloxy)[(benzyloxy)carbonyl]amino]-2-[5-(4-chlorophenyl)-1,3,4-oxadiazol-2-yl]piperidine-1-carboxylate To a solution of tert-butyl (2S,5R)-5-[(benzyloxy)[(benzyloxy)carbonyl]amino]-2-{[(4-chlorophenyl)formohydrazido]carbonyl}piperidine-1-carboxylate (91% purity, 640 mg, 0.91 mmol) in ACN (5 mL) was added DIPEA (0.12 mL, 0.669 mmol) and TsCl (191 mg, 1.0 mmol) and the mixture was stirred at r.t. for 48 h. 15% aq NH$_4$OH solution (20 mL) was added and the mixture was stirred at r.t. for 15 min. The reaction mixture was concentrated in vacuo, diluted with H$_2$O (20 mL) and extracted with DCM (2×30 mL). The combined organic extracts were washed with brine (30 mL), dried over Na$_2$SO$_4$, and concentrated in vacuo. The residue was purified by chromatography on silica gel (10-80% EtOAc in heptane) to afford the title compound (560 mg, 0.877 mmol, 96% yield) as a white gum; $^1$H NMR (400 MHz, chloroform-d) δ 8.02-7.90 (m, 2H), 7.54-7.47 (m, 2H), 7.47-7.31 (m, 9H), 7.27-7.19 (m, 1H), 5.52 (s, 1H), 5.35-5.20 (m, 2H), 4.99-4.88 (m, 2H), 4.32-4.22 (m, 2H), 3.54-3.45 (m, 1H), 2.58-2.43 (m, 1H), 2.23-2.11 (m, 1H), 2.09-2.01 (m, 2H), 1.41 (s, 9H); M/Z: 641, 643 [M+Na]$^+$, ESI$^+$, RT=1.53 (S1).

Step 23.c: tert-butyl (2S,5R)-5-[(benzyloxy)amino]-2-[5-(4-chlorophenyl)-1,3,4-oxadiazol-2-yl]piperidine-1-carboxylate

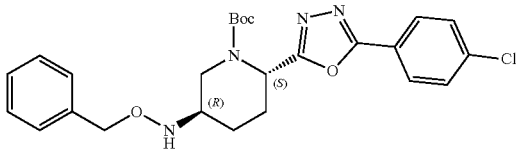

To a solution of tert-butyl (2S,5R)-5-[(benzyloxy)[(benzyloxy)carbonyl]amino]-2-[5-(4-chlorophenyl)-1,3,4-oxadiazol-2-yl]piperidine-1-carboxylate (480 mg, 0.752 mmol) in MeOH (5 mL) was added 2 M aq LiOH solution (10 mL, 20.0 mmol) and the mixture was stirred at r.t. for 15 h. The mixture was then heated to 50° C. for 3 h before allowing to stir at r.t. for 110 h. The reaction mixture was concentrated in vacuo, dissolved in H$_2$O (20 mL) and acidified to pH 9 using 1 M aq HCl solution. The solution was extracted with EtOAc (2×30 mL) and the combined organic extracts were washed with brine (30 mL), dried over Na$_2$SO$_4$, and concentrated in vacuo. The residue was purified by chromatography on silica gel (10-100% EtOAc in heptane) to afford the title compound (92% purity, 195 mg, 0.370 mmol, 49% yield); $^1$H NMR (500 MHz, chloroform-d) δ 8.00-7.88 (m, 2H), 7.53-7.41 (m, 2H), 7.39-7.23 (m, 5H), 4.81-4.61 (m, 2H), 4.41 (d, J=72.2 Hz, 2H), 3.14 (d, J=65.3 Hz, 2H), 2.73 (s, 1H), 2.51-2.40 (m, 1H), 2.23-2.08 (m, 1H), 1.93-1.66 (m, 2H), 1.55-1.44 (m, 9H); M/Z: 485, 487 [M+H]$^+$, ESI$^+$, RT=1.39 (S1).

Intermediate 46 (Step 23.d): tert-butyl (2S,5R)-5-amino-2-[5-(4-chlorophenyl)-1,3,4-oxadiazol-2-yl]piperidine-1-carboxylate Intermediate 46

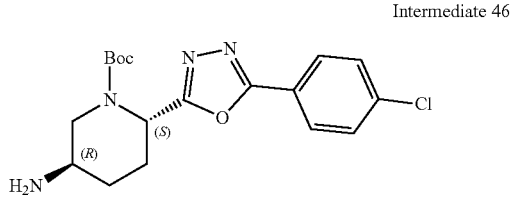

To a solution of tert-butyl (2S,5R)-5-[(benzyloxy)amino]-2-[5-(4-chlorophenyl)-1,3,4-oxadiazol-2-yl]piperidine-1-carboxylate (92% purity, 160 mg, 0.304 mmol) in MeOH (20 mL) at −10° C. was added NiCl$_2$·6H$_2$O (291 mg, 1.21 mmol) followed by NaBH$_4$ (344 mg, 9.11 mmol) and the mixture was stirred at r.t. for 5 h. The reaction mixture was concentrated in vacuo and purified by prep. HPLC (Method 5) to afford the title compound (50 mg, 0.132 mmol, 43% yield) as a colourless gum; M/Z: 379, 381 [M+H]$^+$, ESI$^+$, RT=0.97 (S1).

The intermediate in Table 8 was synthesised according to general route 23 as exemplified by Intermediate 46 using the corresponding starting material.

TABLE 8

| Intermediate | Structure | Name | Starting material | LCMS data | $^1$H NMR |
|---|---|---|---|---|---|
| 47 | (structure shown) | tert-butyl (2R,5S)-5-amino-2-[5-(3,3,3-trifluoropropoxy)-1,3,4-oxadiazol-2-yl]piperidine-1-carboxylate | (2R,5S)-5-[(benzyloxy)[(benzyloxy)carbonyl]amino]-1-[(tert-butoxy)carbonyl]piperidine-2-carboxylic acid (Intermediate 44) and (3,3,3-trifluoropropoxy)carbohydrazide (Intermediate 38) | | $^1$H NMR (500 MHz, chloroform-d) δ 5.91-5.32 (m, 3H), 4.68 (t, J = 6.2 Hz, 2H), 4.42-4.18 (m, 1H), 3.65-3.49 (m, 1H), 3.27-2.98 (m, 1H), 2.70 (qt, J = 10.2, 6.2 Hz, 2H), 2.51-2.34 (m, 1H), 2.19-2.07 (m, 2H), 2.06-1.92 (m, 1H), 1.46 (s, 9H). |

Scheme for route 24

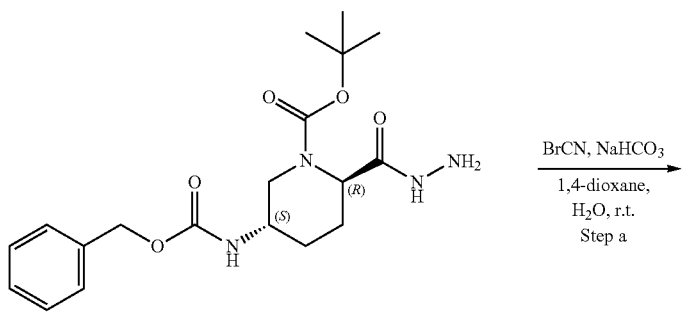

Intermediate 30

BrCN, NaHCO$_3$
1,4-dioxane, H$_2$O, r.t.
Step a

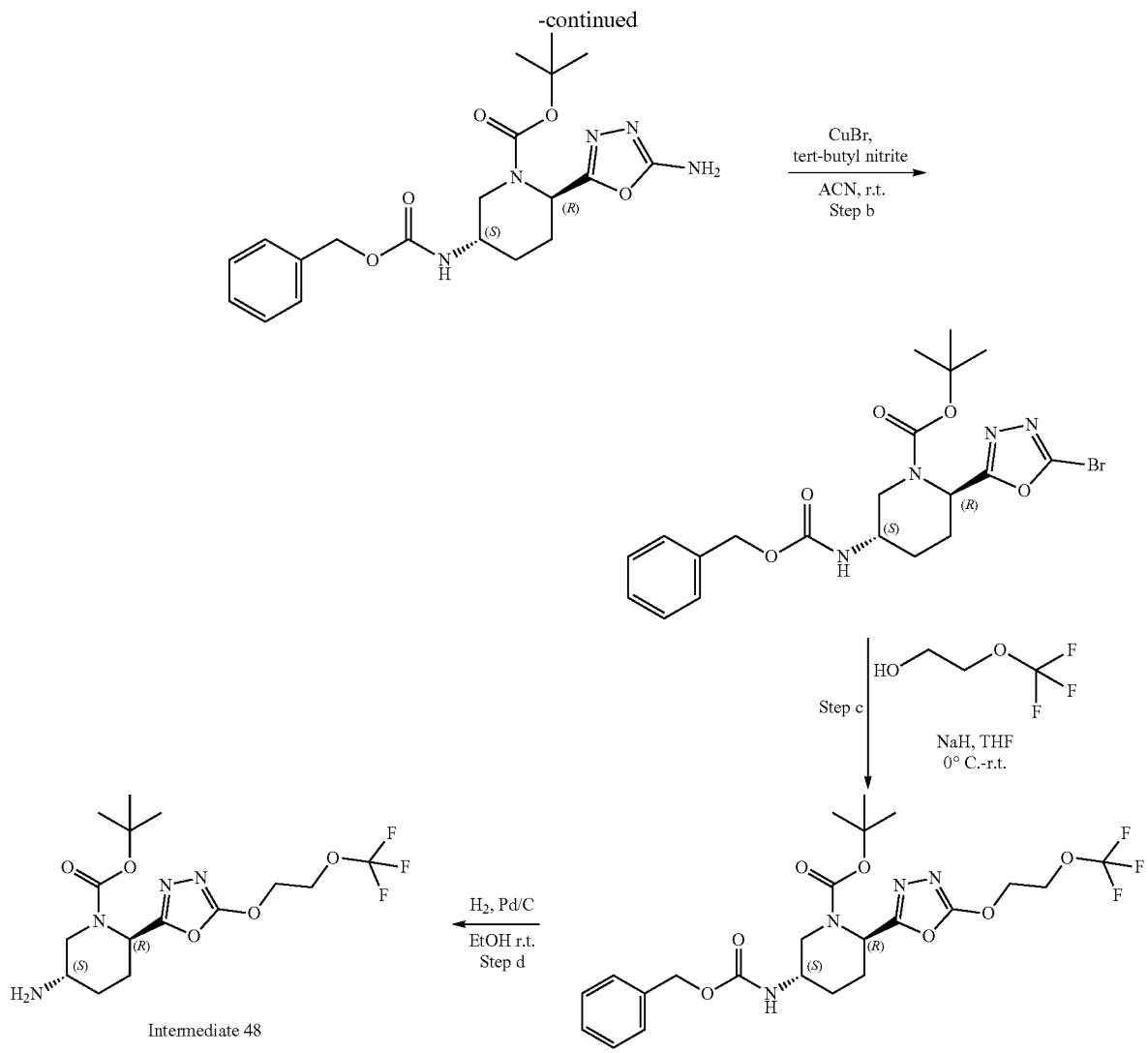

Step 24.a: tert-butyl (2R,5S)-2-(5-amino-1,3,4-oxadiazol-2-yl)-5-{[(benzyloxy)carbonyl]amino}piperidine-1-carboxylate

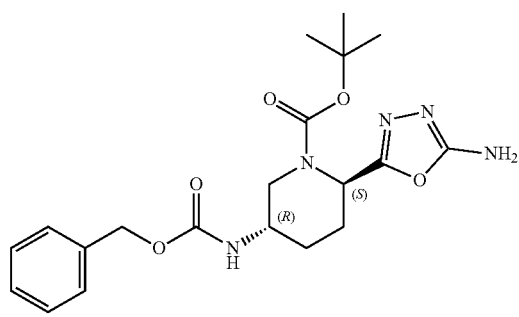

To a solution of tert-butyl (2R,5S)-5-{[(benzyloxy)carbonyl]amino}-2-(hydrazinecarbonyl)piperidine-1-carboxylate (79% purity, 10.2 g, 20.5 mmol, Intermediate 30) in 1,4-dioxane (70 mL) was added a solution of $NaHCO_3$ (2.58 g, 30.8 mmol) in $H_2O$ (20 mL), followed by BrCN (2.17 g, 20.5 mmol), and the mixture was stirred at r.t. for 2.5 h. The reaction mixture was diluted with $H_2O$ and the resultant precipitate was filtered under vacuum, washing with $H_2O$, to afford the title compound in quantitative yield (84% purity, 11.02 g, 22.2 mmol) as an off-white powder; $^1$H NMR (400 MHz, DMSO-$d_6$) δ 7.51-7.42 (m, 1H), 7.41-7.27 (m, 5H), 7.05-6.95 (m, 2H), 5.30 (s, 1H), 5.09-4.97 (m, 2H), 4.11-3.98 (m, 1H), 2.86-2.76 (m, 1H), 2.29-2.14 (m, 1H), 1.95-1.79 (m, 2H), 1.65-1.53 (m, 1H), 1.44-1.30 (m, 10H); M/Z: 318 [M-Boc+H]$^+$, ESI$^+$, RT=0.86 (S2).

Step 24.b: tert-butyl (2R,5S)-5-{[(benzyloxy)carbonyl]amino}-2-(5-bromo-1,3,4-oxadiazol-2-yl)piperidine-1-carboxylate

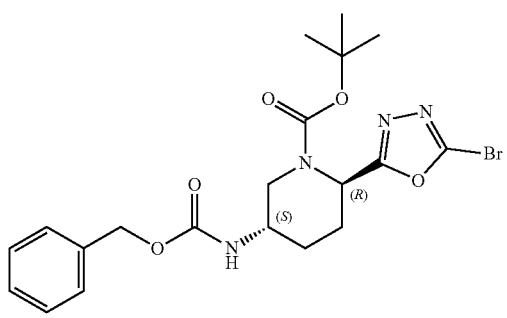

To a solution of tert-butyl (2R,5S)-2-(5-amino-1,3,4-oxadiazol-2-yl)-5-{[(benzyloxy)carbonyl]amino}piperidine-1-carboxylate (84% purity, 11.02 g, 22.2 mmol) and CuBr (3 eq, 9.54 g, 66.5 mmol) in anhydrous ACN (400 mL) was added tert-butyl nitrite (90%, 17.6 mL, 133.0 mmol) and the mixture was stirred at r.t for 5 h. Further portions of CuBr (1.5 eq, 4.77 g, 33.3 mmol) and tert-butyl nitrite (90%, 8.79 mL, 66.5 mmol) were added and the mixture was stirred at r.t. for 19 h. The reaction mixture was diluted with EtOAc (250 mL) and washed with Rochelle salt (2×200 mL) and H$_2$O (3×200 mL). The organic extracts were dried over Na$_2$SO$_4$, concentrated in vacuo, and purified by chromatography on silica gel (0-100% EtOAc in heptane) to afford the title compound (2.02 g, 4.03 mmol, 18% yield) as a beige solid; $^1$H NMR (400 MHz, DMSO-d$_6$) δ 7.52 (d, J=6.2 Hz, 1H), 7.41-7.28 (m, 5H), 5.57-5.41 (m, 1H), 5.05 (s, 2H), 4.08-3.91 (m, 1H), 3.65-3.53 (m, 1H), 2.96-2.84 (m, 1H), 2.33-2.23 (m, 1H), 1.99-1.90 (m, 1H), 1.88-1.72 (m, 1H), 1.65-1.57 (m, 1H), 1.38 (s, 9H); M/Z: 383 [M-Boc+H]$^+$, ESI$^+$, RT=1.09 (S2).

Step 24.c: tert-butyl (2R,5S)-5-{[(benzyloxy)carbonyl]amino}-2-{5-[2-(trifluoromethoxy)ethoxy]-1,3,4-oxadiazol-2-yl}piperidine-1-carboxylate

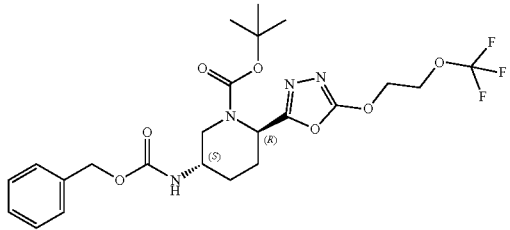

To a solution of 2-(trifluoromethoxy)ethan-1-ol (13% in THF/toluene, 4.50 g, 4.43 mmol) in anhydrous THF (15 mL) at 0° C. was added NaH (60%, 322 mg, 8.06 mmol) and the mixture was stirred at 0° C. for 10 min. tert-Butyl (2R,5S)-5-{[(benzyloxy)carbonyl]amino}-2-(5-bromo-1,3,4-oxadiazol-2-yl)piperidine-1-carboxylate (2.02 g, 4.03 mmol) in anhydrous THF (10 mL) was added and the mixture was stirred at r.t. for 2 h. The reaction mixture was diluted with H$_2$O (50 mL) and extracted with EtOAc (3×100 mL). The combined organic extracts were dried over MgSO$_4$, concentrated in vacuo, and purified by chromatography on silica gel (0-100% EtOAc in heptane) to afford the title compound (85% purity, 1.60 g, 2.56 mmol, 64% yield) as a yellow oil; $^1$H NMR (400 MHz, DMSO-d$_6$) δ 7.50 (d, J=6.1 Hz, 1H), 7.43-7.26 (m, 5H), 5.46-5.29 (m, 1H), 5.04 (s, 2H), 4.80-4.58 (m, 2H), 4.57-4.41 (m, 2H), 4.43-4.26 (m, 1H), 3.73-3.51 (m, 1H), 2.96-2.80 (m, 1H), 2.32-2.16 (m, 1H), 1.96-1.73 (m, 2H), 1.69-1.49 (m, 1H), 1.37 (s, 9H); M/Z: 531 [M-Boc+H]$^+$, ESI$^+$, RT=3.83 (S4).

Intermediate 48 (Step 24.d): tert-butyl (2R,5S)-5-amino-2-{5-[2-(trifluoromethoxy)ethoxy]-1,3,4-oxadiazol-2-yl}piperidine-1-carboxylate Intermediate 48

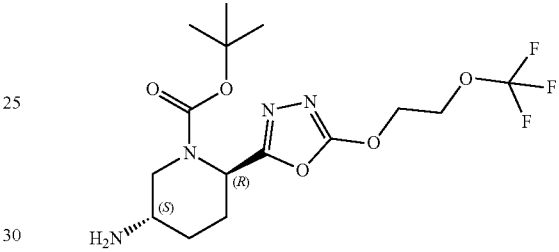

To a solution of tert-butyl (2R,5S)-5-{[(benzyloxy)carbonyl]amino}-2-{5-[2-(trifluoromethoxy)ethoxy]-1,3,4-oxadiazol-2-yl}piperidine-1-carboxylate (85% purity, 1.60 g, 2.56 mmol) in EtOH (45 mL) under N$_2$ was added 10% Pd/C (3.27 g, 3.08 mmol) and the mixture was stirred under H$_2$ at r.t. for 18 h. The reaction mixture was filtered through a pad of Celite and concentrated in vacuo to afford the title compound (49% purity, 843 mg, 1.04 mmol, 41% yield) as a light brown oil; $^1$H NMR (400 MHz, DMSO-d$_6$) δ 5.39-5.26 (m, 1H), 4.76-4.64 (m, 2H), 4.54-4.42 (m, 2H), 4.43-4.25 (m, 1H), 3.74-3.60 (m, 1H), 3.20-2.91 (m, 3H), 2.30-2.09 (m, 1H), 1.93-1.78 (m, 1H), 1.75-1.59 (m, 1H), 1.53-1.25 (m, 11H); M/Z: 397 [M+H]$^+$, ESI$^+$, RT=1.76 (S4).

Scheme for route 25

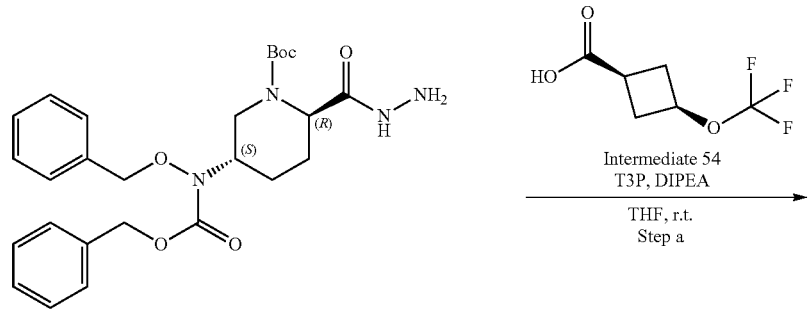

Intermediate 29

-continued

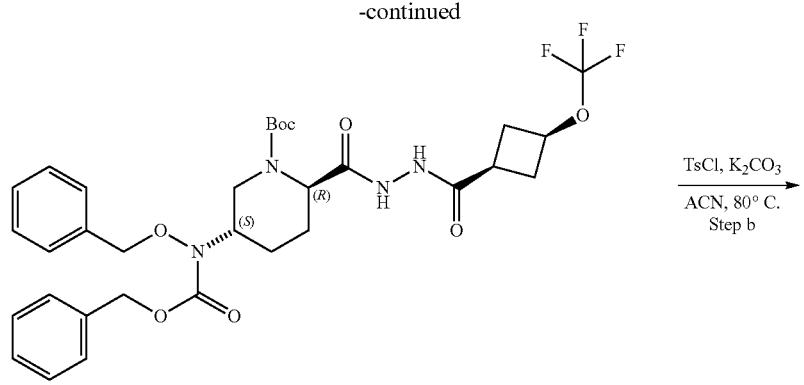

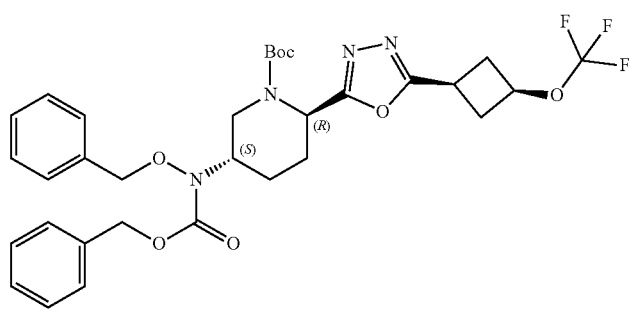

Intermediate 49

Step 25.a: tert-butyl (2R,5S)-5-[(benzyloxy)[(benzyloxy)carbonyl]amino]-2-{N'-[(1s,3s)-3-(trifluoromethoxy)cyclobutanecarbonyl]hydrazinecarbonyl}piperidine-1-carboxylate

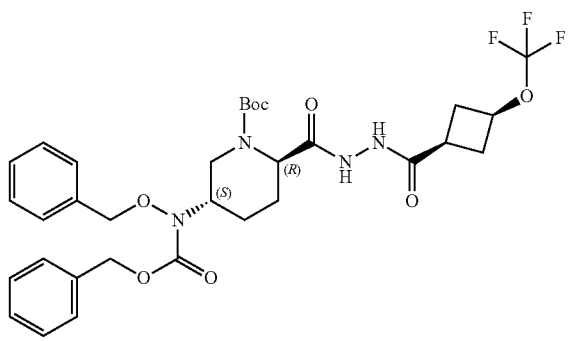

To a solution of (1s,3s)-3-(trifluoromethoxy)cyclobutane-1-carboxylic acid (500 mg, 2.63 mmol, Intermediate 54) in THF (20 mL) was added DIPEA (1.4 mL, 7.90 mmol), T3P (50% in EtOAc, 4.7 mL, 7.90 mmol) and tert-butyl (2R,5S)-5-[(benzyloxy)[(benzyloxy)carbonyl]amino]-2-(hydrazinecarbonyl)piperidine-1-carboxylate (60% purity, 2.30 g, 2.77 mmol, Intermediate 29) and the mixture was stirred at r.t. for 18 h. The reaction mixture was diluted with $H_2O$ (50 mL) and extracted with EtOAc (2×100 mL). The combined organic extracts were dried over $Na_2SO_4$, concentrated in vacuo, and purified by chromatography on silica gel (0-100% EtOAc in heptane) to afford the title compound (1.60 g, 2.29 mmol, 87% yield) as a white solid; $^1$H NMR (400 MHz, DMSO-$d_6$) δ 10.01-9.69 (m, 2H), 7.49-7.21 (m, 10H), 5.21 (s, 2H), 4.92-4.74 (m, 3H), 4.52-4.17 (m, 2H), 4.01-3.70 (m, 2H), 2.76-2.68 (m, 1H), 2.29-1.99 (m, 2H), 1.93-1.47 (m, 4H), 1.42-1.34 (m, 2H), 1.30 (s, 9H); M/Z: 687 [M+Na]$^+$, ESI$^+$, RT=1.21 (S2).

Step 25.b: tert-butyl (2R,5S)-5-[(benzyloxy)](benzyloxy)carbonyl]amino]-2-{5-[(1s,3s)-3-(trifluoromethoxy)cyclobutyl]-1,3,4-oxadiazol-2-yl}piperidine-1-carboxylate

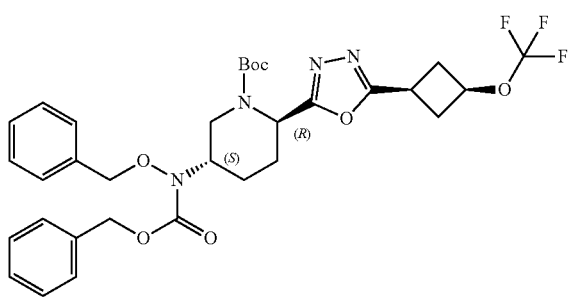

A suspension of tert-butyl (2R,5S)-5-[(benzyloxy)](benzyloxy)carbonyl]amino]-2-{N-[(1s,3s)-3-(trifluoromethoxy)cyclobutanecarbonyl]hydrazinecarbonyl}piperidine-1-carboxylate (1.6 g, 2.29 mmol), K₂CO₃ (2.0 g, 14.4 mmol) and TsCl (1.40 g, 7.22 mmol) in ACN (18 mL) was stirred at 80° C. for 1.5 h. The reaction mixture was partitioned between EtOAc (100 mL) and H₂O (50 mL), and the organic layer was isolated and washed with brine (30 mL). The organic extracts were dried over MgSO₄, concentrated in vacuo, and purified by chromatography on silica gel (0-50% EtOAc in heptane) to afford the title compound (92% purity, 1.05 g, 1.49 mmol, 62% yield) as a yellow oil; $^1$H NMR (400 MHz, DMSO-d₆) δ 7.48-7.27 (m, 10H), 5.36-5.27 (m, 1H), 5.21 (s, 2H), 4.96-4.83 (m, 3H), 4.19-4.09 (m, 1H), 4.01-3.93 (m, 1H), 3.51-3.40 (m, 1H), 2.91-2.79 (m, 2H), 2.31-2.21 (m, 1H), 2.07-1.96 (m, 2H), 1.96-1.87 (m, 2H), 1.41 (s, 2H), 1.28 (d, J=5.8 Hz, 9H); M/Z: 547 [M-Boc+H]⁺, ESI⁺, RT=1.27 (S2).

Intermediate 49 (Step 25.c): tert-butyl (2R,5S)-5-amino-2-{5-[(1s,3s)-3-(trifluoromethoxy)cyclobutyl]-1,3,4-oxadiazol-2-yl}piperidine-1-carboxylate Intermediate 49

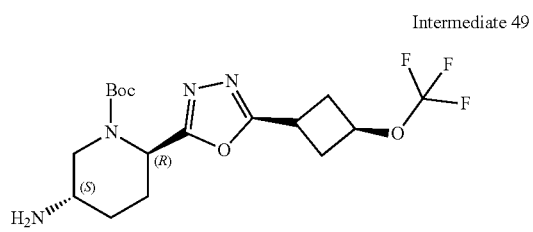

To a solution of tert-butyl (2R,5S)-5-[(benzyloxy)](benzyloxy)carbonyl]amino]-2-{5-[(1s,3s)-3-(trifluoromethoxy)cyclobutyl]-1,3,4-oxadiazol-2-yl}piperidine-1-carboxylate (0.93 g, 1.43 mmol) in anhydrous EtOH (30 mL) was added 10% Pd/C (0.15 g, 0.144 mmol) and the resultant mixture was stirred at r.t. under H₂ for 24 h. A further portion of 10% Pd/C (0.15 g, 0.144 mmol) was added and the reaction mixture was stirred at r.t. under H₂ for 24 h. A further portion of 10% Pd/C (0.15 g, 0.144 mmol) was added and the reaction mixture was stirred at r.t. under H₂ for 24 h. The reaction mixture was warmed to 40° C. and filtered through a pad of Celite, washing copiously with EtOH. The filtrate was concentrated in vacuo and purified by chromatography on silica gel (0-20% MeOH in DCM) to afford the title compound (321 mg, 0.774 mmol, 54% yield) as a pale yellow oil; $^1$H NMR (400 MHz, DMSO-d₆) δ 5.39 (s, 1H), 4.90 (p, J=7.5 Hz, 1H), 3.69 (d, J=13.1 Hz, 1H), 3.52-3.36 (m, 2H), 3.06-2.92 (m, 2H), 2.92-2.76 (m, 2H), 2.32-2.13 (m, 2H), 1.96-1.85 (m, 1H), 1.80-1.59 (m, 1H), 1.49 (d, J=13.6 Hz, 1H), 1.41 (s, 9H); M/Z: 407 [M+H]⁺, ESI⁺, RT=0.71-0.76 (S2).

Scheme for route 26

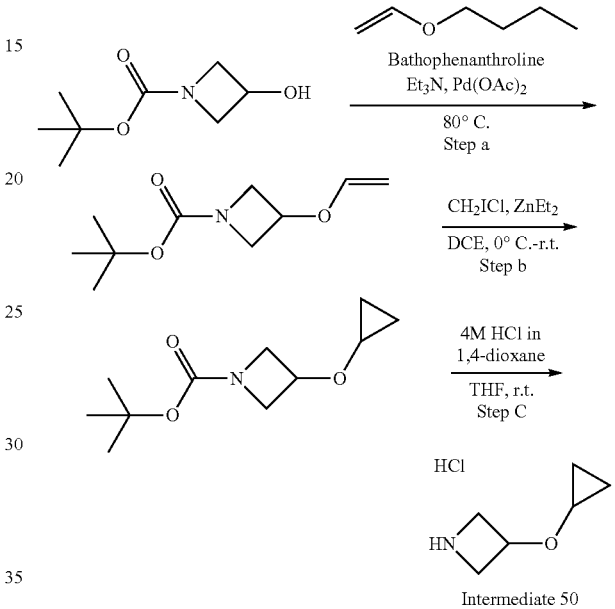

Intermediate 50

Step 26.a: tert-butyl 3-(ethenyloxy)azetidine-1-carboxylate

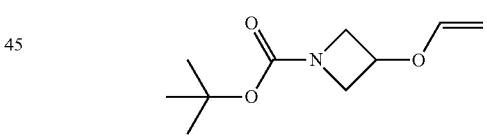

A mixture of tert-butyl 3-hydroxyazetidine-1-carboxylate (5.0 g, 28.9 mmol), 1-(ethenyloxy)butane (56 mL, 0.433 mol), Bathophenanthroline (480 mg, 1.44 mmol), Pd(OAc)₂ (981 mg, 1.44 mmol) and Et₃N (1.7 mL, 12.1 mmol), split over four pressure tubes, was degassed using N₂ for 5 min, prior to being sealed and heated at 80° C. for 24 h. The reaction mixture was cooled to r.t. and filtered through a pad of Celite, washing with EtOAc.

The filtrate was concentrated in vacuo, and purified by chromatography on silica gel (0-25% EtOAc in heptane) to afford the title compound (93% purity, 3.60 g, 16.8 mmol, 58% yield) as a yellow oil; $^1$H NMR (500 MHz, chloroform-d) δ 6.37 (dd, J=14.5, 6.9 Hz, 1H), 4.58 (tt, J=6.5, 4.2 Hz, 1H), 4.17 (ddd, J=9.7, 6.5, 1.0 Hz, 2H), 4.08 (dd, J=6.9, 2.5 Hz, 1H), 3.96 (dd, J=14.5, 2.5 Hz, 2H), 3.90 (ddd, J=9.8, 4.2, 0.9 Hz, 2H), 1.44 (s, 9H); M/Z: no mas ion observed [M+H]⁺, ESI⁺, RT=0.94 (S2).

Step 26.b: tert-butyl 3-cyclopropoxyazetidine-1-carboxylate

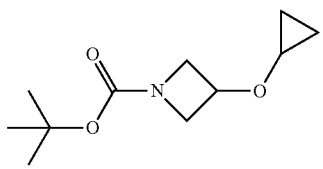

To a solution of tert-butyl 3-(ethenyloxy)azetidine-1-carboxylate (93% purity, 3.60 g, 16.8 mmol) and chloro(iodo)methane (9.48 g, 53.8 mmol) in DCE (14 mL) at −5° C. was added a solution of 0.9 M diethylzinc in hexanes (30 mL, 26.9 mmol) dropwise over 60 mins while maintaining an internal temperature between 0 and −5° C. The mixture was warmed to r.t. and stirred for 30 min. The reaction mixture was cooled to 0° C. and quenched using satd aq NH$_4$Cl solution (5 mL), followed by NH$_4$OH solution (5 mL). The solution was extracted with methyl tert-butyl ether (3×20 mL) and the combined organic extracts were washed with brine (25 mL), dried over MgSO$_4$, and concentrated in vacuo. The residue was purified by chromatography on silica gel (0-25% EtOAc in heptane) to afford the title compound (1.05 g, 4.92 mmol, 29% yield) as a colourless oil; $^1$H NMR (500 MHz, chloroform-d) δ 4.25 (tt, J=6.6, 4.5 Hz, 1H), 4.02 (ddd, J=9.4, 6.6, 0.9 Hz, 2H), 3.82-3.72 (m, 2H), 3.17 (tt, J=6.1, 3.0 Hz, 1H), 1.36 (s, 9H), 0.53 (dq, J=5.0, 3.4, 2.6 Hz, 2H), 0.45-0.37 (m, 2H).

Intermediate 50 (Step 26.c): 3-cyclopropoxyazetidine hydrochloride

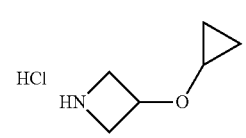

Intermediate 50

To a solution of tert-butyl 3-cyclopropoxyazetidine-1-carboxylate (1.05 g, 4.92 mmol) in THF (3 mL) at 0° C. was added 4 M HCl in 1,4-dioxane (4.9 mL, 19.7 mmol) dropwise and the mixture was stirred at r.t. for 3 h. The reaction mixture was concentrated in vacuo, and azeotroped using 2-propanol, to afford the title compound (75% purity, 0.75 g, 3.73 mmol, 76% yield) as a beige powder; $^1$H NMR (500 MHz, methanol-d$_4$) δ 4.62-4.52 (m, 1H), 4.35-4.27 (m, 2H), 4.04-3.97 (m, 2H), 3.40 (tt, J=6.0, 3.0 Hz, 1H), 0.64-0.59 (m, 2H), 0.56-0.50 (m, 2H).

Scheme for route 27

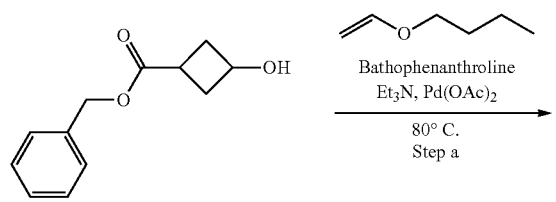

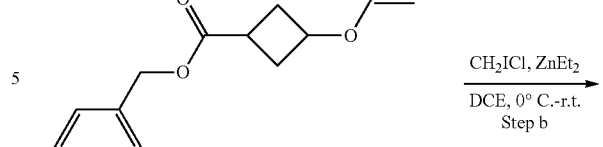

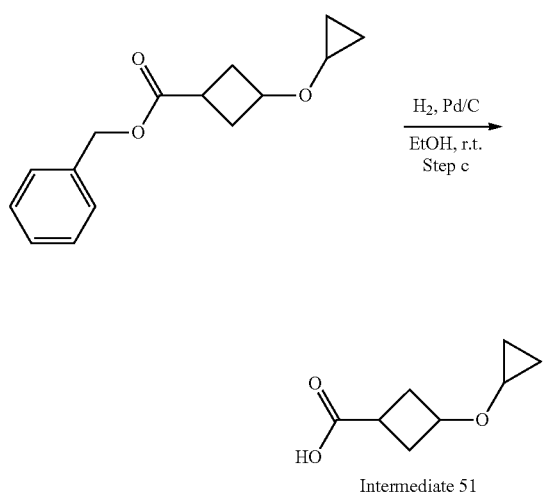

Intermediate 51

Step 27.a: benzyl 3-(ethenyloxy)cyclobutane-1-carboxylate

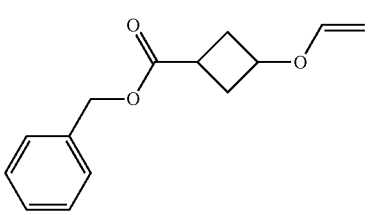 [SMILES: C=COC1CC(C(=O)OCc2ccccc2)C1]

A mixture of benzyl 3-hydroxycyclobutane-1-carboxylate (5.0 g, 24.2 mmol), 1-(ethenyloxy)butane (47 mL, 0.364 mol), Bathophenanthroline (403 mg, 1.21 mmol), Pd(OAc)$_2$ (824 mg, 1.21 mmol) and Et$_3$N (1.4 mL, 10.2 mmol) was stirred under N$_2$ at 80° C. for 24 h. The reaction mixture was cooled to r.t. and filtered through Celite, washing with EtOAc (100 mL). The filtrate was concentrated in vacuo and the resultant residue was purified by chromatography on silica gel (0-50% EtOAc in heptane) to afford the title compound (80% purity, 4.64 g, 16.0 mmol, 66% yield) as a yellow oil; $^1$H NMR (400 MHz, DMSO-d$_6$) δ 7.47-7.27 (m, 5H), 6.37 (dd, J=14.4, 6.9 Hz, 1H), 5.12 (s, 2H), 4.40-4.27 (m, 1H), 4.12 (dd, J=14.4, 1.8 Hz, 1H), 4.00 (dd, J=6.8, 1.8 Hz, 1H), 2.92-2.79 (m, 1H), 2.67-2.56 (m, 2H), 2.17-2.04 (m, 2H); M/Z: 233 [M+H]$^+$, ESI$^+$, RT=1.01 (S2).

Step 27.b: benzyl 3-cyclopropoxycyclobutane-1-carboxylate

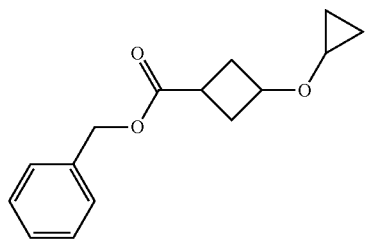 [SMILES: O=C(OCc1ccccc1)C1CC(OC2CC2)C1]

To a solution of benzyl 3-(ethenyloxy)cyclobutane-1-carboxylate (80% purity, 4.64 g, 16.0 mmol) in DCE (40 mL) at 0° C. was added chloro(iodo)methane (3.7 mL, 51.1 mmol) followed by 0.9 M ZnEt$_2$ in hexanes (28 mL, 25.6 mmol) dropwise and the mixture was stirred at r.t. for 2 h. The reaction mixture was cooled to 0° C. and quenched using satd aq NH$_4$Cl solution (30 mL) followed by NH$_4$OH solution (30 mL). The aqueous solution was extracted with EtOAc (3×100 mL) and the combined organic extracts were dried over Na$_2$SO$_4$ and concentrated in vacuo. The residue was purified by chromatography on silica gel (0-50% EtOAc in heptane) to afford the title compound (90% purity, 1.55 g, 5.66 mmol, 35% yield) as a colourless oil; $^1$H NMR (500 MHz, DMSO-d$_6$) δ 7.40-7.31 (m, 5H), 5.09 (s, 2H), 4.00-3.91 (m, 1H), 3.23-3.16 (m, 1H), 2.82-2.71 (m, 1H), 2.48-2.44 (m, 2H), 2.08-1.94 (m, 2H), 0.48-0.40 (m, 2H), 0.43-0.35 (m, 2H); M/Z: 247 [M+H]$^+$, ESI$^+$, RT=1.00 (S2).

Intermediate 51 (Step 27.c): 3-cyclopropoxycyclobutane-1-carboxylic acid

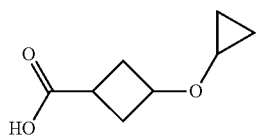

Intermediate 51

To a solution of benzyl 3-cyclopropoxycyclobutane-1-carboxylate (90% purity, 1.55 g, 5.66 mmol) in anhydrous EtOH (20 mL) was added 10% Pd/C (606 mg, 0.570 mmol) and the mixture was stirred at r.t. under H$_2$ for 24 h. The reaction mixture was filtered over Celite, washing with EtOAc (50 mL), and the filtrate was concentrated in vacuo to afford the title compound (90% purity, 981 mg, 5.65 mmol) in quantitative yield as a colourless oil; $^1$H NMR (400 MHz, DMSO-d$_6$) δ 11.88 (s, 1H), 4.14-3.97 (m, 1H), 3.97-3.88 (m, 1H), 3.21-3.17 (m, 1H), 2.43-2.38 (m, 2H), 1.99-1.88 (m, 2H), 0.48-0.35 (m, 4H); M/Z: 157 [M+H]$^+$, ESI$^+$, RT=0.64 (S2).

Scheme for route 28

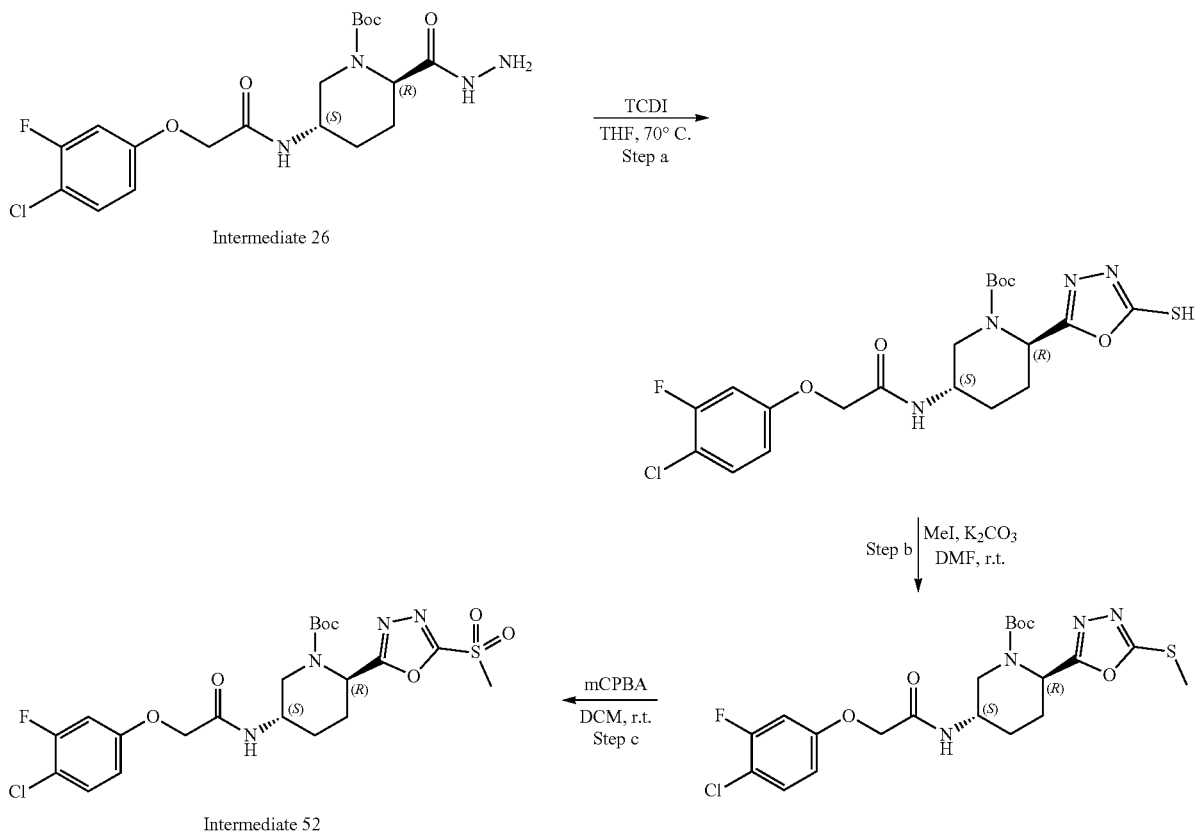

Step 28.a: tert-butyl (2R,5S)-5-[2-(4-chloro-3-fluorophenoxy)acetamido]-2-(5-sulfanyl-1,3,4-oxadiazol-2-yl)piperidine-1-carboxylate

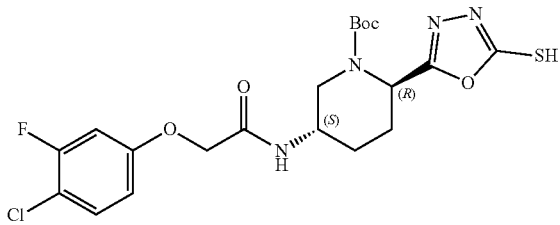

To a solution of tert-butyl (2R,5S)-5-[2-(4-chloro-3-fluorophenoxy)acetamido]-2-(hydrazinecarbonyl)piperidine-1-carboxylate (300 mg, 0.674 mmol, Intermediate 26) in anhydrous THF (15 mL) was added TCDI (144 mg, 0.809 mmol) and the mixture was stirred at 70° C. for 12 h. The reaction mixture was cooled to r.t., diluted with H$_2$O (20 mL) and extracted with EtOAc (2×30 mL). The combined organic extracts were dried over MgSO$_4$ and concentrated in vacuo to afford the title compound (85% purity, 360 mg, 0.628 mmol, 93% yield) as a beige powder; $^1$H NMR (500 MHz, DMSO-d$_6$) δ 8.06 (d, J=6.9 Hz, 1H), 7.98 (s, 1H), 7.48 (t, J=8.9 Hz, 1H), 7.18 (s, 2H), 7.05 (dd, J=11.4, 2.8 Hz, 1H), 6.83 (dd, J=9.0, 2.0 Hz, 1H), 5.31 (s, 1H), 3.89 (s, 2H), 2.97 (d, J=12.0 Hz, 1H), 2.15 (dd, J=11.6, 6.6 Hz, 1H), 1.94 (d, J=13.9 Hz, 1H), 1.78 (t, J=13.5 Hz, 1H), 1.62 (d, J=12.4 Hz, 1H), 1.39 (s, 9H); M/Z: 485, 487 [M−H]$^−$, ESI$^−$, RT=0.98 (S2).

Step 28.b: tert-butyl (2R,5S)-5-[2-(4-chloro-3-fluorophenoxy)acetamido]-2-[5-(methylsulfanyl)-1,3,4-oxadiazol-2-yl]piperidine-1-carboxylate

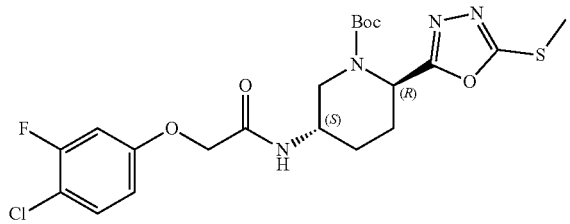

MeI (0.43 mL, 6.98 mmol) was added dropwise to a suspension of tert-butyl (2R,5S)-5-[2-(4-chloro-3-fluorophenoxy)acetamido]-2-(5-sulfanyl-1,3,4-oxadiazol-2-yl)piperidine-1-carboxylate (85% purity, 2.0 g, 3.49 mmol), K$_2$CO$_3$ (965 mg, 6.98 mmol) and DMF (15 mL) and the mixture was stirred at r.t. for 3 h. The reaction mixture was diluted with 1 M aq NaOH solution (10 mL) and extracted with DCM (2×30 mL). The combined organic extracts were dried over MgSO$_4$ and concentrated in vacuo to afford the title compound (1.80 g, 3.41 mmol, 98% yield) as a white solid; $^1$H NMR (400 MHz, DMSO-d$_6$) δ 8.11 (d, J=7.0 Hz, 1H), 7.48 (t, J=8.9 Hz, 1H), 7.05 (dd, J=11.4, 2.9 Hz, 1H), 6.90-6.72 (m, 1H), 5.48 (s, 1H), 4.69-4.52 (m, 2H), 3.91 (d, J=12.7 Hz, 2H), 2.97 (d, J=12.4 Hz, 1H), 2.70 (s, 3H), 2.33-2.16 (m, 1H), 2.02 (d, J=19.2 Hz, 1H), 1.88-1.69 (m, 1H), 1.65 (d, J=13.0 Hz, 1H), 1.39 (s, 9H); M/Z: 401, 403 [M−Boc+H]$^+$, ESI$^+$, RT=1.02 (S2).

Intermediate 52 (Step 28.c): tert-butyl (2R,5S)-5-[2-(4-chloro-3-fluorophenoxy)acetamido]-2-(5-methanesulfonyl-1,3,4-oxadiazol-2-yl)piperidine-1-carboxylate Intermediate 52

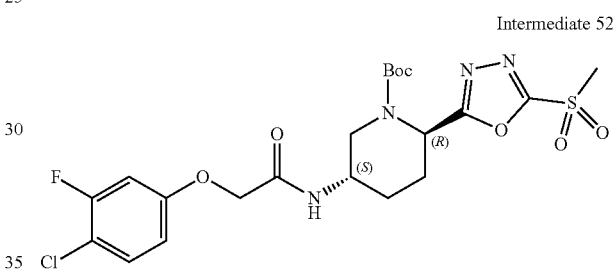

A solution of tert-butyl (2R,5S)-5-[2-(4-chloro-3-fluorophenoxy)acetamido]-2-[5-(methylsulfanyl)-1,3,4-oxadiazol-2-yl]piperidine-1-carboxylate (1.80 g, 3.41 mmol) and m-CPBA (60% purity, 2.95 g, 10.2 mmol) in DCM (40 mL) was stirred at r.t. for 48 h. The reaction mixture was diluted with DCM (20 mL) and satd Na$_2$SO$_3$ solution and stirred at r.t. for 15 min. The organic layer was isolated using a phase separator and then concentrated in vacuo. The residue was purified by chromatography on silica gel (0-40% EtOAc in heptane) to afford the title compound (89% purity, 1.07 g, 1.79 mmol, 52% yield) as a light brown solid; M/Z: 433, 435 [M−Boc+H]$^+$, ESI$^+$, RT=0.99 (S2).

Scheme for route 29

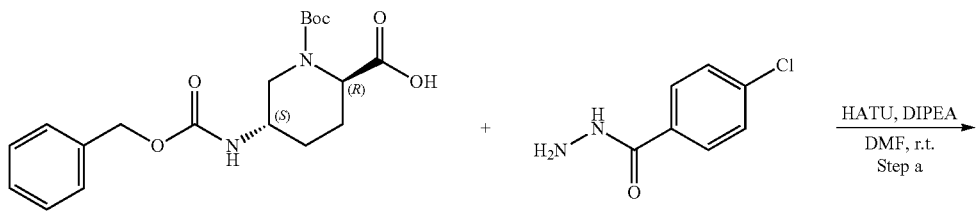

Intermediate 4

-continued

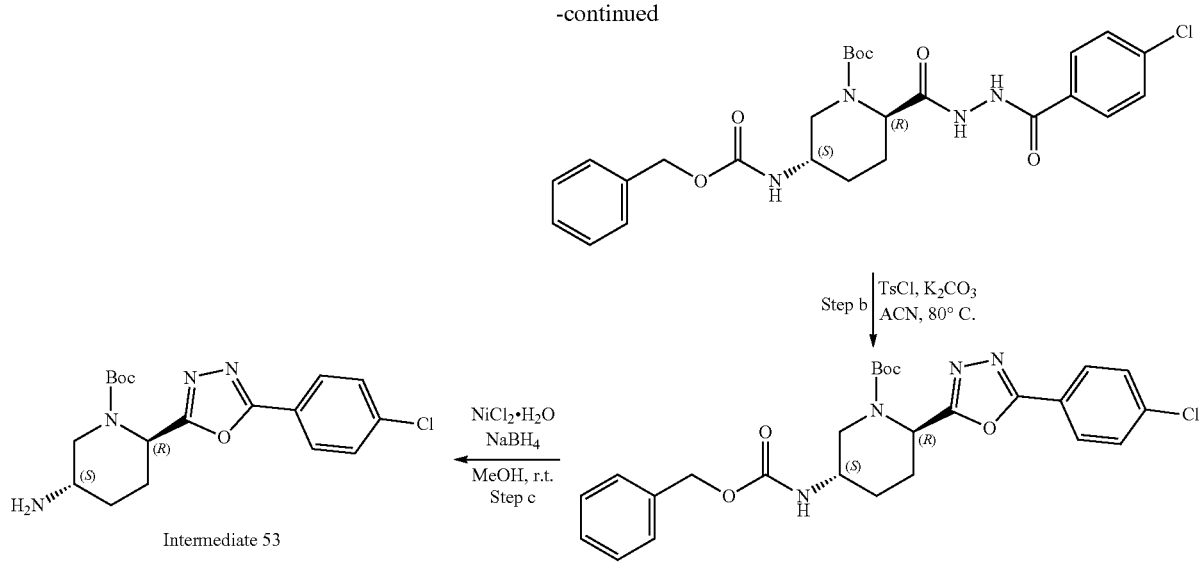

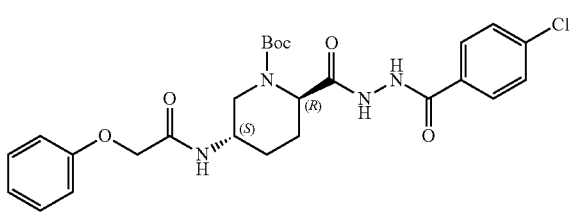

Step 29.a: tert-butyl (2R,5S)-5-{[(benzyloxy)carbonyl]amino}-2-[N'-(4-chlorobenzoyl)hydrazinecarbonyl]piperidine-1-carboxylate To a solution of (2R,5S)-5-{[(benzyloxy)carbonyl]amino}-1-[(tert-butoxy)carbonyl]piperidine-2-carboxylic acid (94% purity, 2.21 g, 5.93 mmol, Intermediate 4), DIPEA (2.1 mL, 11.9 mmol) and 4-chlorobenzohydrazide (1.11 g, 6.52 mmol) in anhydrous DMF (20 mL) was added HATU (2.71 g, 7.11 mmol) and the mixture was stirred at r.t. for 20 h. The reaction mixture was diluted with satd aq NaHCO₃ solution (20 mL) and extracted with EtOAc (2×50 mL). The combined organic extracts were washed with brine, dried over Na₂SO₄, and concentrated in vacuo. The residue was purified by chromatography on silica gel (0-100% EtOAc in heptane) to afford the title compound (76% purity, 1.61 g, 2.43 mmol, 41% yield) as a yellow oil; M/Z: 403, 405 [M-Boc+H]⁺, ESI⁺, RT=0.98 (S2).

Step 29.b: tert-butyl (2R,5S)-5-{[(benzyloxy)carbonyl]amino}-2-[5-(4-chlorophenyl)-1,3,4-oxadiazol-2-yl]piperidine-1-carboxylate

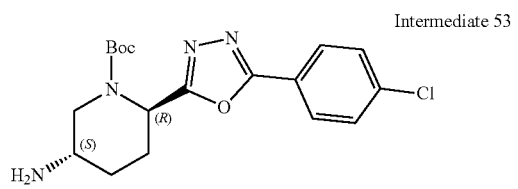

Intermediate 53

A mixture of tert-butyl (2R,5S)-5-{[(benzyloxy)carbonyl]amino}-2-[N-(4-chlorobenzoyl)hydrazinecarbonyl]piperidine-1-carboxylate (76%, 1.61 g, 2.43 mmol), K₂CO₃ (2.02 g, 14.6 mmol) and TsCl (1.39 g, 7.30 mmol) in ACN (12 mL) was stirred at 80° C. for 1.5 h. The reaction mixture was cooled to r.t., diluted with H₂O (10 mL) and brine (10 mL), and extracted with EtOAc (2×30 mL). The combined organic extracts were dried over Na₂SO₄, concentrated in vacuo and purified by chromatography on silica gel (0-50% EtOAc in heptane) to afford the title compound (85% purity, 410 mg, 0.719 mmol, 30% yield) as a beige gum; M/Z: 485, 487 [M+H]⁺, ESI⁺, RT=1.71 (S1).

Intermediate 53 (Step 29.c): tert-butyl (2R,5S)-5-amino-2-[5-(4-chlorophenyl)-1,3,4-oxadiazol-2-yl]piperidine-1-carboxylate To a solution of tert-butyl (2R,5S)-5-{[(benzyloxy)carbonyl]amino}-2-[5-(4-chlorophenyl)-1,3,4-oxadiazol-2-yl]piperidine-1-carboxylate (410 mg, 0.845 mmol) in MeOH (40 mL) at 0° C. was added NiCl₂·H₂O (811 mg, 3.38 mmol) followed by NaBH₄ (959 mg, 25.36 mmol) and the mixture was stirred at r.t. for 18 h. The reaction mixture was concentrated in vacuo, dissolved in H₂O and EtOAc and the resultant suspension was filtered through Celite. The phases were separated and the aqueous layer was further extracted with EtOAc. The combined organic extracts were washed with brine, dried over Na₂SO₄ and concentrated in vacuo. The residue was purified by prep. HPLC (Method 7) to afford the title compound (142 mg, 0.375 mmol, 44% yield); ¹H NMR (500 MHz, chloroform-d) δ 8.40 (s, 1H), 7.93 (d, J=8.5 Hz, 2H), 7.48 (d, J=8.4 Hz, 2H), 5.65 (s, 1H), 4.31 (d, J=13.4 Hz, 1H), 3.61 (s, 1H), 3.24 (s, 1H), 2.45 (s, 1H), 2.25 (d, J=13.3 Hz, 1H), 2.08 (s, 2H), 1.45 (s, 9H); M/Z: 379, 381 [M+H]⁺, ESI⁺, RT=0.73 (S2).

Scheme for route 30

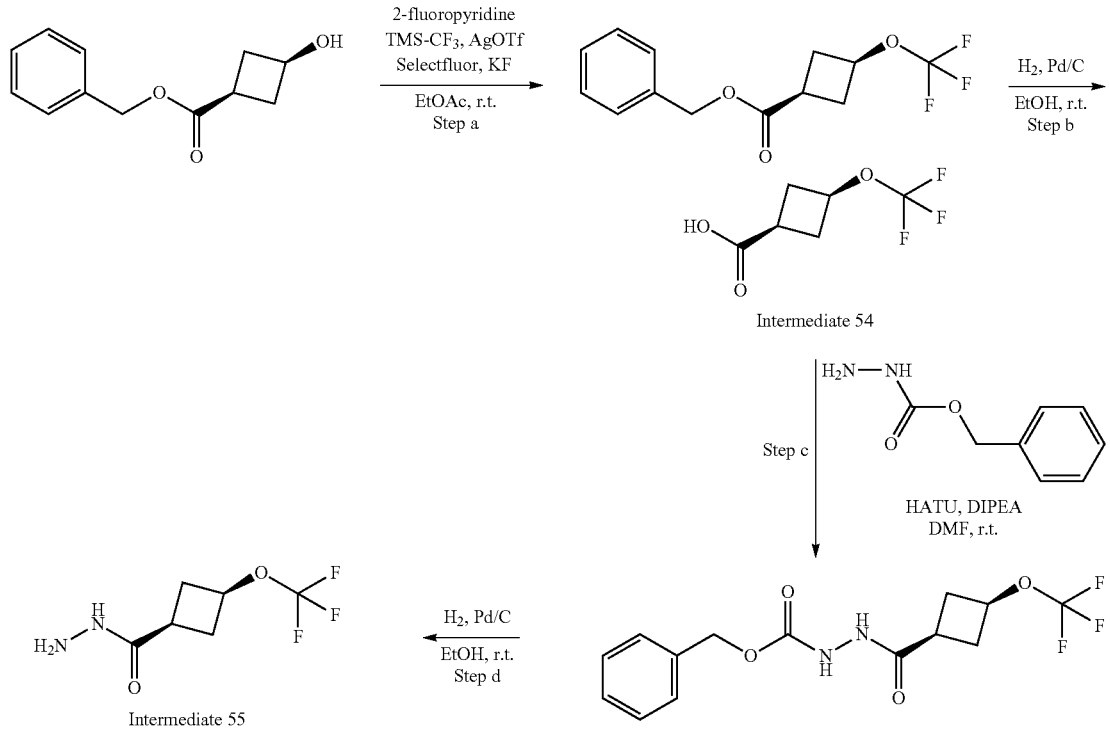

Intermediate 54

Intermediate 55

Step 30.a: benzyl (1s,3s)-3-(trifluoromethoxy)cyclobutane-1-carboxylate

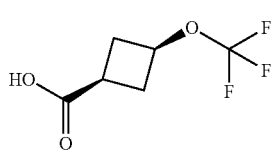

2-Fluoropyridine (15 mL, 0.180 mol) and TMS-CF$_3$ (27 mL, 0.180 mol) were successively added dropwise to a solution of benzyl (1s,3s)-3-hydroxycyclobutane-1-carboxylate (12.4 g, 59.9 mmol), AgOTf (46.3 g, 0.180 mol), Selecfluor (31.8 g, 89.8 mmol) and KF (13.9 g, 0.240 mol) in EtOAc (500 mL) and the mixture was stirred at r.t. under N$_2$ for 20 h in a foil covered flask. The reaction mixture was filtered through Celite, washing with EtOAc (100 mL), and concentrated in vacuo. The residue was purified by chromatography on silica gel (5-30% EtOAc in heptane) to afford the title compound (7.47 g, 27.2 mmol, 45% yield) as a colourless oil; $^1$H NMR (400 MHz, chloroform-d) δ 7.43-7.29 (m, 5H), 5.14 (s, 2H), 4.57 (p, J=7.5 Hz, 1H), 2.82-2.69 (m, 1H), 2.64 (dtd, J=10.0, 7.3, 2.6 Hz, 2H), 2.53 (qd, J=9.8, 9.4, 2.0 Hz, 2H); 19F NMR (376 MHz, chloroform-d) δ −59.56.

Intermediate 54 (Step 30.b): (1s,3s)-3-(trifluoromethoxy)cyclobutane-1-carboxylic acid Intermediate 54

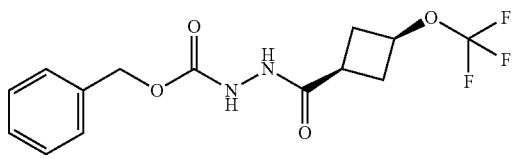 [SMILES: O=C(NNC(=O)[C@H]1C[C@@H](OC(F)(F)F)C1)OCc1ccccc1]

A suspension of benzyl (1s,3s)-3-(trifluoromethoxy)cyclobutane-1-carboxylate (7.85 g, 28.6 mmol) and 5% Pd/C (3.05 g, 1.43 mmol) in EtOH (250 mL) was stirred under H$_2$ at r.t. for 18 h. The reaction mixture was filtered through Celite and concentrated in vacuo to afford the title compound (5.09 g, 27.6 mmol, 97% yield) as a yellow oil; $^1$H NMR (400 MHz, chloroform-d) δ 4.60 (p, J=7.5 Hz, 1H), 2.89-2.61 (m, 4H), 2.61-2.37 (m, 2H); $^{19}$F NMR (376 MHz, chloroform-d) δ −59.62 (3F, s).

Step 30.c: ({[(benzyloxy)carbonyl]amino}amino)[(1s,3s)-3-(trifluoromethoxy)cyclobutyl]methanone To a solution of (1s,3s)-3-(trifluoromethoxy)cyclobutane-1-carboxylic acid (1.00 g, 5.43 mmol, Intermediate 54) in anhydrous DMF (10 mL) at 0° C. was added HATU (2.27 g, 5.97 mmol) followed by DIPEA (1.9 mL, 10.9 mmol) and stirred for 10 min. Benzyl hydrazinecarboxylate (0.90 g, 5.43 mmol) was added and the mixture was stirred at r.t. for 20 h. The reaction mixture was diluted with H$_2$O (20 mL) and extracted with EtOAc (2×50 mL). The combined organic extracts were dried over Na$_2$SO$_4$ and concentrated in vacuo. Purification by chromatography on silica gel (15-100% EtOAc in heptane) afforded the title compound (1.03 g, 3.07 mmol, 56% yield) as a white powder; $^1$H NMR (400 MHz, DMSO-d$_6$) δ 9.78 (s, 1H), 9.35-8.75 (m, 1H), 7.52-

7.16 (m, 5H), 5.16-4.96 (m, 2H), 4.89-4.66 (m, 1H), 2.75-2.57 (m, 1H), 2.50 (s, 2H), 2.35-2.14 (m, 2H); M/Z: 333 [M+H]⁺, ESI⁺, RT=0.88 (S2).

Intermediate 55 (Step 30.d): (1s,3s)-3-(trifluoromethoxy)cyclobutane-1-carbohydrazide

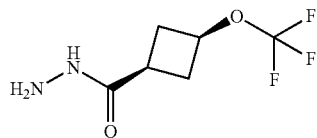

Intermediate 55

A mixture of ({[(benzyloxy)carbonyl]amino}amino)[(1s,3s)-3-(trifluoromethoxy)cyclobutyl]methanone (1.03 g, 3.07 mmol) and 10% Pd/C (100 mg, 3.07 mmol) in EtOH (10 mL) was stirred under H₂ at r.t. for 18 h. The reaction mixture was filtered through Celite and concentrated in vacuo to afford the title compound (0.56 g, 2.68 mmol, 87% yield) as a grey solid; ¹H NMR (400 MHz, DMSO-d₆) δ 9.08 (s, 1H), 4.82-4.66 (m, 1H), 4.30 (s, 2H), 2.60-2.51 (m, 1H), 2.48-2.38 (m, 2H), 2.33-2.21 (m, 2H); M/Z: 199 [M+H]⁺, ESI⁺, RT=0.54 (S2).

Scheme for route 31

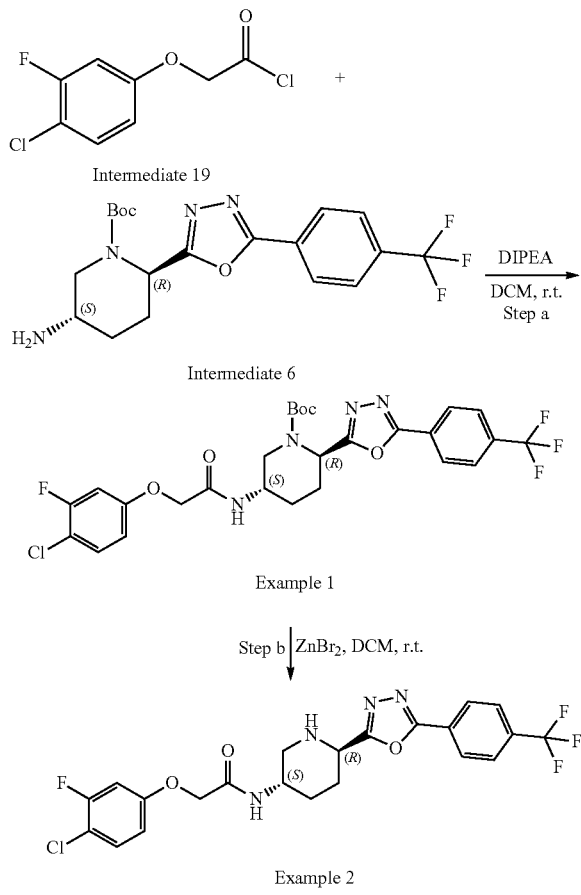

Example 1 (Step 31.a): tert-butyl (2R,5S)-5-[2-(4-chloro-3-fluorophenoxy)acetamido]-2-{5-[4-(trifluoromethyl)phenyl]-1,3,4-oxadiazol-2-yl}piperidine-1-carboxylate

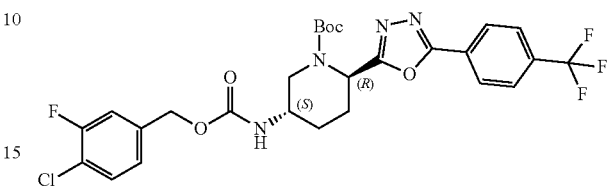

Example 1

To a solution of 2-(4-chloro-3-fluorophenoxy)acetyl chloride (90% purity, 70 mg, 0.282 mmol, Intermediate 19) in DCM (2 mL) was added tert-butyl (2R,5S)-5-amino-2-{5-[4-(trifluoromethyl)phenyl]-1,3,4-oxadiazol-2-yl}piperidine-1-carboxylate (123 mg, 0.282 mmol, Intermediate 6) and DIPEA (0.099 mL, 0.565 mmol) and the mixture was stirred at r.t. for 4 h. The reaction mixture was diluted with H₂O (5 mL) and extracted with DCM (3×5 mL). The combined organic extracts were dried over MgSO₄, concentrated in vacuo and purified by chromatography on silica gel (17-100% EtOAc in heptane) to afford the title compound (78 mg, 0.130 mmol, 46% yield) as a brown powder; M/Z: 499, 501 [M-Boc+H]⁺, ESI⁺, RT=1.20 (S2).

Example 2 (Step 31.b): 2-(4-chloro-3-fluorophenoxy)-N-[(3S,6R)-6-{5-[4-(trifluoromethyl)phenyl]-1,3,4-oxadiazol-2-yl}piperidin-3-yl]acetamide

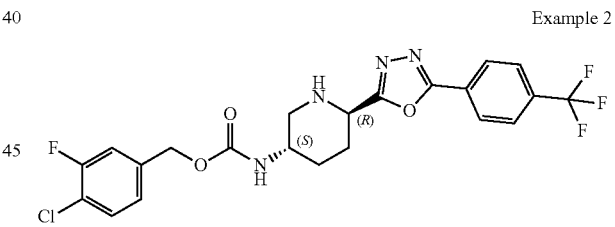

Example 2

To a solution of tert-butyl (2R,5S)-5-[2-(4-chloro-3-fluorophenoxy)acetamido]-2-{5-[4-(trifluoromethyl)phenyl]-1,3,4-oxadiazol-2-yl}piperidine-1-carboxylate (78 mg, 0.130 mmol, Example 1) in DCM (2 mL) was added ZnBr₂ (88 mg, 0.391 mmol) and the mixture was stirred at r.t. for 18 h. The reaction mixture was diluted with satd aq NaHCO₃ solution (3 mL) and extracted with DCM:IPA (80:20) (3×3 mL). The combined organic extracts were dried using a phase separator, concentrated in vacuo, and purified by prep. HPLC (Method 4) to afford the title compound (8.0 mg, 0.0152 mmol, 12% yield) as a white powder; ¹H NMR (500 MHz, DMSO-d₆) δ 8.26-8.17 (m, 2H), 8.04-7.94 (m, 3H), 7.50 (t, J=8.9 Hz, 1H), 7.08 (dd, J=11.4, 2.8 Hz, 1H), 6.89-6.83 (m, 1H), 4.54 (s, 2H), 4.05-3.98 (m, 1H), 3.81-3.69 (m, 1H), 3.07-2.96 (m, 2H), 2.15-2.06 (m, 1H), 1.99-1.91 (m, 1H), 1.85-1.73 (m, 1H), 1.63-1.51 (m, 1H); M/Z: 499, 501 [M+H]⁺, ESI⁺, RT=2.47 (S4).

Scheme for route 32

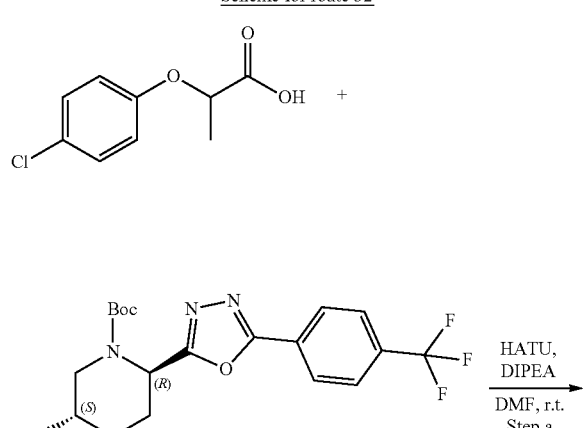

Intermediate 6

Example 3

Step b | TFA, DCM, r.t.

Example 4

Example 3 (Step 32.a): tert-butyl (2R,5S)-5-[2-(4-chlorophenoxy)propanamido]-2-{5-[4-(trifluoromethyl)phenyl]-1,3,4-oxadiazol-2-yl}piperidine-1-carboxylate To a solution of 2-(4-chlorophenoxy)propanoic acid (69 mg, 0.343 mmol) in DMF (1 mL) was added DIPEA (0.18 mL, 1.03 mmol) and HATU (143 mg, 0.377 mmol) and stirred at r.t. for 10 min. tert-butyl (2R,5S)-5-amino-2-{5-[4-(trifluoromethyl)phenyl]-1,3,4-oxadiazol-2-yl}piperidine-1-carboxylate (141 mg, 0.343 mmol, Intermediate 6) was added and the mixture was stirred at r.t. for 20 h. The reaction mixture was diluted with H$_2$O (5 mL) and extracted with EtOAc (3×5 mL). The combined organic extracts were washed with brine (2×15 mL), dried over MgSO$_4$ and concentrated in vacuo. The residue was purified by chromatography on silica gel (12-100% EtOAc in heptane) to afford the title compound (90% purity, 123 mg, 0.186 mmol, 54% yield) as a clear oil; M/Z: 495, 497 [M-Boc+H]$^+$, ESI$^+$, RT=1.22 (S2).

Example 4 (Step 32.b): 2-(4-chlorophenoxy)-N-[(3S,6R)-6-{5-[4-(trifluoromethyl)phenyl]-1,3,4-oxadiazol-2-yl}piperidin-3-yl]propanamide To a solution of tert-butyl (2R,5S)-5-[2-(4-chlorophenoxy)propanamido]-2-{5-[4-(trifluoromethyl)phenyl]-1,3,4-oxadiazol-2-yl}piperidine-1-carboxylate (107 mg, 0.181 mmol, Example 3) in DCM (2 mL) was added TFA (70 μL, 0.947 mmol) and the mixture was stirred at r.t. for 18 h. The reaction mixture was concentrated in vacuo, dissolved in satd aq NaHCO$_3$ solution (10 mL) and extracted with EtOAc (3×10 mL). The combined organic extracts were dried over MgSO$_4$, concentrated in vacuo and triturated using DMSO:MeCN:H$_2$O (60:30:10), washing with MeCN (1 mL), to afford the title compound (19 mg, 0.0383 mmol, 21% yield) as a white powder; $^1$H NMR (500 MHz, DMSO-d$_6$) δ 8.25-8.19 (m, 2H), 8.03-7.94 (m, 3H), 7.36-7.30 (m, 2H), 6.96-6.89 (m, 2H), 4.72-4.64 (m, 1H), 4.02-3.95 (m, 1H), 3.74-3.63 (m, 1H), 3.03-2.91 (m, 2H), 2.13-2.00 (m, 1H), 1.96-1.82 (m, 1H), 1.82-1.69 (m, 1H), 1.60-1.46 (m, 1H), 1.43 (d, J=6.6 Hz, 3H); M/Z: 495, 497 [M+H]$^+$, ESI$^+$, RT=2.47 (S4).

The example compound in Table 9 was synthesised according to the synthetic steps of general route 32 as exemplified by Example 4 using the corresponding intermediates.

TABLE 9

| Ex | Structure | Name | Intermediates | LCMS data | ¹H NMR |
|---|---|---|---|---|---|
| 5 | 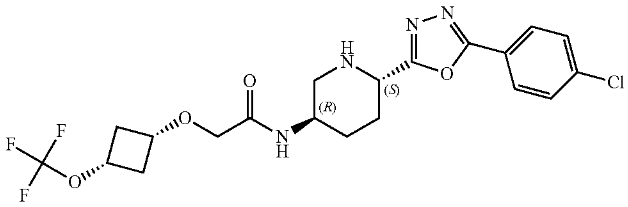 | N-[(3R,6S)-6-[5-(4-chloro-phenyl)-1,3,4-oxa-diazol-2-yl]piperidin-3-yl]-2-[(1s,3s)-3-(trifluoro-methoxy)cyclo-butoxy]acetamide | tert-butyl (2S,5R)-5-amino-2-[5-(4-chlorophenyl)-1,3,4-oxadiazol-2-yl]piperidine-1-carboxylate (Intermediate 46) and 2-[(1s,3s)-3-(trifluoro methoxy)cyclo-butoxy]acectic acid (described in WO2019032743 A1) | M/Z: 475, 477 [M + H]⁺, ESI⁺, RT = 2.32 (S4) | ¹H NMR (500 MHz, DMSO-d₆) δ 8.08-7.98 (m, 2H), 7.72-7.66 (m, 2H), 7.62 (d, J = 8.1 Hz, 1H), 4.51-4.41 (m, 1H), 4.26-4.20 (m, 1H), 3.78 (s, 3H), 3.75-3.66 (m, 1H), 3.08 (s, 1H), 2.86-2.79 (m, 1H), 2.78-2.69 (m, 2H), 2.66-2.61 (m, 1H), 2.17-2.12 (m, 1H), 2.12-2.01 (m, 2H), 1.94-1.84 (m, 1H), 1.77-1.69 (m, 2H). |

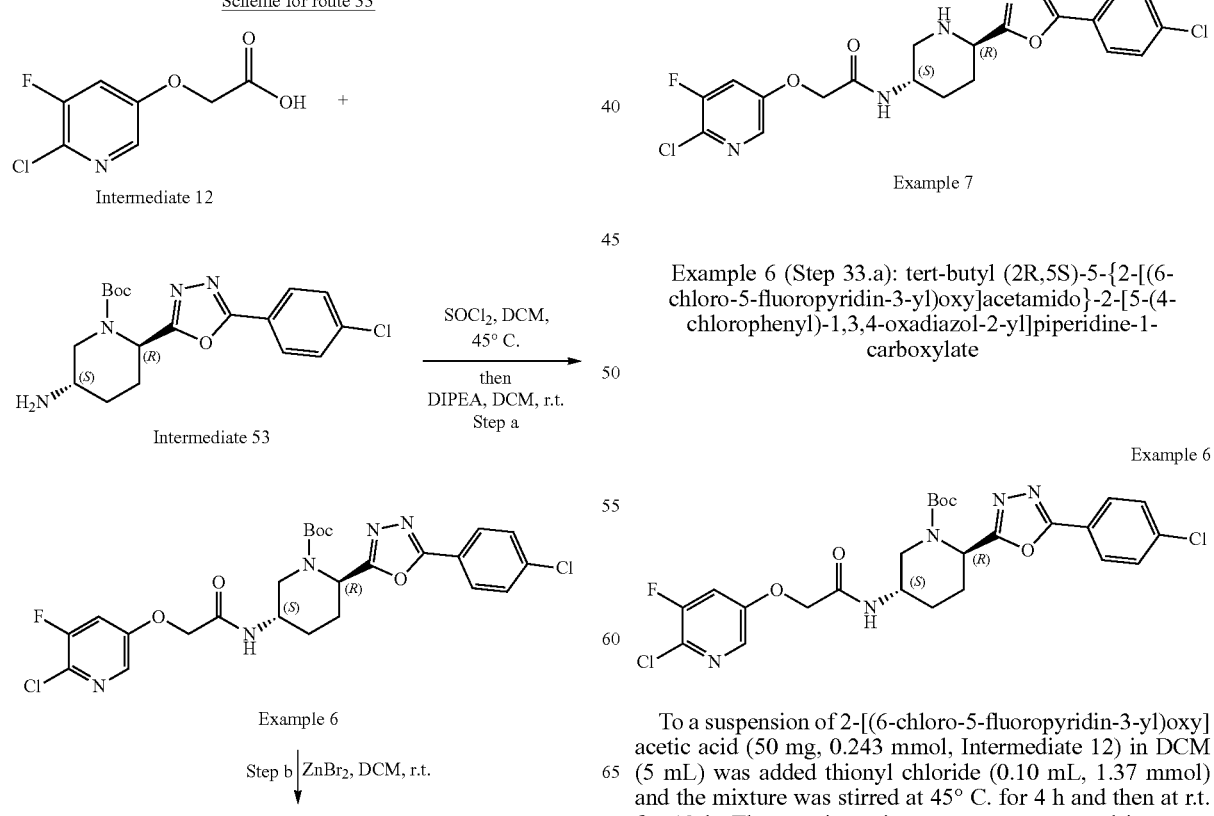

Example 6 (Step 33.a): tert-butyl (2R,5S)-5-{2-[(6-chloro-5-fluoropyridin-3-yl)oxy]acetamido}-2-[5-(4-chlorophenyl)-1,3,4-oxadiazol-2-yl]piperidine-1-carboxylate To a suspension of 2-[(6-chloro-5-fluoropyridin-3-yl)oxy]acetic acid (50 mg, 0.243 mmol, Intermediate 12) in DCM (5 mL) was added thionyl chloride (0.10 mL, 1.37 mmol) and the mixture was stirred at 45° C. for 4 h and then at r.t. for 18 h. The reaction mixture was concentrated in vacuo and azetroped using heptane. The resultant residue was dissolved in DCM (5 mL) and added to a solution of tert-butyl (2R,5S)-5-amino-2-[5-(4-chlorophenyl)-1,3,4-oxadiazol-2-yl]piperidine-1-carboxylate (71 mg, 0.187 mmol, Intermediate 53) and DIPEA (0.16 mL, 0.937 mmol) in DCM (5 mL). The reaction mixture was stirred at r.t. for 2 h, then poured on to satd. aq NaHCO$_3$ solution (10 mL). The aqueous solution was extracted with DCM (2×20 mL) and the combined organic extracts were dried over Na$_2$SO$_4$ and concentrated in vacuo. Purification by chromatography on silica gel (20-100% EtOAc in heptane) afforded the title compound (27 mg, 0.0467 mmol, 25% yield) as a colorless oil; $^1$H NMR (400 MHz, chloroform-d) δ 8.00 (d, J=2.6 Hz, 1H), 7.96 (d, J=8.6 Hz, 2H), 7.49 (d, J=8.5 Hz, 2H), 7.14 (dd, J=8.8, 2.6 Hz, 1H), 4.60-4.48 (m, 2H), 4.24-4.08 (m, 2H), 2.30 (d, J=13.0 Hz, 1H), 2.14-1.95 (m, 2H), 1.66 (s, 1H), 1.49 (s, 9H), 1.28-1.22 (m, 2H); M/Z: 588, 590, 592 [M+Na]$^+$, ESI$^+$, RT=1.09 (S2).

Example 7 (Step 33.b): 2-[(6-chloro-5-fluoropyridin-3-yl)oxy]-N-[(3S,6R)-6-[5-(4-chlorophenyl)-1,3,4-oxadiazol-2-yl]piperidin-3-yl]acetamide Example 7

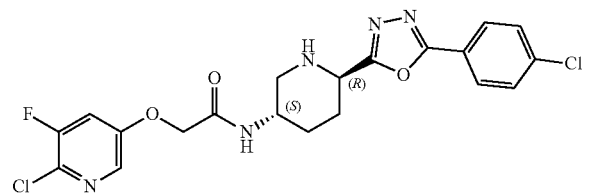

To a solution of tert-butyl (2R,5S)-5-{2-[(6-chloro-5-fluoropyridin-3-yl)oxy]acetamido}-2-[5-(4-chlorophenyl)-1,3,4-oxadiazol-2-yl]piperidine-1-carboxylate (48 mg, 0.0830 mmol, Example 6) in DCM (2 mL) was added ZnBr$_2$ (56 mg, 0.249 mmol) and the reaction mixture was stirred at r.t. for 48 h. The reaction mixture was filtered under vacuum, washing with DCM, and the filtrate concentrated in vacuo. The residue was purified by prep. HPLC (Method 1) to afford the title compound (11 mg, 0.0211 mmol, 25% yield) as a white solid; $^1$H NMR (500 MHz, DMSO-d$_6$) δ 8.20 (d, J=7.7 Hz, 1H), 8.09 (d, J=2.6 Hz, 1H), 8.03 (d, J=8.6 Hz, 2H), 7.75-7.68 (m, 2H), 4.68 (s, 2H), 4.38 (s, 1H), 3.90 (s, 1H), 3.22 (d, J=11.4 Hz, 1H), 2.71 (t, J=11.1 Hz, 1H), 2.24 (d, J=11.1 Hz, 1H), 1.99 (d, J=10.3 Hz, 1H), 1.94-1.84 (m, 1H), 1.69-1.59 (m, 1H); M/Z: 466, 468, 470 [M+H]$^+$, ESI$^+$, RT=2.01 (S4).

Scheme for route 34

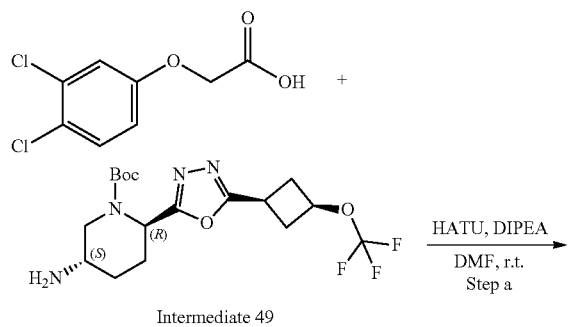

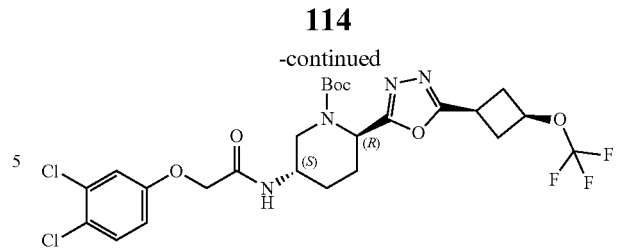

Example 8

Step b | ZnBr$_2$, DCM, r.t.

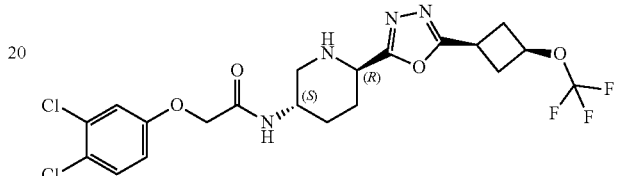

Example 9

Example 8 (Step 34.a): tert-butyl (2R,5S)-5-[2-(3,4-dichlorophenoxy)acetamido]-2-{5-[(1s,3s)-3-(trifluoromethoxy)cyclobutyl]-1,3,4-oxadiazol-2-yl}piperidine-1-carboxylate Example 8

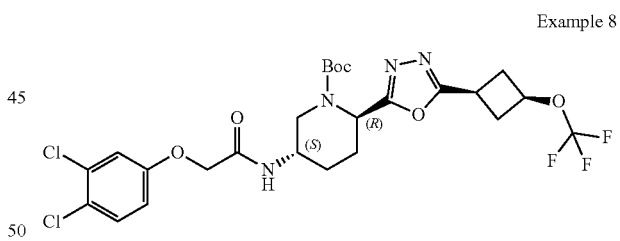

To a solution of 2-(3,4-dichlorophenoxy)acetic acid (104 mg, 0.472 mmol) in DMF (4 mL) was added HATU (180 mg, 0.472 mmol) and DIPEA (0.21 mL, 1.18 mmol) and stirred at r.t. for 10 min. tert-butyl (2R,5S)-5-amino-2-{5-[(1s,3s)-3-(trifluoromethoxy)cyclobutyl]-1,3,4-oxadiazol-2-yl}piperidine-1-carboxylate (160 mg, 0.394 mmol, Intermediate 49) was added and the mixture was stirred at r.t. for 3 h. The reaction mixture was diluted with H$_2$O (10 mL) and extracted with EtOAc (2×20 mL). The combined organic extracts were dried over Na$_2$SO$_4$ and concentrated in vacuo to afford the title compound (52% purity, 105 mg, 0.0896 mmol, 23% yield) as yellow oil; M/Z: 509, 511 [M-$^t$Butyl+H]$^+$, ESI$^+$, RT=1.17 (S2).

Example 9 (Step 34.b): 2-(3,4-dichlorophenoxy)-N-[(3S,6R)-6-{5-[(1s,3s)-3-(trifluoromethoxy)cyclobutyl]-1,3,4-oxadiazol-2-yl}piperidin-3-yl]acetamide Example 9

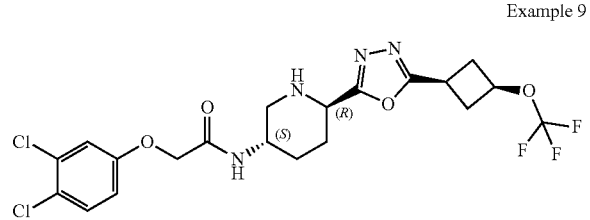

To a solution of tert-butyl (2R,5S4-5-[2-(3,4-dichlorophenoxy)acetamido]-2-{5-[(1s,3s)-3-(trifluoromethoxy)cyclobutyl]-1,3,4-oxadiazol-2-yl}piperidine-1-carboxylate (520 purity, 105 mg, 0.0896 mmol, Example 8) in DCM (1 mL) was added ZnBr$_2$ (61 mg, 0.269 mmol) and the mixture was stirred at r.t. for 6 h. The reaction mixture was diluted with H$_2$O (10 mL) and extracted with DCM/IPA (9:1, 2×20 mL). The combined organic extracts were dried over MgSO$_4$, concentrated in vacuo and purified by prep. HPLC (Method 3) to afford the title compound (6.7 mg, 0.0130 mmol, 15% yield) as a white powder; $^1$H NMR (400 MHz, DMSO-d$_6$) δ 7.98 (d, J=8.0 Hz, 1H), 7.55 (d, J=8.9 Hz, 1H), 7.26 (d, J=2.9 Hz, 1H), 6.99 (dd, J=8.9, 2.9 Hz, 1H), 4.98-4.87 (m, 1H), 4.53 (s, 2H), 3.86 (dd, J=10.5, 2.7 Hz, 1H), 3.71 (s, 1H), 3.45 (d, J=2.1 Hz, 1H), 2.99 (dd, J=11.8, 2.9 Hz, 1H), 2.89-2.80 (m, 3H), 2.43 (s, 3H), 2.00-1.97 (m, 1H), 1.92-1.88 (i, 1H), 1.69-1.64 (m, 1H), 1.54-1.49 (m, 1H); M/Z: 509, 511 [M+H]$^+$, ESI$^+$, RT=2.42 (S4).

Example compounds in Table 10 were synthesised according to the synthetic steps of general route 34 as exemplified by Example 9 using the corresponding intermediates.

TABLE 10

| Ex | Structure | Name | Intermediates | LCMS data | $^1$H NMR |
|---|---|---|---|---|---|
| 10 | 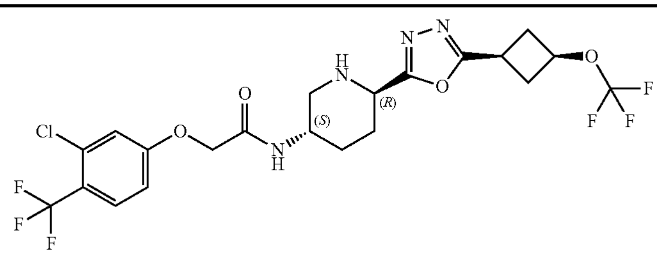 | 2-[3-chloro-4-(trifluoromethyl)phenoxy]-N-[(3S,6R)-6-{5-[(1s,3s)-3-(trifluoromethoxy)cyclobutyl]-1,3,4-oxadiazol-2-yl}piperidin-3-yl]acetamide | tert-butyl (2R,5S)-5-amino-2-{5-[(1s,3s)-3-(trifluoromethoxy)cyclobutyl]-1,3,4-oxadiazol-2-yl}piperidine-1-carboxylate (Intermediate 49) and 2-[3-chloro-4-(trifluoromethyl)phenoxy] acetic acid (Intermediate 7) | M/Z: 543, 545 [M + H]$^+$, ESI$^+$, RT = 2.53 (S4) | $^1$H NMR (400 MHz, DMSO-d$_6$) δ 8.03 (d, J = 8.0 Hz, 1H), 7.79 (d, J = 8.9 Hz, 1H), 7.31 (d, J = 2.4 Hz, 1H), 7.09 (dd, J = 8.7, 2.3 Hz, 1H), 5.02-4.83 (m, 1H), 4.64 (s, 2H), 3.87 (dd, J = 10.6, 2.7 Hz, 1H), 3.78-3.66 (m, 1H), 3.45-3.39 (m, 1H), 3.00 (dd, J = 11.8, 3.1 Hz, 1H), 2.91-2.79 (m, 3H), 2.44 (d, J = 11.7 Hz, 3H), 2.11-1.97 (m, 1H), 1.95-1.87 (m, 1H), 1.75-1.63 (m, 1H), 1.55-1.47 (m, 1H). |
| 11 | 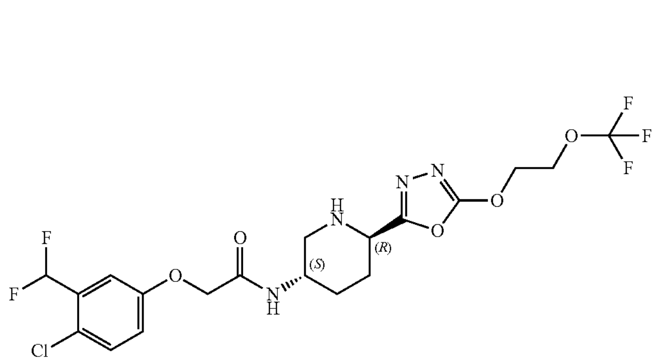 | 2-[4-chloro-3-(difluoromethyl)phenoxy]-N-[(3S,6R)-6-{5-[2-(trifluoromethoxy)ethoxy]-1,3,4-oxadiazol-2-yl}piperidin-3-yl]acetamide | tert-butyl (2R,5S)-5-amino-2-{5-[2-(trifluoromethoxy)ethoxy]-1,3,4-oxadiazol-2-yl}piperidine-1-carboxylate (Intermediate 48) and 2- | M/Z: 515, 517 [M + H]$^+$, ESI$^+$, RT = 2.27 (S4) | $^1$H NMR (400 Hz, DMSO-d$_6$) δ 8.01 (d, J = 8.1 Hz, 1H), 7.57-7.45 (m, 1H), 7.31-7.02 (m, 2H), 4.74-4.62 (m, 2H), 4.56 (s, 2H), 4.51-4.39 (m, 2H), 3.82-3.62 (m, 2H), 3.05-2.90 (m, 1H), 2.86-2.72 (m, 1H), 2.44-2.38 (m, 1H), 2.01-1.83 (m, 2H), 1.73-1.56 (m, 1H), 1.56-1.41 |

TABLE 10-continued

| Ex | Structure | Name | Intermediates | LCMS data | ¹H NMR |
|---|---|---|---|---|---|
| | | | [4-chloro-3-(difluoromethyl)phenoxy]acetic acid (Intermediate 17) | | (m, 1H). |
| 12 | 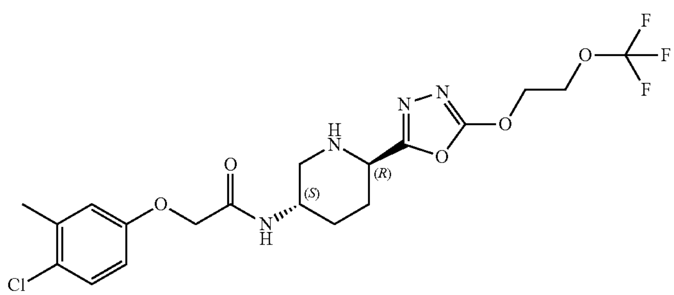 | 2-(4-chloro-3-methylphenoxy)-N-[(3S,6R)-6-{5-[2-(trifluoromethoxy)ethoxy]-1,3,4-oxadiazol-2-yl}piperidin-3-yl]acetamide | tert-butyl (2R,5S)-5-amino-2-{5-[2-(trifluoromethoxy)ethoxy]-1,3,4-oxadiazol-2-yl}piperidine-1-carboxylate (Intermediate 48) and 2-(4-chloro-3-methylphenoxy)acetic acid (Intermediate 14) | M/Z: 479, 481 [M + H]⁺, ESI⁺, RT = 2.34 (S4) | ¹H NMR (500 MHz, chloroform-d) δ 7.27 (s, 1H), 6.84-6.80 (m, 1H), 6.78-6.73 (m, 1H), 6.71 (dd, J = 8.7, 3.0 Hz, 1H), 4.72-4.67 (m, 2H), 4.45 (s, 2H), 4.36-4.31 (m, 2H), 4.09-4.01 (m, 1H), 3.98 (dd, J = 7.9, 3.4 Hz, 1H), 3.30 (dd, J = 12.0, 3.5 Hz, 1H), 2.62 (dd, J = 12.0, 7.8 Hz, 1H), 2.36 (s, 3H), 2.13-2.02 (m, 2H), 2.00-1.86 (m, 2H), 1.66-1.58 (m, 1H). |
| 13 | 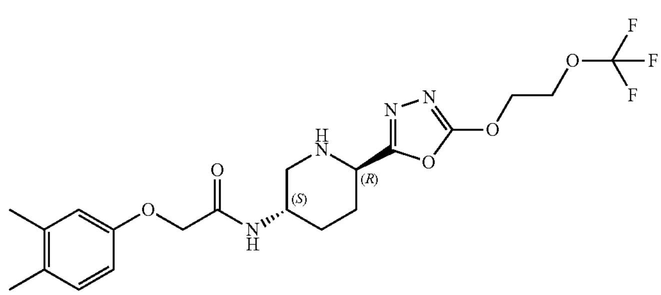 | 2-(3,4-dimethylphenoxy)-N-[(3S,6R)-6-{5-[2-(trifluoromethoxy)ethoxy]-1,3,4-oxadiazol-2-yl}piperidin-3-yl]acetamide | tert-butyl (2R,5S)-5-amino-2-{5-[2-(trifluoromethoxy)ethoxy]-1,3,4-oxadiazol-2-yl}piperidine-1-carboxylate (Intermediate 48) and 2-(3,4-dimethylphenoxy)acetic acid | M/Z: 459 [M + H]⁺, ESI⁺, RT = 2.26 (S4) | ¹H NMR (500 MHz, chloroform-d) δ 7.08-7.03 (m, 1H), 6.82-6.76 (m, 1H), 6.76-6.73 (m, 1H), 6.66 (dd, J = 8.2, 2.7 Hz, 1H), 4.72-4.67 (m, 2H), 4.45 (s, 2H), 4.36-4.31 (m, 2H), 4.08-4.00 (m, 1H), 3.97 (dd, 8.2, 3.1 Hz, 1H), 3.30 (dd, J = 12.0, 3.5 Hz, 1H), 2.61 (dd, J = 12.0, 8.0 Hz, 1H), 2.25 (s, 3H), 2.21 (s, 3H), 2.09 (dd, J = 11.4, 4.4 Hz, 2H), 1.96-1.85 (m, 2H), 1.64-1.57 (m, 2H). |

TABLE 10-continued

| Ex | Structure | Name | Intermediates | LCMS data | ¹H NMR |
|---|---|---|---|---|---|
| 14 | 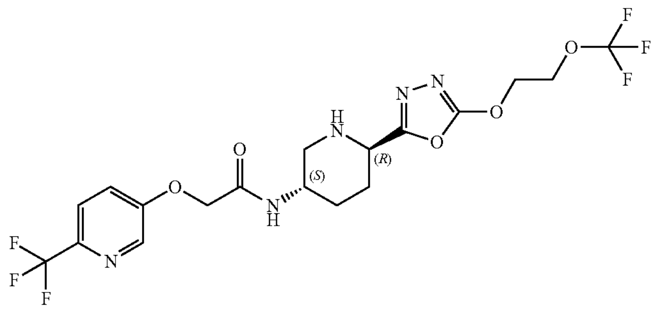 | N-[(3S,6R)-6-{5-[2-(trifluoromethoxy)ethoxy]-1,3,4-oxadiazol-2-yl}piperidin-3-yl]-2-{[6-(trifluoromethyl)pyridin-3-yl]oxy}acetamide | tert-butyl (2R,5S)-5-amino-2-{5-[2-(trifluoromethoxy)ethoxy]-1,3,4-oxadiazol-2-yl}piperidine-1-carboxylate (Intermediate 48) and 2-{[6-(trifluoromethyl)pyridin-3-yl]oxy}acetic acid (Intermediate 13) | M/Z: 500 [M + H]⁺, ESI⁺, RT = 1.84 (S4) | ¹H NMR (500 MHz, DMSO-$d_6$) δ 8.47 (d, J = 2.8 Hz, 1H), 8.08 (d, J = 8.0 Hz, 1H), 7.87 (d, J = 8.7 Hz, 1H), 7.56 (dd, J = 8.7, 2.8 Hz, 1H), 4.71 (s, 2H), 4.70-4.66 (m, 2H), 4.50-4.45 (m, 2H), 3.81-3.74 (m, 1H), 3.74-3.66 (m, 1H), 2.99 (d, J = 11.9 Hz, 1H), 2.81 (s, 1H), 2.47-2.40 (m, 1H), 2.01-1.86 (m, 2H), 1.71-1.60 (m, 1H), 1.54-1.43 (m, 1H). |
| 15 | 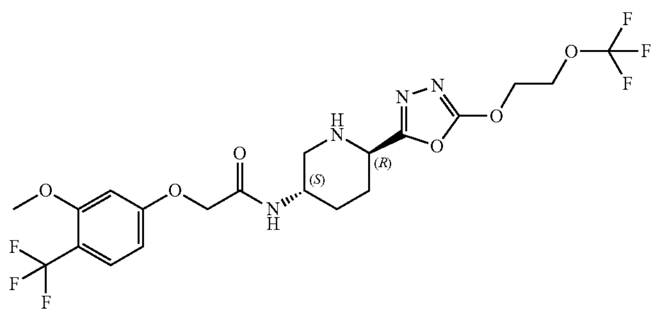 | 2-[3-methoxy-4-(trifluoromethyl)phenoxy]-N-[(3S,6R)-6-{5-[2-(trifluoromethoxy)ethoxy]-1,3,4-oxadiazol-2-yl}piperidin-3-yl]acetamide | tert-butyl (2R,5S)-5-amino-2-{5-[2-(trifluoromethoxy)ethoxy]-1,3,4-oxadiazol-2-yl}piperidine-1-carboxylate (Intermediate 48) and 2-[3-methoxy-4-(trifluoromethyl)phenoxy]acetic acid (Intermediate 15) | M/Z: 529, 531 [M + H]⁺, ESI⁺, RT = 2.28 (S4) | ¹H NMR (500 MHz, DMSO-$d_6$) δ 8.00 (d, J = 8.1 Hz, 1H), 7.53 (d, J = 8.8 Hz, 1H), 6.81 (d, J = 2.0 Hz, 1H), 6.63 (dd, J = 8.7, 2.2 Hz, 1H), 4.73-4.65 (m, 2H), 4.59 (s, 2H), 4.50-4.46 (m, 2H), 3.87 (s, 3H), 3.80-3.68 (m, 2H), 3.04-2.95 (m, 1H), 2.85-2.78 (m, 1H), 2.46-2.41 (m, 1H), 1.99-1.88 (m, 2H), 1.71-1.61 (m, 1H), 1.57-1.47 (m, 1H). |
| 112 | 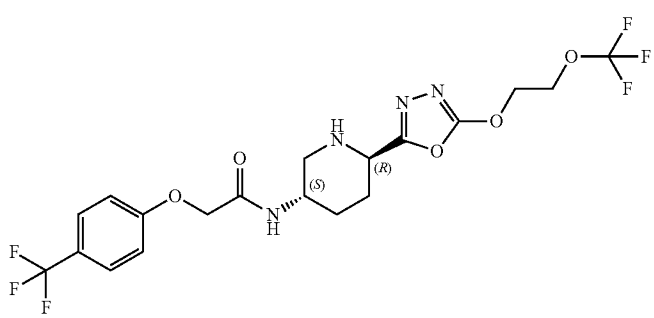 | N-[(3S,6R)-6-{5-[2-(trifluoromethoxy)ethoxy]-1,3,4-oxadiazol-2-yl}piperidin-3-yl]-2-[4-(trifluoromethyl)phenoxy]acetamide | tert-butyl (2R,5S)-5-amino-2-{5-[2-(trifluoromethoxy)ethoxy]-1,3,4-oxadiazol-2-yl}piperidine-1-carboxylate (Intermediate | M/Z: 499 [M + H]⁺, ESI⁺, RT = 2.18 (S4) | ¹H NMR (500 MHz, DMSO-$d_6$) δ 8.02 (d, J = 8.0 Hz, 1H), 7.68 (d, J = 8.7 Hz, 2H), 7.13 (d, J = 8.6 Hz, 2H), 4.73-4.65 (m, 2H), 4.59 (s, 2H), 4.51-4.42 (m, 2H), 3.81-3.74 (m, 1H), 3.74-3.64 (m, 1H), 3.03-2.93 (m, 1H), 2.84-2.76 (m, 1H), 2.48- |

TABLE 10-continued

| Ex | Structure | Name | Intermediates | LCMS data | ¹H NMR |
|---|---|---|---|---|---|
| | | | 48) and 2-[4-(trifluoromethyl)phenoxy]acetic acid (Intermediate 18) | | 2.39 (m, 1H), 2.01-1.85 (m, 2H), 1.72-1.59 (m, 1H), 1.56-1.44 (m, 1H). |
| 113 | 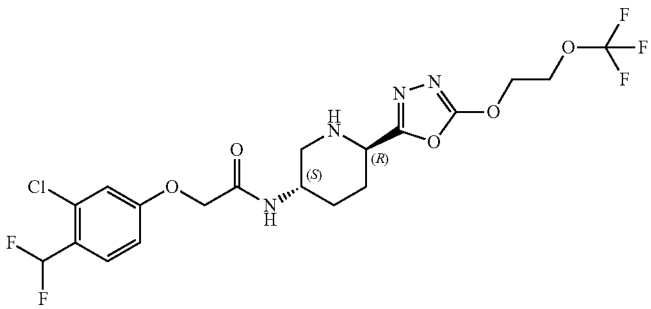 | 2-[3-chloro-4-(difluoromethyl)phenoxy]-N-[(3S,6R)-6-{5-[2-(trifluoromethoxy)ethoxy]-1,3,4-oxadiazol-2-yl}piperidin-3-yl]acetamide | tert-butyl (2R,5S)-5-amino-2-{5-[2-(trifluoromethoxy)ethoxy]-1,3,4-oxadiazol-2-yl}piperidine-1-carboxylate (Intermediate 48) and 2-[3-chloro-4-(difluoromethyl)phenoxy]acetic acid (Intermediate 56) | M/Z: 515, 517 [M + H]⁺, ESI⁺, RT = 2.24 (S4) | ¹H NMR (500 MHz, DMSO-d₆) δ 8.01 (d, J = 8.1 Hz, 1H), 7.65-7.58 (m, 1H), 7.27-6.99 (m, 3H), 4.71-4.64 (m, 2H), 4.59 (s, 2H), 4.51-4.43 (m, 2H), 3.80-3.74 (m, 1H), 3.73-3.65 (m, 1H), 3.01-2.94 (m, 1H), 2.80 (s, 1H), 2.46-2.39 (m, 1H), 2.00-1.92 (m, 1H), 1.93-1.85 (m, 1H), 1.71-1.59 (m, 1H), 1.55-1.43 (m, 1H). |
| 114 | 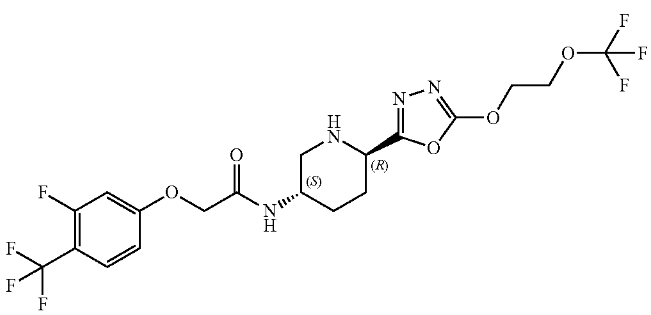 | 2-[3-fluoro-4-(trifluoromethyl)phenoxy]-N-[(3S,6R)-6-{5-[2-(trifluoromethoxy)ethoxy]-1,3,4-oxadiazol-2-yl}piperidin-3-yl]acetamide | tert-butyl (2R,5S)-5-amino-2-{5-[2-(trifluoromethoxy)ethoxy]-1,3,4-oxadiazol-2-yl}piperidine-1-carboxylate (Intermediate 48) and 2-[3-fluoro-4-(trifluoromethyl)phenoxy]acetic acid (Intermediate 8) | M/Z: 517 [M + H]⁺, ESI⁺, RT = 2.20 (S4) | ¹H NMR (400 MHz, chloroform-d) δ 7.57 (t, J = 8.2 Hz, 1H), 6.80 (d, J = 9.8 Hz, 2H), 6.73 (d, J = 7.5 Hz, 1H), 4.74-4.66 (m, 2H), 4.53 (s, 2H), 4.37-4.30 (m, 2H), 4.07 (ddt, J = 11.4, 8.0, 3.9 Hz, 1H), 4.01 (dd, J = 7.4, 3.5 Hz, 1H), 3.30 (dd, J = 12.0, 3.4 Hz, 1H), 2.64 (dd, J = 12.0, 7.4 Hz, 1H), 2.08 (qt, J = 10.8, 5.4 Hz, 2H), 1.95 (ddd, J = 16.9, 10.4, 6.1 Hz, 2H), 1.71-1.58 (m, 1H). |

Scheme for route 35

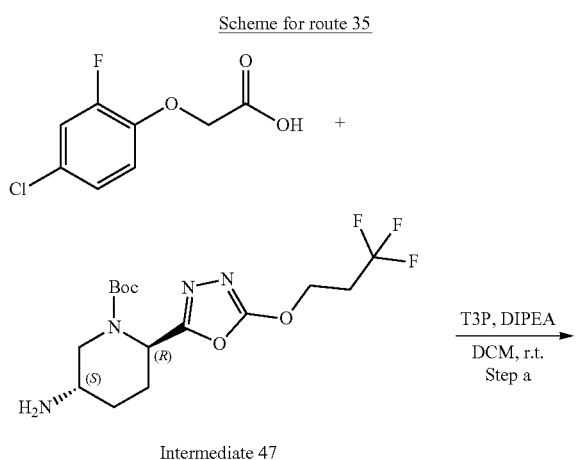

Intermediate 47

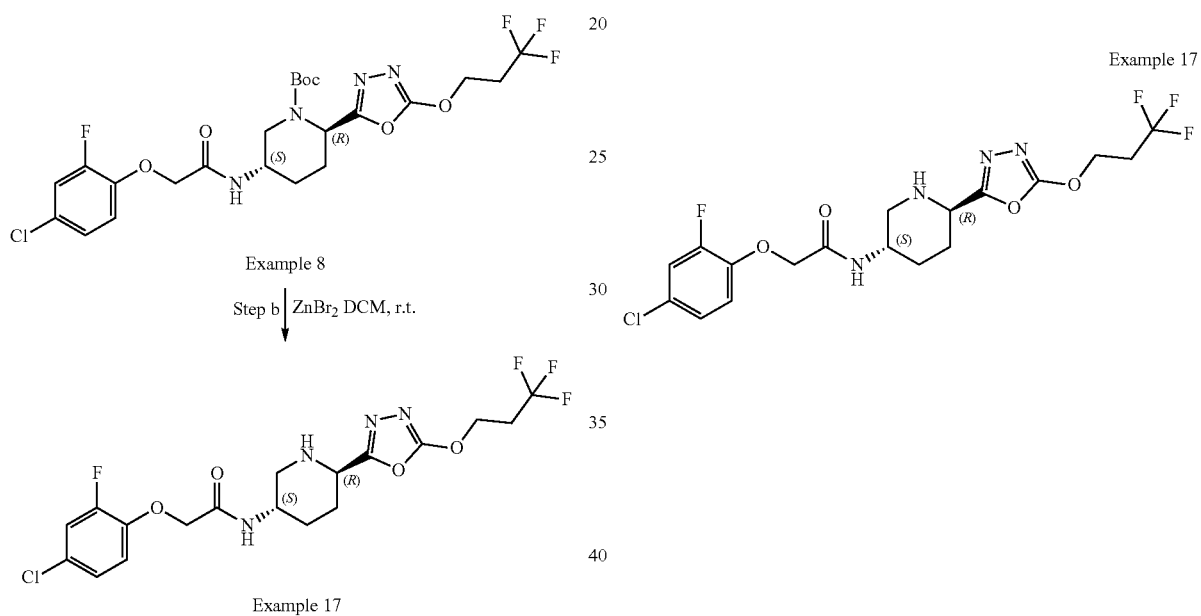

Example 16 (Step 35.a): tert-butyl (2R,5S)-5-[2-(4-chloro-2-fluorophenoxy)acetamido]-2-[5-(3,3,3-trifluoropropoxy)-1,3,4-oxadiazol-2-yl]piperidine-1-carboxylate

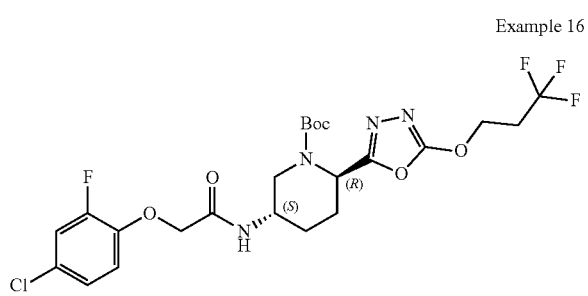

Example 16

To a solution of 2-(4-chloro-2-fluorophenoxy)acetic acid (20 mg, 0.0999 mmol) in DCM (1 mL) was added T3P (50% in EtOAc, 713 µL, 0.120 mmol) and DIPEA (41 µL, 0.233 mmol) and stirred at r.t. for 10 min. tert-butyl (2R,5S)-5-amino-2-[5-(3,3,3-trifluoropropoxy)-1,3,4-oxadiazol-2-yl]piperidine-1-carboxylate (38 mg, 0.10 mmol, Intermediate 47) was added and the resultant mixture was stirred at r.t. for 72 h. The reaction mixture was diluted with $H_2O$ (1 mL) and extracted with DCM (2 mL). The combined organic extracts were dried over $Na_2SO_4$ and concentrated in vacuo to afford an orange solid. The crude material was taken forward without purification.

Example 17 (Step 35.b): 2-(4-chloro-2-fluorophenoxy)-N-[(3S,6R)-6-[5-(3,3,3-trifluoropropoxy)-1,3,4-oxadiazol-2-yl]piperidin-3-yl]acetamide To a solution of tert-butyl (2R,5S)-5-[2-(4-chloro-2-fluorophenoxy)acetamido]-2-[5-(3,3,3-trifluoropropoxy)-1,3,4-oxadiazol-2-yl]piperidine-1-carboxylate (57 mg, 0.10 mmol, Example 16) in anhydrous DCM (1 mL) was added $ZnBr_2$ (90 mg, 0.40 mmol) and the mixture was stirred at r.t. for 18 h. The reaction mixture was diluted with satd aq $NaHCO_3$ solution and extracted with DCM/IPA (4:1, 2×2 mL). The combined organic extracts were concentrated in vacuo and purified by prep. HPLC (Method 4) to afford the title compound (88% purity, 1.7 mg, 0.0032 mmol, 3% yield) as a white solid; $^1$H NMR (400 MHz, chloroform-d) δ 1.59-1.64 (m, 2H), 1.89-2.01 (m, 1H), 2.14 (dq, J=12.8, 4.6, 4.0, 2H), 2.66 (dd, J=12.0, 7.9, 1H), 2.68-2.79 (m, 2H), 3.34 (dd, J=12.0, 3.5, 1H), 4.02 (dd, J=8.1, 3.4, 1H), 4.08 (ddt, J=12.3, 8.2, 4.1, 1H), 4.53 (s, 2H), 4.72 (t, J=6.2, 2H), 6.86-6.97 (m, 2H), 7.11 (ddd, J=8.7, 2.4, 1.7, 1H), 7.19 (dd, J=10.6, 2.5, 1H); M/Z: 467, 469 [M+H]$^+$, ESI$^+$, RT=1.98 (S4).

Example compounds in Table 11 were synthesised according to the synthetic steps of general route 35 as exemplified by Example 17 using the corresponding intermediate

TABLE 11

| Ex | Structure | Name | Intermediates | LCMS data | ¹H NMR |
|---|---|---|---|---|---|
| 18 | 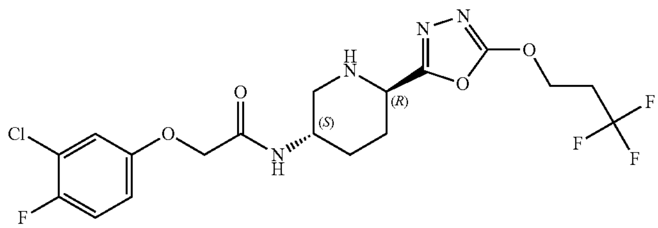 | 2-(3-chloro-4-fluoro-phenoxy)-N-[(3S,6R)-6-[5-(3,3,3-trifluoro-propoxy)-1,3,4-oxadiazol-2-yl]piperidin-3-yl]acetamide | tert-butyl (2R,5S)-5-amino-2-[5-(3,3,3-trifluoro-propoxy)-1,3,4-oxadiazol-2-yl]piperidine-1-carboxylate (Intermediate 47) and 2-(3-chloro-4-fluoro-phenoxy)acetic acid | M/Z: 467, 469 [M + H]⁺, ESI⁺, RT = 2.00 (S4) | ¹H NMR (400 MHz, chloroform-d) δ 1.59-1.66 (m, 2H), 1.88-2.01 (m, 1H), 2.03-2.16 (m, 2H), 2.65 (dd, J = 12.1, 7.6, 1H), 2.73 (qt, J = 10.3, 6.2, 2H), 3.32 (dd, J = 12.0, 3.4, 1H), 4.02 (dd, J = 7.7, 3.4, 1H), 4.04-4.13 (m, 1H), 4.47 (s, 2H), 4.72 (t, J = 6.2, 2H), 6.77 (d, J = 7.8, 1H), 6.83 (dt, J = 9.1, 3.4, 1H), 7.03 (dd, J = 5.9, 3.1, 1H), 7.08-7.16 (m, 1H). |
| 19 | 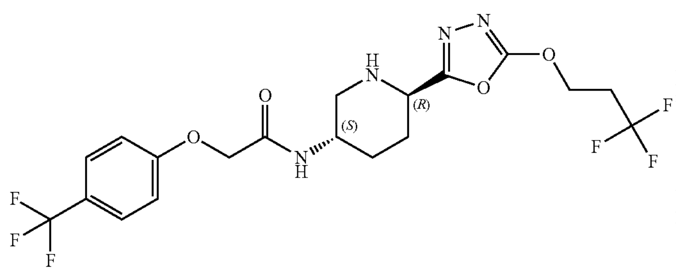 | 2-[4-(trifluoro-methyl)phenoxy]-N-[(3S,6R)-6-[5-(3,3,3-trifluoro-propoxy)-1,3,4-oxadiazol-2-yl]piperidin-3-yl]acetamide | tert-butyl (2R,5S)-5-amino-2-[5-(3,3,3-trifluoro-propoxy)-1,3,4-oxadiazol-2-yl]piperidine-1-carboxylate (Intermediate 47) and 2-[4-(trifluoro-methyl)phenoxy]acetic acid | M/Z: 483 [M + H]⁺, ESI⁺, RT = 2.12 (S4) | ¹H NMR (400 MHz, chloroform-d) δ 1.58-1.68 (m, 2H), 1.90-2.00 (m, 1H), 2.04-2.16 (m, 2H), 2.65 (dd, J = 12.1, 7.7, 1H), 2.68-2.80 (m, 2H), 3.32 (dd, J = 12.0, 3.4, 1H), 4.01 (dd, J = 7.7, 3.4, 1H), 4.04-4.14 (m, 1H), 4.56 (s, 2H), 4.72 (t, J = 6.2, 2H), 6.78 (d, J = 8.0, 1H), 7.05 (d, J = 8.5, 2H), 7.63 (d, J = 8.5, 2H). |
| 20 | 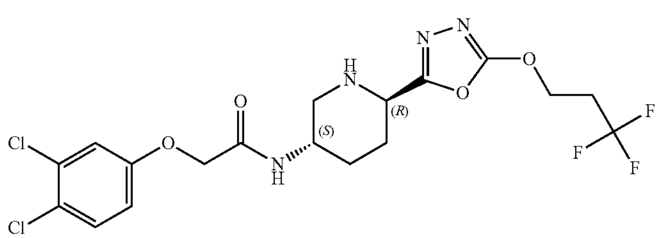 | 2-(3,4-dichloro-phenoxy)-N-[(3S,6R)-6-[5-(3,3,3-trifluoro-propoxy)-1,3,4-oxadiazol-2-yl]piperidin-3-yl]acetamide | tert-butyl (2R,5S)-5-amino-2-[5-(3,3,3-trifluoro-propoxy)-1,3,4-oxadiazol-2-yl]piperidine-1-carboxylate (Intermediate 47) and 2-(3,4-dichloro-phenoxy)acetic acid | M/Z: 483, 485, 487 [M + H]⁺, ESI⁺, RT = 2.16 (S4) | ¹H NMR (400 MHz, chloroform-d) δ 1.60-1.67 (m, 2H), 1.89-2.00 (m, 1H), 2.10 (dtq, J = 10.5, 6.9, 3.7, 2H), 2.65 (dd, J = 12.1, 7.6, 1H), 2.73 (qt, J = 10.3, 6.2, 2H), 3.32 (dd, J = 12.0, 3.5, 1H), 4.02 (dd, J = 7.7, 3.5, 1H), 4.08 (ddq, J = 11.5, 8.0, 3.5, 1H), 4.49 (s, 2H), 4.72 (t, J = 6.2, 2H), 6.75 (d, J = 8.1, 1H), 6.83 (dd, J = 8.9, 2.9, 1H), 7.10 |

TABLE 11-continued

| Ex | Structure | Name | Intermediates | LCMS data | ¹H NMR |
|---|---|---|---|---|---|
| | | | | | (d, J = 2.9, 1H), 7.41 (d, J = 8.9, 1H). |
| 21 | 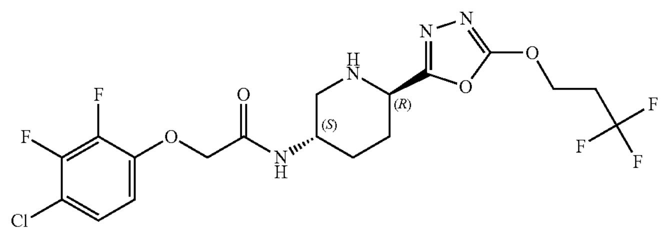 | 2-(4-chloro-2,3-difluoro-phenoxy)-N-[(3S,6R)-6-[5-(3,3,3-trifluoro-propoxy)-1,3,4-oxadiazol-2-yl]piperidin-3-yl]acetamide | tert-butyl (2R,5S)-5-amino-2-[5-(3,3,3-trifluoro-propoxy)-1,3,4-oxadiazol-2-yl]piperidine-1-carboxylate (Intermediate 47) and 2-(4-chloro-2,3-difluoro-phenoxy)acetic acid (Intermediate 10) | M/Z: 485, 487 [M + H]⁺, ESI⁺, RT = 2.08 (S4) | ¹H NMR (400 MHz, chloroform-d) δ 1.64-1.72 (m, 2H), 1.91-2.01 (m, 1H), 2.05-2.19 (m, 2H), 2.63-2.79 (m, 3H), 3.33 (dd, J = 12.0, 3.4, 1H), 3.99-4.15 (m, 2H), 4.55 (s, 2H), 4.72 (t, J = 6.2, 2H), 6.70-6.78 (m, 1H), 6.88 (d, J = 7.9, 1H), 7.16 (ddd, J = 9.2, 7.5, 2.5, 1H). |
| 22 | 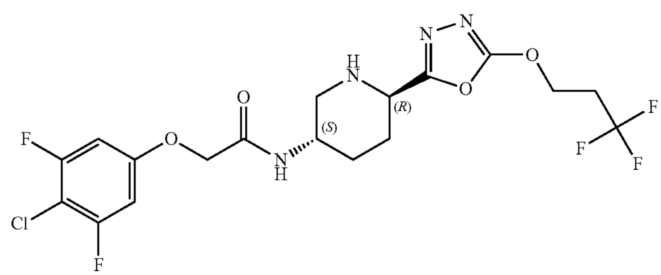 | 2-(4-chloro-3,5-difluoro-phenoxy)-N-[(3S,6R)-6-[5-(3,3,3-trifluoro-propoxy)-1,3,4-oxadiazol-2-yl]piperidin-3-yl]acetamide | tert-butyl (2R,5S)-5-amino-2-[5-(3,3,3-trifluoro-propoxy)-1,3,4-oxadiazol-2-yl]piperidine-1-carboxylate (Intermediate 47) and 2-(4-chloro-3,5-difluoro-phenoxy)acetic acid (Intermediate 11) | M/Z: 485, 487 [M + H]⁺, ESI⁺, RT = 2.12 (S4) | ¹H NMR (400 MHz, chloroform-d) δ 1.61-1.67 (m, 2H), 1.91-2.02 (m, 1H), 2.03-2.17 (m, 2H), 2.58-2.80 (m, 3H), 3.32 (dd, J = 12.0, 3.4, 1H), 4.00-4.15 (m, 2H), 4.48 (s, 2H), 4.72 (t, J = 6.2, 2H), 6.60-6.68 (m, 2H), 6.71 (d, J = 8.0, 1H). |
| 23 | 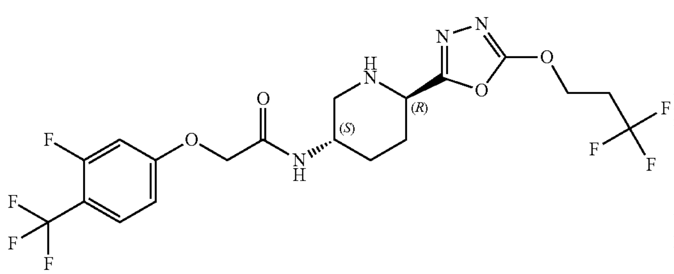 | 2-[3-fluoro-4-(trifluoromethyl)phenoxy]-N-[(3S,6R)-6-[5-(3,3,3-trifluoro-propoxy)-1,3,4-oxadiazol-2-yl]piperidin-3-yl]acetamide | tert-butyl (2R,5S)-5-amino-2-[5-(3,3,3-trifluoro-propoxy)-1,3,4-oxadiazol-2-yl]piperidine-1-carboxylate (Intermediate 47) and 2-[3-fluoro-4-(trifluoromethyl) | M/Z: 501 [M + H]⁺, ESI⁺, RT = 2.18 (S4) | ¹H NMR (400 MHz, chloroform-d) δ 1.66-1.74 (m, 2H), 1.89-2.02 (m, 1H), 2.12 (ddd, J = 12.1, 7.0, 3.3, 2H), 2.61-2.81 (m, 3H), 3.32 (dd, J = 12.0, 3.4, 1H), 4.03 (dd, J = 7.6, 3.5, 1H), 4.05-4.14 (m, 1H), 4.55 (s, 2H), 4.72 (t, J = 6.2, 2H), 6.75 (d, J = 7.9, 1H), 6.82 (d, J = 9.8, 2H), |

TABLE 11-continued

| Ex | Structure | Name | Intermediates | LCMS data | ¹H NMR |
|---|---|---|---|---|---|
| | | phenoxy] acetic acid (Intermediate 8) | | | 7.59 (t, J = 8.2, 1H). |
| 24 | 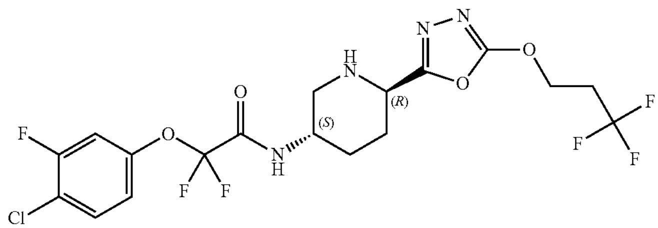 | 2-(4-chloro-3-fluoro-phenoxy)-2,2-difluoro-N-[(3S,6R)-6-[5-(3,3,3-trifluoro-propoxy)-1,3,4-oxadiazol-2-yl]piperidin-3-yl]acetamide | tert-butyl (2R,5S)-5-amino-2-[5-(3,3,3-trifluoro-propoxy)-1,3,4-oxadiazol-2-yl]piperidine-1-carboxylate (Intermediate 47) and 2-(4-chloro-3-fluoro-phenoxy)-2,2-difluoro-acetic acid | M/Z: 503, 505 [M + H]⁺, ESI⁺, RT = 2.33 (S4) | ¹H NMR (400 MHz, chloroform-d) δ 1.76 (dt, J = 13.9, 7.0, 1H), 1.96-2.21 (m, 4H), 2.66-2.81 (m, 3H), 3.31 (dd, J = 12.1, 3.1, 1H), 4.02-4.14 (m, 2H), 4.73 (t, J = 6.1, 2H), 6.89 (d, J = 7.3, 1H), 7.05 (d, J = 8.9, 1H), 7.12 (dd, J = 9.3, 2.6, 1H), 7.37-7.48 (m, 1H). |
| 25 | 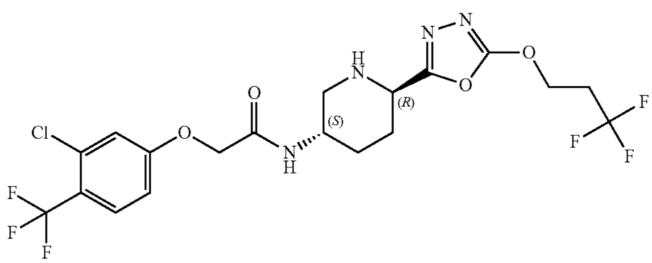 | 2-[3-chloro-4-(trifluoro-methyl)phenoxy]-N-[(3S,6R)-6-[5-(3,3,3-trifluoro-propoxy)-1,3,4-oxadiazol-2-yl]piperidin-3-yl]acetamide | tert-butyl (2R,5S)-5-amino-2-[5-(3,3,3-trifluoro-propoxy)-1,3,4-oxadiazol-2-yl]piperidine-1-carboxylate (Intermediate 47) and 2-[3-chloro-4-(trifluoro-methyl)phenoxy]acetic acid (Intermediate 7) | M/Z: 517, 519 [M + H]⁺, ESI⁺, RT = 2.3 (S4) | ¹H NMR (400 MHz, chloroform-d) δ 1.60-1.67 (m, 2H), 1.90-2.01 (m, 1H), 2.04-2.16 (m, 2H), 2.62-2.80 (m, 3H), 3.32 (dd, J = 12.0, 3.4, 1H), 4.03 (dd, J = 7.6, 3.5, 1H), 4.09 (ddq, J = 11.4, 7.8, 3.5, 1H), 4.55 (s, 2H), 4.72 (t, J = 6.2, 2H), 6.75 (d, J = 7.9, 1H), 6.92 (dd, J = 8.7, 2.2, 1H), 7.13 (d, J = 2.4, 1H), 7.68 (d, J = 8.8, 1H). |
| 26 | 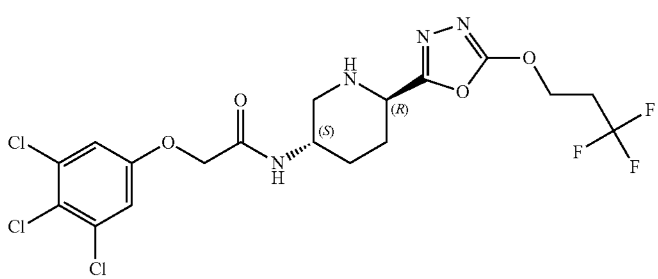 | 2-(3,4,5-trichloro-phenoxy)-N-[(3S,6R)-6-[5-(3,3,3-trifluoro-propoxy)-1,3,4-oxadiazol-2-yl]piperidin-3-yl]acetamide | tert-butyl (2R,5S)-5-amino-2-[5-(3,3,3-trifluoro-propoxy)-1,3,4-oxadiazol-2-yl]piperidine-1-carboxylate (Intermediate 47) and 2-(3,4,5-trichloro-phenoxy)acetic acid | M/Z: 517, 519, 521, 523 [M + H]⁺, ESI⁺, RT = 2.39 (S4) | ¹H NMR (400 MHz, chloroform-d) δ 1.58 (dd, J = 16.6, 8.2, 2H), 1.80-1.92 (m, 2H), 1.93-2.06 (m, 2H), 2.56 (dd, J = 11.9, 7.3, 1H), 2.59-2.70 (m, 2H), 3.22 (dd, J = 12.0, 3.4, 1H), 3.93 (dd, J = 7.5, 3.6, 1H), 4.00 (ddt, J = 11.9, 8.1, 4.0, 1H), 4.38 (s, 2H), 4.63 (t, J = 6.2, |

TABLE 11-continued

| Ex | Structure | Name | Intermediates | LCMS data | ¹H NMR |
|---|---|---|---|---|---|
| | | | (Intermediate 9) | | 2H), 6.63 (d, J = 8.0, 1H), 6.95 (s, 2H). |
| 27 | 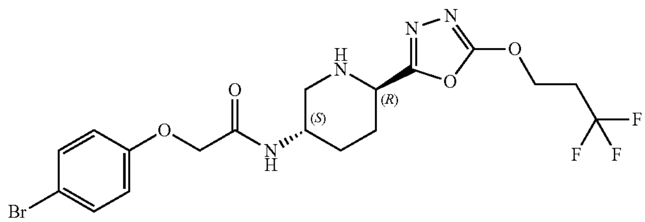 | 2-(4-bromophenoxy)-N-[(3S,6R)-6-[5-(3,3,3-trifluoropropoxy)-1,3,4-oxadiazol-2-yl]piperidin-3-yl]acetamide | tert-butyl (2R,5S)-5-amino-2-[5-(3,3,3-trifluoropropoxy)-1,3,4-oxadiazol-2-yl]piperidine-1-carboxylate (Intermediate 47) and 2-(4-bromophenoxy)acetic acid | M/Z: 493, 495 [M + H]⁺, ESI⁺, RT = 1.98 (S4) | ¹H NMR (400 MHz, chloroform-d) δ 1.57-1.63 (m, 2H), 1.88-1.99 (m, 1H), 2.04-2.15 (m, 2H), 2.64 (dd, J = 12.0, 7.8, 1H), 2.73 (qt, J = 10.2, 6.2, 2H), 3.32 (dd, J = 12.0, 3.5, 1H), 4.00 (dd, J = 7.9, 3.3, 1H), 4.07 (ddq, J = 11.6, 8.1, 3.4, 1H), 4.49 (s, 2H), 4.72 (t, J = 6.2, 2H), 6.77 (d, J = 8.0, 1H), 6.80-6.90 (m, 2H), 7.40-7.50 (m, 2H). |
| 28 | 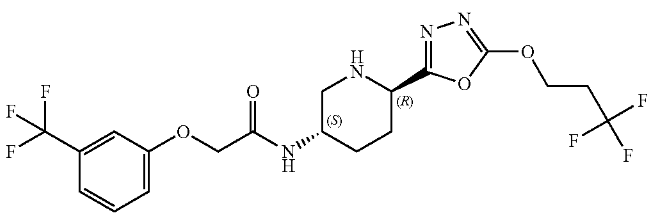 | 2-[3-(trifluoromethyl)phenoxy]-N-[(3S,6R)-6-[5-(3,3,3-trifluoropropoxy)-1,3,4-oxadiazol-2-yl]piperidin-3-yl]acetamide | tert-butyl (2R,5S)-5-amino-2-[5-(3,3,3-trifluoropropoxy)-1,3,4-oxadiazol-2-yl]piperidine-1-carboxylate (Intermediate 47) and 2-[3-(trifluoromethyl)phenoxy]acetic acid | M/Z: 483 [M + H]⁺, ESI⁺, RT = 2.11 (S4) | ¹H NMR (400 MHz, chloroform-d) δ 1.60-1.67 (m, 2H), 1.89-2.00 (m, 1H), 2.03-2.15 (m, 2H), 2.65 (dd, J = 12.0, 7.5, 1H), 2.69-2.80 (m, 2H), 3.32 (dd, J = 12.0, 3.4, 1H), 4.01 (dd, J = 7.7, 3.4, 1H), 4.09 (dq, J = 8.1, 4.6, 4.1, 1H), 4.56 (s, 2H), 4.72 (t, J = 6.2, 2H), 6.80 (d, J = 8.1, 1H), 7.14 (dd, J = 8.3, 2.5, 1H), 7.23 (s, 1H), 7.33 (d, J = 7.7, 1H), 7.48 (t, J = 8.0, 1H). |
| 29 | 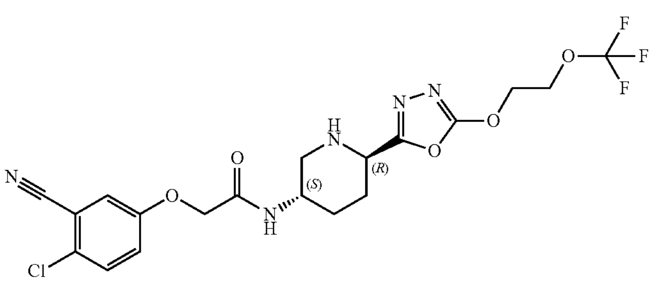 | 2-(4-chloro-3-cyanophenoxy)-N-[(3S,6R)-6-{5-[2-(trifluoromethoxy)ethoxy]-1,3,4-oxadiazol-2-yl}piperidin-3-yl]acetamide | tert-butyl (2R,5S)-5-amino-2-{5-[2-(trifluoromethoxy)ethoxy]-1,3,4-oxadiazol-2-yl}piperidine-1-carboxylate (Intermediate 48) and 2-(4-chloro-3-cyano- | M/Z: 490, 492 [M+ H]⁺, ESI⁺, RT = 2.04 (S4) | ¹H NMR (400 MHz, DMSO-d₆) δ 7.99 (d, J = 8.1 Hz, 1H), 7.67 (d, J = 9.0 Hz, 1H), 7.59 (d, J = 3.0 Hz, 1H), 7.34 (dd, J = 9.0, 3.1 Hz, 1H), 4.73-4.65 (m, 2H), 4.59 (s, 2H), 4.51-4.43 (m, 2H), 3.77 (ddd, J = 9.1, 5.9, 2.8 Hz, 1H), 3.74-3.63 (m, 1H), 3.04-2.93 (m, 1H), |

TABLE 11-continued

| Ex | Structure | Name | Intermediates | LCMS data | ¹H NMR |
|----|-----------|------|---------------|-----------|--------|
| | | phenoxy) acetic acid (Intermediate 16) | | | 2.86-2.75 (m, 1H), 2.46-2.37 (m, 1H), 2.01-1.83 (m, 2H), 1.72-1.58 (m, 1H), 1.56-1.42 (m, 1H). |

Scheme for route 36

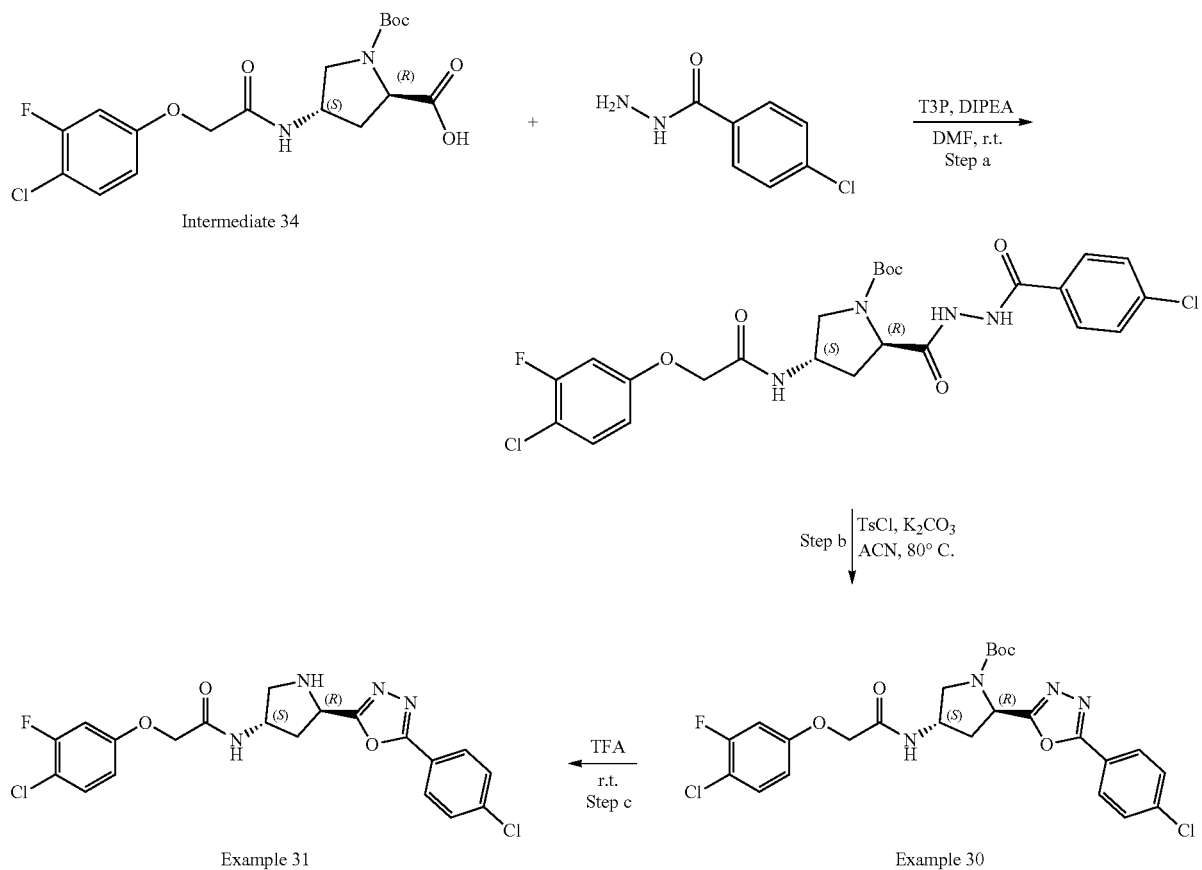

Step 36.a: tert-butyl (2R,4S)-4-[2-(4-chloro-3-fluorophenoxy)acetamido]-2-{[(4-chlorophenyl)formohydrazido]carbonyl}pyrrolidine-d-carboxylate

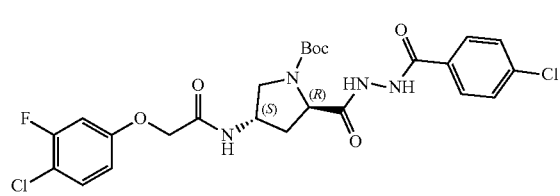

To a solution of (2R,4S)-1-[(tert-butoxy)carbonyl]-4-[2-(4-chloro-3-fluorophenoxy)acetamido]pyrrolidine-2-carboxylic acid (80% purity, 200 mg, 0.384 mmol, Intermediate 34), 4-chlorobenzohydrazide (65 mg, 0.384 mmol) and DIPEA (0.080 mL, 0.461 mmol) in DMF (1 mL) was added T3P (50% in EtOAc, 0.25 mL, 0.422 mmol) and the mixture was stirred at r.t. for 1 h. The reaction mixture was diluted with H₂O (20 mL) and extracted with EtOAc (2×20 mL). The combined organic extracts were washed with brine, dried over MgSO₄, and concentrated in vacuo. The residue was purified by chromatography on silica gel (0-100% EtOAc in heptane) to afford the title compound (89% purity, 158 mg, 0.247 mmol, 64% yield) as a pale yellow gum; ¹H NMR (400 MHz, DMSO-d₆) δ 10.52 (d, J=48.5 Hz, 1H), 10.05 (d, J=9.9 Hz, 1H), 8.34 (t, J=6.4 Hz, 1H), 7.98-7.85 (m, 2H), 7.58 (dd, J=8.5, 4.7 Hz, 2H), 7.50 (t, J=8.9 Hz, 1H), 7.08 (d, J=11.5 Hz, 1H), 6.91-6.80 (m, 1H), 4.55 (s, 2H), 4.52-4.39 (m, 1H), 4.34 (dq, J=12.6, 4.4 Hz, 1H), 3.73-3.59 (m, 1H), 3.25-3.11 (m, 1H), 2.31-2.11 (m, 2H), 1.40 (s, 9H); M/Z: 469, 471, 473 [M-Boc+H]⁺, ESI⁺, RT=0.95 (S2).

Example 30 (Step 36.b): tert-butyl (2R,4S)-4-[2-(4-chloro-3-fluorophenoxy)acetamido]-2-[5-(4-chlorophenyl)-1,3,4-oxadiazol-2-yl]pyrrolidine-1-carboxylate

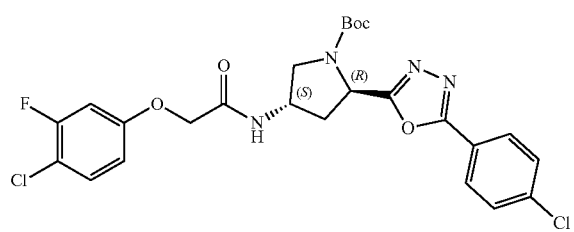

Example 30

A suspension of tert-butyl (2R,4S)-4-[2-(4-chloro-3-fluorophenoxy)acetamido]-2-{[(4-chlorophenyl)formohydrazido]carbonyl}pyrrolidine-1-carboxylate (89% purity, 158 mg, 0.247 mmol), $K_2CO_3$ (205 mg, 1.48 mmol) and TsCl (0.012 mL, 0.741 mmol) in ACN (2 mL) was stirred at 80° C. for 2.5 h. The reaction mixture was partitioned between EtOAc (30 mL) and $H_2O$ (20 mL). The organic layer was isolated, washed with brine, dried over $MgSO_4$, and concentrated in vacuo. The residue was purified by chromatography on silica gel (0-100% EtOAc in heptane) to afford the title compound (119 mg, 0.208 mmol, 84% yield) as a pale yellow gum; $^1$H NMR (400 MHz, DMSO-$d_6$) δ 8.49 (s, 1H), 8.01 (d, J=8.5 Hz, 2H), 7.70 (d, J=8.6 Hz, 2H), 7.50 (t, J=8.9 Hz, 1H), 7.08 (dd, J=11.4, 2.8 Hz, 1H), 6.87 (dd, J=9.0, 1.7 Hz, 1H), 5.30-5.18 (m, 1H), 4.66-4.47 (m, 3H), 3.82-3.69 (m, 1H), 3.44-3.40 (m, 1H), 2.44-2.35 (m, 2H), 1.42-1.18 (m, 9H); M/Z: 595, 597 [M+ MeCN+H]$^+$, ESI$^+$, RT=1.11 (S2).

Example 31 (Step 36.c): 2-(4-chloro-3-fluorophenoxy)-N-[(3S,5R)-5-[5-(4-chlorophenyl)-1,3,4-oxadiazol-2-yl]pyrrolidin-3-yl]acetamide

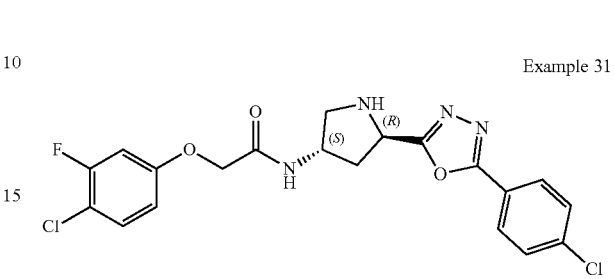

Example 31

A solution of tert-butyl (2R,4S)-4-[2-(4-chloro-3-fluorophenoxy)acetamido]-2-[5-(4-chlorophenyl)-1,3,4-oxadiazol-2-yl]pyrrolidine-1-carboxylate (119 mg, 0.207 mmol, Example 30) and TFA (0.15 mL, 2.07 mmol) in DCM (2.5 mL) was stirred at r.t. for 4 h. The reaction mixture was partitioned between DCM and satd aq $NaHCO_3$ solution, and the organic layer was isolated using a phase separator and concentrated in vacuo. The residue was purified by prep. HPLC (Method 3) and then triturated using $Et_2O$ to afford the title compound (44 mg, 0.0965 mmol, 47% yield) as a white solid; $^1$H NMR (500 MHz, DMSO-$d_6$) δ 8.26 (d, J=7.2 Hz, 1H), 8.04-7.98 (m, 2H), 7.72-7.65 (m, 2H), 7.51 (t, J=8.9 Hz, 1H), 7.10 (dd, J=11.4, 2.8 Hz, 1H), 6.90-6.85 (m, 1H), 4.65 (s, 1H), 4.55 (s, 2H), 4.46-4.37 (m, 1H), 3.16-3.07 (m, 2H), 2.87-2.79 (m, 1H), 2.44-2.38 (m, 1H), 2.19-2.10 (m, 1H); M/Z: 451, 453, 455 [M+H]$^+$, ESI$^+$, RT=2.26 (S4).

Scheme for route 37

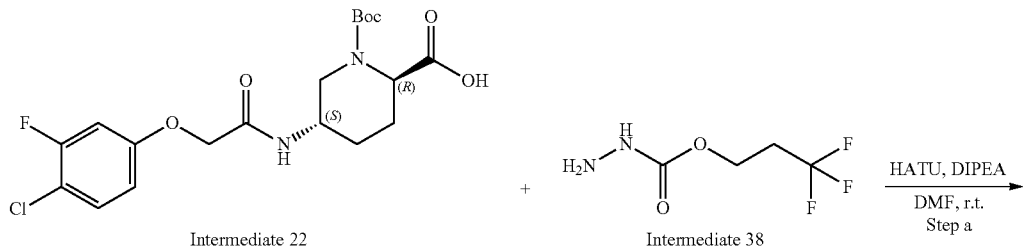

Intermediate 22 + Intermediate 38 →(HATU, DIPEA / DMF, r.t.) Step a

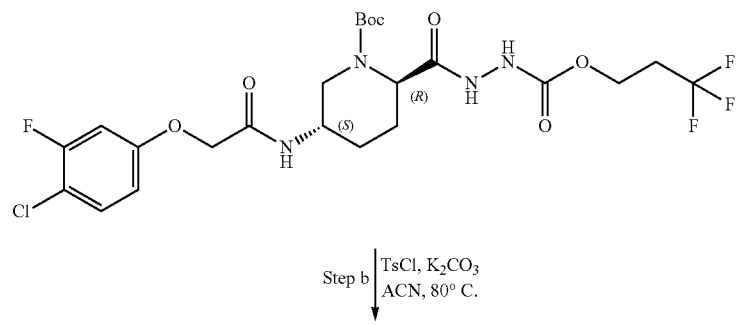

Step b | TsCl, $K_2CO_3$ / ACN, 80° C.

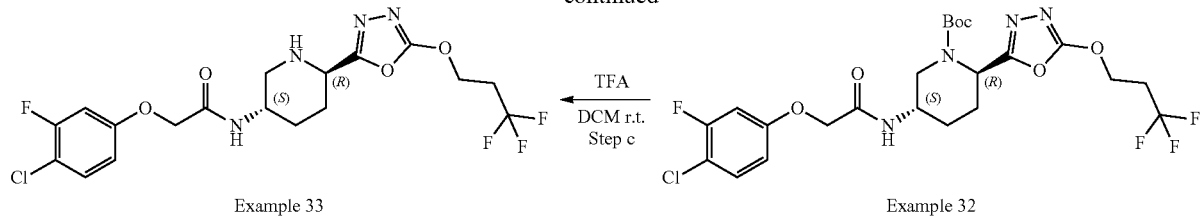

Example 33 ← TFA / DCM r.t. Step c — Example 32

Step 37.a: tert-butyl (2R,5S)-5-[[2-(4-chloro-3-fluoro-phenoxy)acetyl]amino]-2-[(3,3,3-trifluoro-propoxycarbonylamino)carbamoyl]piperidine-1-carboxylate

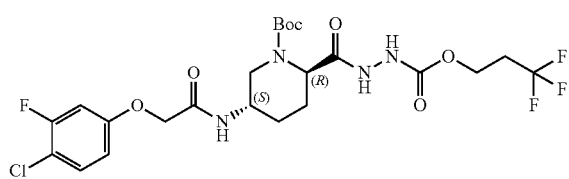

To a solution of (2R,5S)-1-[(tert-butoxy)carbonyl]-5-[2-(4-chloro-3-fluorophenoxy) acetamido]piperidine-2-carboxylic acid (500 mg, 1.10 mmol, Intermediate 22) in anhydrous DMF (6 mL) was added DIPEA (0.40 mL, 2.29 mmol) and HATU (503 mg, 1.32 mmol) and stirred at r.t. for 10 min. (3,3,3-trifluoropropoxy)carbohydrazide (273 mg, 1.43 mmol, Intermediate 38) was added and the mixture was stirred at r.t. for 12 h. The reaction mixture was diluted with EtOAc (20 mL) and washed with brine (20 mL). The combined organic extracts were dried over MgSO$_4$, concentrated in vacuo, and purified by chromatography on silica gel (0-80% EtOAc in heptane) to afford the title compound (91% purity, 646 mg, 1.00 mmol, 91% yield) as a colourless oil; M/Z: 485, 487 [M-Boc+H]$^+$, ESI$^+$, RT=0.96 (S2).

Example 32 (Step 37.b): tert-butyl (2R,5S)-5-[2-(4-chloro-3-fluorophenoxy)acetamido]-2-[5-(3,3,3-trifluoropropoxy)-1,3,4-oxadiazol-2-yl]piperidine-1-carboxylate

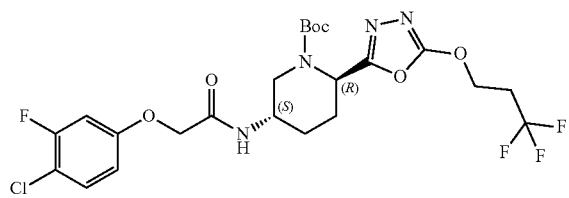

A suspension of tert-butyl (2R,5S)-5-[[2-(4-chloro-3-fluoro-phenoxy)acetyl]amino]-2-[(3,3,3-trifluoropropoxy-carbonylamino)carbamoyl]piperidine-1-carboxylate (91% purity, 646 mg, 1.0 mmol), K$_2$CO$_3$ (833 mg, 6.03 mmol) and TsCl (576 mg, 3.02 mmol) in ACN (5 mL) was stirred at 80° C. for 3 h. The reaction mixture was diluted with EtOAc (20 mL) and washed with brine (20 mL). The organic layer was dried over MgSO$_4$, concentrated in vacuo, and purified by chromatography on silica gel (0-100% EtOAc in heptane) to afford the title compound (252 mg, 0.440 mmol, 44% yield) as a white powder; $^1$H NMR (400 MHz, DMSO-d$_6$) δ 8.08 (d, J=7.0 Hz, 1H), 7.48 (t, J=8.9 Hz, 1H), 7.04 (dd, J=11.4, 2.9 Hz, 1H), 6.82 (ddd, J=9.0, 2.8, 1.1 Hz, 1H), 5.38 (s, 1H), 4.65 (t, J=5.7 Hz, 2H), 4.62-4.52 (m, 2H), 3.96-3.85 (m, 2H), 2.99-2.85 (m, 3H), 2.25-2.11 (m, 1H), 2.03-1.94 (m, 1H), 1.86-1.73 (m, 1H), 1.63 (d, J=13.5 Hz, 1H), 1.37 (s, 9H); M/Z: 467, 469 [M-Boc+H]$^+$, ESI$^+$, RT=1.07 (S2).

Example 33 (Step 37.c): 2-(4-chloro-3-fluorophenoxy)-N-[(3S,6R)-6-[5-(3,3,3-trifluoropropoxy)-1,3,4-oxadiazol-2-yl]piperidin-3-yl]acetamide

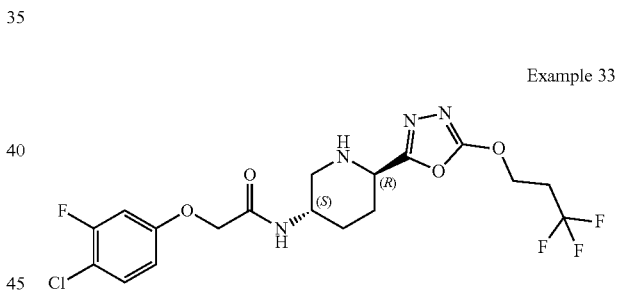

A solution of tert-butyl (2R,5S)-5-[2-(4-chloro-3-fluorophenoxy)acetamido]-2-[5-(3,3,3-trifluoropropoxy)-1,3,4-oxadiazol-2-yl]piperidine-1-carboxylate (107 mg, 0.185 mmol, Example 32) and TFA (0.14 mL, 1.85 mmol) in DCM (2 mL) was stirred at r.t. for 6 h. The reaction mixture was partitioned between DCM (5 mL) and satd aq NaHCO$_3$ solution (5 mL). The organic layer was isolated, concentrated in vacuo, and purified by prep. HPLC (Method 3) to afford the title compound (15 mg, 0.0298 mmol, 16a yield) as a white solid; MH NMR (400 MHz, DMSO-d$_6$) δ 7.97 (d, J=8.0 Hz, 1H), 7.50 (t, J=8.9 Hz, H), 7.07 (dd, J=11.4, 2.8 Hz, 1H), 6.85 (ddd, J=9.0, 2.9, 1.2 Hz, 1H), 4.74-4.58 (m, 2H), 4.53 (s, 2H), 3.79 (dd, J=10.5, 2.5 Hz, 1H), 3.76-3.62 (i, 1H), 3.06-2.80 (i, 3H), 2.47-2.41 (i, 1H), 2.05-1.81 (m, 2H), 1.76-1.59 (i, (H), 1.50 (qd, J=12.3, 3.7 Hz, 1H); M/Z: 467, 469 [M+H]$^+$, ESI$^+$, RT=3.12 (S6).

Example compounds in Table 12 were synthesized according to the synthetic steps of general route 37 as exemplified by Example 33 using the corresponding intermediates.

TABLE 12

| Ex | Structure | Name | Intermediates | LCMS data | ¹H NMR |
|---|---|---|---|---|---|
| 34 | 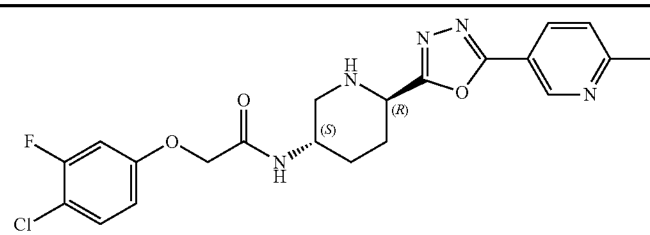 | 2-(4-chloro-3-fluoro-phenoxy)-N-[(3S,6R)-6-[5-(6-methyl-pyridin-3-yl)-1,3,4-oxa-diazol-2-yl]piperidin-3-yl]acetamide | (2R,5S)-1-[(tert-butoxy)carbonyl]-5-[2-(4-chloro-3-fluoro-phenoxy)acetamido]piperidine-2-carboxylic acid (Intermediate 22) and 6-methyl-3-pyridine-carboxylic acid hydrazide | M/Z: 446, 448 [M + H]⁺, ESI⁺, RT = 2.76 (S4) | ¹H NMR (500 MHz, chloroform-d) δ 9.13 (d, J = 2.1 Hz, 1H), 8.23 (dd, J = 8.1, 2.3 Hz, 1H), 7.38-7.29 (m, 2H), 6.80 (dd, J = 10.3, 2.8 Hz, 1H), 6.71 (ddd, J = 8.9, 2.8, 1.2 Hz, 2H), 4.48 (s, 2H), 4.21 (dd, J = 8.0, 3.8 Hz, 1H), 4.11 (ddq, J = 11.9, 8.0, 3.7 Hz, 1H), 3.38 (dd, J = 12.1, 3.4 Hz, 1H), 2.69 (dd, J = 6.8, 5.3 Hz, 1H), 2.66 (s, 3H), 2.25-2.17 (m, 1H), 2.17-2.09 (m, 1H), 2.09-2.00 (m, 1H), 1.72-1.63 (m, 2H). |
| 35 | 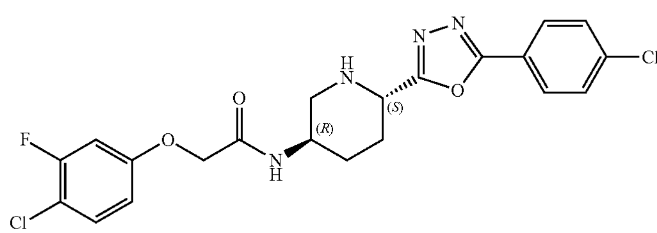 | 2-(4-chloro-3-fluoro-phenoxy)-N-[(3R,6S)-6-[5-(4-chloro-phenyl)-1,3,4-oxa-diazol-2-yl]piperidin-3-yl]acetamide | (5R)-1-[(tert-butoxy)carbonyl]-5-[2-(4-chloro-3-fluoro-phenoxy)acetamido]piperidine-2-carboxylic acid (Intermediate 23) and 4-chloro-benzo-hydrazide | M/Z: 465, 467, 469 [M + H]⁺, ESI⁺, RT = 2.23 (S4) | ¹H NMR (500 MHz, DMSO-d₆) δ 8.06-7.94 (m, 3H), 7.69 (d, J = 8.6 Hz, 2H), 7.50 (t, J = 8.9 Hz, 1H), 7.08 (dd, J = 11.4, 2.8 Hz, 1H), 6.86 (dd, J = 8.9, 1.9 Hz, 1H), 4.54 (s, 2H), 3.99 (dd, J = 10.6, 2.8 Hz, 1H), 3.83-3.69 (m, 1H), 3.13-2.83 (m, 2H), 2.14-2.05 (m, 1H), 2.00-1.87 (m, 1H), 1.86-1.71 (m, 1H), 1.56 (qd, J = 12.5, 3.9 Hz, 1H). |
| 36 | 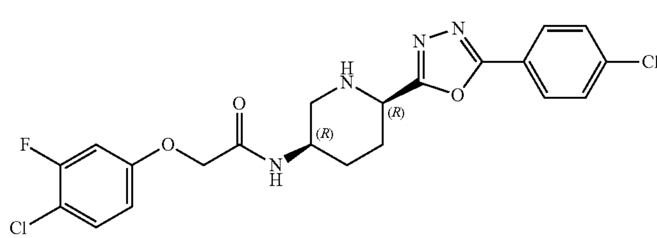 | 2-(4-chloro-3-fluoro-phenoxy)-N-[(3R,6R)-6-[5-(4-chloro-phenyl)-1,3,4-oxa-diazol-2-yl]piperidin-3-yl]acetamide | (5R)-1-[tert-butoxy)carbonyl]-5-[2-(4-chloro-3-fluoro-phenoxy)acetamido]piperidine-2-carboxylic acid (Intermediate 23) and 4-chloro-benzo-hydrazide | M/Z: 465, 467, 469 [M + H]⁺, ESI⁺, RT = 2.44 (S4) | ¹H NMR (500 MHz, DMSO-d₆) δ 8.19 (s, 1H), 8.06-8.00 (m, 2H), 8.00-7.93 (m, 1H), 7.74-7.63 (m, 2H), 7.47 (t, J = 8.9 Hz, 1H), 7.05 (dd, J = 11.4, 2.8 Hz, 1H), 6.83 (dd, J = 8.9, 1.8 Hz, 1H), 4.53 (s, 2H), 4.29-4.17 (m, 1H), 3.90-3.74 (m, 1H), 2.85 (dd, J = 12.2, |

TABLE 12-continued

| Ex | Structure | Name | Intermediates | LCMS data | 1H NMR |
|---|---|---|---|---|---|
| | | | | | 3.5 Hz, 1H), 2.70-2.59 (m, 1H), 2.14-2.01 (m, 1H), 1.96-1.82 (m, 1H), 1.80-1.65 (m, 2H). |
| 37 | 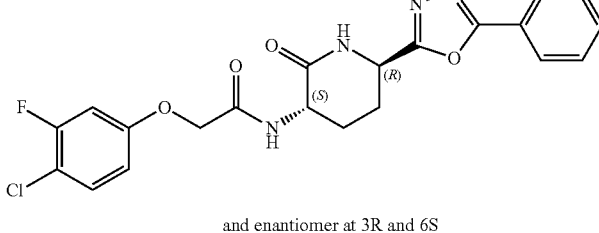 and enantiomer at 3R and 6S | rac-2-(4-chloro-3-fluoro-phenoxy)-N-[(3R,6S)-6-[5-(4-chloro-phenyl)-1,3,4-oxa-diazol-2-yl]-2-oxo-piperidin-3-yl]acetamide | 5-[2-(4-chloro-3-fluoro-phenoxy)acetamido]-6-oxo-piperidine-2-carboxylic acid (Intermediate 41) and 4-chloro-benzo-hydrazide following steps 37.a and 37.b | M/Z: 479, 481, 483 [M + H]+, ESI+, RT = 3.13 (S4) | 1H NMR (500 MHz, DMSO-d6) δ 8.43 (d, J = 8.2 Hz, 1H), 8.28 (s, 1H), 8.11-8.03 (m, 2H), 7.76-7.65 (m, 2H), 7.51 (t, J = 8.9 Hz, 1H), 7.12 (dd, J = 11.4, 2.8 Hz, 1H), 6.90 (dd, J = 8.9, 1.9 Hz, 1H), 4.98 (dd, J = 9.7, 4.8 Hz, 1H), 4.65-4.55 (m, 2H), 4.43-4.34 (m, 1H), 2.34-2.27 (m, 1H), 2.21-2.11 (m, 1H), 2.11-2.04 (m, 1H), 2.02-1.91 (m, 1H). |
| 38 | 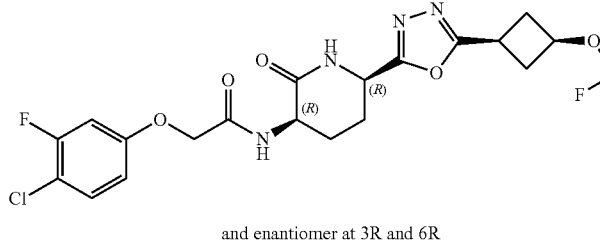 and enantiomer at 3R and 6R | rac-2-(4-chloro-3-fluoro-phenoxy)-N-[(3R,6R)-2-oxo-6-{5-[(1s,3s)-3-(trifluoro-methoxy)cyclo-butyl]-1,3,4-oxa-diazol-2-yl}piperidin-3-yl]acetamide | 5-[2-(4-chloro-3-fluoro-phenoxy)acetamido]-6-oxo-piperidine-2-carboxylic acid (Intermediate 41) and (1s,3s)-3-(trifluoro-methoxy)cyclo-butane-1-carbo-hydrazide (Intermediate 55) following steps 37.a and 37.b | M/Z: 507, 509 [M + H]+, ESI+, RT = 3.07 (S4) | 1H NMR (500 MHz, DMSO-d6) δ 8.40 (d, J = 8.2 Hz, 1H), 8.27-8.15 (m, 1H), 7.54-7.44 (m, 1H), 7.14-7.05 (m, 1H), 6.91-6.83 (m, 1H), 4.96-4.88 (m, 1H), 4.88-4.83 (m, 1H), 4.63-4.51 (m, 2H), 4.41-4.27 (m, 1H), 3.51-3.39 (m, 1H), 2.90-2.80 (m, 2H), 2.57-2.52 (m, 1H), 2.33-1.80 (m, 5H). |
| 39 | 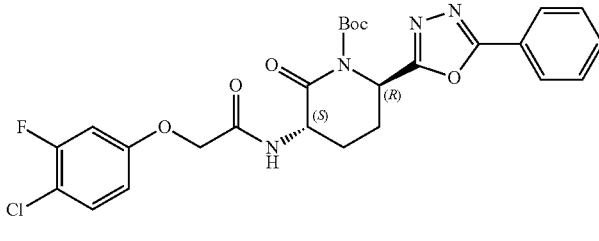 | tert-butyl (2R,5S)-5-[2-(4-chloro-3-fluoro-phenoxy)acetamido]-2-[5-(4-chloro-phenyl)-1,3,4-oxa-diazol-2-yl]piperidine-1-carboxy- | (2R,5S)-1-[(tert-butoxy)carbonyl]-5-[2-(4-chloro-3-fluoro-phenoxy)acetamido]piperidine-2-carboxylic acid (Inter-mediate | M/Z: 465, 467, 469 [M − BOC + H]+, ESI+, RT = 1.39 (S1) | 1H NMR (500 MHz, chloro-form-d) δ 1.51 (s, 9H), 1.91-2.16 (m, 3H), 2.25-2.37 (m, 1H), 3.18-3.37 (m, 1H), 4.02-4.19 (m, 1H), 4.19-4.29 (m, 1H), 4.45-4.57 (m, 2H), 5.74 (s, 1H), 6.71 (ddd, J = 8.9, 2.8, 1.1 Hz, |

TABLE 12-continued

| Ex | Structure | Name | Intermediates | LCMS data | ¹H NMR |
|---|---|---|---|---|---|
| | | late | 22) and 4-cloro-benzo-hydrazide following steps 37.a and 37.b | | 1H), 6.75-6.99 (m, 2H), 7.37 (t, J = 8.6 Hz, 1H), 7.51 (d, J = 8.6 Hz, 2H), 7.93-8.04 (m, 2H). |
| 40 | 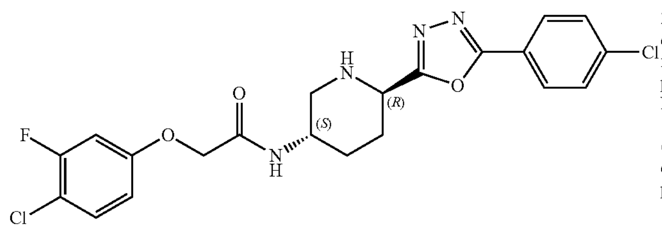 | 2-(4-chloro-3-fluoro-phenoxy)-N-[(3S,6R)-6-[5-(4-chloro-phenyl)-1,3,4-oxa-diazol-2-yl]piperidin-3-yl]acetamide | From tert-butyl (2R,5S)-5-[2-(4-chloro-3-fluoro-phenoxy)acetamido]-2-[5-(4-chloro-phenyl)-1,3,4-oxa-diazol-2-yl]piperidine-1-carboxy-late (Example 39) following step 37.c | M/Z: 465, 467, 469 [M + H]⁺, ESI⁺, RT = 2.25 (S4) | ¹H NMR (500 MHz, DMSO-d₆) δ = 1.77 (qd, J = 13.2, 12.8, 3.9 Hz, 1H), 1.95-2.10 (m, 2H), 2.31 (s, 3H), 2.42 (dd, J = 10.9, 3.5 Hz, 1H), 3.01 (t, J = 11.8 Hz, 1H), 3.42 (dd, J = 12.1, 3.6 Hz, 1H), 4.04-4.19 (m, 1H), 4.58 (s, 2H), 4.82-4.94 (m, 1H), 6.81-6.93 (m, 1H), 7.09 (dd, J = 11.3, 2.8 Hz, 1H), 7.51 (t, J = 8.9 Hz, 1H), 7.69-7.79 (m, 2H), 8.01-8.10 (m, 2H), 8.35 (d, J = 7.8 Hz, 1H), 9.72 (s, 2H). |

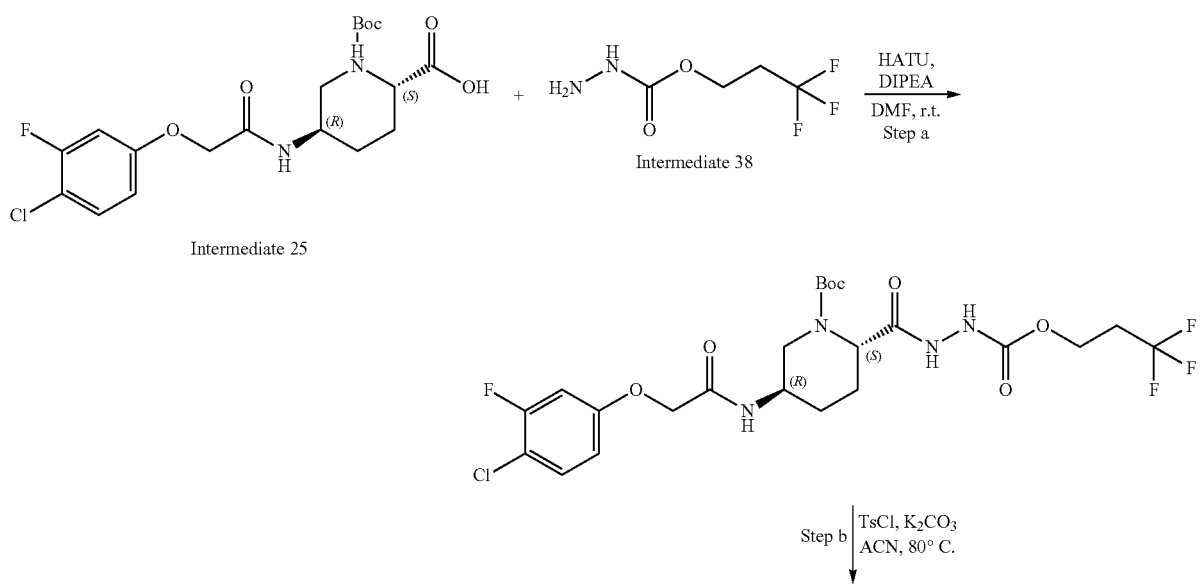

Scheme for route 38

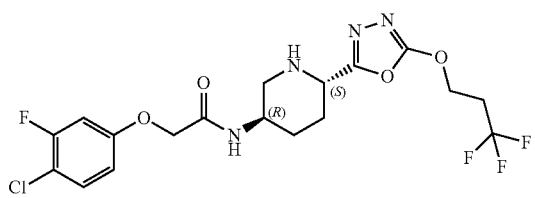

Example 42

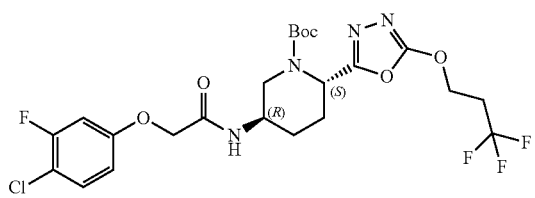

Example 41

Step 38.a: tert-butyl (2S,5R)-5-[2-(4-chloro-3-fluorophenoxy)acetamido]-2-{N'-[(3,3,3-trifluoropropoxy)carbonyl]hydrazinecarbonyl}piperidine-1-carboxylate

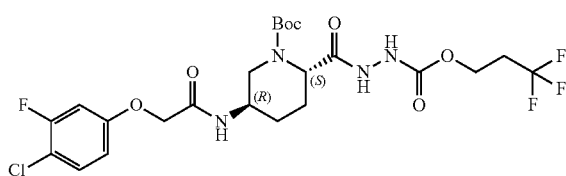

To a solution of (2S,5R)-1-[(tert-butoxy)carbonyl]-5-[2-(4-chloro-3-fluorophenoxy)acetamido]piperidine-2-carboxylic acid (450 mg, 1.04 mmol, Intermediate 25) in anhydrous DMF (5 mL) was added HATU (477 mg, 1.25 mmol) and DIPEA (0.36 mL, 2.09 mmol) and the mixture was stirred at r.t. for 10 min. (3,3,3-trifluoropropoxy)carbohydrazide (90% purity, 260 mg, 1.36 mmol, Intermediate 38) was then added and the mixture was stirred at r.t. for 18 h. The reaction mixture was partitioned between EtOAc (25 mL) and 1 M aq HCl solution (25 mL). The organic layer was isolated, washed with satd aq NaHCO₃ (25 mL) and brine (2×25 mL), dried over MgSO₄ and concentrated in vacuo. The residue was purified by chromatography on silica gel (20-100% EtOAc in heptane) to afford the title compound (85% purity, 268 mg, 0.389 mmol, 37% yield) as a clear oil; $^1$H NMR (400 MHz, DMSO-$d_6$) δ 9.78 (s, 1H), 9.22 (s, 1H), 7.98 (d, J=7.1 Hz, 1H), 7.48 (m 1H), 7.05 (dd, J=11.4, 2.8 Hz, 1H), 6.82 (dd, J=8.9, 1.8 Hz, 1H), 4.74-4.44 (m, 3H), 4.22 (m, 2H), 3.87 (m, 2H), 2.63 (m, 2H), 2.02 (m, 2H), 1.85 (m, 1H), 1.58 (s, 2H), 1.37 (s, 9H); M/Z: 485, 487 [M-Boc+H]$^+$, ESI$^+$, RT=0.96 (S2).

Example 41 (Step 38.b): tert-butyl (2S,5R)-5-[2-(4-chloro-3-fluorophenoxy)acetamido]-2-[5-(3,3,3-trifluoropropoxy)-1,3,4-oxadiazol-2-yl]piperidine-1-carboxylate

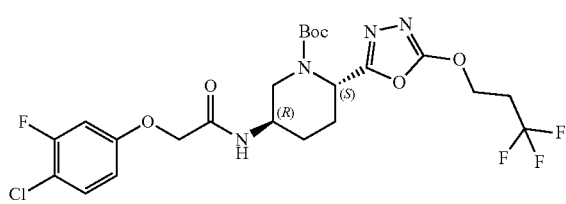

Example 41

A suspension of tert-butyl (2S,5R)-5-[2-(4-chloro-3-fluorophenoxy)acetamido]-2-{N-[(3,3,3-trifluoropropoxy)carbonyl]hydrazinecarbonyl}piperidine-1-carboxylate (85% purity, 265 mg, 0.385 mmol), K₂CO₃ (319 mg, 2.31 mmol) and TsCl (220 mg, 1.16 mmol) in ACN (2.5 mL) was stirred at 80° C. for 24 h. The reaction mixture was diluted with H₂O (10 mL) and extracted with EtOAc (3×10 mL). The combined organic extracts were washed with brine (3×10 mL), dried over MgSO₄, and concentrated in vacuo. The resultant residue was purified by chromatography on silica gel (0-100% EtOAc in heptane) to afford the title compound (88% purity, 68 mg, 0.106 mmol, 27% yield) as a brown oil; $^1$H NMR (500 MHz, DMSO-$d_6$) δ 8.08 (d, J=7.0 Hz, 1H), 7.48 (t, J=8.9 Hz, 1H), 7.04 (dd, J=11.4, 2.8 Hz, 1H), 6.85-6.78 (m, 1H), 5.38 (s, 1H), 4.65 (t, J=5.7 Hz, 2H), 4.62-4.51 (m, 2H), 3.96-3.84 (m, 2H), 3.02-2.85 (m, 2H), 2.24-2.13 (m, 1H), 2.04-1.94 (m, 2H), 1.84-1.74 (m, 1H), 1.68-1.57 (m, 1H), 1.38 (s, 9H); M/Z: 467, 469 [M-Boc+H]$^+$, ESI$^+$, RT=1.31 (S1).

Example 42 (Step 38.c): 2-(4-chloro-3-fluorophenoxy)-N-[(3R,6S)-6-[5-(3,3,3-trifluoropropoxy)-1,3,4-oxadiazol-2-yl]piperidin-3-yl]acetamide Example 42

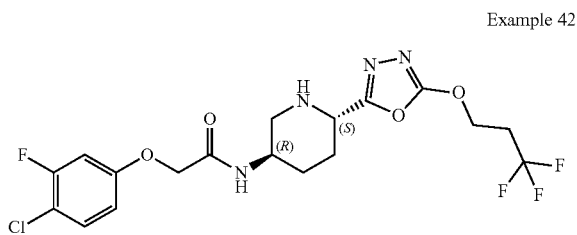

To a solution of tert-butyl (2S,5R)-5-[2-(4-chloro-3-fluorophenoxy)acetamido]-2-[5-(3,3,3-trifluoropropoxy)-1,3,4-oxadiazol-2-yl]piperidine-1-carboxylate (88% purity, 55 mg, 0.0854 mmol) in DCM (1 mL) was added ZnBr₂ (77 mg, 0.341 mmol) and the mixture was stirred under N₂ at r.t. for 18 h. The reaction mixture was diluted with satd aq NaHCO₃ solution (3 mL) and extracted with DCM:IPA (80:20) (3×3 mL). The combined organic extracts were washed with brine (5 mL), dried over MgSO₄, and concentrated in vacuo. The resultant residue was purified by prep. HPLC (Method 3) to afford the title compound (12 mg, 0.0249 mmol, 29% yield) as a white powder; $^1$H NMR (500 MHz, DMSO-$d_6$) δ 7.96 (d, J=7.8 Hz, 1H), 7.49 (t, J=8.8 Hz, 1H), 7.07 (dd, J=11.4, 2.5 Hz, 1H), 6.87-6.81 (m, 1H), 4.64 (t, J=5.5 Hz, 2H), 4.52 (s, 2H), 3.80-3.63 (m, 2H), 3.02-2.83 (m, 3H), 2.83-2.75 (m, 1H), 2.46-2.39 (m, 1H), 2.00-1.83 (m, 2H), 1.70-1.57 (m, 1H), 1.54-1.43 (m, 1H); M/Z: 467, 469, [M+H]$^+$, ESI$^+$, RT=3.12 (S6).

The example compound in Table 13 was synthesized according to the synthetic steps of general route 38 as exemplified by Example 42 using the corresponding intermediates.

TABLE 13

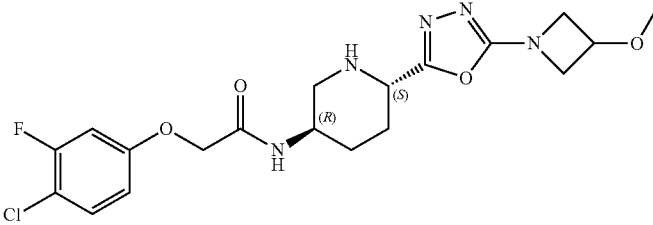

| Ex | Structure | Name | Intermediates | LCMS data | $^1$H NMR |
|---|---|---|---|---|---|
| 43 | 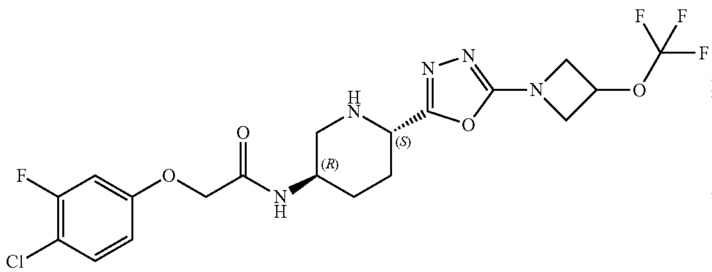 | 2-(4-chloro-3-fluoro-phenoxy)-N-[(3R,6S)-6-[5-[3-(trifluoro-methoxy)azetidin-1-yl]-1,3,4-oxa-diazol-2-yl}piperidin-3-yl]acetamide | (2S,5R)-1-[(tert-butoxy)carbonyl]-5-[2-(4-chloro-3-fluoro-phenoxy)acetamido]-piperidine-2-carboxylic acid (Intermediate 25) and 3-(trifluoro-methoxy)azetidine-1-carbo-hydrazide (Intermediate 37) | M/Z: 494, 496 [M + H]$^+$, ESI$^+$, RT = 3.12 (S6) | $^1$H NMR (500 MHz, DMSO-d$_6$) δ 7.96 (d, J = 8.1 Hz, 1H), 7.49 (t, J = 8.9 Hz, 1H), 7.07 (dd, J = 11.4, 2.8 Hz, 1H), 6.85 (ddd, J = 9.0, 2.8, 1.1 Hz, 1H), 5.33 (tt, J = 7.0, 4.1 Hz, 1H), 4.51 (s, 2H), 4.50-4.42 (m, 2H), 4.24-4.15 (m, 2H), 3.76-3.63 (m, 2H), 3.02-2.92 (m, 1H), 2.74-2.65 (m, 1H), 2.45-2.38 (m, 1H), 1.98-1.84 (m, 2H), 1.69-1.57 (m, 1H), 1.53-1.42 (m, 1H). |

Scheme for route 39

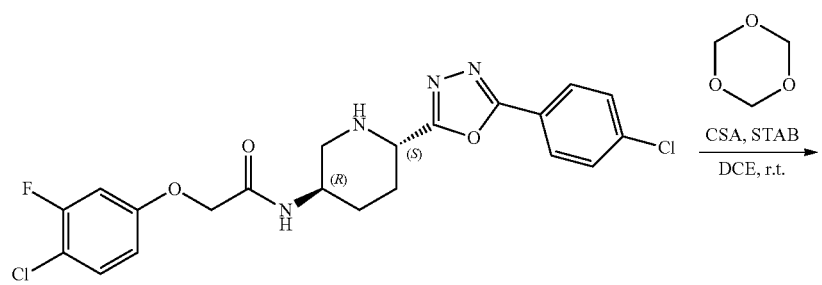

Example 35

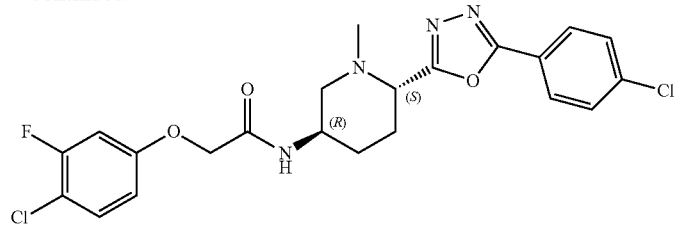

Example 44

Example 44: 2-(4-chloro-3-fluorophenoxy)-N-[(3R,6S)-6-[5-(4-chlorophenyl)-1,3,4-oxadiazol-2-yl]-1-methylpiperidin-3-yl]acetamide A solution of CSA (200 μL, 0.0172 mmol), 2-(4-chloro-3-fluorophenoxy)-N-[(3R,6S)-6-[5-(4-chlorophenyl)-1,3,4-oxadiazol-2-yl]piperidin-3-yl]acetamide (40 mg, 0.0860 mmol, Example 35) and 1,3,5-trioxane (25 μL, 0.215 mmol) in DCE (0.5 mL) was stirred at r.t. under $N_2$ for 45 min. STAB (55 mg, 0.258 mmol) was added and the reaction mixture was stirred at r.t. for 3 days. The reaction mixture was diluted with DCM (5 mL) and satd aq $NaHCO_3$ solution (5 mL). The organic layer was isolated, concentrated in vacuo, and purified by prep. HPLC (Method 2) to afford the title compound (9.8 mg, 0.0194 mmol, 23% yield) as a white solid; $^1$H NMR (500 MHz, DMSO-$d_6$) δ 8.10 (d, J=8.0 Hz, 1H), 8.06-7.98 (m, 2H), 7.73-7.64 (m, 2H), 7.50 (t, J=8.9 Hz, 1H), 7.08 (dd, J=11.4, 2.8 Hz, 1H), 6.86 (dd, J=8.9, 2.0 Hz, 1H), 4.55 (s, 2H), 4.00-3.86 (m, 1H), 3.52 (dd, J=9.9, 3.0 Hz, 1H), 2.97 (dd, J=11.0, 3.7 Hz, 1H), 2.14-2.04 (m, 4H), 2.02-1.81 (m, 3H), 1.57-1.39 (m, 1H); M/Z: 479, 481, 482 [M+H]$^+$, ESI$^+$, RT=3.00 (S4).

Example compounds in Table 14 were synthesized according to the general route 39 as exemplified by Example 44 using the corresponding intermediates.

TABLE 14

| Ex | Structure | Name | Intermediates | LCMS data | $^1$H NMR |
|---|---|---|---|---|---|
| 45 | 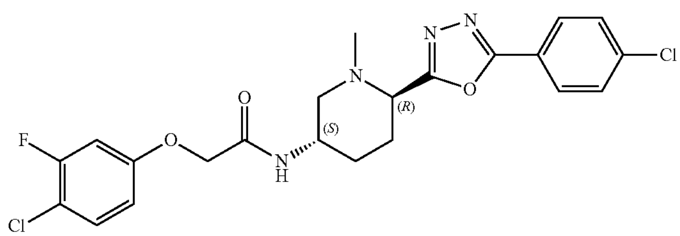 | 2-(4-chloro-3-fluoro-phenoxy)-N-[(3S,6R)-6-[5-(4-chloro-phenyl)-1,3,4-oxa-diazol-2-yl]-1-methyl-piperidin-3-yl] acetamide | 2-(4-chloro-3-fluoro-phenoxy)-N-[(3S,6R)-6-[5-(4-chloro-phenyl)-1,3,4-oxa-diazol-2-yl] piperidin-3-yl] acetamide (Example 40) | M/Z: 479, 481, 483 [M + H]$^+$, ESI$^+$, RT = 2.99 (S4) | $^1$H NMR (500 MHz, DMSO-$d_6$) δ 1.43-1.54 (m, 1H), 1.83-1.94 (m, 2H), 1.94-2.03 (m, 1H), 2.07-2.12 (m, 4H), 2.98 (dd, J = 11.1, 3.7 Hz, 1H), 3.53 (dd, J = 9.8, 3.0 Hz, 1H), 3.86-4.00 (m, 1H), 4.56 (s, 2H), 6.83-6.91 (m, 1H), 7.09 (dd, J = 11.4, 2.8 Hz, 1H), 7.51 (t, J = 8.9 Hz, 1H), 7.64-7.73 (m, 2H), 8.00-8.08 (m, 2H), 8.11 (d, J = 8.0 Hz, 1H). |

TABLE 14-continued

| Ex | Structure | Name | Intermediates | LCMS data | ¹H NMR |
|---|---|---|---|---|---|
| 46 | 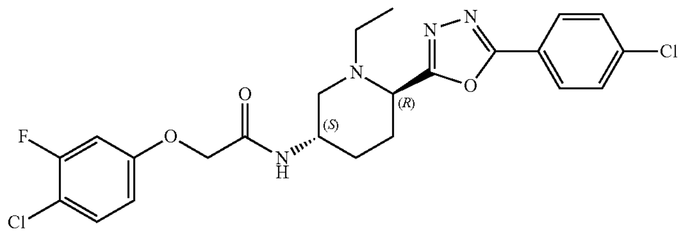 | 2-(4-chloro-3-fluoro-phenoxy)-N-[(3S,6R)-6-[5-(4-chloro-phenyl)-1,3,4-oxa-diazol-2-yl]-1-ethyl-piperidin-3-yl] acetamide | 2-(4-chloro-3-fluoro-phenoxy)-N-[(3S,6R)-6-[5-(4-chloro-phenyl)-1,3,4-oxa-diazol-2-yl] piperidin-3-yl] acetamide (Example 40) and acetaldehyde | M/Z: 493, 495, 497 [M + H]$^+$, ESI$^+$, RT = 3.13 (S4) | ¹H NMR (500 MHz, DMSO-$d_6$) δ 0.93 (t, J = 7.1 Hz, 3H), 1.51 (dt, J = 15.6, 7.7 Hz, 1H), 1.90 (td, J = 9.4, 8.9, 3.1 Hz, 2H), 2.00 (dt, J = 7.6, 4.0 Hz, 1H), 2.20 (dd, J = 11.1, 8.9 Hz, 1H), 2.29 (dq, J = 13.9, 7.0 Hz, 1H), 2.45 (dt, J = 14.3, 7.1 Hz, 1H), 2.99 (dd, J = 11.2, 3.5 Hz, 1H), 3.87 (dd, J = 8.7, 3.4 Hz, 1H), 3.90-4.00 (m, 1H), 4.57 (s, 2H), 6.87 (ddd, J = 9.0, 2.8, 1.0 Hz, 1H), 7.10 (dd, J = 11.4, 2.8 Hz, 1H), 7.52 (t, J = 8.9 Hz, 1H), 7.63-7.72 (m, 2H), 7.97-8.07 (m, 3H). |

Scheme for route 40

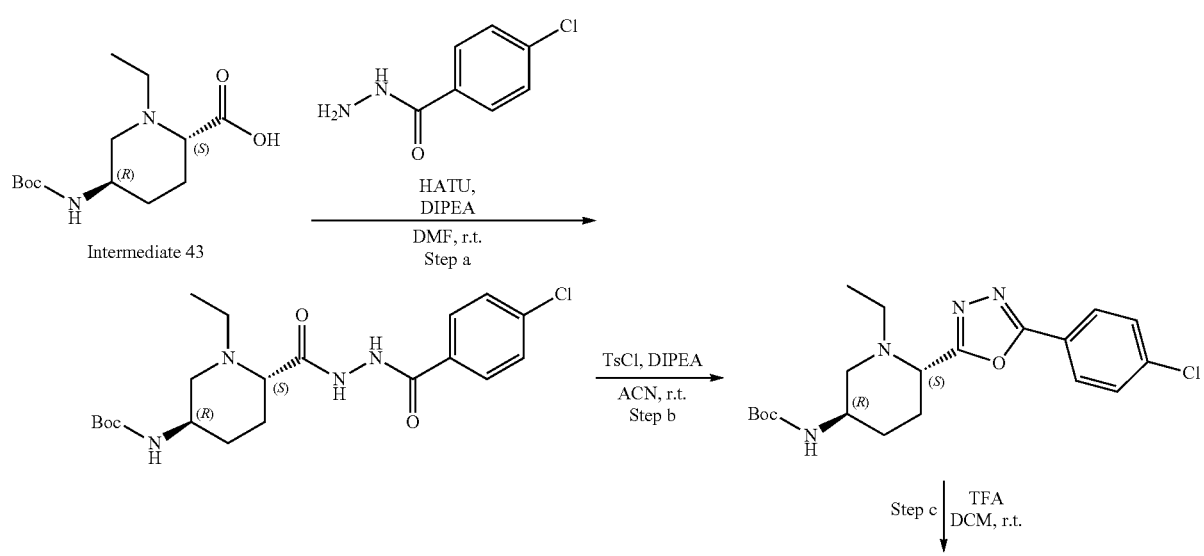

-continued

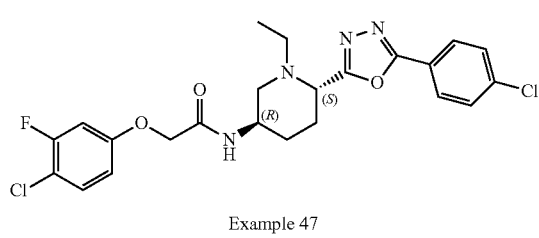

Example 47

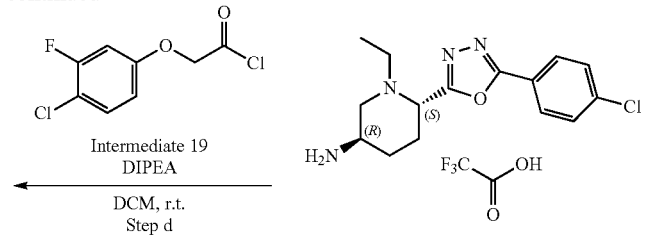

Step 40.a: tert-butyl N-[(3R,6S)-6-{[(4-chlorophenyl)formohydrazido]carbonyl}-1-ethylpiperidin-3-yl]carbamate

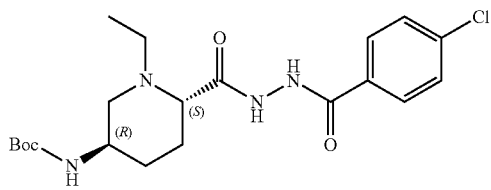

To a solution of (2S,5R)-5-{[(tert-butoxy)carbonyl]amino}-1-ethylpiperidine-2-carboxylic acid (50 mg, 0.183 mmol, Intermediate 43) in DMF (5 mL) at 0° C. was added 4-chlorobenzohydrazide (41 mg, 0.238 mmol), followed by HATU (83 mg, 0.220 mmol) and DIPEA (0.064 mL, 0.366 mmol), and the mixture was stirred r.t. for 3 h. The reaction mixture was diluted with $H_2O$ (30 mL) and extracted with EtOAc (2×20 mL). The combined organic extracts were washed with brine (30 mL), dried over $Na_2SO_4$, and concentrated in vacuo. The residue was purified by chromatography on silica gel (10-100% EtOAc in heptane) to afford the title compound (75% purity, 100 mg, 0.177 mmol, 96% yield); M/Z: 425, 427 [M+H]+, ESI+, RT=0.87 (S1).

Step 40.b: tert-butyl N-[(3R,6S)-6-[5-(4-chlorophenyl)-1,3,4-oxadiazol-2-yl]-1-ethylpiperidin-3-yl]carbamate

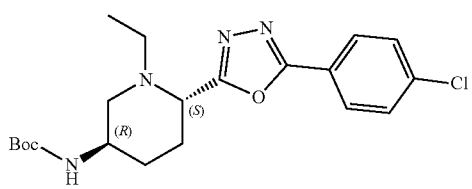

To a solution of tert-butyl N-[(3R,6S)-6-{[(4-chlorophenyl)formohydrazido]carbonyl}-1-ethylpiperidin-3-yl]carbamate (75% purity, 100 mg, 0.177 mmol) in anhydrous ACN (10 mL) was added TsCl (101 mg, 0.530 mmol) followed by DIPEA (0.092 mL, 0.530 mmol) and the mixture was stirred at r.t. for 16 h. 15% aq $NH_4OH$ solution (10 mL) was added and the reaction mixture was concentrated in vacuo. The residue was dissolved in $H_2O$ (20 mL) and extracted with DCM (2×30 mL). The combined organic extracts were washed with brine (30 mL), dried over $Na_2SO_4$, and concentrated in vacuo. The residue was purified by chromatography on silica gel (10-100% EtOAc in heptane) to afford the title compound (81% purity, 82 mg, 0.163 mmol, 92% yield) as a white solid; M/Z: 407, 409 [M+H]+, ESI+, RT=1.02 (S1).

Step 40.c: (3R,6S)-6-[5-(4-chlorophenyl)-1,3,4-oxadiazol-2-yl]-1-ethylpiperidin-3-amine; trifluoroacetic acid

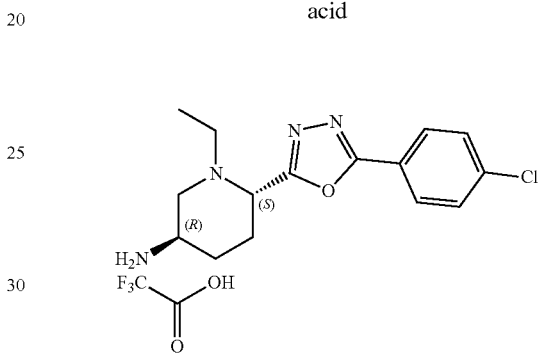

To a solution of tert-butyl N-[(3R,6S)-6-[5-(4-chlorophenyl)-1,3,4-oxadiazol-2-yl]-1-ethylpiperidin-3-yl]carbamate (81% purity, 82 mg, 0.163 mmol) in DCM (1 mL) at 0° C. was added TFA (1.0 mL, 13.5 mmol) and the mixture was stirred at r.t. for 3 h. The reaction mixture was concentrated in vacuo to afford the title compound (28% purity, 160 mg, 0.106 mmol, 65% yield) as a beige gum; M/Z: 307, 309 [M+H]+, ESI+, RT=0.84 (S1).

Example 47 (Step 40.d): 2-(4-chloro-3-fluorophenoxy)-N-[(3R,6S)-6-[5-(4-chlorophenyl)-1,3,4-oxadiazol-2-yl]-1-ethylpiperidin-3-yl]acetamide Example 47

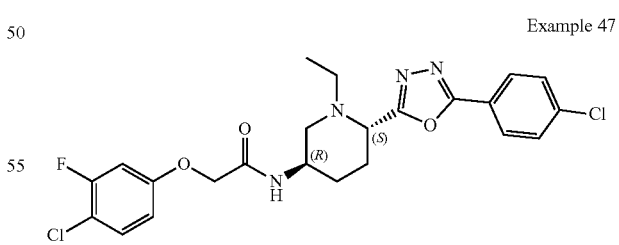

To a solution of (3R,6S)-6-[5-(4-chlorophenyl)-1,3,4-oxadiazol-2-yl]-1-ethyl-piperidin-3-amine trifluoroacetic acid (28% purity, 160 mg, 0.106 mmol) in DCM (5 mL) at 0° C. was added DIPEA (0.056 mL, 0.319 mmol) followed by a solution of 2-(4-chloro-3-fluoro-phenoxy)acetyl chloride (29 mg, 0.128 mmol, Intermediate 19) in DCM (1 mL), and the mixture was stirred at r.t. for 5 h. The reaction mixture was diluted with $H_2O$ (10 mL), extracted with DCM (2×10 mL), and the combined organic extracts were dried over Na₂SO₄ and concentrated in vacuo. The residue was purified by prep. HPLC (Method 5) to afford the title compound (20 mg, 0.0397 mmol, 37% yield) as a white powder; ¹H NMR (400 MHz, DMSO-d₆) δ 8.10-7.89 (m, 3H), 7.76-7.60 (m, 2H), 7.51 (t, J=8.9 Hz, 1H), 7.13-7.05 (m, 1H), 6.91-6.83 (m, 1H), 4.56 (s, 2H), 3.99-3.83 (m, 2H), 3.03-2.94 (m, 1H), 2.49-2.39 (m, 1H), 2.34-2.15 (m, 2H), 2.04-1.82 (m, 3H), 1.57-1.43 (m, 1H), 0.92 (t, J=7.1 Hz, 3H); M/Z: 493, 495, 497 [M+H]⁺, ESI⁺, RT=3.12 (S4).

The example compound in Table 15 was synthesized according to the general route 40 as exemplified by Example 47 using the corresponding intermediate.

TABLE 15

| Ex | Structure | Name | Intermediates | LCMS data | ¹H NMR |
|----|-----------|------|---------------|-----------|--------|
| 48 | 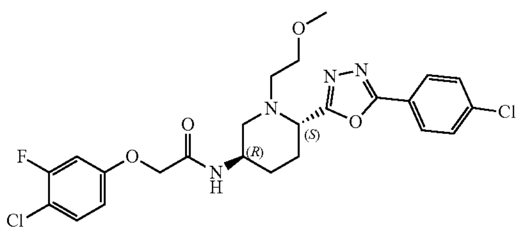 | 2-(4-chloro-3-fluoro-phenoxy)-N-[(3R,6S)-6-[5-(4-chlorophenyl)-1,3,4-oxadiazol-2-yl]-1-(2-methoxyethyl)piperidin-3-yl]acetamide | (2S,5R)-5-{[{tert-butoxy)carbonyl]amino}-1-(2-methoxy-ethyl)piperidine-2-carboxylic acid (Intermediate 45) | M/Z: 523, 525, 527 [M + H]⁺, ESI⁺, RT = 3.66 (S4) | ¹H NMR (400 MHz, DMSO-d₆) δ 8.06-7.95 (m, 3H), 7.68 (d, J = 8.7 Hz, 2H), 7.51 (t, J = 8.9 Hz, 1H), 7.09 (dd, J = 11.4, 2.8 Hz, 1H), 6.87 (ddd, J = 9.0, 2.9, 1.2 Hz, 1H), 4.56 (s, 2H), 4.02-3.85 (m, 2H), 3.14 (s, 3H), 3.06 (dd, J = 11.5, 3.5 Hz, 1H), 2.62-2.54 (m, 1H), 2.34 (dd, J = 11.4, 8.4 Hz, 1H), 2.05-1.94 (m, 1H), 1.94-1.77 (m, 2H), 1.59-1.44 (m, 1H). |

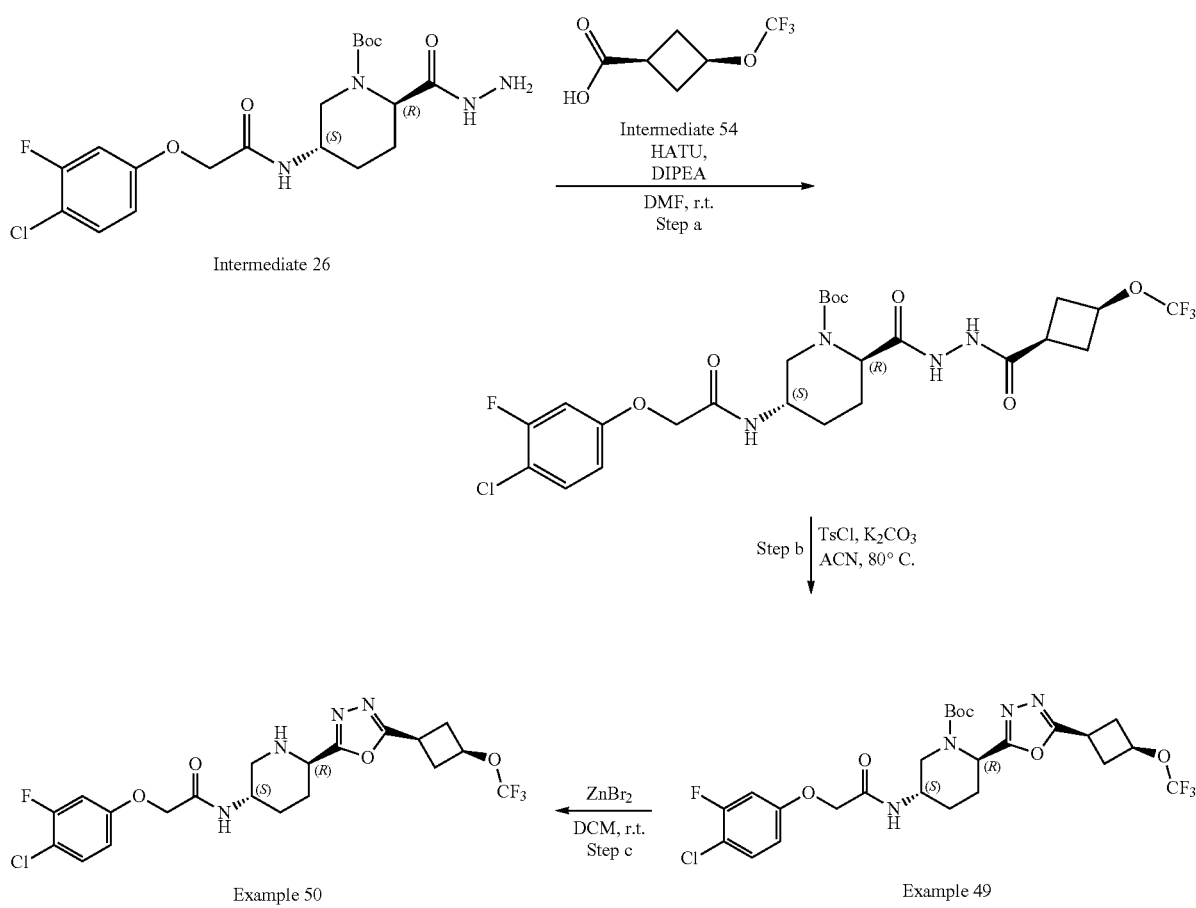

Scheme for route 41

Step 41.a: tert-butyl (2R,5S)-5-[2-(4-chloro-3-fluorophenoxy)acetamido]-2-{N'-[(1s,3s)-3-(trifluoromethoxy)cyclobutanecarbonyl]hydrazinecarbonyl}piperidine-1-carboxylate

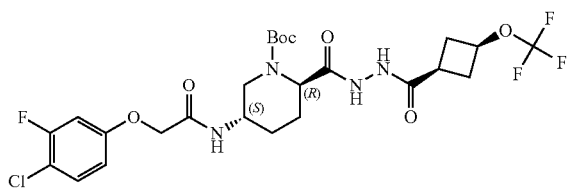

To a solution of (1s,3s)-3-(trifluoromethoxy)cyclobutane-1-carboxylic acid (397 mg, 2.16 mmol, Intermediate 54) and DIPEA (0.94 mL, 5.39 mmol) in anhydrous DMF (12 mL) was added HATU (820 mg, 2.16 mmol) and the mixture was stirred at r.t. for 10 min. A solution of tert-butyl (2R,5S)-5-[2-(4-chloro-3-fluorophenoxy)acetamido]-2-(hydrazinecarbonyl)piperidine-1-carboxylate (800 mg, 1.80 mmol, Intermediate 26) in DMF (7 mL) was added and the mixture was stirred at r.t. for 12 h. The reaction mixture was diluted with H$_2$O (50 mL) and extracted with EtOAc (2×50 mL). The combined organic extracts were washed with brine (2×50 mL), dried over Na$_2$SO$_4$ and concentrated in vacuo. The residue was purified by chromatography on silica gel (0-100% EtOAc in heptane) to afford the title compound (86% purity, 970 mg, 1.37 mmol, 76% yield) as an off-white solid; $^1$H NMR (400 MHz, DMSO-d$_6$) δ 9.84 (s, 2H), 7.98 (d, J=7.1 Hz, 1H), 7.47 (t, J=8.9 Hz, 1H), 7.04 (dd, J=11.4, 2.9 Hz, 1H), 6.82 (dd, J=8.9, 1.8 Hz, 1H), 4.86-4.73 (m, 1H), 4.68-4.45 (m, 3H), 3.98-3.75 (m, 2H), 2.73-2.62 (m, 4H), 2.36-2.21 (m, 2H), 2.12-1.77 (m, 2H), 1.70-1.50 (m, 2H), 1.37 (s, 9H); M/Z: 609, 611 [M-Boc+H]$^+$, ESI$^+$, RT=0.99 (S2).

Example 49 (Step 41.b): tert-butyl (2R,5S)-5-[2-(4-chloro-3-fluorophenoxy)acetamido]-2-{5-[(1s,3s)-3-(trifluoromethoxy)cyclobutyl]-1,3,4-oxadiazol-2-yl}piperidine-1-carboxylate

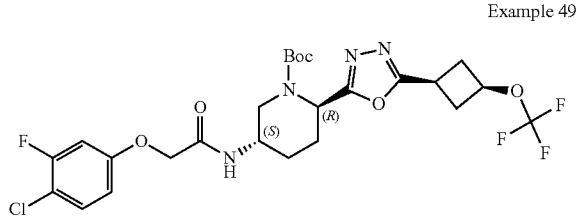

A suspension of tert-butyl (2R,5S)-5-[[2-(4-chloro-3-fluoro-phenoxy)acetyl]amino]-2-[[[(1S,3S)-3-(trifluoromethoxy)cyclobutanecarbonyl]amino]carbamoyl]piperidine-1-carboxylate (86% purity, 970 mg, 1.37 mmol), K$_2$CO$_3$ (1132 mg, 8.19 mmol) and TsCl (781 mg, 4.10 mmol) in ACN (10 mL) was stirred at 80° C. for 3 h. The reaction mixture was partitioned between EtOAc (100 mL) and H$_2$O (100 mL), and the organic layer was isolated, washed with brine (100 mL), dried over MgSO$_4$, and concentrated in vacuo. The residue was purified by chromatography on silica gel (0-100% EtOAc in heptane) to afford the title compound (317 mg, 0.524 mmol, 38% yield) as an off-white powder; $^1$H NMR (500 MHz, DMSO-d$_6$) δ 8.12 (d, J=7.1 Hz, 1H), 7.48 (t, J=8.9 Hz, 1H), 7.05 (dd, J=11.4, 2.8 Hz, 1H), 6.82 (dd, J=8.9, 1.9 Hz, 1H), 5.46 (s, 1H), 4.90 (p, J=7.5 Hz, 1H), 4.64-4.54 (m, 2H), 3.90 (d, J=12.2 Hz, 2H), 3.44 (tt, J=9.8, 7.9 Hz, 1H), 3.35-3.29 (m, 1H), 2.96 (d, J=7.8 Hz, 1H), 2.90-2.78 (m, 2H), 2.23 (ddq, J=13.7, 9.7, 4.4 Hz, 1H), 2.05 (d, J=11.4 Hz, 1H), 1.75 (m, J=13.7, 10.1, 4.1 Hz, 1H), 1.64 (d, J=13.3 Hz, 1H), 1.39 (s, 10H); M/Z: 493, 495 [M-Boc+H]$^+$, ESI$^+$, RT=1.12 (S2).

Example 50 (Step 41.c): 2-(4-chloro-3-fluorophenoxy)-N-[(3S,6R)-6-{5-[(1s,3s)-3-(trifluoromethoxy)cyclobutyl]-1,3,4-oxadiazol-2-yl}piperidin-3-yl]acetamide

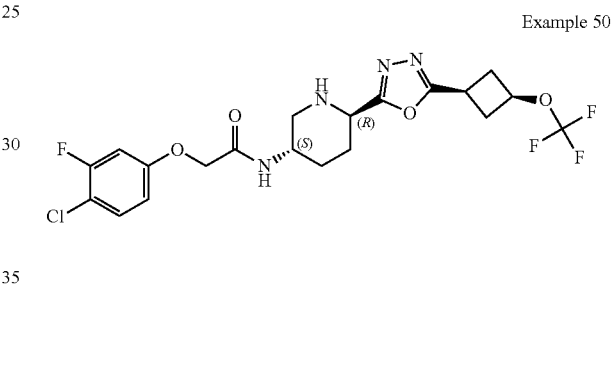

To a solution of tert-butyl (2R,5S)-5-[2-(4-chloro-3-fluorophenoxy)acetamido]-2-{5-[(1s,3s)-3-(trifluoromethoxy)cyclobutyl]-1,3,4-oxadiazol-2-yl}piperidine-1-carboxylate (317 mg, 0.524 mmol, Example 49) in DCM (10 mL) was added ZnBr$_2$ (714 mg, 3.14 mmol) and the mixture was stirred at r.t. under N$_2$ for 20 h. The reaction mixture was diluted with satd aq NaHCO$_3$ solution (10 mL) and 20% IPA in DCM (10 mL). The organic layer was isolated, concentrated in vacuo, and purified by chromatography on silica gel (0-20% MeOH in DCM) to afford the title compound (240 mg, 0.467 mmol, 89% yield) as an off-white powder; $^1$H NMR (400 MHz, DMSO-d$_6$) δ 7.97 (d, J=8.1 Hz, 1H), 7.50 (t, J=8.9 Hz, 1H), 7.07 (dd, J=11.4, 2.8 Hz, 1H), 6.85 (m, J=9.0, 2.9, 1.2 Hz, 1H), 4.96-4.85 (m, 1H), 4.52 (s, 2H), 3.92-3.82 (m, 1H), 3.79-3.63 (m, 1H), 3.48-3.37 (m, 1H), 3.00 (d, J=12.3 Hz, 1H), 2.91-2.77 (m, 3H), 2.49-2.40 (m, 3H), 2.06-1.97 (m, 1H), 1.96-1.86 (m, 1H), 1.77-1.61 (m, 1H), 1.58-1.43 (m, 1H); M/Z: 493, 495 [M+H]$^+$, ESI$^+$, RT=1.12 (S4).

Example compounds in Table 16 were synthesised according to the general route 41 as exemplified by Example 50 using the corresponding intermediates.

TABLE 16

| Ex | Structure | Name | Intermediates | LCMS data | ¹H NMR |
|----|-----------|------|---------------|-----------|--------|
| 51 | 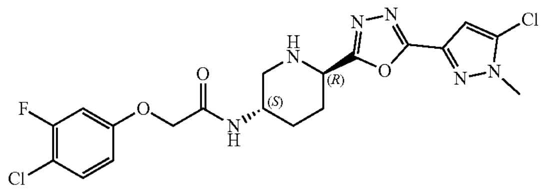 | N-[(3S,6R)-6-[5-(5-chloro-1-methyl-1H-pyrazol-3-yl)-1,3,4-oxadiazol-2-yl]piperidin-3-yl]-2-(4-chloro-3-fluorophenoxy)acetamide | tert-butyl (2R,5S)-5-[2-(4-chloro-3-fluorophenoxy)acetamido]-2-(hydrazinecarbonyl)piperidine-1-carboxylate (Intermediate 26) and 5-chloro-1-methyl-1H-pyrazole-3-carboxylic acid | M/Z: 469, 471, 473 [M + H]⁺, ESI⁺, RT = 1.98 (S4) | ¹H NMR (400 MHz, chloroform-d) δ 7.34 (t, J = 8.6 Hz, 1H), 6.88 (s, 1H), 6.79 (dd, J = 10.3, 2.9 Hz, 2H), 6.73-6.67 (m, 1H), 4.47 (s, 2H), 4.22-4.16 (m, 1H), 4.13-4.04 (m, 1H), 3.96 (s, 3H), 3.32 (dd, J = 12.0, 3.4 Hz, 1H), 2.70-2.61 (m, 1H), 2.25-1.99 (m, 4H), 1.72-1.62 (m, 1H). |
| 52 | 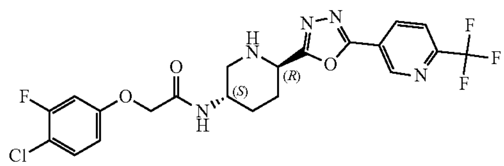 | 2-(4-chloro-3-fluorophenoxy)-N-[(3S,6R)-6-{5-[6-(trifluoromethyl)pyridin-3-yl]-1,3,4-oxadiazol-2-yl}piperidin-3-yl]acetamide | tert-butyl (2R,5S)-5-[2-(4-chloro-3-fluorophenoxy)acetamido]-2-(hydrazinecarbonyl)piperidine-1-carboxylate (Intermediate 26) and 6-(trifluoromethyl)pyridine-3-carboxylic acid | M/Z: 500, 502, [M + H]⁺, ESI⁺, RT = 2.21 (S4) | ¹H NMR (500 MHz, DMSO-d₆) δ 9.37 (d, J = 1.9 Hz, 1H), 8.67 (dd, J = 8.1, 1.9 Hz, 1H), 8.17 (d, J = 8.2 Hz, 1H), 8.03 (d, J = 8.1 Hz, 1H), 7.51 (t, J = 8.9 Hz, 1H), 7.09 (dd, J = 11.4, 2.8 Hz, 1H), 6.87 (ddd, J = 9.0, 2.8, 1.1 Hz, 1H), 4.55 (s, 2H), 4.09-3.99 (m, 1H), 3.83-3.71 (m, 1H), 3.10-2.96 (m, 2H), 2.54 (s, 1H), 2.18-2.09 (m, 1H), 2.08 (s, 1H), 2.01-1.91 (m, 1H), 1.81 (qd, J = 12.9, 3.8 Hz, 1H), 1.58 (qd, J = 12.5, 4.0 Hz, 1H). |
| 53 | 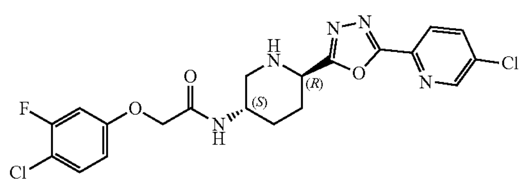 | 2-(4-chloro-3-fluorophenoxy)-N-[(3S,6R)-6-[5-(5-chloropyridin-2-yl)-1,3,4-oxadiazol-2-yl]piperidin-3-yl]acetamide | tert-butyl (2R,5S)-5-[2-(4-chloro-3-fluorophenoxy)acetamido]-2-(hydrazinecarbonyl)piperidine-1-carboxylate (Intermediate 26) and 5-chloropyridine-2-carboxylic acid | M/Z: 466, 468, [M + H]⁺, ESI⁺, RT = 2.00 (S4) | ¹H NMR (500 MHz, DMSO-d₆) δ 8.85 (t, J = 1.6 Hz, 1H), 8.20 (d, J = 1.6 Hz, 2H), 8.01 (d, J = 8.1 Hz, 1H), 7.51 (t, J = 8.9 Hz, 1H), 7.09 (dd, J = 11.4, 2.8 Hz, 1H), 6.87 (ddd, J = 9.0, 2.8, 1.1 Hz, 1H), 4.54 (s, 2H), 4.07-3.99 (m, 1H), 3.82-3.69 (m, 1H), 3.04 (d, J = 11.5 Hz, 1H), 2.97 (s, 1H), 2.57-2.52 (m, 1H), 2.10 (dt, J = 11.4, 2.9 Hz, 1H), 1.99-1.91 (m, 1H), 1.78 (qd, J = 12.8, 3.7 Hz, 1H), 1.57 (qd, J = 12.5, 3.9 Hz, 1H). |
| 54 | 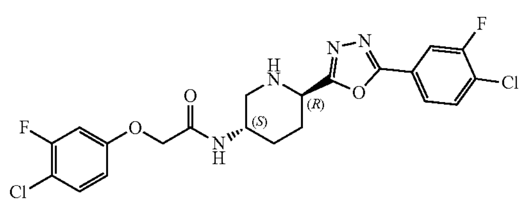 | 2-(4-chloro-3-fluorophenoxy)-N-[(3S,6R)-6-[5-(4-chloro-3-fluorophenyl)-1,3,4-oxadiazol-2-yl]piperidin-3-yl]acetamide | tert-butyl (2R,5S)-5-[2-(4-chloro-3-fluorophenoxy)acetamido]-2-(hydrazinecarbonyl)piperidine-1-carboxylate (Intermediate 26) and 4-chloro-3-fluorobenzoic acid | M/Z: 483, 485, [M + H]⁺, ESI⁺, RT = 2.39 (S4) | ¹H NMR (400 MHz, DMSO-d₆) δ 8.05-7.97 (m, 2H), 7.90-7.82 (m, 2H), 7.50 (t, J = 8.9 Hz, 1H), 7.08 (dd, J = 11.4, 2.8 Hz, 1H), 6.89-6.83 (m, 1H), 4.53 (s, 2H), 4.04-3.94 (m, 1H), 3.81-3.70 (m, 1H), 3.08-2.94 (m, 2H), 2.14-2.05 (m, 1H), 1.94 (dd, J = 12.9, 2.8 Hz, 1H), 1.85-1.70 (m, 1H), 1.56 (qd, J = 12.4, 3.8 Hz, 1H). |

TABLE 16-continued

| Ex | Structure | Name | Intermediates | LCMS data | ¹H NMR |
|---|---|---|---|---|---|
| 55 | 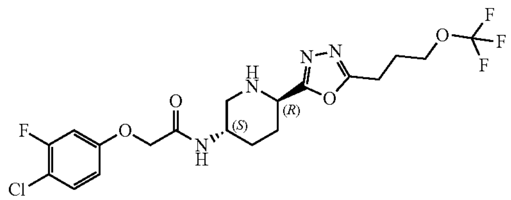 | 2-(4-chloro-3-fluorophenoxy)-N-[(3S,6R)-6-{5-[3-(trifluoromethoxy)propyl]-1,3,4-oxadiazol-2-yl}piperidin-3-yl]acetamide | tert-butyl (2R,5S)-5-[2-(4-chloro-3-fluorophenoxy)acetamido]-2-(hydrazinecarbonyl)piperidine-1-carboxylate (Intermediate 26) and 4-(trifluoromethoxy)butanoic acid (Intermediate 35) | M/Z: 481, 483, [M + H]⁺, ESI⁺, RT = 3.22 (S6) | ¹H NMR (400 MHz, methanol-d) δ 8.38-8.08 (m, 1H), 7.39 (t, J = 8.7 Hz, 1H), 6.95 (dd, J = 10.9, 2.8 Hz, 1H), 6.84 (ddd, J = 8.9, 2.8, 1.2 Hz, 1H), 4.54 (s, 2H), 4.20-3.87 (m, 4H), 3.25-3.19 (m, 1H), 3.02 (t, J = 7.4 Hz, 1H), 2.70-2.59 (m, 1H), 2.26-2.00 (m, 4H), 1.94-1.79 (m, 1H), 1.73-1.58 (m, 1H). |

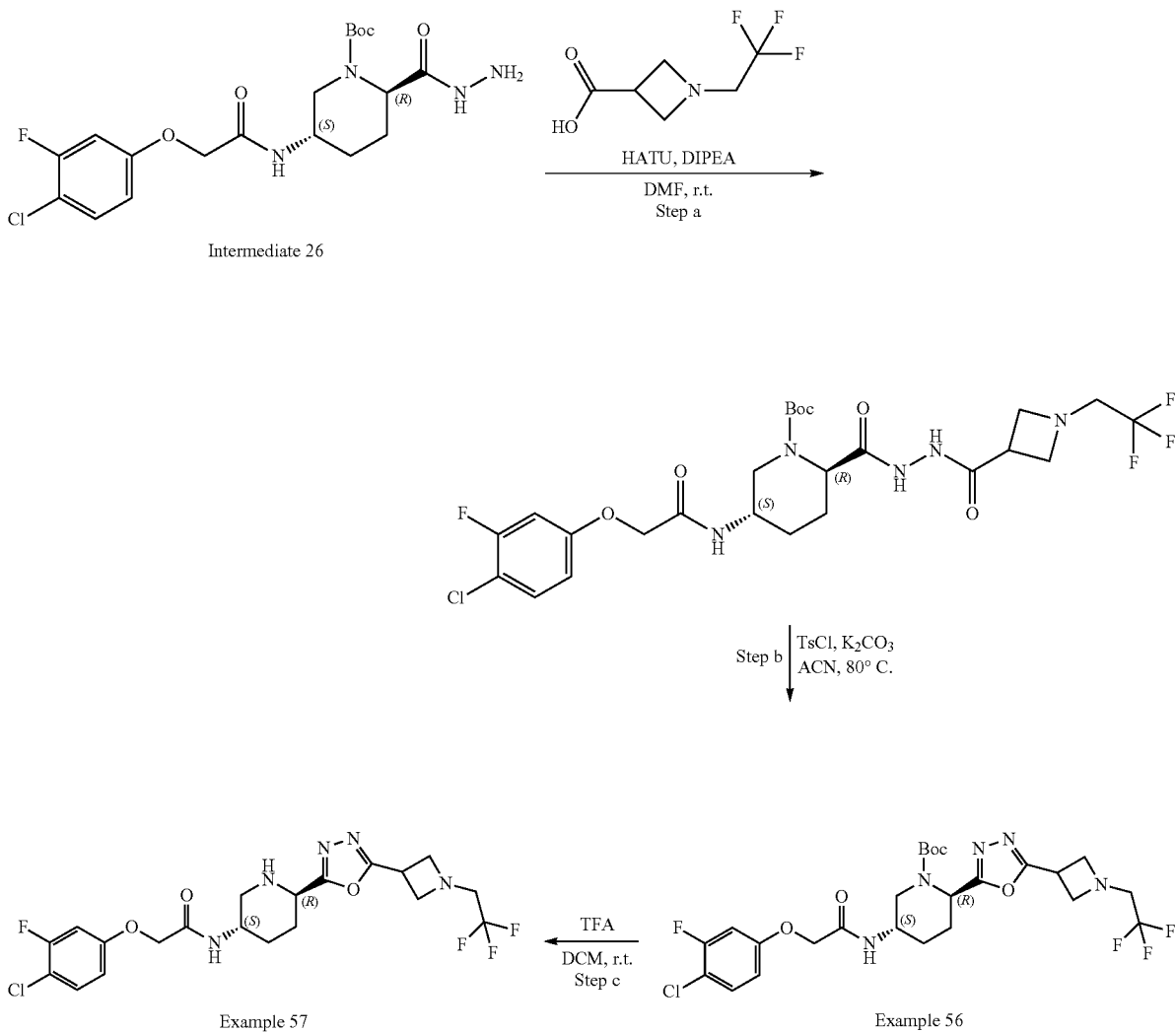

Scheme for route 42

Step 42.a: tert-butyl (2R,5S)-5-[2-(4-chloro-3-fluorophenoxy)acetamido]-2-{N'-[1-(2,2,2-trifluoroethyl)azetidine-3-carbonyl]hydrazinecarbonyl}piperidine-1-carboxylate

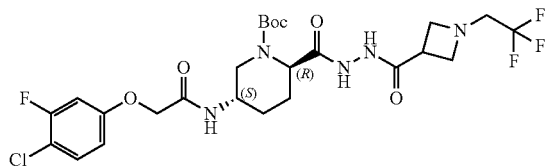

To a solution of 1-(2,2,2-trifluoroethyl)azetidine-3-carboxylic acid (74 mg, 0.405 mmol) in anhydrous DMF (2 mL) was added HATU (185 mg, 0.486 mmol) followed by DIPEA (0.14 mL, 0.809 mmol) and the mixture was stirred at r.t. for 10 min. tert-butyl (2R,5S)-5-[2-(4-chloro-3-fluorophenoxy)acetamido]-2-(hydrazinecarbonyl)piperidine-1-carboxylate (90% purity, 200 mg, 0.405 mmol, Intermediate 26) was added and the mixture was stirred at r.t. for 20 h. The reaction mixture was diluted with H₂O (5 mL) and extracted with EtOAc (2×20 mL). The combined organic extracts were washed with brine (20 mL), dried over MgSO₄, and concentrated in vacuo. The residue was purified by chromatography on silica gel (0-100% EtOAc in heptane, followed by 0-20% MeOH in EtOAc) to afford the title compound (90% purity, 206 mg, 0.303 mmol, 75% yield) as a pale yellow gum; ¹H NMR (400 MHz, DMSO-d₆) δ 9.81 (s, 2H), 8.05-7.93 (m, 1H), 7.48 (t, J=8.9 Hz, 1H), 7.05 (dd, J=11.4, 2.8 Hz, 1H), 6.83 (dd, J=9.0, 1.8 Hz, 1H), 4.75-4.48 (m, 3H), 3.99-3.76 (m, 2H), 3.55 (t, J=7.4 Hz, 2H), 3.17 (q, J=10.2 Hz, 2H), 2.11-2.01 (m, 1H), 1.96-1.81 (m, 1H), 1.70-1.50 (m, 2H), 1.37 (s, 9H); M/Z: 610, 612 [M+H]⁺, ESI⁺, RT=0.85 (S2).

Example 56 (Step 42.b): tert-butyl (2R,5S)-5-[2-(4-chloro-3-fluorophenoxy)acetamido]-2-{5-[1-(2,2,2-trifluoroethyl)azetidin-3-yl]-1,3,4-oxadiazol-2-yl}piperidine-1-carboxylate

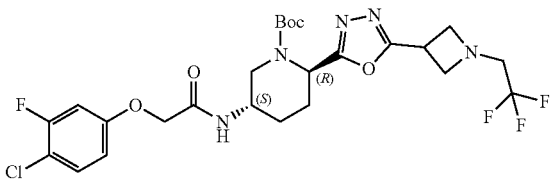

Example 56

A suspension of tert-butyl (2R,5S)-5-[2-(4-chloro-3-fluorophenoxy)acetamido]-2-{N-[1-(2,2,2-trifluoroethyl)azetidine-3-carbonyl]hydrazinecarbonyl}piperidine-1-carboxylate (90% purity, 206 mg, 0.303 mmol), K₂CO₃ (252 mg, 1.82 mmol) and TsCl (0.012 mL, 0.910 mmol) in ACN (1.5384 mL) was stirred at 80° C. for 45 min. The reaction mixture was diluted with H₂O (5 mL) and extracted with EtOAc (2×20 mL). The combined organic extracts were washed with brine (20 mL), dried over MgSO₄, and concentrated in vacuo. The residue was purified by chromatography on silica gel (0-100% EtOAc in heptane) to afford the title compound (110 mg, 0.179 mmol, 59% yield) as a colourless gum; ¹H NMR (400 MHz, DMSO-d₆) δ 8.11 (d, J=7.0 Hz, 1H), 7.48 (t, J=8.9 Hz, 1H), 7.05 (dd, J=11.4, 2.8 Hz, 1H), 6.87-6.79 (m, 1H), 5.48 (s, 1H), 4.65-4.49 (m, 2H), 4.00-3.94 (m, 1H), 3.92 (d, J=11.6 Hz, 1H), 3.78 (t, J=7.7 Hz, 2H), 3.56 (q, J=6.8 Hz, 2H), 3.27 (dd, J=20.3, 10.2 Hz, 2H), 3.09-2.93 (m, 1H), 2.31-2.17 (m, 1H), 2.11-2.00 (m, 1H), 1.76 (t, J=13.7 Hz, 1H), 1.70-1.59 (m, 1H), 1.39 (s, 9H); M/Z: 592, 594 [M+H]⁺, ESI⁺, RT=0.66 (S2).

Example 57 (Step 42.c): 2-(4-chloro-3-fluorophenoxy)-N-[(3S,6R)-6-{5-[1-(2,2,2-trifluoroethyl)azetidin-3-yl]-1,3,4-oxadiazol-2-yl}piperidin-3-yl]acetamide

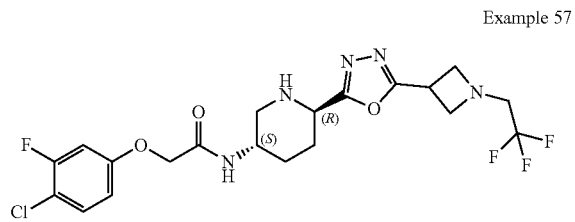

Example 57

A solution of tert-butyl (2R,5S)-5-[2-(4-chloro-3-fluorophenoxy)acetamido]-2-{5-[1-(2,2,2-trifluoroethyl)azetidin-3-yl]-1,3,4-oxadiazol-2-yl}piperidine-1-carboxylate (110 mg, 0.179 mmol, Example 56) and TFA (133 μL, 1.79 mmol) in DCM (2 mL) was stirred at r.t. for 3 h. The reaction mixture was diluted with satd aq NaHCO₃ solution (3 mL) and extracted with DCM (2×5 mL). The combined organic extracts were dried using a phase separator, concentrated in vacuo, and purified by prep. HPLC (Method 3) to afford the title compound (24 mg, 0.0478 mmol, 27% yield) as a white solid; ¹H NMR (500 MHz, DMSO-d₆) δ 7.99 (d, J=8.1 Hz, 1H), 7.50 (t, J=8.9 Hz, 1H), 7.08 (dd, J=11.4, 2.8 Hz, 1H), 6.86 (ddd, J=9.0, 2.8, 1.1 Hz, 1H), 4.53 (s, 2H), 4.01-3.92 (m, 1H), 3.88 (ddd, J=10.4, 6.1, 2.9 Hz, 1H), 3.78 (t, J=7.7 Hz, 2H), 3.76-3.66 (m, 1H), 3.56 (t, J=6.9 Hz, 2H), 3.28 (q, J=10.2 Hz, 2H), 3.00 (d, J=11.5 Hz, 1H), 2.83 (q, J=6.0 Hz, 1H), 2.48-2.42 (m, 1H), 2.06-1.97 (m, 1H), 1.95-1.87 (m, 1H), 1.75-1.64 (m, 1H), 1.52 (qd, J=12.5, 3.9 Hz, 1H); M/Z: 492, 494 [M+H]⁺, ESI⁺, RT=1.88 (S4).

Scheme for route 43

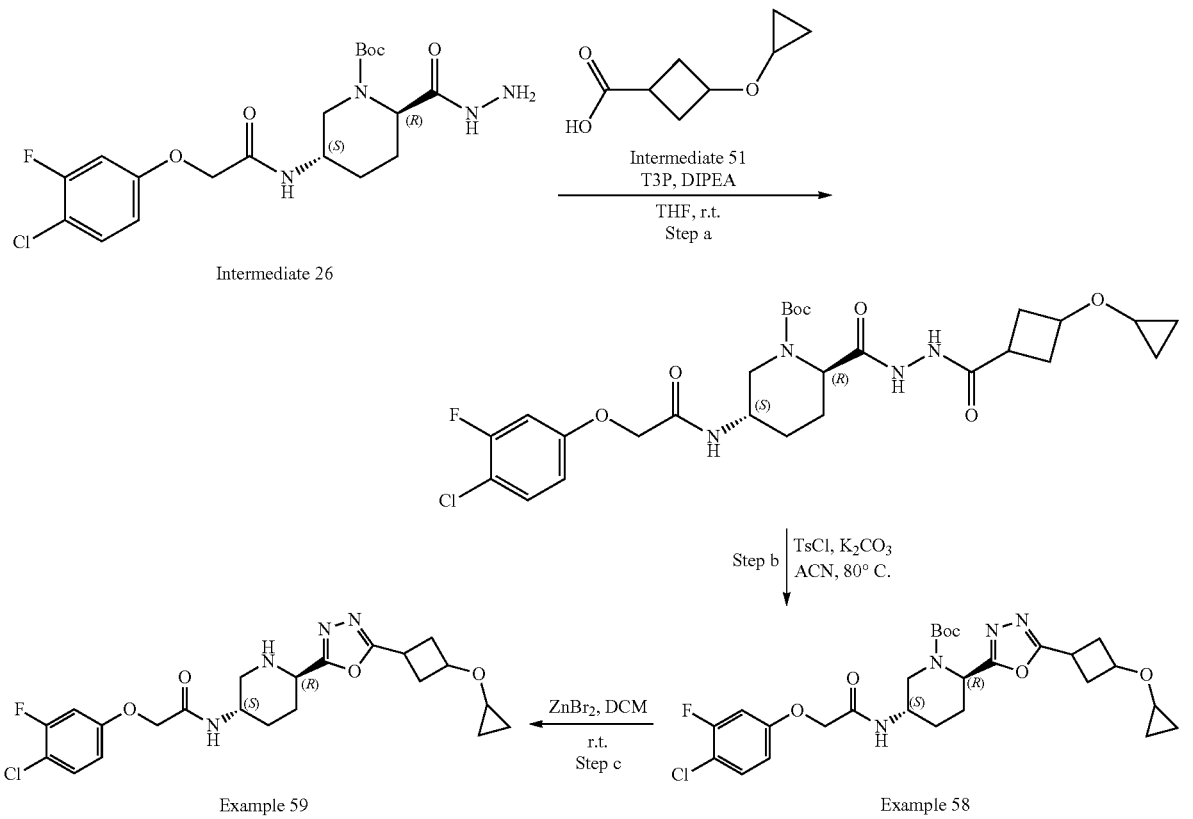

Step 43.a: tert-butyl (2R,5S)-5-[2-(4-chloro-3-fluorophenoxy)acetamido]-2-[N'-(3-cyclopropoxycyclobutanecarbonyl)hydrazinecarbonyl]piperidine-1-carboxylate Example 58 (Step 43.b): tert-butyl (2R,5S)-5-[2-(4-chloro-3-fluorophenoxy)acetamido]-2-[5-(3-cyclopropoxycyclobutyl)-1,3,4-oxadiazol-2-yl]piperidine-1-carboxylate

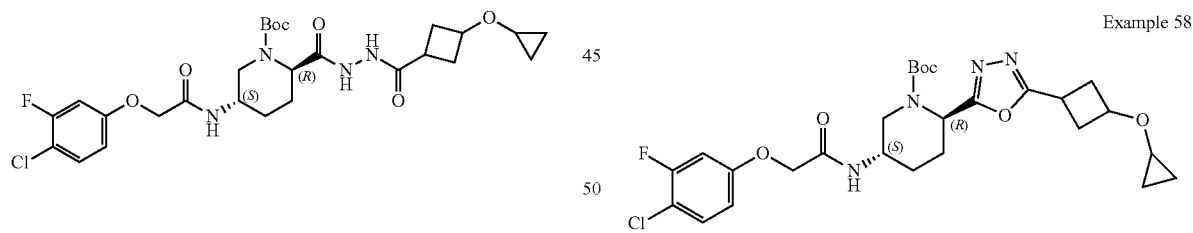

To a solution of 3-cyclopropoxycyclobutane-1-carboxylic acid (90% purity, 100 mg, 0.576 mmol, Intermediate 51) in THF (5 mL) was added DIPEA (302 µL, 1.73 mmol), T3P (50%, 1.0 mL, 1.73 mmol) and tert-butyl (2R,5S)-5-[2-(4-chloro-3-fluorophenoxy)acetamido]-2-(hydrazinecarbonyl)piperidine-1-carboxylate (256 mg, 0.576 mmol, Intermediate 26) and the mixture was stirred at r.t. for 18 h. The reaction mixture was diluted with H$_2$O (30 mL) and extracted with EtOAc (2×50 mL). The combined organic extracts were dried over Na$_2$SO$_4$ and concentrated in vacuo to afford a colourless solid. Purification by chromatography on silica gel (0-100% EtOAc in heptane) afforded the title compound (85% purity, 143 mg, 0.208 mmol, 36% yield) as a white solid; M/Z: 583, 585 [M+H]$^+$, ESI$^+$, RT=3.18 (S4).

To a solution of tert-butyl (2R,5S)-5-[2-(4-chloro-3-fluorophenoxy)acetamido]-2-[N-(3-cyclopropoxycyclobutanecarbonyl)hydrazinecarbonyl]piperidine-1-carboxylate (85% purity, 143 mg, 0.208 mmol) in anhydrous ACN (10 mL) was added TsCl (79 mg, 0.417 mmol) and K$_2$CO$_3$ (144 mg, 1.04 mmol) and the mixture was stirred at 80° C. for 5 h. The reaction mixture was diluted with H$_2$O (30 mL) and extracted with EtOAc (2×50 mL). The combined organic extracts were dried over Na$_2$SO$_4$ and concentrated in vacuo to afford a pale orange oil. Purification by chromatography on silica gel (0-100% EtOAc in heptane) afforded the title compound (70% purity, 111 mg, 0.138 mmol, 66% yield) as a colourless solid; M/Z: 565, 567 [M+H]$^+$, ESI$^+$, RT=3.85 (S4).

Example 59 (Step 43.c): 2-(4-chloro-3-fluorophenoxy)-N-[(3S,6R)-6-[5-(3-cyclopropoxycyclobutyl)-1,3,4-oxadiazol-2-yl]piperidin-3-yl]acetamide

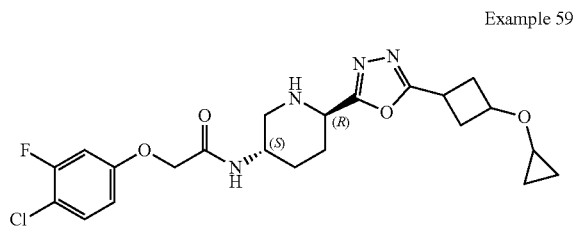

Example 59

To a solution of tert-butyl (2R,5S)-5-[2-(4-chloro-3-fluorophenoxy)acetamido]-2-[5-(3-cyclopropoxycyclobutyl)-1,3,4-oxadiazol-2-yl]piperidine-1-carboxylate (70% purity, 110 mg, 0.136 mmol, Example 58) in DCM (5 mL) was added ZnBr$_2$ (92 mg, 0.409 mmol) and the resultant mixture was stirred at r.t. for 16 h. The reaction mixture was diluted with NaHCO$_3$ (30 mL), extracted with DCM/IPA (2:1, 2×50 mL), and the combined organic extracts were dried over Na$_2$SO$_4$ and concentrated in vacuo. The residue was purified by prep. HPLC (Method 3) to afford the title compound (26 mg, 0.0559 mmol, 4100 yield) as a white powder; δ $^1$H NMR (400 MHz, methanol-d$_4$) δ 7.44-7.35 (m, 1H), 6.97 (dd, J=11.0, 2.8 Hz, 1H), 6.86 (ddd, J=8.9, 2.8, 1.2 Hz, 1H), 4.55 (s, 2H), 4.27-4.15 (m, 1H), 4.05-3.92 (m, 2H), 3.41-3.34 (m, 2H), 3.25-3.19 (m, 1H), 2.81-2.60 (m, 3H), 2.40-2.26 (m, 2H), 2.23-2.06 (m, 2H), 1.94-1.81 (m, 1H), 1.73-1.59 (m, 1H), 0.60-0.42 (in, 4H); M/Z: 465, 467 [M+H]$^+$, ESI$^+$, RT=1.97 (S4).

Example compounds in Table 17 were synthesised according to general route 43 as exemplified by Example 59 using the corresponding intermediates.

TABLE 17

| Ex | Structure | Name | Intermediates | LCMS data | $^1$H NMR |
|---|---|---|---|---|---|
| 60 | 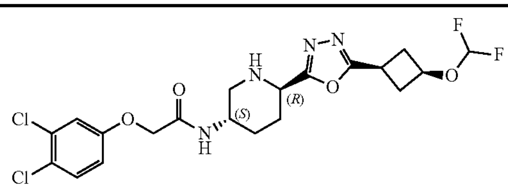 | 2-(3,4-dichlorophenoxy)-N-[(3S,6R)-6-(5-[(1s,3s)-3-(difluoromethoxy)cyclobutyl]-1,3,4-oxadiazol-2-yl}piperidin-3-yl]acetamide | tert-butyl (2R,5S)-5-[2-(3,4-dichlorophenoxy)acetamido]-2-(hydrazinecarbonyl)piperidine-1-carboxylate (Intermediate 27) and (1s,3s)-3-(difluoromethoxy)cyclobutane-1-carboxylic acid | M/Z: 491, 493, 495 [M + H]$^+$, ESI$^+$, RT = 2.12 (S4) | $^1$H NMR (500 MHz, DMSO-d$_6$) δ 8.02 (d, J = 7.4 Hz, 1H), 7.56 (d, J = 8.9 Hz, 1H), 7.26 (d, J = 2.9 Hz, 1H), 6.99 (dd, J = 8.9, 2.9 Hz, 1H), 6.68 (t, J = 75.4 Hz, 1H), 4.68 (q, J = 7.5 Hz, 1H), 4.55 (s, 2H), 4.05-3.68 (m, 2H), 3.47-3.37 (m, 2H), 3.10-2.98 (m, 1H), 2.81-2.73 (m, 2H), 2.53-2.52 (m, 1H), 2.41-2.36 (m, 2H), 2.11-1.96 (m, 1H), 1.96-1.88 (m, 1H), 1.77-1.65 (m, 1H), 1.60-1.48 (m, 1H). |
| 61 | 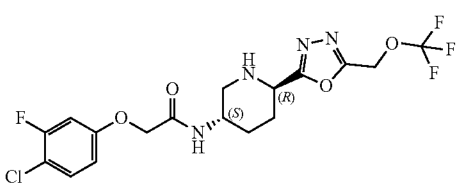 | 2-(4-chloro-3-fluorophenoxy)-N-[(3S,6R)-6-(5-[(trifluoromethoxy)methyl]-1,3,4-oxadiazol-2-yl}piperidin-3-yl]acetamide | tert-butyl (2R,5S)-5-[2-(4-chloro-3-fluorophenoxy)acetamido]-2-(hydrazinecarbonyl)piperidine-1-carboxylate (Intermediate 26) and 2-(trifluoromethoxy)acetic acid | M/Z: 453, 455 [M + H]$^+$, ESI$^+$, RT = 2.05 (S4) | $^1$H NMR (400 MHz, chloroform-d) δ 7.34 (t, J = 8.6 Hz, 1H), 6.79 (dd, J = 10.3, 2.9 Hz, 1H), 6.70 (ddd, J = 8.9, 2.9, 1.2 Hz, 2H), 5.17 (s, 2H), 4.47 (s, 2H), 4.16 (dd, J = 7.8, 3.8 Hz, 1H), 4.08 (ddq, J = 11.8, 7.9, 3.6 Hz, 1H), 3.32 (dd, J = 12.1, 3.2 Hz, 1H), 2.66 (dd, J = 12.1, 7.7 Hz, 1H), 2.23-1.93 (m, 4H), 1.71-1.61 (m, 1H). |

Scheme for route 44

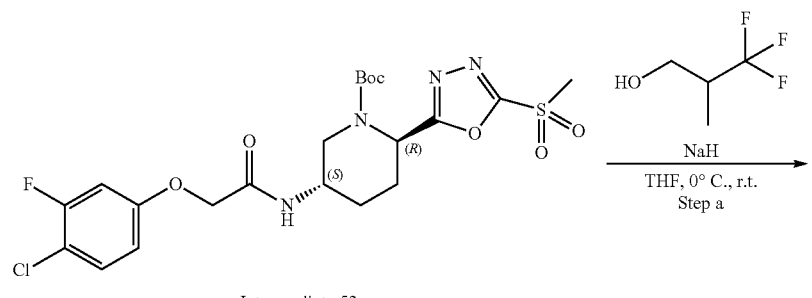

Intermediate 52

-continued

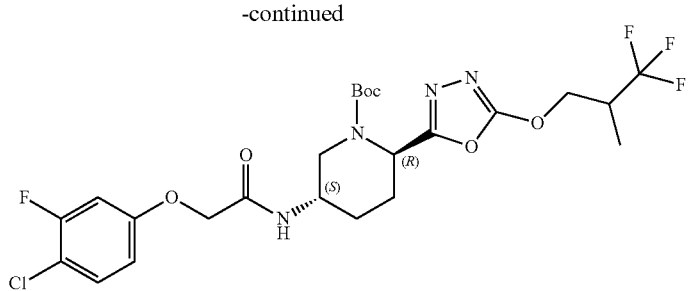

Intermediate 62

Step b | ZnBr₂, DCM
r.t.

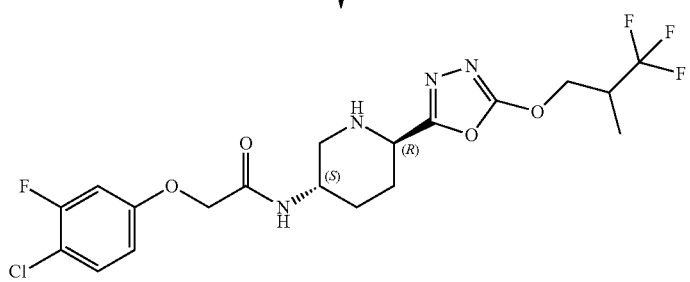

Intermediate 63

Example 62 (Step 44.a): tert-butyl (2R,5S)-5-[2-(4-chloro-3-fluorophenoxy)acetamido]-2-[5-(3,3,3-trifluoro-2-methylpropoxy)-1,3,4-oxadiazol-2-yl]piperidine-1-carboxylate

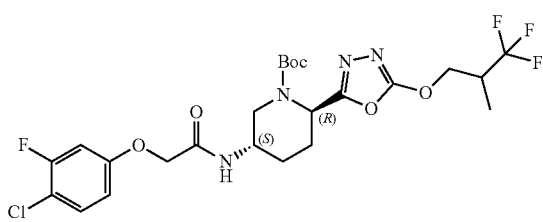

Example 62

A suspension of 3,3,3-trifluoro-2-methylpropan-1-ol (34 mg, 0.266 mmol) in anhydrous THF at 0° C. (1 mL) was treated with NaH (60%, 11 mg, 0.271 mmol) and stirred at 0° C. under $N_2$ for 5 min. tert-butyl (2R,5S)-5-[2-(4-chloro-3-fluorophenoxy)acetamido]-2-(5-methanesulfonyl-1,3,4-oxadiazol-2-yl)piperidine-1-carboxylate (71 mg, 0.133 mmol, Intermediate 52) in anhydrous THF (1 mL) was added and the mixture was stirred at r.t. for 45 min. The reaction mixture was diluted with satd aq NaHCO₃ solution (1 mL) and extracted with EtOAc (2×3 mL). The combined organic extracts were dried over Na₂SO₄ and concentrated in vacuo to afford the title compound (77 mg, 0.133 mmol) in quantitative yield. The crude material was taken forward without purification.

Example 63 (Step 44.b): 2-(4-chloro-3-fluorophenoxy)-N-[(3S,6R)-6-[5-(3,3,3-trifluoro-2-methylpropoxy)-1,3,4-oxadiazol-2-yl]piperidin-3-yl]acetamide

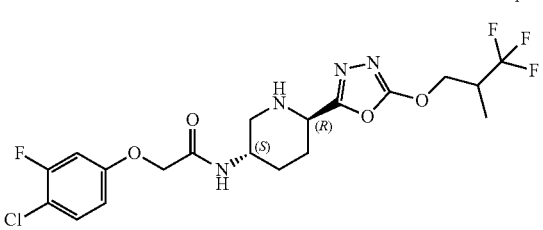

Example 63

To a solution of tert-butyl (2R,5S)-5-[2-(4-chloro-3-fluorophenoxy)acetamido]-2-[5-(3,3,3-trifluoro-2-methylpropoxy)-1,3,4-oxadiazol-2-yl]piperidine-1-carboxylate (77 mg, 0.133 mmol, Example 62) in DCM (2 mL) was added ZnBr₂ (180 mg, 0.799 mmol) and the mixture was stirred at r.t. for 17 h. The reaction mixture was diluted with satd aq NaHCO₃ solution (10 mL) and extracted with DCM/IPA (8:2, 2×3 mL). The combined organic extracts were dried using a phase separator, concentrated in vacuo, and purified by prep. HPLC (Method 3) to afford the title compound (94% purity, 7.0 mg, 0.0143 mmol, 11% yield) as a white powder; $^1$H NMR (500 MHz, DMSO-$d_6$) δ 7.95 (d, J=8.0 Hz, 1H), 7.49 (t, J=8.9 Hz, 1H), 7.06 (dd, J=11.4, 2.8 Hz, 1H), 6.85 (ddd, J=9.0, 2.8, 1.1 Hz, 1H), 4.55 (d, J=5.0 Hz, 2H), 4.52 (s, 2H), 3.78-3.73 (m, 1H), 3.73-3.65 (m, 1H), 3.13-3.01 (m, 1H), 3.00-2.92 (m, 1H), 2.83-2.76 (m, 1H), 2.46-2.39 (m, 1H), 1.99-1.86 (m, 2H), 1.70-1.59 (m, 1H), 1.53-1.45 (m, 1H), 1.19 (d, J=7.1 Hz, 3H); M/Z: 481, 483 [M+H]⁺, ESI⁺, RT=2.15 (S4).

Example compounds in Table 18 were synthesised according to the general route 44 as exemplified by Example 63 using the corresponding intermediates.

TABLE 18

| Ex | Structure | Name | Starting materials | LCMS data | $^1$H NMR |
|---|---|---|---|---|---|
| 64 | 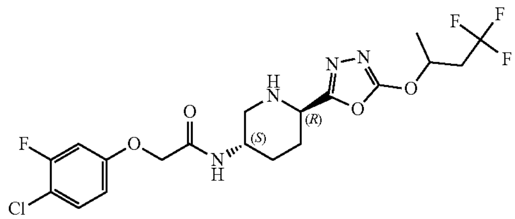 | 2-(4-chloro-3-fluorophenoxy)-N-[(3S,6R)-6-{5-[(4,4,4-trifluorobutan-2-yl)oxy]-1,3,4-oxadiazol-2-yl}piperidin-3-yl]acetamide | tert-butyl (2R,5S)-5-[2-(4-chloro-3-fluorophenoxy)acetamido]-2-(5-methanesulfonyl-1,3,4-oxadiazol-2-yl)piperidine-1-carboxylate (Intermediate 52) and 4,4,4-trifluorobutan-2-ol | M/Z: 481, 483 [M + H]$^+$, ESI$^+$, RT = 2.15 (S4) | $^1$H NMR (500 MHz, chloroform-d) δ 7.33 (t, J = 8.6 Hz, 1H), 6.78 (dd, J = 10.3, 2.9 Hz, 1H), 6.74-6.67 (m, 2H), 5.38-5.16 (m, 1H), 4.46 (s, 2H), 4.06 (ddq, J = 11.4, 7.8, 3.4 Hz, 1H), 4.00-3.96 (m, 1H), 3.30 (dt, J = 11.9, 3.7 Hz, 1H), 2.80-2.67 (m, 1H), 2.68-2.55 (m, 1H), 2.52-2.43 (m, 1H), 2.08 (dt, J = 5.8, 3.1 Hz, 2H), 1.96-1.88 (m, 1H), 1.63 (d, J = 8.5 Hz, 2H), 1.59 (d, J = 6.3 Hz, 3H). |
| 65 | 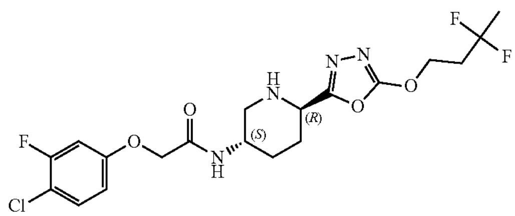 | 2-(4-chloro-3-fluorophenoxy)-N-[(3S,6R)-6-[5-(3,3-difluorobutoxy)-1,3,4-oxadiazol-2-yl]piperidin-3-yl]acetamide | tert-butyl (2R,5S)-5-[2-(4-chloro-3-fluorophenoxy)acetamido]-2-(5-methanesulfonyl-1,3,4-oxadiazol-2-yl)piperidine-1-carboxylate (Intermediate 52) and 3,3-difluorobutan-1-ol | M/Z: 463, 465 [M + H]$^+$, ESI$^+$, RT = 2.00 (S4) | $^1$H NMR (400 MHz, DMSO-d$_6$) δ 7.96 (d, J = 8.1 Hz, 1H), 7.50 (t, J = 8.9 Hz, 1H), 7.07 (dd, J = 11.4, 2.8 Hz, 1H), 6.85 (ddd, J = 9.0, 2.8, 1.1 Hz, 1H), 4.59 (t, J = 6.1 Hz, 2H), 4.52 (s, 2H), 3.74 (s, 2H), 3.01-2.94 (m, 1H), 2.82-2.75 (m, 1H), 2.44 (d, J = 6.5 Hz, 1H), 2.00-1.86 (m, 2H), 1.68 (t, J = 19.2 Hz, 5H), 1.55-1.43 (m, 2H). |
| 66 | 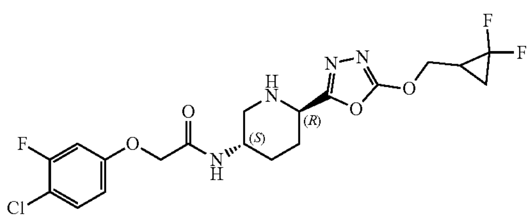 | 2-(4-chloro-3-fluorophenoxy)-N-[(3S,6R)-6-{5-[(2,2-difluoro-cyclopropyl)methoxy]-1,3,4-oxadiazol-2-yl}piperidin-3-yl]acetamide | tert-butyl (2R,5S)-5-[2-(4-chloro-3-fluorophenoxy)acetamido]-2-(5-methanesulfonyl-1,3,4-oxadiazol-2-yl)piperidine-1-carboxylate (Intermediate 52) and (2,2-difluoro-cyclopropyl)methanol | M/Z: 461, 463 [M + H]$^+$, ESI$^+$, RT = 1.99 (S4) | $^1$H NMR (400 MHz, DMSO-d$_6$) δ 7.95 (d, J = 8.1 Hz, 1H), 7.49 (t, J = 8.9 Hz, 1H), 7.07 (dd, J = 11.4, 2.8 Hz, 1H), 6.85 (ddd, J = 9.0, 2.8, 1.1 Hz, 1H), 4.63-4.55 (m, 1H), 4.52 (s, 2H), 4.45-4.37 (m, 1H), 3.80-3.64 (m, 2H), 3.01-2.93 (m, 1H), 2.83-2.74 (m, 1H), 2.45-2.37 (m, 1H), 2.37-2.27 (m, 1H), 2.00-1.84 (m, 2H), 1.85-1.72 (m, 1H), 1.71-1.58 (m, 2H), 1.55-1.41 (m, 1H). |
| 67 | 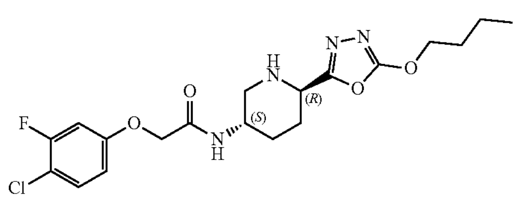 | N-[(3S,6R)-6-(5-butoxy-1,3,4-oxadiazol-2-yl)piperidin-3-yl]-2-(4-chloro-3-fluorophenoxy)acetamide | tert-butyl (2R,5S)-5-[2-(4-chloro-3-fluorophenoxy)acetamido]-2-(5-methanesulfonyl-1,3,4-oxadiazol-2-yl)piperidine-1-carboxylate (Intermediate 52) and butan-1-ol | M/Z: 427, 429 [M + H]$^+$, ESI$^+$, RT = 2.07 (S4) | $^1$H NMR (500 MHz, DMSO-d$_6$) δ 7.95 (d, J = 8.1 Hz, 1H), 7.49 (t, J = 8.9 Hz, 1H), 7.07 (dd, J = 11.4, 2.8 Hz, 1H), 6.85 (ddd, J = 9.0, 2.8, 1.1 Hz, 1H), 4.52 (s, 2H), 4.42 (t, J = 6.5 Hz, 2H), 3.77-3.64 (m, 2H), 3.00-2.93 (m, 1H), 2.79-2.73 (m, 1H), 2.44-2.38 (m, 1H), 1.99-1.85 (m, 2H), 1.77-1.70 (m, 2H), 1.68-1.58 (m, 1H), 1.48 (qd, J = 12.3, 3.7 Hz, 1H), 1.40 (h, J = 7.4 Hz, 2H), 0.92 (t, J = 7.4 Hz, 3H). |

TABLE 18-continued

| Ex | Structure | Name | Starting materials | LCMS data | ¹H NMR |
|---|---|---|---|---|---|
| 68 | 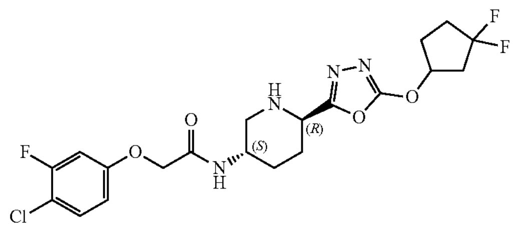 | 2-(4-chloro-3-fluorophenoxy)-N-[(3S,6R)-6-{5-[(3,3-difluoro-cyclopentyl)oxy]-1,3,4-oxadiazol-2-yl}piperidin-3-yl]acetamide | tert-butyl (2R,5S)-5-[2-(4-chloro-3-fluorophenoxy)acetamido]-2-(5-methanesulfonyl-1,3,4-oxadiazol-2-yl)piperidine-1-carboxylate (Intermediate 52) and 3,3-difluorocyclo-pentan-1-ol | M/Z: 475, 477 [M + H]⁺, ESI⁺, RT = 2.05 (S4) | ¹H NMR (400 MHz, DMSO-d₆) δ 7.95 (d, J = 8.1 Hz, 1H), 7.49 (t, J = 8.9 Hz, 1H), 7.06 (dd, J = 11.4, 2.8 Hz, 1H), 6.85 (ddd, J = 9.0, 2.9, 1.2 Hz, 1H), 5.32 (s, 1H), 4.52 (s, 2H), 3.79-3.63 (m, 2H), 3.00-2.93 (m, 1H), 2.81-2.74 (m, 1H), 2.71-2.64 (m, 1H), 2.46-2.38 (m, 2H), 2.34-2.19 (m, 3H), 2.16-2.07 (m, 1H), 1.99-1.85 (m, 2H), 1.70-1.58 (m, 1H), 1.48 (qd, J = 12.1, 3.4 Hz, 1H). |
| 69 | 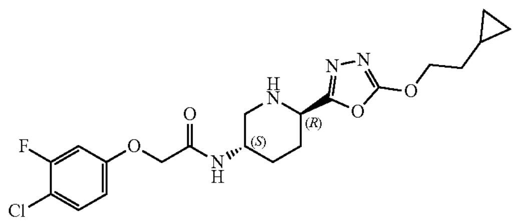 | 2-(4-chloro-3-fluorophenoxy)-N-[(3S,6R)-6-[5-(2-cyclopropyl-ethoxy)-1,3,4-oxadiazol-2-yl]piperidin-3-yl]acetamide | tert-butyl (2R,5S)-5-[2-(4-chloro-3-fluorophenoxy)acetamido]-2-(5-methanesulfonyl-1,3,4-oxadiazol-2-yl)piperidine-1-carboxylate (Intermediate 52) and 2-cyclopropyl-ethan-1-ol | M/Z: 439, 441 [M + H]⁺, ESI⁺, RT = 2.16 (S4) | ¹H NMR (400 MHz, DMSO-d6) δ 7.95 (d, J = 8.2 Hz, 1H), 7.49 (t, J = 8.9 Hz, 1H), 7.07 (dd, J = 11.4, 2.9 Hz, 1H), 6.85 (dd, J = 8.9, 1.7 Hz, 1H), 4.52 (s, 2H), 4.46 (t, J = 6.5 Hz, 2H), 3.78-3.64 (m, 2H), 3.00-2.93 (m, 1H), 2.81-2.74 (m, 1H), 2.42 (d, J = 4.0 Hz, 1H), 1.98-1.86 (m, 2H), 1.67 (q, J = 6.6 Hz, 2H), 1.55-1.41 (m, 2H), 0.82-0.72 (m, 1H), 0.47-0.39 (m, 2H), 0.15-0.07 (m, 2H). |
| 70 | 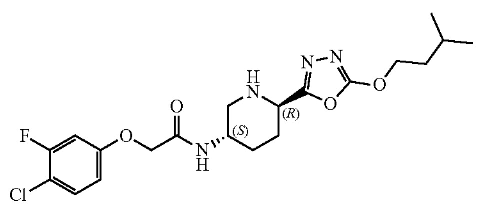 | 2-(4-chloro-3-fluorophenoxy)-N-[(3S,6R)-6-[5-(3-methylbutoxy)-1,3,4-oxadiazol-2-yl]piperidin-3-yl]acetamide | tert-butyl (2R,5S)-5-[2-(4-chloro-3-fluorophenoxy)acetamido]-2-(5-methanesulfonyl-1,3,4-oxadiazol-2-yl)piperidine-1-carboxylate (Intermediate 52) and 3-methylbutan-1-ol | M/Z: 441, 443 [M + H]⁺, ESI⁺, RT = 2.28 (S4) | ¹H NMR (400 MHz, DMSO-d6) δ 7.95 (d, J = 8.1 Hz, 1H), 7.49 (t, J = 8.9 Hz, 1H), 7.06 (dd, J = 11.4, 2.8 Hz, 1H), 6.85 (ddd, J = 9.0, 2.8, 1.1 Hz, 1H), 4.52 (s, 2H), 4.45 (t, J = 6.5 Hz, 2H), 3.77-3.63 (m, 2H), 3.00-2.93 (m, 1H), 2.80-2.73 (m, 1H), 2.46-2.37 (m, 1H), 1.99-1.85 (m, 2H), 1.68 (tq, J = 12.5, 6.6, 5.9 Hz, 4H), 1.54-1.42 (m, 1H), 0.92 (d, J = 6.4 Hz, 6H). |
| 71 | 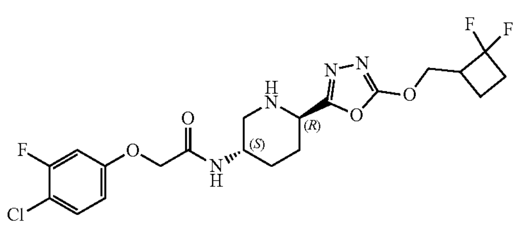 | 2-(4-chloro-3-fluorophenoxy)-N-[(3S,6R)-6-{5-[(2,2-difluoro-cyclobutyl)methoxy]-1,3,4-oxadiazol-2-yl}piperidin-3-yl]acetamide | tert-butyl (2R,5S)-5-[2-(4-chloro-3-fluorophenoxy)acetamido]-2-(5-methanesulfonyl-1,3,4-oxadiazol-2-yl)piperidine-1-carboxylate (Intermediate 52) and (2,2-difluoro-cyclobutyl)methanol | M/Z: 475, 477 [M + H]⁺, ESI⁺, RT = 2.05 (S4) | ¹H NMR (400 MHz, DMSO-d6) δ 7.95 (d, J = 8.0 Hz, 1H), 7.49 (t, J = 8.9 Hz, 1H), 7.06 (dd, J = 11.4, 2.8 Hz, 1H), 6.85 (ddd, J = 9.0, 2.8, 1.2 Hz, 1H), 4.60-4.48 (m, 4H), 3.79-3.63 (m, 3H), 2.96 (d, J = 11.9 Hz, 1H), 2.79 (s, 1H), 2.43-2.38 (m, 1H), 2.01-1.83 (m, 4H), 1.70-1.55 (m, 3H), 1.48 (qd, J = 12.3, 3.7 Hz, 1H). |

TABLE 18-continued

| Ex | Structure | Name | Starting materials | LCMS data | ¹H NMR |
|---|---|---|---|---|---|
| 72 | 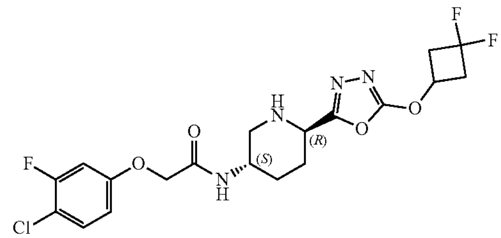 | 2-(4-chloro-3-fluorophenoxy)-N-[(3S,6R)-6-[5-(3,3-difluoro-cyclobutoxy)-1,3,4-oxadiazol-2-yl]piperidin-3-yl]acetamide | tert-butyl (2R,5S)-5-[2-(4-chloro-3-fluorophenoxy)acetamido]-2-(5-methanesulfonyl-1,3,4-oxadiazol-2-yl)piperidine-1-carboxylate (Intermediate 52) and 3,3-difluorocyclo-butan-1-ol | M/Z: 461, 463 [M + H]⁺, ESI⁺, RT = 1.96 (S4) | ¹H NMR (400 MHz, DMSO-d₆) δ 7.95 (d, J = 8.2 Hz, 1H), 7.49 (t, J = 8.9 Hz, 1H), 7.06 (dd, J = 11.4, 2.8 Hz, 1H), 6.85 (ddd, J = 9.0, 2.8, 1.1 Hz, 1H), 5.20-5.09 (m, 1H), 4.52 (s, 2H), 3.80-3.64 (m, 2H), 3.25-3.14 (m, 2H), 3.02-2.85 (m, 3H), 2.81-2.73 (m, 1H), 2.45-2.38 (m, 1H), 2.01-1.84 (m, 2H), 1.70-1.59 (m, 1H), 1.54-1.43 (m, 1H). |
| 73 | 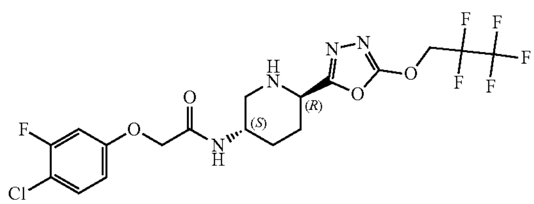 | 2-(4-chloro-3-fluorophenoxy)-N-[(3S,6R)-6-[5-(2,2,3,3,3-pentafluoro-propoxy)-1,3,4-oxadiazol-2-yl]piperidin-3-yl]acetamide | tert-butyl (2R,5S)-5-[2-(4-chloro-3-fluorophenoxy)acetamido]-2-(5-methanesulfonyl-1,3,4-oxadiazol-2-yl)piperidine-1-carboxylate (Intermediate 52) and 2,2,3,3,3-pentafluoro-propan-1-ol | M/Z: 503, 505 [M + H]⁺, ESI⁺, RT = 2.29 (S4) | ¹H NMR (500 MHz, chloroform-d) δ 7.33 (t, J = 8.6 Hz, 1H), 6.78 (dd, J = 10.3, 2.9 Hz, 1H), 6.74-6.67 (m, 2H), 4.94-4.86 (m, 2H), 4.46 (s, 2H), 4.10-4.00 (m, 2H), 3.30 (dd, J = 12.0, 3.4 Hz, 1H), 2.63 (dd, J = 12.1, 7.6 Hz, 1H), 2.13-2.02 (m, 2H), 1.98-1.90 (m, 1H), 1.67-1.61 (m, 2H). |
| 74 | 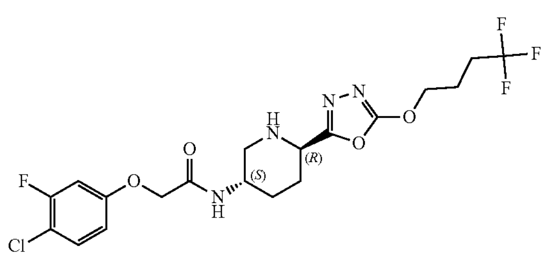 | 2-(4-chloro-3-fluorophenoxy)-N-[(3S,6R)-6-[5-(4,4,4-trifluorobutoxy)-1,3,4-oxadiazol-2-yl]piperidin-3-yl]acetamide | tert-butyl (2R,5S)-5-[2-(4-chloro-3-fluorophenoxy)acetamido]-2-(5-methanesulfonyl-1,3,4-oxadiazol-2-yl)piperidine-1-carboxylate (Intermediate 52) and 4,4,4-trifluorobutan-1-ol | M/Z: 481, 483 [M + HCO₂H⁺], ESI⁺, RT = 2.21 (S4) | ¹H NMR (500 MHz, DMSO-d₆) δ 7.94 (d, J = 7.7 Hz, 1H), 7.49 (t, J = 8.9 Hz, 1H), 7.07 (dd, J = 11.4, 2.8 Hz, 1H), 6.89-6.76 (m, 1H), 4.52 (s, 2H), 4.48 (t, J = 6.3 Hz, 2H), 3.79-3.64 (m, 2H), 3.01-2.89 (m, 1H), 2.77 (s, 1H), 2.45-2.38 (m, 3H), 2.06-1.83 (m, 4H), 1.71-1.58 (m, 1H), 1.56-1.45 (m, 1H). |
| 75 | 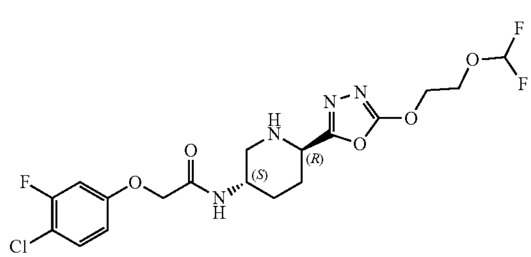 | 2-(4-chloro-3-fluorophenoxy)-N-[(3S,6R)-6-{5-[2-(difluoromethoxy)ethoxy]-1,3,4-oxadiazol-2-yl}piperidin-3-yl]acetamide | tert-butyl (2R,5S)-5-[2-(4-chloro-3-fluorophenoxy)acetamido]-2-(5-methanesulfonyl-1,3,4-oxadiazol-2-yl)piperidine-1-carboxylate (Intermediate 52) and 2-(difluoromethoxy)ethan-1-ol (Intermediate 39) | M/Z: 465, 467 [M + H]⁺, ESI⁺, RT = 2.23 (S4) | ¹H NMR(500 MHz, chloroform-d) δ 7.33 (t, J = 8.6 Hz, 1H), 6.78 (dd, J = 10.3, 2.9 Hz, 1H), 6.74 (d, J = 7.3 Hz, 1H), 6.69 (ddd, J = 8.9, 2.9, 1.2 Hz, 1H), 6.27 (t, J = 73.4 Hz, 1H), 4.69-4.65 (m, 2H), 4.46 (s, 2H), 4.26-4.22 (m, 2H), 4.10-4.02 (m, 1H), 4.00 (dd, J = 7.6, 3.5 Hz, 1H), 3.29 (dd, J = 12.2, 3.4 Hz, 1H), 2.62 (dd, J = 12.0, 7.5 Hz, 1H), 2.11-2.03 (m, 2H), 1.98-1.89 (m, 1H), 1.69-1.60 (m, 2H). |

Scheme for route 45

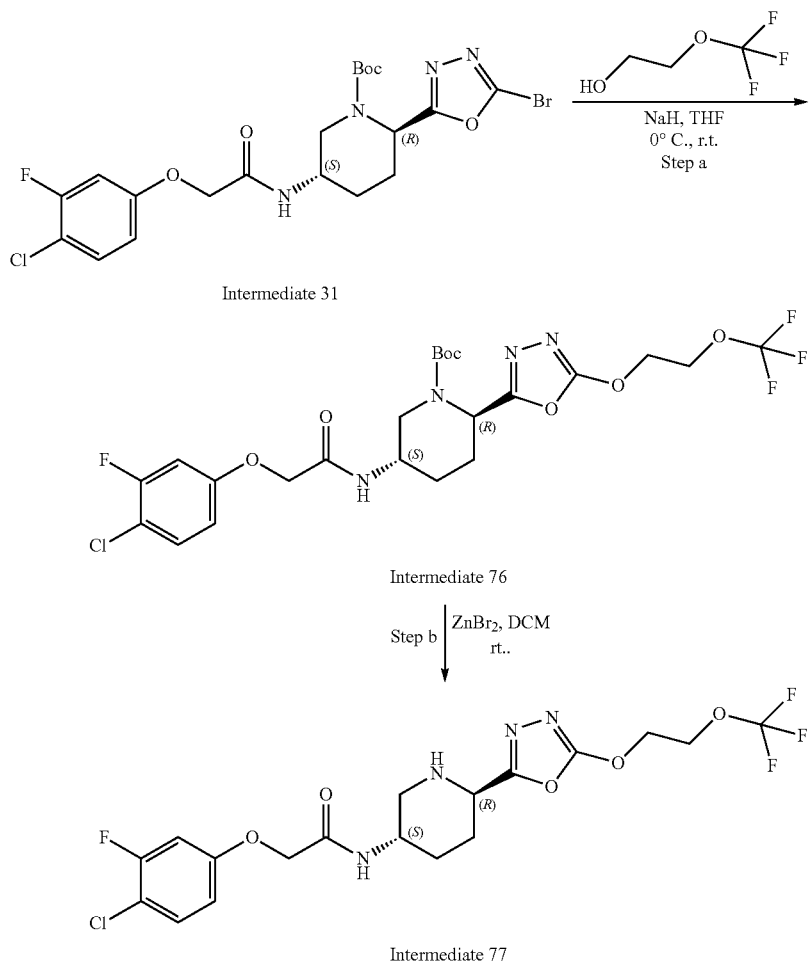

Example 76 (Step 45.a): tert-butyl (2R,5S)-5-[2-(4-chloro-3-fluorophenoxy)acetamido]-2-{5-[2-(trifluoromethoxy)ethoxy]-1,3,4-oxadiazol-2-yl}piperidine-1-carboxylate Example 76

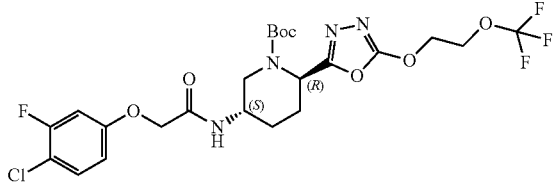

To a solution of 2-(trifluoromethoxy)ethanol (139 mg, 1.07 mmol) in anhydrous THF (6 mL) at 0° C. was added NaH (60%, 43 mg, 1.07 mmol) and the mixture was stirred for 10 min. A solution of tert-butyl (2R,5S)-2-(5-bromo-1,3,4-oxadiazol-2-yl)-5-[[2-(4-chloro-3-fluoro-phenoxy)acetyl]amino]piperidine-1-carboxylate (500 mg, 0.890 mmol, Intermediate 31) in anhydrous THF (6 mL) was added and the mixture was stirred at r.t. for 2 h. The reaction mixture was poured on to water (15 mL) and extracted with EtOAc (3×15 mL). The combined organic extracts were dried over MgSO₄ and concentrated in vacuo to afford the title compound (80% purity, 627 mg, 0.860 mmol, 97% yield) as a yellow oil; $^1$H NMR (400 MHz, chloroform-d) δ 7.33 (t, J=8.6 Hz, 1H), 6.91-6.61 (m, 3H), 5.48 (d, J=25.4 Hz, 1H), 4.77-4.65 (m, 2H), 4.44 (dd, J=14.2, 4.1 Hz, 2H), 4.38-4.29 (m, 2H), 4.22-4.01 (m, 2H), 3.17 (s, 1H), 2.27-2.06 (m, 1H), 1.91 (d, J=26.1 Hz, 3H), 1.45 (s, 9H); M/Z: 483, 485 [M-Boc+H]⁺, ESI⁺, RT=1.11 (S2).

Example 77 (Step 45.b): 2-(4-chloro-3-fluorophenoxy)-N-[(3S,6R)-6-{5-[2-(trifluoromethoxy)ethoxy]-1,3,4-oxadiazol-2-yl}piperidin-3-yl]acetamide Example 77

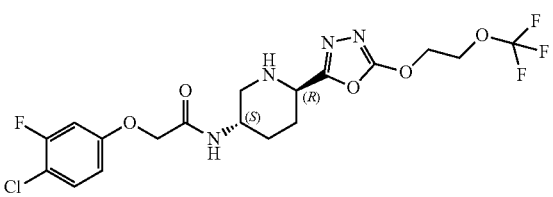

To a solution of tert-butyl (2R,5S)-5-[2-(4-chloro-3-fluorophenoxy)acetamido]-2-{5-[2-(trifluoromethoxy)ethoxy]-

1,3,4-oxadiazol-2-yl}piperidine-1-carboxylate (80% purity, 627 mg, 0.860 mmol, Example 76) in DCM (9 mL) was added ZnBr$_2$ (581 mg, 2.58 mmol) and the mixture was stirred at r.t. for 12 h. The reaction was poured onto H$_2$O (20 mL) and extracted with 10% IPA in DCM (3×20 mL). The combined organic extracts were dried over MgSO$_4$ and concentrated in vacuo. The residue was purified by prep. HPLC (Method 4) to afford the title compound (194 mg, 0.394 mmol, 46% yield) as a white solid; $^1$H NMR (500 MHz, DMSO-d$_6$) δ 7.99 (d, J=8.1 Hz, 1H), 7.48 (t, J=8.9 Hz, 1H), 7.06 (dd, J=11.4, 2.8 Hz, 1H), 6.84 (m, J=9.0, 2.8, 1.1 Hz, 1H), 4.70-4.65 (m, 2H), 4.51 (s, 2H), 4.49-4.44 (m, 2H), 3.79-3.73 (m, 1H), 3.73-3.65 (m, 1H), 2.96 (dd, J=11.5, 3.2 Hz, 1H), 2.79 (s, 1H), 2.47-2.38 (m, 1H), 1.99-1.84 (m, 2H), 1.69-1.58 (m, 1H), 1.54-1.44 (m, 1H); M/Z: 483, 485 [M+H]$^+$, ESI$^+$, RT=2.19 (S4).

Example compounds in Table 19 were synthesised according to the general route 45 as exemplified by Example 77 using the corresponding intermediates.

TABLE 19

| Ex | Structure | Name | Starting materials | LCMS data | $^1$H NMR |
|---|---|---|---|---|---|
| 78 | 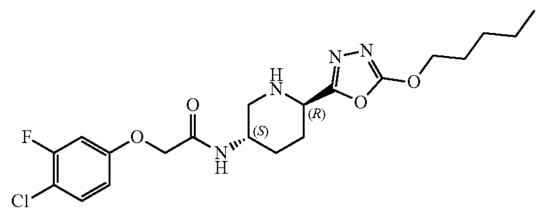 | 2-(4-chloro-3-fluorophenoxy)-N-[(3S,6R)-6-[5-(pentyloxy)-1,3,4-oxadiazol-2-yl]piperidin-3-yl]acetamide | tert-butyl (2R,5S)-2-(5-bromo-1,3,4-oxadiazol-2-yl)-5-[[2-(4-chloro-3-fluoro-phenoxy)acetyl]amino]piperidine-1-carboxylate (Intermediate 31) and pentan-1-ol | M/Z: 441, 443 [M + H]$^+$, ESI$^+$, RT = 2.32 (S4) | $^1$H NMR (400 MHz, chloroform-d) δ 7.33 (t, J = 8.6 Hz, 1H), 6.78 (dd, J = 10.3, 2.9 Hz, 1H), 6.72-6.62 (m, 2H), 4.46 (s, 2H), 4.21 (t, J = 5.1 Hz, 2H), 4.11-3.93 (m, 2H), 3.72 (t, J = 5.1 Hz, 2H), 3.33 (dd, J = 12.0, 3.5 Hz, 1H), 3.17 (s, 3H), 2.60 (dd, J = 11.9, 8.1 Hz, 1H), 2.15-1.86 (m, 4H), 1.64-1.57 (m, 1H). |
| 79 | 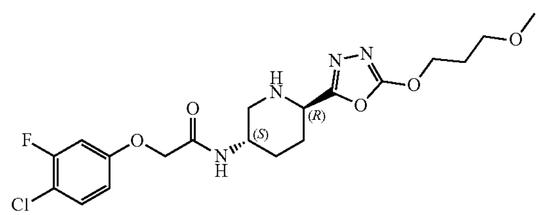 | 2-(4-chloro-3-fluorophenoxy)-N-[(3S,6R)-6-[5-(3-methoxy-propoxy)-1,3,4-oxadiazol-2-yl]piperidin-3-yl]acetamide | tert-butyl (2R,5S)-2-(5-bromo-1,3,4-oxadiazol-2-yl)-5-[[2-(4-chloro-3-fluoro-phenoxy)acetyl]amino]piperidine-1-carboxylate (Intermediate 31) and 3-methoxypropan-1-ol | M/Z: 443, 445 [M + H]$^+$, ESI$^+$, RT = 1.86 (S4) | $^1$H NMR (400 MHz, chloroform-d) δ 7.33 (t, J = 8.6 Hz, 1H), 6.81-6.67 (m, 3H), 4.57 (t, J = 6.3 Hz, 2H), 4.46 (s, 2H), 4.11-3.92 (m, 2H), 3.52 (t, J = 6.0 Hz, 2H), 3.37-3.25 (m, 4H), 2.62 (dd, J = 12.0, 7.5 Hz, 1H), 2.19-1.83 (m, 6H), 1.61 (q, J = 8.3 Hz, 1H). |
| 80 | 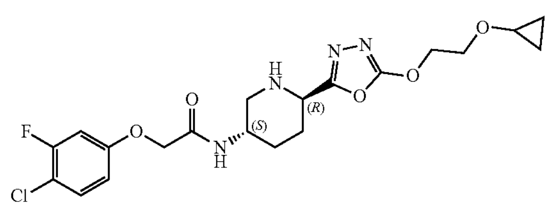 | 2-(4-chloro-3-fluorophenoxy)-N-[(3S,6R)-6-[5-(2-cyclopro-poxythoxy)-1,3,4-oxadiazol-2-yl]piperidin-3-yl]acetamide | tert-butyl (2R,5S)-2-(5-bromo-1,3,4-oxadiazol-2-yl)-5-[[2-(4-chloro-3-fluoro-phenoxy)acetyl]amino]piperidine-1-carboxylate (Intermediate 31) and 2-cyclopropoxy-ethan-1-ol | M/Z: 455, 457 [M + H]$^+$, ESI$^+$, RT = 1.97 (S4) | $^1$H NMR (400 MHz, chloroform-d) δ 7.33 (t, J = 8.6 Hz, 1H), 6.81-6.66 (m, 3H), 4.63-4.57 (m, 2H), 4.46 (s, 2H), 4.10-3.96 (m, 2H), 3.90-3.84 (m, 2H), 3.37 (tt, J = 6.0, 3.0 Hz, 1H), 3.28 (dd, J = 12.0, 3.4 Hz, 1H), 2.62 (dd, J = 12.0, 7.4 Hz, 1H), 2.12-1.86 (m, 4H), 1.67-1.58 (m, 1H), 0.64-0.47 (m, 4H). |
| 81 | 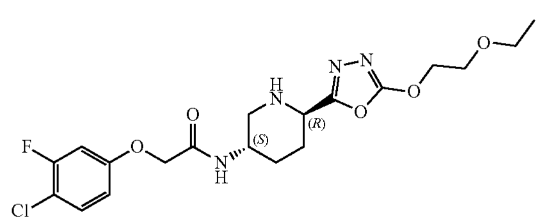 | 2-(4-chloro-3-fluorophenoxy)-N-[(3S,6R)-6-[5-(2-ethoxyethoxy)-1,3,4-oxadiazol-2-yl]piperidin-3-yl]acctamide | tert-butyl (2R,5S)-2-(5-bromo-1,3,4-oxadiazol-2-yl)-5-[[2-(4-chloro-3-fluoro-phenoxy)acetyl]amino]piperidine-1-carboxylate (Intermediate 31) and 2-ethoxyethan-1-ol | M/Z: 443, 445 [M + H]$^+$, ESI$^+$, RT = 1.88 (S4) | $^1$H NMR (400 MHz, chloroform-d) δ 7.33 (t, J = 8.6 Hz, 1H), 6.81-6.66 (m, 3H), 4.64-4.57 (m, 2H), 4.46 (s, 2H), 4.10-4.02 (m, 1H), 4.02-3.97 (m, 1H), 3.84-3.77 (m, 2H), 3.57 (q, J = 7.0 Hz, 2H), 3.28 (dd, J = 12.0, 3.4 Hz, 1H), 2.62 (dd, J = 12.0, 7.5 Hz, 1H), 2.24-1.99 (m, 3H), 1.97-1.86 (m, 1H), 1.68-1.55 (m, 1H), 1.23 (t, J = 7.0 Hz, 3H). |

TABLE 19-continued

| Ex | Structure | Name | Starting materials | LCMS data | ¹H NMR |
|---|---|---|---|---|---|
| 82 | 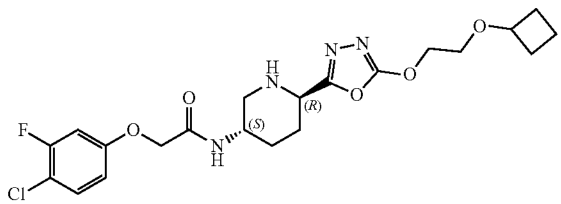 | 2-(4-chloro-3-fluorophenoxy)-N-[(3S,6R)-6-[5-(2-cyclobutoxy-ethoxy)-1,3,4-oxadiazol-2-yl]piperidin-3-yl]acetamide | tert-butyl (2R,5S)-2-(5-bromo-1,3,4-oxadiazol-2-yl)-5-[[2-(4-chloro-3-fluoro-phenoxy)acetyl] amino] piperidine-1-carboxylate (Intermediate 31) and 2-cyclobutoxy-ethan-1-ol | M/Z: 469, 471 [M + H]⁺, ESI⁺, RT = 2.12 (S4) | ¹H NMR (400 MHz, chloroform-d) δ 7.33 (t, J = 8.6 Hz, 1H), 6.81-6.66 (m, 3H), 4.61-4.55 (m, 2H), 4.46 (s, 2H), 4.11-3.94 (m, 3H), 3.74-3.68 (m, 2H), 1.77-1.60 (m, 2H), 3.28 (dd, J = 12.0, 3.4 Hz, 1H), 2.62 (dd, J = 11.9, 7.5 Hz, 1H), 2.26-2.16 (m, 2H), 2.11-1.87 (m, 6H), 1.53-1.47 (m, 1H). |
| 83 | 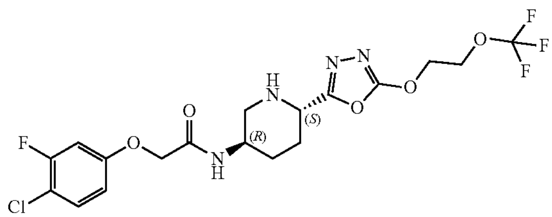 | 2-(4-chloro-3-fluorophenoxy)-N-[(3R,6S)-6-{5-[2-(trifluoro-methoxy)ethoxy]-1,3,4-oxadiazol-2-yl}piperidin-3-yl]acetamide | tert-butyl (2S,5R)-2-(5-bromo-1,3,4-oxadiazol-2-yl)-5-[2-(4-chloro-3-fluorophenoxy)acetamido]piperidine-1-carboxylate (Intermediate 33) and 2-(trifluoro-methoxy)ethan-1-ol | M/Z: 483, 485 [M + H]⁺, ESI⁺, RT = 2.13 (S4) | ¹H NMR (500 MHz, DMSO-d₆) δ 7.97 (d, J = 8.0 Hz, 1H), 7.50 (t, J = 8.9 Hz, 1H), 7.07 (dd, J = 11.4, 2.8 Hz, 1H), 6.86 (ddd, J = 9.0, 2.8, 1.1 Hz, 1H), 4.71-4.67, (m, 2H), 4.53 (s, 2H), 4.50-4.45 (m, 2H), 3.80-3.74 (m, 1H), 3.74-3.65 (m, 1H), 3.02-2.94 (m, 1H), 2.84-2.77 (m, 1H), 2.47-2.39 (m, 1H), 2.00-1.93 (m, 1H), 1.93-1.86 (m, 1H), 1.65 (qd, J = 12.6, 3.5 Hz, 1H), 1.50 (qd, J = 12.4, 3.8 Hz, 1H). |
| 84 | 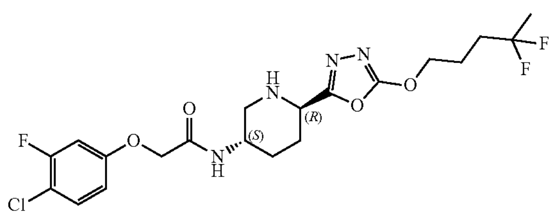 | 2-(4-chloro-3-fluorophenoxy)-N-[(3S,6R)-6-{5-[(4,4-difluoropentyl)oxy]-1,3,4-oxadiazol-2-yl}piperidin-3-yl]acetamide | tert-butyl (2R,5S)-2-(5-bromo-1,3,4-oxadiazol-2-yl)-5-[[2-(4-chloro-3-fluoro-phenoxy)acetyl] amino] piperidine-1-carboxylate (Intermediate 31) and 4,4-difluoropentan-1-ol | M/Z: 477, 479 [M + H]⁺, ESI⁺, RT = 2.20 (S4) | ¹H NMR (500 MHz, chloroform-d) δ 7.33 (t, J = 8.6 Hz, 1H), 6.78 (dd, J = 10.3, 2.9 Hz, 1H), 6.74-6.66 (m, 2H), 4.52 (t, J = 6.0 Hz, 2H), 4.46 (s, 2H), 4.10-4.02 (m, 1H), 3.98 (dd, J = 7.7, 3.3 Hz, 1H), 3.30 (dd, J = 12.0, 3.4 Hz, 1H), 2.62 (dd, J = 12.0, 7.6 Hz, 1H), 2.11-1.89 (m, 8H), 1.68-1.58 (m, 4H). |

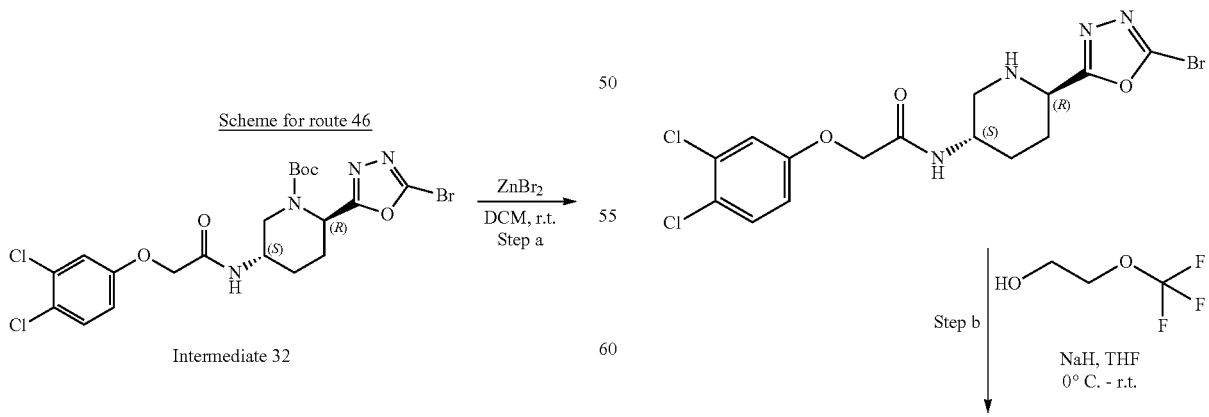

Scheme for route 46

-continued

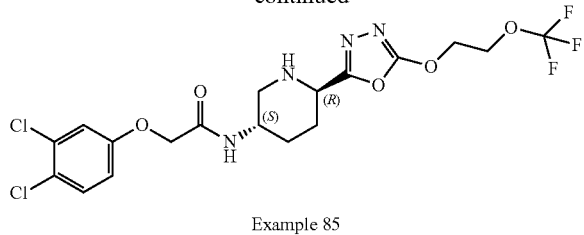

Example 85

Step 46.a: N-[(3S,6R)-6-(5-bromo-1,3,4-oxadiazol-2-yl)piperidin-3-yl]-2-(3,4-dichlorophenoxy)acetamide

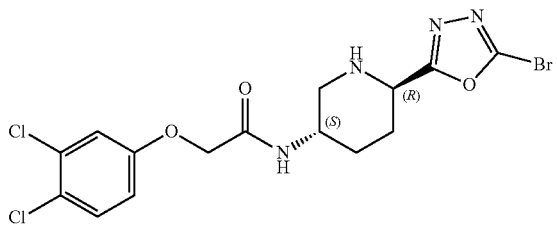

To a solution of tert-butyl (2R,5S)-2-(5-bromo-1,3,4-oxadiazol-2-yl)-5-[2-(3,4-dichlorophenoxy)acetamido]piperidine-1-carboxylate (400 mg, 0.712 mmol, Intermediate 32) in DCM (10 mL) was added ZnBr₂ (642 mg, 2.85 mmol) and the mixture was stirred at r.t. for 6 h. A further portion of ZnBr₂ (642 mg, 2.85 mmol) was added and the mixture was stirred at r.t. for 48 h. The reaction mixture was diluted with H₂O (50 mL) and extracted with DCM/IPA (2:1, 3×50 mL). The combined organic extracts were dried over Na₂SO₄ and concentrated in vacuo to afford the title compound (80% purity, 269 mg, 0.478 mmol, 67% yield) as a pale yellow powder; M/Z: 451, 453, 455 [M+H]⁺, ESI⁺, RT=0.77 (S2).

Example 85 (Step 46.b): 2-(3,4-dichlorophenoxy)-N-[(3S,6R)-6-{5-[2-(trifluoromethoxy)ethoxy]-1,3,4-oxadiazol-2-yl}piperidin-3-yl]acetamide

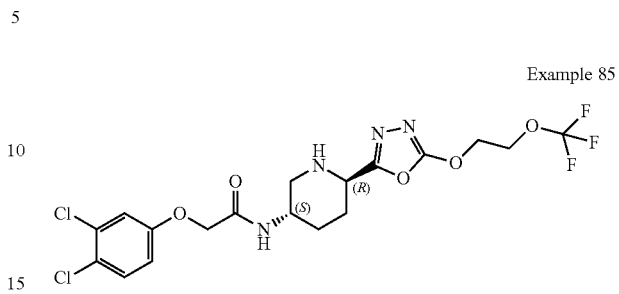

Example 85

To a solution of 2-(trifluoromethoxy)ethanol (43 µL, 0.427 mmol) in anhydrous THF (3 mL) at 0° C. was added NaH (60%, 17 mg, 0.427 mmol) and the solution was stirred at r.t. for 5 min. N-[(3S,6R)-6-(5-bromo-1,3,4-oxadiazol-2-yl)piperidin-3-yl]-2-(3,4-dichlorophenoxy)acetamide (80% purity, 200 mg, 0.355 mmol) was added and the resultant mixture was stirred at r.t. for 1 h. The reaction mixture was diluted with H₂O (30 mL) and extracted with EtOAc (2×50 mL). The combined organic extracts were dried over Na₂SO₄ and concentrated in vacuo to afford an orange oil. The residue was purified by chromatography on silica gel (0-100% EtOAc in heptane), followed by prep. HPLC (Method 3) to afford the title compound (17 mg, 0.0337 mmol, 10% yield) as a white powder; ¹H NMR (400 MHz, methanol-d₄) δ 7.46 (d, J=8.9 Hz, 1H), 7.22 (d, J=2.9 Hz, 1H), 6.98 (dd, J=8.9, 2.9 Hz, 1H), 4.74-4.70 (m, 2H), 4.55 (s, 2H), 4.46-4.42 (m, 2H), 4.01-3.93 (m, 1H), 3.92-3.87 (m, 1H), 3.24-3.18 (m, 1H), 2.66-2.57 (m, 1H), 2.19-2.06 (m, 21H), 1.91-1.80 (m, 11H), 1.70-1.58 (in, 11H); M/Z: 499, 501, 503 [M+H]⁺, ESI⁺, RT=2.30 (S4).

Example compounds in Table 20 were synthesised according to general route 46 as exemplified by Example 85 using the corresponding intermediates.

TABLE 20

| Ex | Structure | Name | Intermediates | LCMS data | ¹H NMR |
|---|---|---|---|---|---|
| 86 | 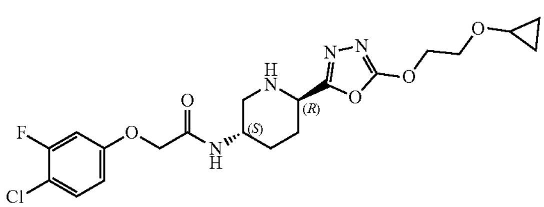 | N-[(3S,6R)-6-[5-(2-cyclopropoxyethoxy)-1,3,4-oxadiazol-2-yl]piperidin-3-yl]-2-(3,4-dichlorophenoxy)acetamide | tert-butyl (2R,5S)-2-(5-bromo-1,3,4-oxadiazol-2-yl)-5-[2-(3,4-dichlorophenoxy)acetamido]piperidine-1-carboxylate (Intermediate 32) and 2-cyclopropoxyethan-1-ol | M/Z: 471, 473, 475 [M + H]⁺, ESI⁺, RT = 2.11 (S4) | ¹H NMR (400 MHz, methanol-d₄) δ 7.46 (d, J = 8.9 Hz, 1H), 7.22 (d, J = 2.9 Hz, 1H), 6.98 (dd, J = 8.9, 2.9 Hz, 1H), 4.62-4.56 (m, 2H), 4.55 (s, 2H), 4.01-3.91 (m, 1H), 3.91-3.85 (m, 3H), 3.45-3.37 (m, 1H), 3.24-3.16 (m, 1H), 2.67-2.56 (m, 1H), 2.19-2.03 (m, 2H), 1.92-1.77 (m, 1H), 1.71-1.57 (m, 1H), 0.60-0.46 (m, 4H). |

TABLE 20-continued

| Ex | Structure | Name | Intermediates | LCMS data | ¹H NMR |
|---|---|---|---|---|---|
| 87 | 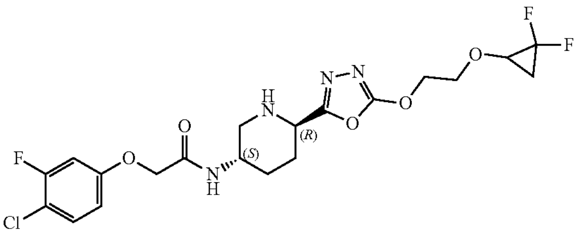 | 2-(4-chloro-3-fluorophenoxy)-N-[(3S,6R)-6-{5-[2-(2,2-difluorocyclopropoxy)ethoxy]-1,3,4-oxadiazol-2-yl}piperidin-3-yl]acetamide | tert-butyl (2R,5S)-2-(5-bromo-1,3,4-oxadiazol-2-yl)-5-[[2-(4-chloro-3-fluoro-phenoxy)acetyl]amino]piperidine-1-carboxylate (Intermediate 31) and 2-(2,2-difluorocyclopropoxy)ethan-1-ol (Intermediate 40) | M/Z: 491, 493 [M + H]⁺, ESI⁺, RT = 2.08 (S4) | ¹H NMR (500 MHz, DMSO-d₆) δ 7.97 (d, J = 8.1 Hz, 1H), 7.49 (t, J = 8.9 Hz, 1H), 7.09-7.03 (m, 1H), 6.87-6.82 (m, 1H), 4.57 (t, J = 4.4 Hz, 2H), 4.52 (s, 2H), 4.00-3.93 (m, 1H), 3.93-3.86 (m, 2H), 3.78-3.72 (m, 1H), 3.72-3.64 (m, 1H), 3.00-2.93 (m, 1H), 2.82-2.74 (m, 1H), 2.46-2.38 (m, 1H), 1.98-1.85 (m, 2H), 1.75-1.43 (m, 4H). |
| 88 | 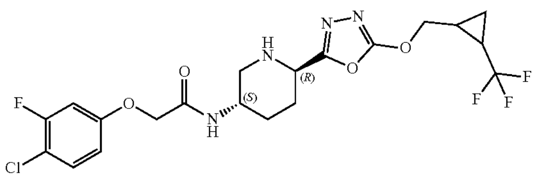 | 2-(4-chloro-3-fluorophenoxy)-N-[(3S,6R)-6-{5-[2-(trifluoromethyl)cyclopropyl]methoxy}-1,3,4-oxadiazol-2-yl)piperidin-3-yl]acetamide | tert-butyl (2R,5S)-2-(5-bromo-1,3,4-oxadiazol-2-yl)-5-[[2-(4-chloro-3-fluorophenoxy)acetyl]amino]piperidine-1-carboxylate (Intermediate 31) and rac-[(1R,2R)-2-(trifluoromethyl)cyclopropyl]methanol | M/Z: 493, 495 [M + H]⁺, ESI⁺, RT = 2.22 (S4) | ¹H NMR (500 MHz, chloroform-d) δ 7.33 (t, J = 8.6 Hz, 1H), 6.78 (dd, J = 10.3, 2.9 Hz, 1H), 6.75-6.65 (m, 2H), 4.49-4.42 (m, 3H), 4.31 (dd, J = 11.2, 7.5 Hz, 1H), 4.10-3.96 (m, 2H), 3.29 (dd, J = 12.0, 3.4 Hz, 1H), 2.62 (dd, J = 12.0, 7.6 Hz, 1H), 2.13-1.87 (m, 4H), 1.85-1.77 (m, 1H), 1.73-1.66 (m, 1H), 1.64-1.58 (m, 1H), 1.21-1.14 (m, 1H), 0.97-0.91 (m, 1H); 70:30 mixture of diastereomers. |

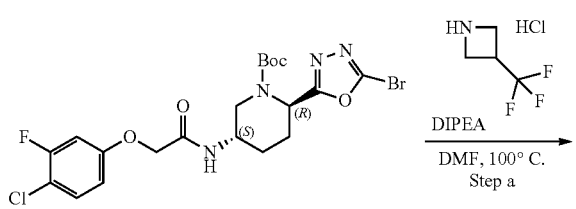

Intermediate 31

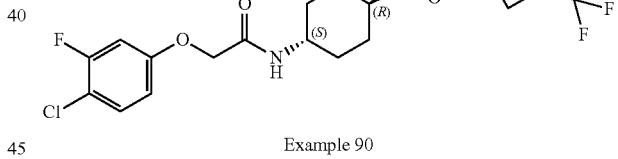

Example 90

Example 89 (Step 47.a): tert-butyl (2R,5S)-5-[2-(4-chloro-3-fluorophenoxy)acetamido]-2-{5-[3-(trifluoromethyl)azetidin-1-yl]-1,3,4-oxadiazol-2-yl}piperidine-1-carboxylate

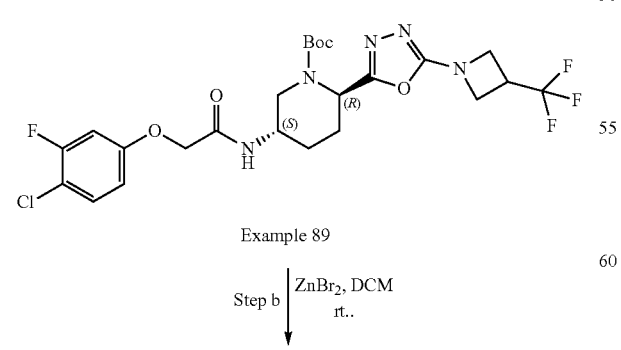

Example 89

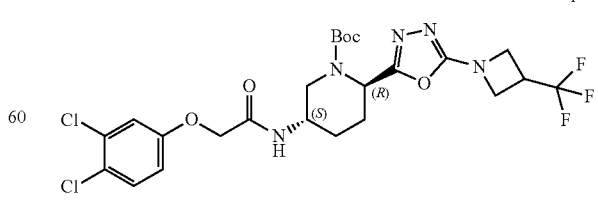

Example 89

To a solution of 3-(trifluoromethyl)azetidine hydrochloride (60 mg, 0.371 mmol) in anhydrous DMF (1 mL) was added DIPEA (0.16 mL, 0.927 mmol) followed by a solution of tert-butyl (2R,5S)-2-(5-bromo-1,3,4-oxadiazol-2-yl)-5-[[2-(4-chloro-3-fluoro-phenoxy)acetyl]amino]piperidine-1-carboxylate (100 mg, 0.185 mmol, Intermediate 31) in anhydrous DMF (1 mL) and the mixture was stirred at 100° C. for 2 h. The reaction mixture was diluted with H$_2$O (10 mL) and extracted with EtOAc (3×10 mL). The combined organic extracts were washed with brine (2×30 mL), dried over MgSO$_4$, and concentrated in vacuo to afford the title compound (87% purity, 117 mg, 0.176 mmol, 95% yield) as a brown oil; M/Z: 478, 480 [M+H]$^+$, ESI$^+$, RT=1.13 (S2).

Example 90 (Step 47.b): 2-(4-chloro-3-fluorophenoxy)-N-[(3S,6R)-6-{5-[3-(trifluoromethyl)azetidin-1-yl]-1,3,4-oxadiazol-2-yl}piperidin-3-yl]acetamide Example 90

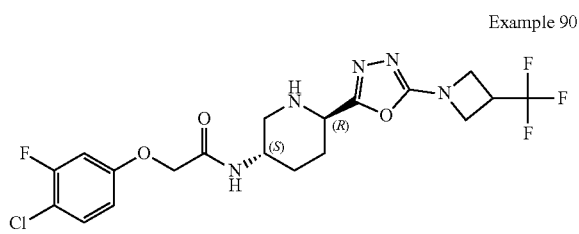

To a solution of tert-butyl (2R,5S)-5-[2-(4-chloro-3-fluorophenoxy)acetamido]-2-{5-[3-(trifluoromethyl)azetidin-1-yl]-1,3,4-oxadiazol-2-yl}piperidine-1-carboxylate (87% purity, 115 mg, 0.173 mmol) in DCM (2 mL) was added ZnBr$_2$ (117 mg, 0.519 mmol) and the mixture was stirred at r.t. for 20 h. The reaction mixture was diluted with satd aq NaHCO$_3$ (3 mL) solution and extracted with DCM:IPA (80:20, 3×3 mL). The combined organic extracts were dried using a phase separator and concentrated in vacuo. The residue was purified by prep. HPLC (Method 4) to afford the title compound (37 mg, 0.0774 mmol, 45% yield) as a white powder; $^1$H NMR (500 MHz, DMSO-d$_6$) δ 7.96 (d, J=8.1 Hz, 1H), 7.49 (t, J=8.9 Hz, 1H), 7.07 (m, 1H), 6.87-6.82 (m, 1H), 4.51 (s, 2H), 4.37-4.30 (m, 2H), 4.10-4.04 (m, 2H), 3.85-3.75 (m, 1H), 3.75-3.64 (m, 2H), 3.01-2.94 (m, 1H), 2.75-2.67 (m, 1H), 2.47-2.37 (m, 1H), 1.97-1.85 (m, 2H), 1.69-1.58 (m, 1H), 1.54-1.42 (m, 1H); M/Z: 480, 482 [M+H]$^+$, ESI$^+$, RT=1.97 (S4).

Example compounds in Table 21 were synthesised according to general route 47 as exemplified by Example 90 using the corresponding intermediates.

TABLE 21

| Ex | Structure | Name | Intermediates | LCMS data | $^1$H NMR |
|---|---|---|---|---|---|
| 91 | 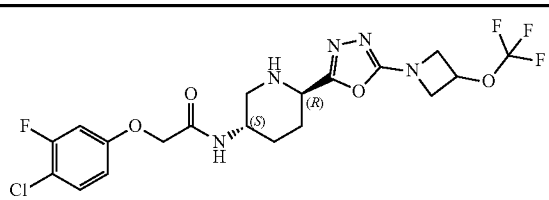 | 2-(4-chloro-3-fluoro-phenoxy)-N-[(3S,6R)-6-{5-[3-(trifluoromethoxy)azetidin-1-yl]-1,3,4-oxadiazol-2-yl}piperidin-3-yl]acetamide | tert-butyl (2R,5S)-2-(5-bromo-1,3,4-oxadiazol-2-yl)-5-[[2-(4-chloro-3-fluoro-phenoxy)acetyl]amino]piperidine-1-carboxylate (Intermediate 31) and 3-(trifluoromethoxy)azetidine | M/Z: 494, 496 [M + H]$^+$, ESI$^+$, RT = 2.16 (S4) | $^1$H NMR (400 MHz, chloroform-d) δ 7.33 (t, J = 8.6 Hz, 1H), 6.83-6.58 (m, 3H), 5.10 (t, J = 4.7 Hz, 1H), 4.50-4.43 (m, 4H), 4.30 (dd, J = 9.8, 4.6 Hz, 2H), 4.10-3.93 (m, 2H), 3.32 (dd, J = 12.2, 3.4 Hz, 1H), 2.60 (dd, J = 12.0, 8.1 Hz, 1H), 2.08 (d, J = 9.1 Hz, 2H), 1.91 (d, J = 8.7 Hz, 2H), 1.59 (s, 1H). |
| 92 | 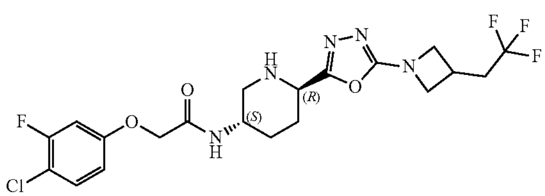 | 2-(4-chloro-3-fluoro-phenoxy)-N-[(3S,6R)-6-{5-[3-(2,2,2-trifluoroethyl)azetidin-1-yl]-1,3,4-oxadiazol-2-yl}piperidin-3-yl]acetamide | tert-butyl (2R,5S)-2-(5-bromo-1,3,4-oxadiazol-2-yl)-5-[[2-(4-chloro-3-fluoro-phenoxy)acetyl]amino]piperidine-1-carboxylate (Intermediate 31) and 3-(2,2,2-trifluoroethyl)azetidine | M/Z: 492, 494 [M + H]$^+$, ESI$^+$, RT = 2.12 (S4) | $^1$H NMR (400 MHz, methanol-d$_4$) δ 7.44-7.37 (m, 1H), 6.96 (dd, J = 11.0, 2.8 Hz, 1H), 6.85 (ddd, J = 9.0, 2.8, 1.2 Hz, 1H), 4.55 (s, 2H), 4.37-4.31 (m, 2H), 4.02-3.91 (m, 3H), 3.89-3.82 (m, 1H), 3.25-3.14 (m, 2H), 2.70-2.57 (m, 3H), 2.15-2.06 (m, 2H), 1.90-1.78 (m, 1H), 1.69-1.57 (m, 1H). |
| 93 | 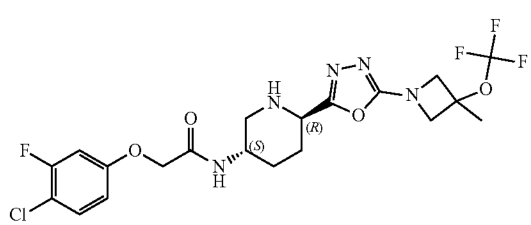 | 2-(4-chloro-3-fluoro-phenoxy)-N-[(3S,6R)-6-{5-[3-methyl-3-(trifluoromethoxy)azetidin-1-yl]-1,3,4-oxadiazol-2-yl}piperidin-3-yl]acetamide | tert-butyl (2R,5S)-2-(5-bromo-1,3,4-oxadiazol-2-yl)-5-[[2-(4-chloro-3-fluoro-phenoxy)acetyl]amino]piperidine-1-carboxylate (Intermediate 31) and 3-methyl-3-(trifluoromethoxy)azetidine hydrochloride (Intermediate 36) | M/Z: 508, 510 [M + H]$^+$, ESI$^+$, RT = 2.16 (S4) | $^1$H NMR (400 MHz, methanol-d$_4$) δ 7.35-7.23 (m, 1H), 6.84 (dd, J = 11.0, 2.8 Hz, 1H), 6.73 (ddd, J = 8.9, 2.8, 1.2 Hz, 1H), 4.43 (s, 2H), 4.28 (d, J = 9.1 Hz, 2H), 4.08 (d, J = 9.6 Hz, 2H), 3.90-3.79 (m, 1H), 3.79-3.70 (m, 1H), 3.13-3.05 (m, 1H), 2.54-2.45 (m, 1H), 2.06-1.93 (m, 2H), 1.78-1.68 (m, 4H), 1.57-1.46 (m, 1H). |

TABLE 21-continued

| Ex | Structure | Name | Intermediates | LCMS data | ¹H NMR |
|---|---|---|---|---|---|
| 94 | 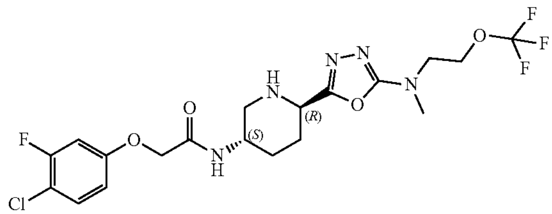 | 2-(4-chloro-3-fluorophenoxy)-N-[(3S,6R)-6-(5-{methyl[2-(trifluoromethoxy)ethyl]amino}-1,3,4-oxadiazol-2-yl)piperidin-3-yl]acetamide | tert-butyl (2R,5S)-2-(5-bromo-1,3,4-oxadiazol-2-yl)-5-[[2-(4-chloro-3-fluorophenoxy)acetyl]amino]piperidine-1-carboxylate (Intermediate 31) and methyl[2-(trifluoromethoxy)ethyl]amine-hydrochloride | M/Z: 496, 498 [M + H]⁺, ESI⁺, RT = 2.1 (S4) | ¹H NMR (400 MHz, chloroform-d) δ 7.33 (t, J = 8.6 Hz, 1H), 6.78 (dd, J = 10.3, 2.9 Hz, 1H), 6.72-6.62 (m, 2H), 4.46 (s, 2H), 4.21 (t, J = 5.1 Hz, 2H), 4.11-3.93 (m, 2H), 3.72 (t, J = 5.1 Hz, 2H), 3.33 (dd, J = 12.0, 3.5 Hz, 1H), 3.17 (s, 3H), 2.60 (dd, J = 11.9, 8.1 Hz, 1H), 2.15-1.86 (m, 4H), 1.64-1.57 (m, 1H). |
| 95 | 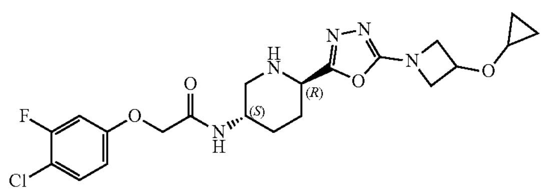 | 2-(4-chloro-3-fluorophenoxy)-N-[(3S,6R)-6-[5-(3-cyclopropoxyazetidin-1-yl)-1,3,4-oxadiazol-2-yl)piperidin-3-yl]acetamide | tert-butyl (2R,5S)-2-(5-bromo-1,3,4-oxadiazol-2-yl)-5-[[2-(4-chloro-3-fluorophenoxy)acetyl]amino]piperidine-1-carboxylate (Intermediate 31) and 3-cyclopropoxy-azetidine hydrochloride (Intermediate 50) | M/Z: 466, 468 [M + H]⁺, ESI⁺, RT = 1.96 (S4) | ¹H NMR (400 MHz, chloroform-d) δ 7.33 (t, J = 8.6 Hz, 1H), 6.78 (dd, J = 10.3, 2.8 Hz, 1H), 6.72-6.60 (m, 2H), 4.58-4.51 (m, 1H), 4.46 (s, 2H), 4.37-4.30 (m, 2H), 4.12-3.99 (m, 3H), 3.95 (dd, J = 8.2, 3.2 Hz, 1H), 3.35-3.24 (m, 2H), 2.59 (dd, J = 12.0, 8.0 Hz, 1H), 2.13-1.85 (m, 4H), 1.62-1.56 (m, 1H), 0.65-0.46 (m, 4H). |
| 96 | 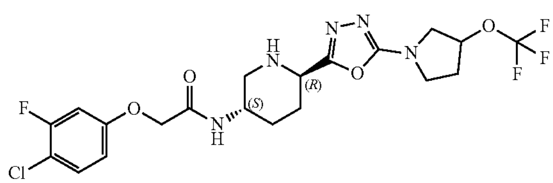 | 2-(4-chloro-3-fluorophenoxy)-N-[(3S,6R)-6-{5-[3-(trifluoromethoxy)pyrrolidin-1-yl]-1,3,4-oxadiazol-2-yl}piperidin-3-yl]acetamide | tert-butyl (2R,5S)-2-(5-bromo-1,3,4-oxadiazol-2-yl)-5-[[2-(4-chloro-3-fluorophenoxy)acetyl]amino]piperidine-1-carboxylate (Intermediate 31) and 3-(trifluoromethoxy)pyrrolidine hydrochloride | M/Z: 508, 510 [M + H]⁺, ESI⁺, RT = 0.70 (S2) | |

Scheme for route 48

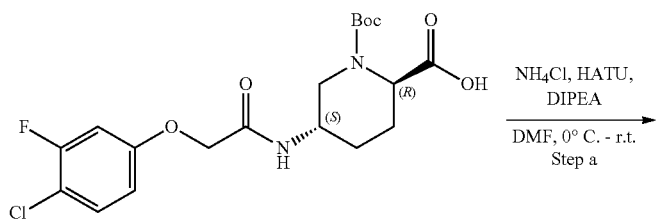

Intermediate 22

NH₄Cl, HATU, DIPEA

DMF, 0° C. - r.t.
Step a

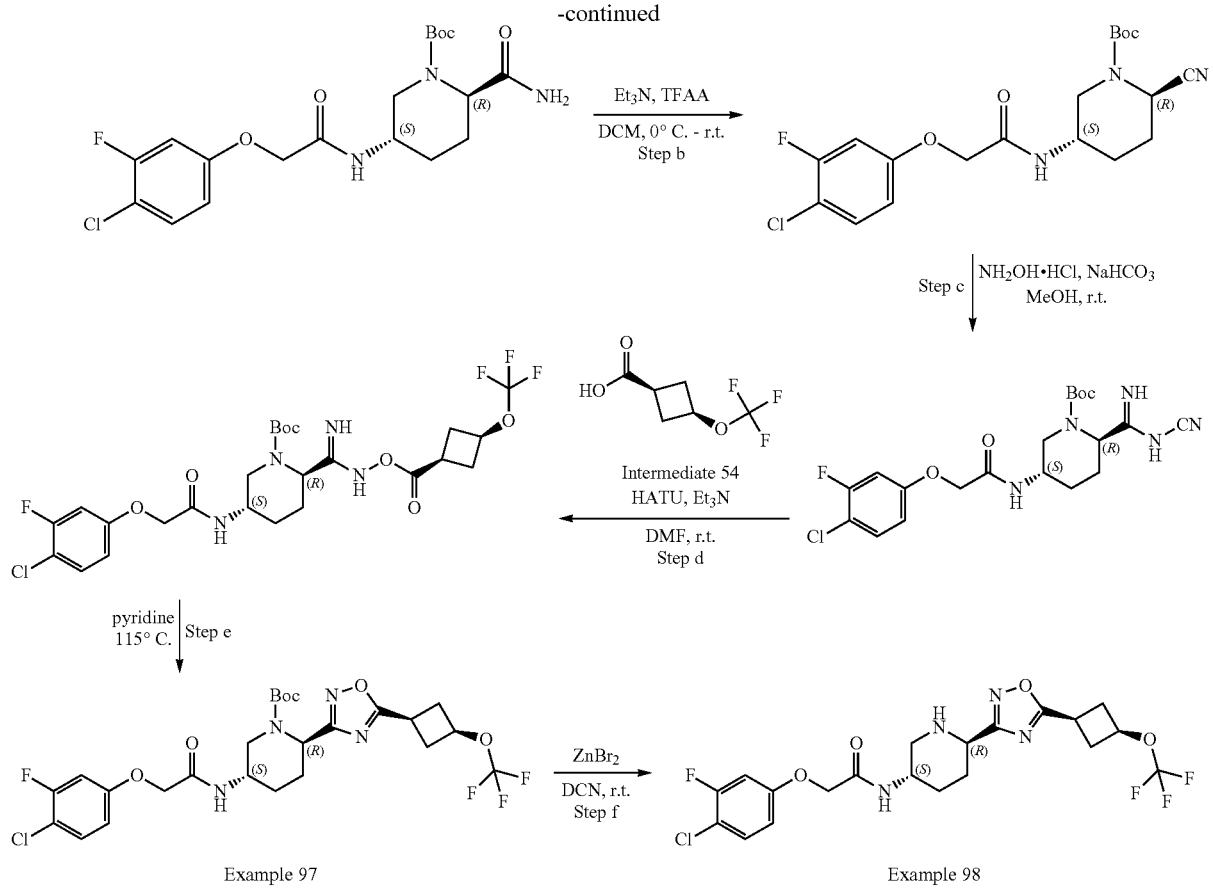

Step 48.a: tert-butyl (2R,5S)-2-carbamoyl-5-[2-(4-chloro-3-fluorophenoxy)acetamido]piperidine-1-carboxylate

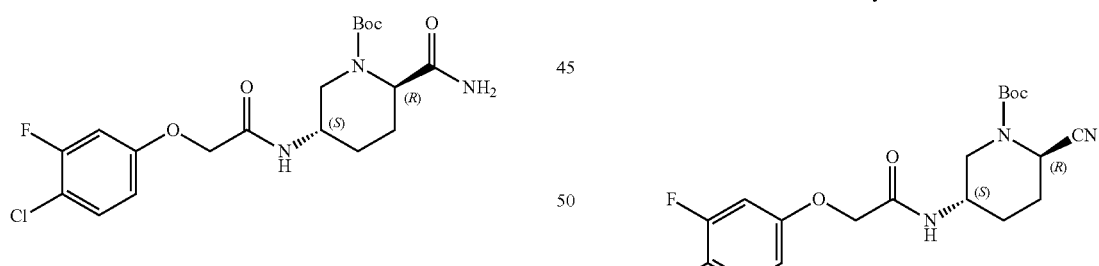

To a solution of (2R,5S)-1-[(tert-butoxy)carbonyl]-5-[2-(4-chloro-3-fluorophenoxy) acetamido]piperidine-2-carboxylic acid (1.86 g, 4.32 mmol, Intermediate 22), NH₄Cl (253 mg, 4.73 mmol) and DIPEA (3.1 mL, 17.7 mmol) in anhydrous DMF (22 mL) at 0° C. was added HATU (1.80 g, 4.73 mmol) and the mixture was stirred at r.t. for 4 h. The reaction mixture was diluted with EtOAc (100 mL) and washed with brine (3×50 mL). The combined organic extracts were dried over MgSO₄, and concentrated in vacuo to afford the title compound (80% purity, 2.36 g, 4.39 mmol) in quantitative yield as colourless crystals; $^1$H NMR (500 MHz, DMSO-$d_6$) δ 7.99-7.93 (m, 1H), 7.47 (t, J=8.9 Hz, 1H), 7.32 (s, 1H), 7.08-6.99 (m, 2H), 6.81 (dd, J=8.9, 1.9 Hz, 1H), 4.63-4.37 (m, 3H), 3.97-3.74 (m, 2H), 3.27-3.08 (m, 1H), 1.98-1.81 (m, 2H), 1.60-1.47 (m, 2H), 1.36 (s, 9H); M/Z: 330, 332 [M+H]⁺, ESI⁺, RT=0.88 (S2).

Step 48.b: tert-butyl (2R,5S)-5-[2-(4-chloro-3-fluorophenoxy)acetamido]-2-cyanopiperidine-1-carboxylate To a solution of tert-butyl (2R,5S)-2-carbamoyl-5-[2-(4-chloro-3-fluorophenoxy)acetamido]piperidine-1-carboxylate (80% purity, 2.17 g, 4.04 mmol) and Et₃N (2.6 mL, 18.7 mmol) in anhydrous DCM (40 mL) at 0° C. was added TFAA (1.2 mL, 8.27 mmol) and the solution was stirred at r.t. for 2 h. The reaction mixture was cooled to 0° C. and quenched with H₂O (20 mL). The solution was diluted with DCM (50 mL) and washed with satd aq NaHCO₃ solution (20 mL). The organic layer was dried using a phase separator, concentrated in vacuo, and purified by chromatography on silica gel (0-50% EtOAc in heptane) to afford the title compound (0.94 g, 2.22 mmol, 55% yield) as a white powder; ¹H NMR (500 MHz, DMSO-d₆) δ 8.06 (d, J=6.9 Hz, 1H), 7.47 (t, J=8.9 Hz, 1H), 7.02 (dd, J=11.4, 2.8 Hz, 1H), 6.80 (dd, J=8.9, 2.0 Hz, 1H), 5.37-5.27 (m, 1H), 4.61-4.50 (m, 2H), 4.03-3.90 (m, 2H), 3.07-2.92 (m, 1H), 2.17-2.04 (m, 1H), 1.84-1.68 (m, 3H), 1.39 (s, 9H); M/Z: 429, 431 [M+NH₄]⁺, ESI⁺, RT=3.69 (S6).

Step 48.c: tert-butyl (2R,5S)-5-[2-(4-chloro-3-fluorophenoxy)acetamido]-2-(N-hydroxycarbamimidoyl)piperidine-1-carboxylate

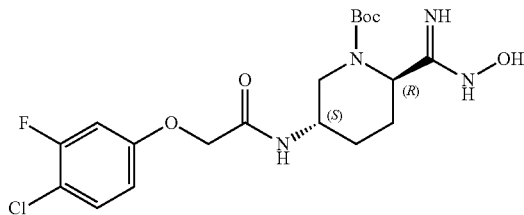

To a solution of tert-butyl (2R,5S)-5-[2-(4-chloro-3-fluorophenoxy)acetamido]-2-cyanopiperidine-1-carboxylate (500 mg, 1.21 mmol) in MeOH (6 mL) at 0° C. was added hydroxylamine hydrochloride (1:1) (125 mg, 1.80 mmol) and NaHCO₃ (225 mg, 2.68 mmol) and the reaction mixture was stirred at r.t. for 40 h. The resulting suspension was filtered under vacuum, washing with MeOH, and the filtrate was concentrated in vacuo to afford the title compound (69% purity, 620 mg, 0.962 mmol, 79% yield) as a white powder; ¹H NMR (500 MHz, DMSO-d₆) δ 8.01-7.90 (m, 1H), 7.48 (t, J=8.9 Hz, 1H), 7.05 (dd, J=11.3, 2.9 Hz, 1H), 6.82 (ddd, J=9.0, 2.8, 0.9 Hz, 1H), 5.22 (s, 1H), 4.67 (s, 1H), 4.62-4.51 (m, 2H), 3.95-3.78 (m, 2H), 3.19-3.11 (m, 1H), 2.00-1.82 (m, 2H), 1.75 (d, J=16.9 Hz, 1H), 1.59-1.47 (m, 1H), 1.37 (s, 9H); M/Z: 345, 347 [M-Boc+H]⁺, ESI⁺, RT=0.78 (S2).

Step 48.d: tert-butyl (2R,5S)-5-[2-(4-chloro-3-fluorophenoxy)acetamido]-2-{N-[(1s,3s)-3-(trifluoromethoxy)cyclobutanecarbonyloxy]carbamimidoyl}piperidine-1-carboxylate

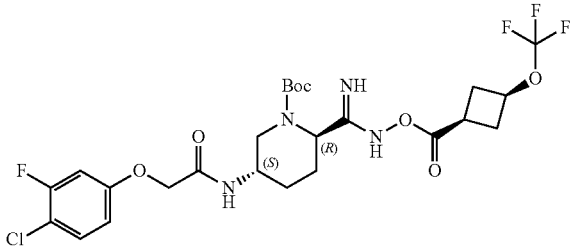

To a solution of (1s,3s)-3-(trifluoromethoxy)cyclobutane-1-carboxylic acid (90 mg, 0.489 mmol, Intermediate 54) in anhydrous DMF (2.5 mL) was added Et₃N (202 μL, 1.45 mmol) followed by HATU (200 mg, 0.526 mmol) and stirred at r.t. for 10 min. tert-butyl (2R,5S)-5-[2-(4-chloro-3-fluorophenoxy)acetamido]-2-(N-hydroxycarbamimidoyl)piperidine-1-carboxylate (69% purity, 310 mg, 0.481 mmol) was added and the resultant mixture was stirred at r.t. for 17 h. The reaction mixture was diluted with EtOAc (30 mL) and washed with brine (3×20 mL). The combined organic extracts were dried over MgSO₄, and concentrated in vacuo to afford the title compound (59% purity, 367 mg, 0.354 mmol, 74% yield) as an orange oil; M/Z: 511, 513 [M-Boc+H]⁺, ESI⁺, RT=1.12 (S2).

Example 97 (Step 48.e): tert-butyl (2R,5S)-5-[2-(4-chloro-3-fluorophenoxy)acetamido]-2-{5-[(1s,3s)-3-(trifluoromethoxy)cyclobutyl]-1,2,4-oxadiazol-3-yl}piperidine-1-carboxylate Example 97

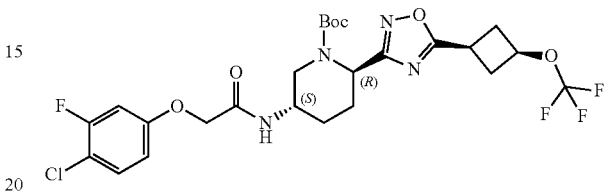

A solution of tert-butyl (2R,5S)-5-[2-(4-chloro-3-fluorophenoxy)acetamido]-2-{N-[(1s,3s)-3-(trifluoromethoxy)cyclobutanecarbonyloxy]carbamimidoyl}piperidine-1-carboxylate (59% purity, 367 mg, 0.354 mmol) in pyridine (3.5 mL) was stirred at 115° C. for 17 h. The reaction mixture was concentrated in vacuo and purified by chromatography on silica gel (0-100% EtOAc in heptane) to afford the title compound (91% purity, 172 mg, 0.264 mmol, 74% yield) as a colourless oil; M/Z: 593, 595 [M+H]⁺, ESI⁺, RT=1.20 (S2).

Example 98 (Step 48.1): 2-(4-chloro-3-fluorophenoxy)-N-[(3S,6R)-6-{5-[(1s,3s)-3-(trifluoromethoxy)cyclobutyl]-1,2,4-oxadiazol-3-yl}piperidin-3-yl]acetamide Example 98

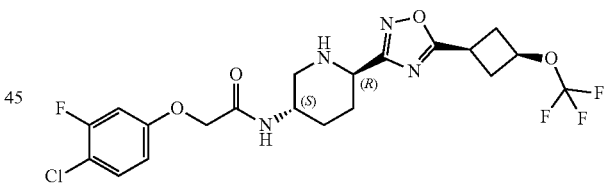

To a solution of tert-butyl (2R,5S)-5-[2-(4-chloro-3-fluorophenoxy)acetamido]-2-{5-[(1s,3s)-3-(trifluoromethoxy)cyclobutyl]-1,2,4-oxadiazol-3-yl}piperidine-1-carboxylate (91% purity, 152 mg, 0.233 mmol, Example 97) in anhydrous DCM (1.5 mL) was added ZnBr₂ (210 mg, 0.924 mmol) and the resultant mixture was stirred at r.t. under N₂ for 17 h. The reaction mixture was diluted with satd aq NaHCO₃ solution (20 mL) and extracted with DCM/IPA 80:20 (3×50 mL). The combined organic extracts were dried using a phase separator, concentrated in vacuo and purified by prep. HPLC (Method 4) to afford the title compound (68 mg, 0.138 mmol, 59% yield) as a white solid; ¹H NMR (400 MHz, chloroform-d) δ 7.33 (t, J=8.6 Hz, 1H), 6.78 (dd, J=10.3, 2.8 Hz, 1H), 6.70 (ddd, J=8.9, 2.8, 1.2 Hz, 1H), 6.60-6.53 (m, 1H), 4.71 (p, J=7.6 Hz, 1H), 4.46 (s, 2H), 4.10-4.00 (m, 1H), 3.94 (dd, J=9.1, 3.0 Hz, 1H), 3.40-3.28 (m, 2H), 2.94-2.85 (m, 2H), 2.78-2.66 (m, 2H), 2.64-2.57

(m, 1H), 2.18-2.01 (m, 3H), 1.94-1.82 (m, 1H), 1.63-1.57 (m, 1H); M/Z: 493, 495 [M+H]⁺, ESI⁺, RT=2.32 (S4).

Scheme for route 49

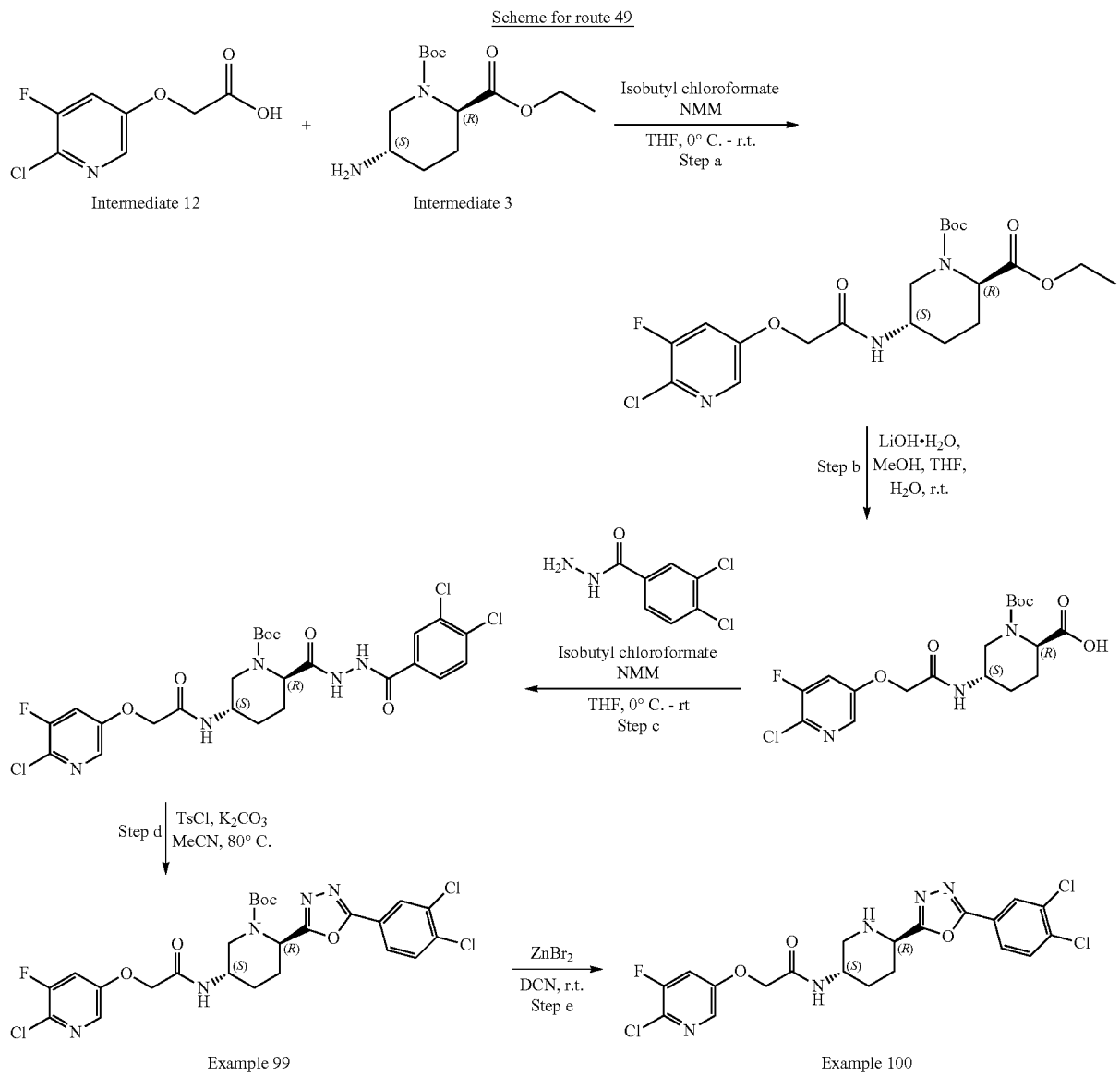

Step 49.a: 1-tert-butyl 2-ethyl (2R,5S)-5-{2-[(6-chloro-5-fluoropyridin-3-yl)oxy]acetamido}piperidine-1,2-dicarboxylate

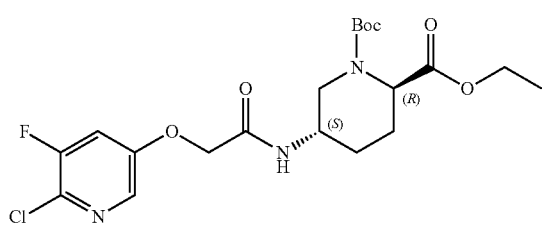

To a solution of 2-[(6-chloro-5-fluoropyridin-3-yl)oxy]acetic acid (400 mg, 1.95 mmol, Intermediate 12) in anhydrous THF (20 mL) at 0° C. was added isobutyl chloroformate (0.24 mL, 1.85 mmol) followed by NMM (0.21 mL, 1.95 mmol). The mixture was stirred for 15 min before 1-tert-butyl 2-ethyl (2R,5S)-5-aminopiperidine-1,2-dicarboxylate (530 mg, 1.95 mmol, Intermediate 3) was added and the resultant mixture was stirred at r.t. for 1 h. The reaction mixture was cooled to 0° C., quenched with H₂O (0.5 mL) and concentrated in vacuo. The residue was partitioned between EtOAc (10 mL) and H₂O (10 mL). The organic layer was isolated, washed with satd aq NaHCO₃ solution (10 mL) and brine (10 mL), dried over Na₂SO₄, and concentrated in vacuo to afford the title compound (90% purity, 805 mg, 1.58 mmol, 81% yield) as an off-white solid; ¹H NMR (400 MHz, chloroform-d) δ 7.98 (d, J=2.6 Hz, 1H), 7.12 (dd, J=8.8, 2.6 Hz, 1H), 6.73 (d, J=43.3 Hz, 1H), 4.52 (s, 2H), 4.28-4.16 (m, 3H), 4.10-3.86 (m, 1H), 3.24 (dd, J=39.3, 13.1 Hz, 1H), 2.15 (d, J=15.8 Hz, 1H), 2.01-1.73 (m, 2H), 1.63-1.51 (m, 2H), 1.45 (s, 9H), 1.32-1.21 (m, 3H).

Step 49.b: (2R,5S)-1-[(tert-butoxy)carbonyl]-5-{2-[(6-chloro-5-fluoropyridin-3-yl)oxy]acetamido}piperidine-2-carboxylic acid

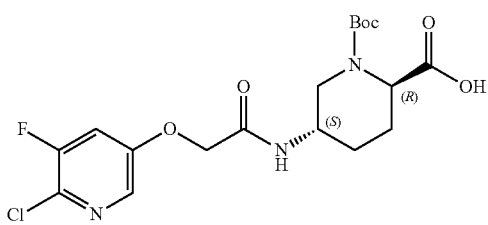

A solution of 1-tert-butyl 2-ethyl (2R,5S)-5-{2-[(6-chloro-5-fluoropyridin-3-yl)oxy]acetamido}piperidine-1,2-dicarboxylate (90% purity, 805 mg, 1.58 mmol) and LiOH·H₂O (81 mg, 1.89 mmol) in THF (2.5 mL)/MeOH (2.5 mL)/H₂O (2.5 mL) was stirred at r.t. for 6 h. The reaction mixture was concentrated in vacuo and the residue was partitioned between EtOAc (20 mL) and H₂O (20 mL). The layers were separated and the organic layer discarded. The aqueous layer was cooled to 0° C. and acidified to pH 2/3 using 1 M aq HCl solution. The resultant solution was extracted with EtOAc (2×25 mL) and the combined organic extracts were washed with H₂O (30 mL), dried over Na₂SO₄, and concentrated in vacuo to afford the title compound (90% purity, 570 mg, 1.19 mmol, 75% yield) as a white solid; ¹H NMR (400 MHz, DMSO-d₆) δ 8.12 (d, J=6.9 Hz, 1H), 8.03 (d, J=2.6 Hz, 1H), 7.66 (dd, J=10.3, 2.3 Hz, 1H), 4.75-4.44 (m, 3H), 3.99-3.71 (m, 2H), 3.15-2.90 (m, 2H), 2.08-1.84 (m, 2H), 1.67-1.55 (m, 1H), 1.54-1.41 (m, 1H), 1.37 (s, 9H).

Step 49.c: tert-butyl (2R,5S)-5-{2-[(6-chloro-5-fluoropyridin-3-yl)oxy]acetamido}-2-[N'-(3,4-dichlorobenzoyl)hydrazinecarbonyl]piperidine-1-carboxylate

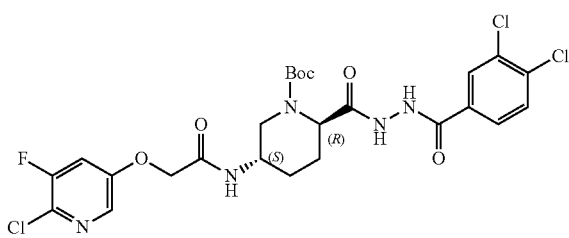

To a solution of (2R,5S)-1-[(tert-butoxy)carbonyl]-5-{2-[(6-chloro-5-fluoropyridin-3-yl)oxy]acetamido}piperidine-2-carboxylic acid (90% purity, 530 mg, 1.10 mmol) in anhydrous THF (11 mL) at 0° C. was added isobutyl chloroformate (0.14 mL, 1.05 mmol) followed by NMM (0.12 mL, 1.10 mmol). The mixture was stirred for 15 min before 3,4-dichlorobenzohydrazide (226 mg, 1.10 mmol) was added and the resultant mixture was stirred at r.t. 1 h. The reaction mixture was cooled to 0° C., quenched with H₂O (0.5 mL) and concentrated in vacuo. The residue was partitioned between EtOAc (15 mL) and H₂O (15 mL). The organic layer was isolated, washed with satd aq NaHCO₃ solution (10 mL) and brine (10 mL), dried over Na₂SO₄, and concentrated in vacuo to afford the title compound (90% purity, 626 mg, 0.910 mmol, 82% yield) as an off-white solid; ¹H NMR (400 MHz, chloroform-d) δ 8.68 (s, 2H), 8.00 (d, J=2.6 Hz, 1H), 7.92 (d, J=1.8 Hz, 1H), 7.66-7.59 (m, 1H), 7.56-7.50 (m, 1H), 7.13 (dd, J=8.8, 2.6 Hz, 1H), 5.00-4.82 (m, 1H), 4.58-4.46 (m, 2H), 4.28-4.08 (m, 2H), 3.33 (d, J=12.5 Hz, 1H), 2.25-2.16 (m, 1H), 2.09-1.84 (m, 2H), 1.83-1.71 (m, 1H), 1.54-1.44 (m, 10H).

Example 99 (Step 49.d): tert-butyl (2R,5S)-5-{2-[(6-chloro-5-fluoropyridin-3-yl)oxy]acetamido}-2-[5-(3,4-dichlorophenyl)-1,3,4-oxadiazol-2-yl]piperidine-1-carboxylate Example 99

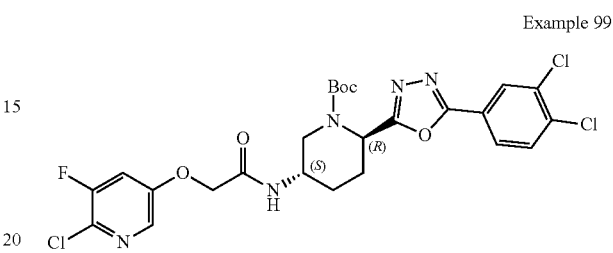

A suspension of tert-butyl (2R,5S)-5-{2-[(6-chloro-5-fluoropyridin-3-yl)oxy]acetamido}-2-[N-(3,4-dichlorobenzoyl)hydrazinecarbonyl]piperidine-1-carboxylate (601 mg, 0.971 mmol), TsCl (555 mg, 2.91 mmol) and K₂CO₃ (805 mg, 5.83 mmol) in anhydrous ACN (10 mL) was stirred at 80° C. for 4 h. The reaction mixture was cooled to r.t. and partitioned between EtOAc (20 mL) and H₂O (20 mL). The layers were separated and the aqueous layer extracted further with EtOAc (10 mL). The combined organic extracts were washed with satd aq NaHCO₃ solution (5×20 mL) and brine (20 mL), dried over Na₂SO₄, and concentrated in vacuo. The residue was purified by chromatography on silica gel (40-90% EtOAc in heptane) to afford the title compound (310 mg, 0.490 mmol, 50% yield) as a off-white solid; ¹H NMR (500 MHz, chloroform-d) δ 8.10 (d, J=2.0 Hz, 1H), 8.01 (d, J=2.6 Hz, 1H), 7.87 (dd, J=8.4, 2.0 Hz, 1H), 7.60 (d, J=8.4 Hz, 1H), 7.14 (dd, J=8.8, 2.6 Hz, 1H), 6.77 (s, 1H), 5.93-5.44 (m, 1H), 4.62-4.48 (m, 2H), 4.29-4.19 (m, 1H), 4.17-4.02 (m, 1H), 3.43-2.98 (m, 1H), 2.38-2.23 (m, 1H), 2.18-1.91 (m, 3H), 1.50 (s, 9H).

Example 100 (Step 49.e): 2-[(6-chloro-5-fluoropyridin-3-yl)oxy]-N-[(3S,6R)-6-[5-(3,4-dichlorophenyl)-1,3,4-oxadiazol-2-yl]piperidin-3-yl]acetamide Example 100

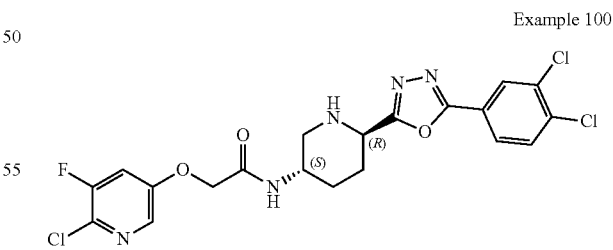

To a solution of tert-butyl (2R,5S)-5-{2-[(6-chloro-5-fluoropyridin-3-yl)oxy]acetamido}-2-[5-(3,4-dichlorophenyl)-1,3,4-oxadiazol-2-yl]piperidine-1-carboxylate (150 mg, 0.250 mmol, Example 99) in DCM (3 mL) was added ZnBr₂ (225 mg, 0.999 mmol) and the resultant mixture was stirred at r.t. for 18 h. The reaction mixture was partitioned between satd aq NaHCO₃ solution (2 mL) and DCM/IPA (4:1, 2 mL) and the layers were separated using a phase separator. The organic layer was concentrated in vacuo and purified by prep. HPLC (Method 4) to afford the title compound (28 mg, 0.0554 mmol, 22% yield) as an off-white powder; $^1$H NMR (500 MHz, chloroform-d) δ 8.17 (d, J=2.0 Hz, 1H), 8.05 (d, J=2.6 Hz, 1H), 7.93 (dd, J=8.4, 2.0 Hz, 1H), 7.63 (d, J=8.4 Hz, 1H), 7.18 (dd, J=8.8, 2.6 Hz, 1H), 6.73 (d, J=7.8 Hz, 1H), 4.57 (s, 2H), 4.27-4.21 (m, 1H), 4.20-4.09 (m, 1H), 3.41 (dd, J=12.1, 3.3 Hz, 1H), 2.73 (dd, J=12.1, 7.7 Hz, 1H), 2.29-2.20 (m, 1H), 2.20-2.04 (m, 3H), 1.78-1.67 (m, 1H); M/Z: 500, 502, 504, 506 [M+H]$^+$, ESI$^+$, RT=2.18 (S4).

Scheme for route 50

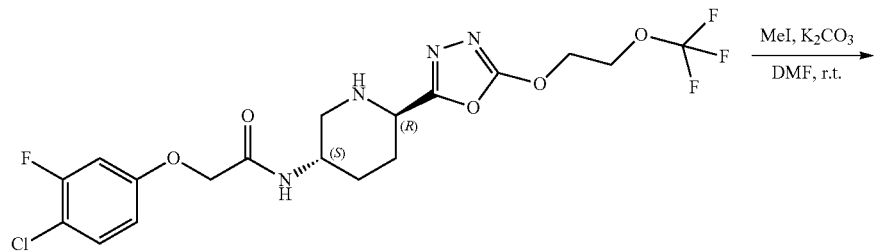

Example 77

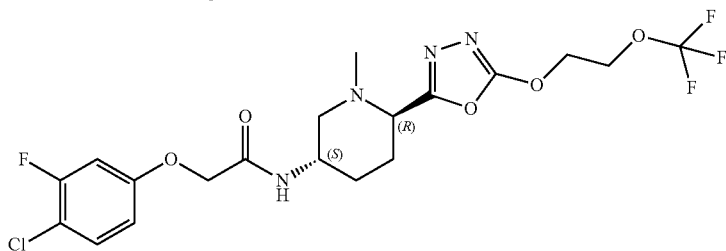

Example 101

Example 101: 2-(4-chloro-3-fluorophenoxy)-N-[(3S, 6R)-1-methyl-6-{5-[2-(trifluoromethoxy)ethoxy]-1,3,4-oxadiazol-2-yl}piperidin-3-yl]acetamide Example 101

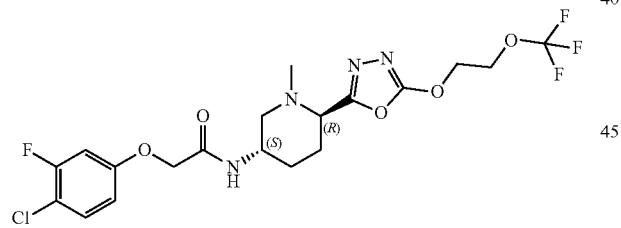

To a solution of 2-(4-chloro-3-fluorophenoxy)-N-[(3S, 6R)-6-{5-[2-(trifluoromethoxy)ethoxy]-1,3,4-oxadiazol-2-yl}piperidin-3-yl]acetamide (100 mg, 0.197 mmol, Example 77) and K$_2$CO$_3$ (57 mg, 0.413 mmol) in DMF (2 mL) was added MeI (134 μL, 2.16 mmol) and the mixture was stirred at r.t. for 5 days. The reaction mixture was quenched with 33% aq NH$_4$OH solution (1 mL) and stirred for 30 min. The solution was diluted with H$_2$O (30 mL), extracted with EtOAc (2×30 mL), and the combined organic extracts were dried over Na$_2$SO$_4$, and concentrated in vacuo. Purification by prep. HPLC (Method 5) afforded the title compound (36 mg, 0.0725 mmol, 37% yield) as a white powder; $^1$H NMR (400 MHz, DMSO-d$_6$) δ 8.05 (d, J=8.0 Hz, 1H), 7.49 (t, J=8.9 Hz, 1H), 7.07 (dd, J=11.4, 2.8 Hz, 1H), 6.89-6.81 (m, 1H), 4.72-4.63 (m, 2H), 4.53 (s, 2H), 4.49-4.42 (m, 2H), 3.91-3.80 (m, 1H), 3.29-3.20 (m, 1H), 2.96-2.88 (m, 1H), 2.12-1.95 (m, 4H), 1.92-1.80 (m, 2H), 1.78-1.67 (m, 1H), 1.49-1.35 (m, 1H); M/Z: 497, 499 [M+H]$^+$, ESI$^+$, RT=2.75 (S4).

Scheme for route 51

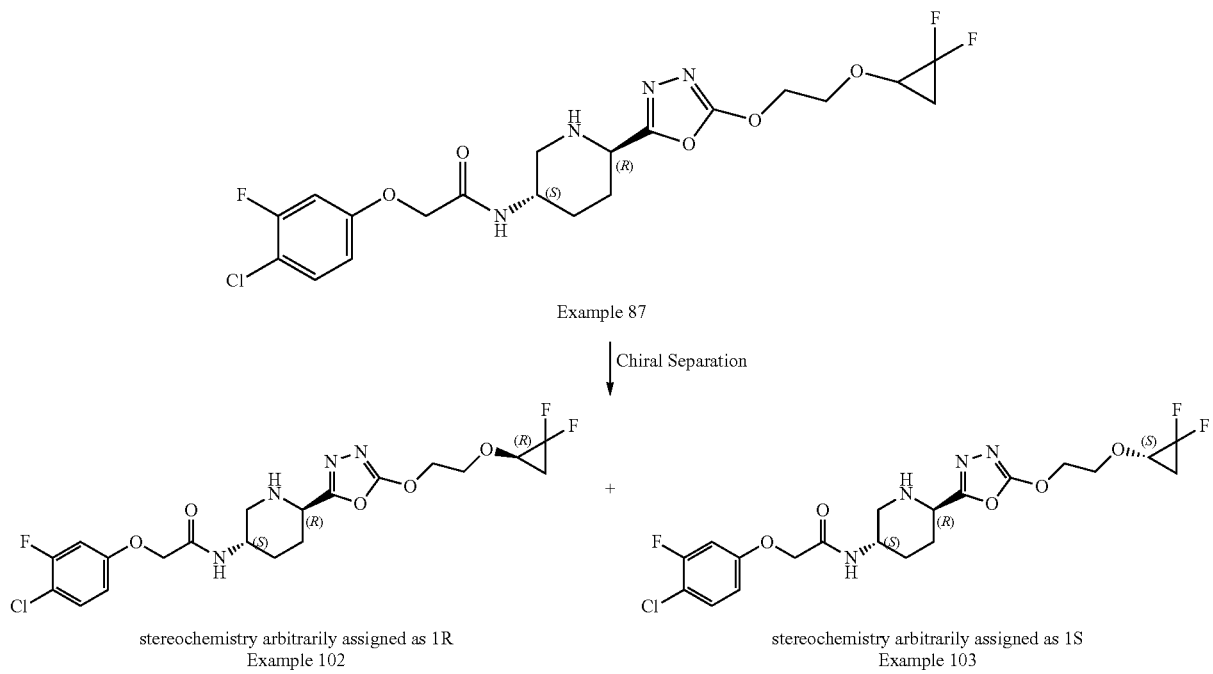

Example 102 and 103 Chiral separation of 2-(4-chloro-3-fluorophenoxy)-N-[(3S,6R)-6-{5-[2-(2,2-difluorocyclopropoxy)ethoxy]-1,3,4-oxadiazol-2-yl}piperidin-3-yl]acetamide (Example 87)

2-(4-chloro-3-fluorophenoxy)-N-[(3S,6R)-6-{5-[2-(2,2-difluorocyclopropoxy)ethoxy]-1,3,4-oxadiazol-2-yl}piperidin-3-yl]acetamide (48 mg, 0.0978 mmol, Example 87) was subjected to chiral purification using Method C4, affording 2-(4-chloro-3-fluorophenoxy)-N-[(3S,6R)-6-(5-{2-[(1R)-2,2-difluorocyclopropoxy]ethoxy}-1,3,4-oxadiazol-2-yl)piperidin-3-yl]acetamide (98% chiral purity, 13.3 mg, 0.0268 mmol, 27% yield) and 2-(4-chloro-3-fluorophenoxy)-N-[(3S,6R)-6-(5-{2-[(1S)-2,2-difluorocyclopropoxy]ethoxy}-1,3,4-oxadiazol-2-yl)piperidin-3-yl]acetamide (10% chiral purity, 12.4 mg, 0.025 mmol), 26% yield) as white powders. The stereochemistry of each compound was arbitrarily assigned.

Example compounds in Table 22 were chirally purified according to the general route 51 as exemplified by Example 102 and 103, using the corresponding intermediates and methods.

TABLE 22

| Ex | Structure | Name | Intermediate and Method | LCMS data | $^1$H NMR |
|---|---|---|---|---|---|
| 102 | stereochemistry arbitrarily assigned as 1R | 2-(4-chloro-3-fluorophenoxy)-N-[(3S,6R)-6-(5-{2-[(1R)-2,2-difluorocyclopropoxy]ethoxy}-1,3,4-oxadiazol-2-yl)piperidin-3-yl]acetamide (stereochemistry arbitrarily assigned as 1R) | 2-(4-chloro-3-fluorophenoxy)-N-[(3S,6R)-6-{5-[2-(2,2-difluorocyclopropoxy)ethoxy]-1,3,4-oxadiazol-2-yl}piperidin-3-yl]acetamide (Example 87) (Method C4) | M/Z: 491, 493 [M + H]$^+$, ESI$^+$, RT = 2.13 (S4) | $^1$H NMR (500 MHz, DMSO-d$_6$) δ 7.96 (d, J = 8.1 Hz, 1H), 7.49 (t, J = 8.9 Hz, 1H), 7.10-7.02 (m, 1H), 6.88-6.81 (m, 1H), 4.57 (t, J = 4.3 Hz, 2H), 4.52 (s, 2H), 4.01-3.85 (m, 3H), 3.78-3.64 (m, 2H), 3.00-2.93 (m, 1H), 2.81-2.74 (m, 1H), 2.46-2.38 (m, 1H), 2.00-1.84 (m, 2H), 1.76-1.59 (m, 2H), 1.59-1.43 (m, 2H). |

TABLE 22-continued

| Ex | Structure | Name | Intermediate and Method | LCMS data | ¹H NMR |
|---|---|---|---|---|---|
| 103 | 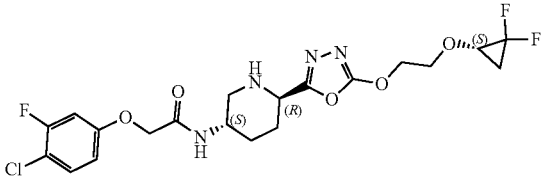<br>stereochemistry arbitrarily assigned as 1S | 2-(4-chloro-3-fluorophenoxy)-N-[(3S,6R)-6-(5-{2-[(1S)-2,2-difluorocyclopropoxy]ethoxy}-1,3,4-oxadiazol-2-yl)piperidin-3-yl]acetamide (stereochemistry arbitrarily assigned as 1S) | 2-(4-chloro-3-fluorophenoxy)-N-[(3S,6R)-6-{5-[2-(2,2-difluorocyclopropoxy)ethoxy]-1,3,4-oxadiazol-2-yl}piperidin-3-yl]acetamide (Example 87) (Method C4) | M/Z: 491, 493 [M + H]⁺, ESI⁺, RT = 2.13 (S4) | ¹H NMR (500 MHz, DMSO-d₆) δ 7.96 (d, J = 8.1 Hz, 1H), 7.49 (t, J = 8.9 Hz, 1H), 7.10-7.03 (m, 1H), 6.88-6.80 (m, 1H), 4.57 (t, J = 4.4 Hz, 2H), 4.52 (s, 2H), 4.01-3.85 (m, 3H), 3.79-3.64 (m, 2H), 3.01-2.92 (m, 1H), 2.82-2.74 (m, 1H), 2.47-2.38 (m, 1H), 1.99-1.83 (m, 2H), 1.77-1.58 (m, 2H), 1.61-1.43 (m, 2H). |
| 104 | 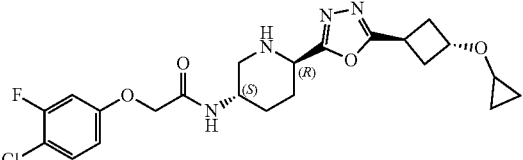<br>stereochemistry arbitrarily assigned as 1r and 3r | 2-(4-chloro-3-fluorophenoxy)-N-[(3S,6R)-6-{5-[(1r,3r)-3-cyclopropoxycyclobutyl]-1,3,4-oxadiazol-2-yl}piperidin-3-yl]acetamide (stereochemistry arbitrarily assigned as 1r and 3r) | 2-(4-chloro-3-fluorophenoxy)-N-[(3S,6R)-6-[5-(3-cyclopropoxycyclobutyl)-1,3,4-oxadiazol-2-yl]piperidin-3-yl]acetamide (Example 59) (Method C3) |  | ¹H NMR (500 MHz, methanol-d₄) δ 7.32-7.25 (m, 1H), 6.85 (dd, J = 11.0, 2.8 Hz, 1H), 6.74 (ddd, J = 8.9, 2.8, 1.2 Hz, 1H), 4.44 (s, 2H), 4.35-4.26 (m, 1H), 3.92-3.82 (m, 2H), 3.61-3.52 (m, 1H), 3.19-3.17 (m, 1H), 3.14-3.08 (m, 1H), 2.59-2.48 (m, 3H), 2.47-2.36 (m, 2H), 2.11-2.04 (m, 1H), 2.03-1.96 (m, 1H), 1.81-1.72 (m, 1H), 1.60-1.51 (m, 1H), 0.46-0.39 (m, 2H), 0.39-0.32 (m, 2H). |
| 105 | 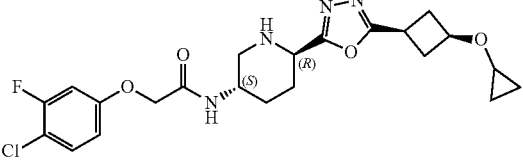<br>stereochemistry arbitrarily assigned as 1s and 3s | 2-(4-chloro-3-fluorophenoxy)-N-[(3S,6R)-6-{5-[(1s,3s)-3-cyclopropoxycyclobutyl]-1,3,4-oxadiazol-2-yl}piperidin-3-yl]acetamide (stereochemistry arbitrarily assigned as 1s and 3s) | 2-(4-chloro-3-fluorophenoxy)-N-[(3S,6R)-6-[5-(3-cyclopropoxycyclobutyl)-1,3,4-oxadiazol-2-yl]piperidin-3-yl]acetamide (Example 59) (Method C3) | M/Z: 465, 467 [M + H]⁺, ESI⁺, RT = 2.08 (S4). | ¹H NMR (500 MHz, methanol-d₄) δ 7.32-7.25 (m, 1H), 6.85 (dd, J = 11.0, 2.8 Hz, 1H), 6.74 (ddd, J = 8.9, 2.8, 1.2 Hz, 1H), 4.43 (s, 2H), 4.13-4.04 (m, 1H), 3.91-3.81 (m, 2H), 3.28-3.22 (m, 2H), 3.13-3.08 (m, 1H), 2.69-2.61 (m, 2H), 2.56-2.48 (m, 1H), 2.26-2.18 (m, 2H), 2.10-2.03 (m, 1H), 2.02-1.95 (m, 1H), 1.80-1.70 (m, 1H), 1.59-1.50 (m, 1H), 0.46-0.39 (m, 2H), 0.39-0.33 (m, 2H). |
| 106 | 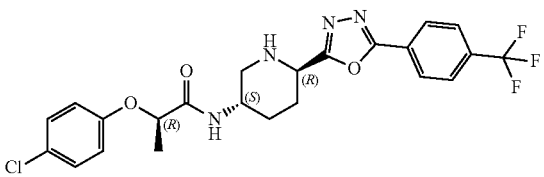<br>stereochemistry arbitrarily assigned as 2R | (2R)-2-(4-chlorophenoxy)-N-[(3S,6R)-6-{5-[4-(trifluoromethyl)phenyl]-1,3,4-oxadiazol-2-yl}piperidin-3-yl]propanamide (stereochemistry arbitrarily assigned as 2R) | 2-(4-chlorophenoxy)-N-[(3S,6R)-6-{5-[4-(trifluoromethyl)phenyl]-1,3,4-oxadiazol-2-yl}piperidin-3-yl]propanamide (Example 4) (Method C5) | M/Z: 495, 497 [M + H]⁺, ESI⁺, RT = 2.49 (S4) | ¹H NMR (500 MHz, DMSO-d₆) δ 8.26-8.16 (m, 2H), 8.04-7.93 (m, 3H), 7.37-7.29 (m, 2H), 6.97-6.88 (m, 2H), 4.69 (q, J = 6.6 Hz, 1H), 4.03-3.95 (m, 1H), 3.73-3.64 (m, 1H), 2.98-2.92 (m, 1H), 2.44-2.37 (m, 1H), 2.14-2.06 (m, 1H), 1.96-1.89 (m, 1H), 1.81-1.72 (m, 1H), 1.60-1.50 (m, 1H), 1.43 (d, J = 6.6 Hz, 3H). |

TABLE 22-continued

| Ex | Structure | Name | Intermediate and Method | LCMS data | ¹H NMR |
|---|---|---|---|---|---|
| 107 | 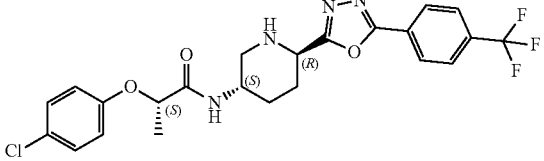 stereochemistry arbitrarily assigned as 2S | (2R)-2-(4-chlorophenoxy)-N-[(3S,6R)-6-{5-[4-(trifluoromethyl)phenyl]-1,3,4-oxadiazol-2-yl}piperidin-3-yl]propanamide (stereochemistry arbitrarily assigned as 2S) | 2-(4-chlorophenoxy)-N-[(3S,6R)-6-{5-[4-(trifluoromethyl)phenyl]-1,3,4-oxadiazol-2-yl}piperidin-3-yl]propanamide (Example 4) (Method C5) | M/Z: 495, 497 [M + H]⁺, ESI⁺, RT = 2.51 (S4) | ¹H NMR (500 MHz, DMSO-d₆) δ 8.25-8.18 (m, 2H), 8.04-7.94 (m, 3H), 7.37-7.29 (m, 2H), 6.96-6.89 (m, 2H), 4.68 (q, J = 6.6 Hz, 1H), 4.02-3.96 (m, 1H), 3.72-3.63 (m, 1H), 3.03-2.92 (m, 2H), 2.08-2.01 (m, 1H), 1.89-1.81 (m, 1H), 1.80-1.70 (m, 1H), 1.53-1.45 (m, 1H), 1.43 (d, J = 6.6 Hz, 3H). |
| 108 | 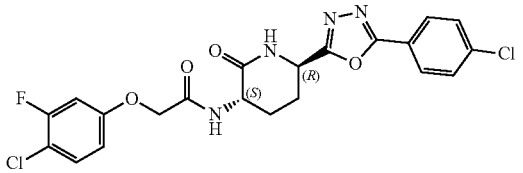 stereochemistry arbitrarily assigned as 3S and 6R | 2-(4-chloro-3-fluorophenoxy)-N-[(3S,6R)-6-[5-(4-chlorophenyl)-1,3,4-oxadiazol-2-yl]-2-oxopiperidin-3-yl]acetamide (stereochemistry arbitrarily assigned as 3S and 6R) | Rac-2-(4-chloro-3-fluorophenoxy)-N-[6-[5-(4-chlorophenyl)-1,3,4-oxadiazol-2-yl]-2-oxopiperidin-3-yl]acetamide (Example 37) (Method C6) | M/Z: 479.2 [M + H]⁺, ESI⁺, RT = 3.18 (S4) | ¹H NMR (500 MHz, DMSO-d₆) δ 8.42 (d, J = 8.2 Hz, 1H), 8.27 (s, 1H), 8.08-8.03 (m, 2H), 7.72-7.67 (m, 2H), 7.51 (t, J = 8.9 Hz, 1H), 7.11 (dd, J = 11.4, 2.8 Hz, 1H), 6.89 (ddd, J = 9.0, 2.8, 1.1 Hz, 1H), 4.97 (dd, J = 9.5, 4.6 Hz, 1H), 4.63-4.55 (m, 2H), 4.37 (ddd, J = 11.0, 8.2, 6.1 Hz, 1H), 2.33-2.27 (m, 1H), 2.19-2.10 (m, 1H), 2.09-2.04 (m, 1H), 2.00-1.92 (m, 1H). |
| 109 | 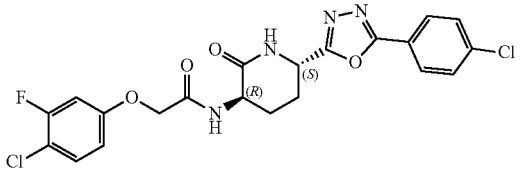 stereochemistry arbitrarily assigned as 3R and 6S | 2-(4-chloro-3-fluorophenoxy)-N-[(3R,6S)-6-[5-(4-chlorophenyl)-1,3,4-oxadiazol-2-yl]-2-oxopiperidin-3-yl]acetamide (stereochemistry arbitrarily assigned as 3R and 6S) | Rac-2-(4-chloro-3-fluorophenoxy)-N-[6-[5-(4-chlorophenyl)-1,3,4-oxadiazol-2-yl]-2-oxopiperidin-3-yl]acetamide (Example 37) (Method C6) | M/Z: 479.2 [M + H]⁺, ESI⁺, RT = 3.18 (S4) | ¹H NMR (500 MHz, DMSO-d₆) δ 8.42 (d, J = 8.2 Hz, 1H), 8.27 (s, 1H), 8.10-8.01 (m, 2H), 7.72-7.67 (m, 2H), 7.51 (t, J = 8.9 Hz, 1H), 7.11 (dd, J = 11.4, 2.8 Hz, 1H), 6.89 (ddd, J = 9.0, 2.8, 1.1 Hz, 1H), 4.97 (dd, J = 9.5, 4.6 Hz, 1H), 4.64-4.53 (m, 2H), 4.37 (ddd, J = 11.1, 8.1, 6.1 Hz, 1H), 2.33-2.27 (m, 1H), 2.19-2.10 (m, 1H), 2.09-2.03 (m, 1H), 1.96 (qd, J = 12.6, 3.4 Hz, 1H). |
| 110 | 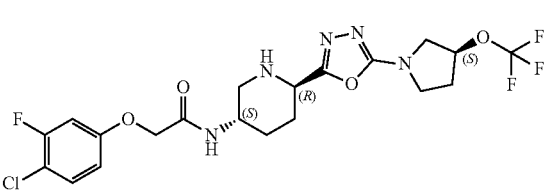 stereochemistry arbitrarily assigned as 3S | 2-(4-chloro-3-fluorophenoxy)-N-[(3S,6R)-6-{5-[(3S)-3-(trifluoromethoxy)pyrrolidin-1-yl]-1,3,4-oxadiazol-2-yl}piperidin-3-yl]acetamide (stereochemistry arbitrarily assigned as 3S) | 2-(4-chloro-3-fluorophenoxy)-N-[(3S,6R)-6-{5-[3-(trifluoromethoxy)pyrrolidin-1-yl]-1,3,4-oxadiazol-2-yl}piperidin-3-yl]acetamide (Example 96) (Method C7) | M/Z: 508, 510 [M + H]⁺, ESI⁺, RT = 2.07 (S4) | ¹H NMR (400 MHz, chloroform-d) δ 7.33 (t, J = 8.6 Hz, 1H), 6.78 (dd, J = 10.3, 2.8 Hz, 1H), 6.72-6.62 (m, 2H), 5.01-4.94 (m, 1H), 4.46 (s, 2H), 4.05 (dp, J = 11.8, 4.0, 3.4 Hz, 1H), 3.97 (dd, J = 8.3, 3.3 Hz, 1H), 3.85-3.63 (m, 4H), 3.33 (dd, J = 11.9, 3.4 Hz, 1H), 2.60 (dd, J = 12.0, 8.1 Hz, 1H), 2.42-2.31 (m, 1H), 2.30-2.19 (m, 1H), 2.14-2.02 (m, 2H), 2.00-1.86 (m, 2H), 1.61-1.52 (m, 1H). |
| 111 | 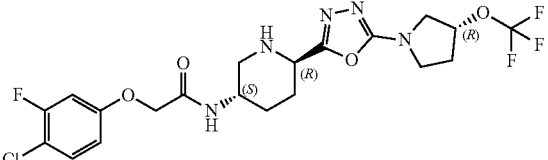 stereochemistry arbitrarily assigned as 3R | 2-(4-chloro-3-fluorophenoxy)-N-[(3S,6R)-6-{5-[(3R)-3-(trifluoromethoxy)pyrrolidin-1-yl]-1,3,4-oxadiazol-2-yl}piperidin- | 2-(4-chloro-3-fluorophenoxy)-N-[(3S,6R)-6-{5-[3-(trifluoromethoxy)pyrrolidin-1-yl]-1,3,4-oxadiazol-2-yl}piperidin- | M/Z: 508, 510 [M + H]⁺, ESI⁺, RT = 2.07 (S4) | ¹H NMR (400 MHz, chloroform-d) δ 7.33 (t, J = 8.6 Hz, 1H), 6.78 (dd, J = 10.3, 2.9 Hz, 1H), 6.73-6.60 (m, 2H), 5.02-4.94 (m, 1H), 4.46 (s, 2H), 4.10-3.93 (m, 2H), 3.81-3.66 (m, 4H), 3.33 (dd, J = 11.9, 3.5 Hz, 1H), 2.60 (dd, J = 11.9, |

TABLE 22-continued

| Ex | Structure | Name | Intermediate and Method | LCMS data | ¹H NMR |
|---|---|---|---|---|---|
| | | 3-yl]acetamide (stereochemistry arbitrarily assigned as 3R) | 3-yl]acetamide (Example 96) (Method C7) | | 8.1 Hz, 1H), 2.41-2.32 (m, 1H), 2.30-2.19 (m, 1H), 2.15-1.87 (m, 4H), 1.58-1.52 (m, 1H). |

II Assays

HEK-ATF4 High Content Imaging Assay

Example compounds were tested in the HEK-ATF4 High Content Imaging assay to assess their pharmacological potency to prevent Tunicamycin induced ISR. Wild-type HEK293 cells were plated in 384-well imaging assay plates at a density of 12,000 cells per well in growth medium (containing DMEM/F12, 10% FBS, 2 mM L-Glutamine, 100 U/mL Penicillin-100 µg/mL Streptomycin) and incubated at 37° C., 5% $CO_2$. 24 h later, the medium was changed to 50 µL assay medium per well (DMEM/F12, 0.3% FBS, 2 mM L-Glutamine, 100 U/mL Penicillin-100 µg/mL Streptomycin). Example compounds were serially diluted in DMSO, spotted into intermediate plates and prediluted with assay medium containing 3.3 µM Tunicamycin to give an 11-fold excess of final assay concentration. In addition to the example compound testing area, the plates also contained multiples of control wells for assay normalization purposes, wells containing Tunicamycin but no example compounds (High control), as well as wells containing neither example compound nor Tunicamycin (Low control). The assay was started by transferring 5 µL from the intermediate plate into the assay plates, followed by incubation for 6 h at 37° C., 5% $CO_2$. Subsequently, cells were fixed (4% PFA in PBS, 20 min at r.t.) and submitted to indirect ATF4 immunofluorescence staining (primary antibody rabbit anti ATF4, clone D4B8, Cell Signaling Technologies; secondary antibody Alexa Fluor 488 goat anti-rabbit IgG (H+L), Thermofisher Scientific). Nuclei were stained using Hoechst dye (Thermofisher Scientific), and plates were imaged on an Opera Phenix High Content imaging platform equipped with 405 nm and 488 nm excitation. Finally, images were analyzed using script based algorithms. The main readout HEK-ATF4 monitored the ATF4 signal ratio between nucleus and cytoplasm. Tunicamycin induced an increase in the overall ATF4 ratio signal, which was prevented by ISR modulating example compounds. In addition, HEK-CellCount readout was derived from counting the number of stained nuclei corresponding to healthy cells. This readout served as an internal toxicity control. The example compounds herein did not produce significant reduction in CellCount.

HEK ATF4 Activity of the tested example compounds is provided in Table 23 as follows: +++=$IC_{50}$ 1-500 nM; ++=$IC_{50}$>500-2000 nM; +=IC50>2000-15000 nM.

TABLE 23

| Example number | HEK-ATF4 Activity |
|---|---|
| 2 | +++ |
| 7 | +++ |
| 9 | +++ |
| 10 | +++ |
| 11 | +++ |
| 12 | +++ |
| 13 | +++ |

TABLE 23-continued

| Example number | HEK-ATF4 Activity |
|---|---|
| 14 | ++ |
| 15 | +++ |
| 17 | + |
| 18 | ++ |
| 19 | ++ |
| 20 | +++ |
| 21 | ++ |
| 22 | ++ |
| 23 | +++ |
| 24 | ++ |
| 25 | +++ |
| 26 | + |
| 27 | +++ |
| 28 | + |
| 29 | ++ |
| 31 | + |
| 33 | +++ |
| 34 | ++ |
| 35 | +++ |
| 36 | ++ |
| 37 | +++ |
| 38 | + |
| 39 | + |
| 40 | +++ |
| 42 | +++ |
| 43 | +++ |
| 44 | +++ |
| 45 | +++ |
| 46 | +++ |
| 47 | +++ |
| 48 | ++ |
| 50 | +++ |
| 51 | ++ |
| 52 | +++ |
| 53 | +++ |
| 54 | +++ |
| 55 | +++ |
| 57 | ++ |
| 59 | ++ |
| 60 | +++ |
| 61 | + |
| 63 | ++ |
| 64 | + |
| 65 | ++ |
| 66 | ++ |
| 67 | +++ |
| 68 | + |
| 69 | +++ |
| 70 | +++ |
| 71 | ++ |
| 72 | + |
| 73 | ++ |
| 74 | +++ |
| 75 | +++ |
| 76 | ++ |
| 77 | +++ |
| 78 | +++ |
| 79 | + |
| 80 | +++ |
| 81 | ++ |
| 82 | +++ |
| 83 | +++ |
| 84 | +++ |
| 85 | +++ |
| 86 | +++ |

TABLE 23-continued

| Example number | HEK-ATF4 Activity |
| --- | --- |
| 87 | +++ |
| 88 | ++ |
| 90 | ++ |
| 91 | +++ |
| 92 | ++ |
| 93 | ++ |
| 94 | + |
| 95 | +++ |
| 98 | +++ |
| 100 | +++ |
| 101 | +++ |
| 102 | ++ |
| 103 | +++ |
| 105 | ++ |
| 106 | + |
| 107 | + |
| 108 | + |
| 109 | +++ |
| 110 | +++ |
| 111 | +++ |
| 112 | +++ |
| 113 | +++ |

Protocol—Thermodynamic (Equilibrium) Solubility in Selected Buffer

Example compounds were tested in the Thermodynamic (Equilibrium) solubility in selected buffer assay. The test compound, in powder form, was weighted into a 4 mL glass vial and a calculated volume of selected medium was added to reach the target concentration of the solubility test (1 mg/mL). The solution was then stirred overnight at r.t. protected from the light. The solution was filtered through a 0.45 μm PTFE membrane at ambient temperature. An aliquot of the resulting filtrate was quantified using UPLC-UV method described below against a reference solution of the test compound, 0.8 mg/mL in DMSO. Media compositions: Phosphate buffer 50 mM (pH=2.0) 690 mg of $NaH_2PO_4$, $H_2O$ in 200 mL of ultrapurified water adjusted at pH 2 with phosphoric acid 85%; Acetate buffer 50 mM (pH=5.5) 820 mg of anhydrous sodium acetate in 200 mL of ultrapurified water adjusted at pH 5.5 with acetic acid 99.8%; Phosphate buffer 50 mM (pH=7.4) 40.5 mL of $Na_2HPO_4$ 0.1 M solution+9.5 mL of $NaH_2PO_4$ 0.1 M solution. Analytical conditions: UPLC-UV-MS analyses were performed with a Waters Acquity UPLC HClass-PDA-QDa system using a reverse phase Acquity BEH C18 column (2.1 mm×50 mm, 1.7 μm; temperature: 40° C.) and a gradient of 10-95% B (A=0.1% formic acid in $H_2O$; B=0.05% formic acid in ACN) over 1.8 min then 100% B for 0.8 min, with an injection volume of 0.4 μL at flow rate of 0.65 mL/min. UV chromatograms were recorded at 220 nm, 254 nm and 290 nm using a photo diode array detector. Mass spectra were recorded in the 150 to 900 M/Z range at a sampling rate of 10 scans per sec using a QDa detector. Data were integrated using Empower®3 software. Data Analysis: Equilibrium solubility of the test compound in the selected medium was calculated through the ratio of the surface area of the UV chromatographic peak of the compound in the filtrate to the surface of the UV chromatographic peak of the compound in the reference solution.

Protocol—Measure of the Effect on hERG Channel by Tail Current Recording Using In Vitro Rapid ICE The potency of the example compounds in inhibiting human ERG potassium channel (hERG) tail current was assessed in a recombinant HEK293 cell line stably transfected with hERG cDNA under an inducible promoter, using Rapid ICE (rapid ion channel electrophysiology) assay. Rapid ICE is an automated patch-clamp assay utilizing the QPatch HTX system (Sophion Bioscience A/S). Briefly, inducible HEK hERG cells were cultivated in minimum essential medium supplemented with 10% FBS, 1% non-essential amino acids, 1% sodium pyruvate, 2 mM 1-glutamine, 15 μg/mL blasticidin, and 100 μg/mL hygromycin. hERG channel expression induction was obtained by adding 10 μg/mL tetracycline for 24, 48, or 72 h before recordings.

On the day of the experiment, cells were detached with TrypLE and prepared to be loaded on the instrument. Cells were resuspended in 7 mL of Serum-Free Media containing 25 mM Hepes and soybean trypsin inhibitor and immediately placed in the cell storage tank of the machine. The composition of the extracellular buffer was (mM): NaCl 137, KCl 4, $CaCl_2$ 1.8, $MgCl_2$ 1.0, d-glucose 10, N-2-hydroxyethylpiperazine-N'-2-ethanesulfonic acid (HEPES) 10, pH 7.4 with 1 M NaOH. The composition of the intracellular solution was (mM): KCl 130, $MgCl_2$ 1.0, ethylene glycol-bis(β-aminoethyl ether)-N,N,N',N'-tetraacetic acid (EGTA) 5, MgATP 5, HEPES 10, pH 7.2 with 1 M KOH. The voltage protocol included the following steps: step from −80 to −50 mV for 200 ms, +20 mV for 4.8 s, step to −50 mV for 5 s, then step to the holding potential of −80 mV. Compounds were dissolved in DMSO and diluted in extracellular buffer to achieve final test concentrations (0.3, 3, and 30 μM) in 0.3% DMSO. The voltage protocol was run and recorded continuously during the experiment. The vehicle, corresponding to 0.3% DMSO in extracellular buffer was then applied for 3 min, followed by the test substance in triplicate. The standard combined exposure time was 5 min. The average of tail current amplitude values recorded from four sequential voltage pulses was used to calculate for each cell the effect of the test substance by calculating the residual current (% control) compared with vehicle pretreatment. Data were reported as % inhibition for each concentration tested, and $IC_{50}$ values were estimated using QPatch software. At least two cells were tested, and even more if results diverged.

Protocol—Log D 7.4 Assay

Phosphate buffer (1 M) was diluted to 20 mM with deionised water and adjusted to pH 7.4 (±0.05) with phosphoric acid or sodium hydroxide. A 1:1 mixture of phosphate buffer (20 mM) and 1-octanol were saturated by tumbling overnight after which time the two phases were separated. Using an automated liquid handler the following procedure was carried out: 20 mM DMSO stocks of assay and control compounds were reformatted to provide cassettes of 4 compounds per well giving a final concentration of 5 mM per compound. In duplicate 5 μL of the cassetted compounds were added to 495 μL 1-octanol (saturated with buffer) followed by 495 μL of buffer (saturated with 1-octanol) in a 96-well plate giving final incubation concentrations of 25 μM (50 μM max concentration in either layer if all compound partitioned into a single matrix). The layers were mixed by aspirating and dispensing the buffer and octanol layers into one another three times. The plate was sealed, shaken for 120 minutes and then centrifuged at 25° C. for 15 min at 4600 rpm. The 1-octanol and buffer layer were sampled separately (ensuring no cross contamination) and the respective samples diluted with 60:40 ACN:0.1 M ammonium acetate pH 7.4 (containing external standard; Sulfisoxazole, assay concentration 120 nM) to obtain final theoretical maximum concentrations of the 1-octanol layer of 0.025 μM, 0.5 μM and a buffer layer concentration of 0.5 μM. The second buffer sample was prepared by diluting the assay buffer layer with acetonitrile (containing external standard; Sulfisoxazole, assay concentration 120 nM) to give a theoretical maximum concentration of 20 μM. The analytical samples were analysed by LC-MS/MS and the Log D calculated as shown:

$$\text{Log}D \text{ (pH 7.4)} = \text{Log}\left(\frac{PA_{analyte\ in\ octanol}/PA_{ES}}{PA_{analyte\ in\ buffer}/PA_{ES}}\right)$$

Where PA=Peak area and ES=External standard

Biological Example: Lipophilicity and Solubility

In recent years there have been numerous reports in the medicinal chemistry literature associating the clinical success of drug candidates with their physicochemical properties. The degree of lipophilicity, in particular, has been highlighted as an important factor in defining the overall properties and likely fate of drug candidates (29), and typically it is beneficial if the log D lies in the range of 1 to 3. With reference to Table 24 selected compounds of the present invention have log D values lying within this range and represent an improvement over previously reported and similar analogues in this respect.

Similarly poor solubility of drug candidates has been associated with increased risk of drug development failures (30). Also with reference to Table 24 the selected compounds of the present invention show a higher aqueous solubility compared to structurally similar compounds of the state of the art. Additional solubility data relating to further example compounds are shown in Table 25 below.

TABLE 24

| Example number | Structure | Solubility (μg/mL) | | | Log D | HEK-ATF4 Activity* | hERG Activity** |
|---|---|---|---|---|---|---|---|
| | | pH 7.4 | pH 5 | pH 2 | | | |
| WO2019046779 Ex 1 | 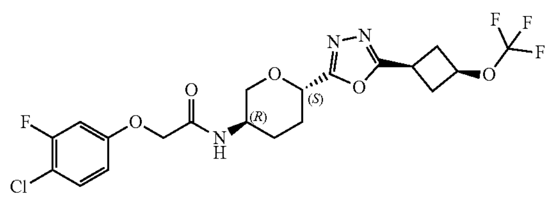 | <1 | <1 | <1 | 3.6 | +++ | ++ |
| 50 | 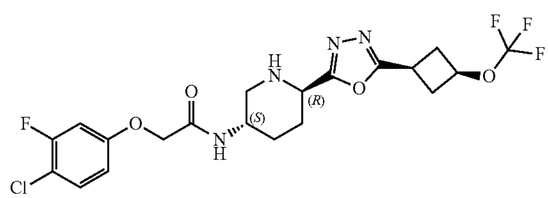 | 63 | 78 | quant.# | 2.7 | +++ | ++ |
| WO2019046779 Ex 30 | 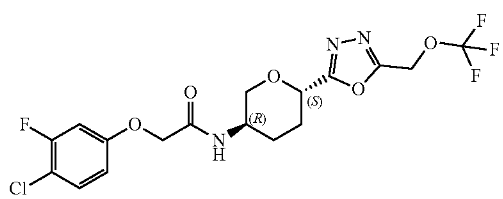 | 3 | 3 | 3 | 2.9 | ++ | +++ |
| 61 | 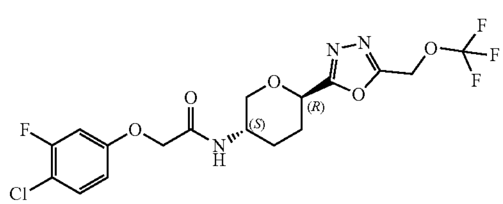 | 90 | 156 | 907 | 2.3 | ++ | ++ |

*ATF4 Activity category: +++ = $IC_{50}$ 1-500 nM; ++ = $IC_{50}$ >500-2000 nM; + = $IC_{50}$ >2000 nM.

**hERG Activity category: +++ = $IC_{50}$ 1-1000 nM; ++ = $IC_{50}$ >1000-5000 nM; + = $IC_{50}$ >5000 nM completely dissolved in assay

TABLE 25

| Example number | Solubility (μg/mL) | | |
|---|---|---|---|
| | pH 2.0 | pH 5.5 | pH 7.4 |
| 5 | quant.# | 215 | 278 |
| 11 | 617 | 60 | 42 |
| 12 | 651 | 113 | 105 |
| 13 | 661 | 318 | 240 |
| 14 | 616 | 814 | 606 |
| 34 | 994 | 239 | 153 |
| 50 | quant.# | 78 | 63 |
| 51 | 945 | 4 | 2 |
| 52 | 839 | 9 | 7 |
| 57 | quant.# | 663 | 501 |
| 60 | 886 | 47 | 91 |
| 61 | 907 | 156 | 90 |
| 68 | 909 | 168 | 102 |
| 75 | 713 | 26 | 22 |
| 77 | 810 | 98 | 76 |
| 84 | 717 | 93 | 62 |
| 85 | 918 | 9 | 6 |
| 90 | quant.# | 294 | 173 |
| 95 | 970 | 378 | 230 |
| 98 | quant.# | 61 | 17 |
| 110 | 982 | 256 | 132 |
| 111 | 911 | 9 | 6 |
| 112 | 812 | 97 | 67 | completely dissolved in assay

Biological Example: hERG Selectivity

Drug-induced QT interval prolongation and the appearance of torsade de pointes (TdP) is well recognised as a clinical risk. Whilst these effects are often multifactorial there is a clear consensus in recognising the role that interactions of drugs with the cardiac hERG $K^+$ channel play in the manifestation of these clinical side-effects. In general it is widely accepted that minimising the interactions of drug molecules with the hERG $K^+$ channel is desirable (31). To this end we have sought to balance the improvements in physicochemical properties mentioned above (i.e. log D and solubility—Tables 24 & 25) with selective modulation of ATF4 relative to the hERG $K^+$ channel.

TABLE 26

| Example number | hERG Activity* |
|---|---|
| 2 | +++ |
| 4 | +++ |
| 7 | +++ |
| 9 | ++ |
| 10 | ++ |
| 11 | + |
| 12 | + |
| 13 | + |
| 14 | + |
| 15 | + |
| 29 | + |
| 31 | +++ |
| 33 | ++ |
| 35 | +++ |
| 38 | + |
| 40 | +++ |
| 42 | ++ |
| 43 | + |
| 44 | +++ |
| 45 | +++ |
| 46 | +++ |
| 47 | +++ |
| 50 | + |
| 52 | +++ |
| 53 | ++ |
| 54 | +++ |
| 55 | + |
| 57 | + |
| 59 | + |
| 60 | +++ |
| 61 | ++ |
| 64 | + |
| 65 | ++ |
| 66 | ++ |
| 67 | ++ |
| 68 | ++ |
| 69 | +++ |
| 70 | ++ |
| 71 | ++ |
| 72 | ++ |
| 75 | ++ |
| 76 | + |
| 77 | ++ |
| 78 | ++ |
| 79 | + |
| 80 | + |
| 81 | + |
| 82 | + |
| 83 | + |
| 84 | ++ |
| 85 | ++ |
| 86 | ++ |
| 87 | ++ |
| 88 | ++ |
| 90 | + |
| 91 | ++ |
| 92 | ++ |
| 93 | + |
| 94 | + |
| 95 | ++ |
| 98 | ++ |
| 100 | ++ |
| 101 | + |
| 102 | ++ |
| 103 | + |
| 105 | + |
| 106 | ++ |
| 108 | +++ |
| 109 | +++ |
| 110 | + |
| 111 | ++ |
| 112 | + |
| 113 | ++ |

*hERG Activity category: +++ = $IC_{50}$ 1-1000 nM; ++ = $IC_{50}$ >1000-5000 nM; + = $IC_{50}$ >5000 nM With reference to Tables 23, 25 and 26 selected compounds of the present invention display an advantageous balance of properties, especially regarding HEK ATF4 Activity and/or solubility and/or selected hERG inhibition.

REFERENCES (1) Pakos-Zebrucka K, Koryga I, Mnich K, Ljujic M, Samali A, Gorman A M. The integrated stress response. EMBO Rep. 2016 October; 17(10):1374-1395. Epub 2016 Sep. 14.
(2) Wek R C, Jiang H Y, Anthony T G. Coping with stress: eIF2 kinases and translational control. Biochem Soc Trans. 2006 February; 34 (Pt 1):7-11.
(3) Donnelly N, Gorman A M, Gupta S, Samali A. The eIF2alpha kinases: their structures and functions. Cell Mol Life Sci. 2013 October; 70(19):3493-511
(4) Jackson R J, Hellen C U, Pestova T V. The mechanism of eukaryotic translation initiation and principles of its regulation. Nat Rev Mol Cell Biol. 2010 February; 11(2): 113-27

(5) Lomakin I B, Steitz T A. The initiation of mammalian protein synthesis and mRNA scanning mechanism. Nature. 2013 Aug. 15; 500(7462):307-11
(6) Pain V M. Initiation of protein synthesis in eukaryotic cells. Eur J Biochem. 1996 Mar. 15; 236(3):747-71
(7) Pavitt G D. Regulation of translation initiation factor eIF2B at the hub of the integrated stress response. Wiley Interdiscip Rev RNA. 2018 November; 9(6):e1491.
(8) Krishnamoorthy T, Pavitt G D, Zhang F, Dever T E, Hinnebusch A G. Tight binding of the phosphorylated alpha subunit of initiation factor 2 (eIF2alpha) to the regulatory subunits of guanine nucleotide exchange factor eIF2B is required for inhibition of translation initiation. Mol Cell Biol. 2001 August; 21(15):5018-30.
(9) Hinnebusch, A. G., Ivanov, I. P., & Sonenberg, N. (2016). Translational control by 5'-untranslated regions of eukaryotic mRNAs. Science, 352(6292), 1413-1416.
(10) Young, S. K., & Wek, R. C. (2016). Upstream open reading frames differentially regulate gene-specific translation in the integrated stress response. The Journal of Biological Chemistry, 291(33), 16927-16935.
(11) Lin J H, Li H, Zhang Y, Ron D, Walter P (2009) Divergent effects of PERK and IRE1 signaling on cell viability. PLoS ONE 4: e4170
(12) Tabas I, Ron D. Nat Cell Biol. 2011 March; 13(3):184-90. Integrating the mechanisms of apoptosis induced by endoplasmic reticulum stress.
(13) Shore G C, Papa F R, Oakes S A. Curr Opin Cell Biol. 2011 April; 23(2):143-9. Signaling cell death from the endoplasmic reticulum stress response.
(14) Bi M, Naczki C, Koritzinsky M, Fels D, Blais J, Hu N, Harding H, Novoa I, Varia M, Raleigh J, Scheuner D, Kaufman R J, Bell J, Ron D, Wouters B G, Koumenis C. EMBO J. 2005 Oct. 5; 24(19):3470-81 ER stress-regulated translation increases tolerance to extreme hypoxia and promotes tumor growth.
(15) Bobrovnikova-Marjon E, Grigoriadou C, Pytel D, Zhang F, Ye J, Koumenis C, Cavener D, Diehl J A. Oncogene. 2010 Jul. 8; 29(27):3881-95 PERK promotes cancer cell proliferation and tumor growth by limiting oxidative DNA damage.
(16) Avivar-Valderas A, Salas E, Bobrovnikova-Marjon E, Diehl J A, Nagi C, Debnath J, Aguirre-Ghiso J A. Mol Cell Biol. 2011 September; 31(17):3616-29. PERK integrates autophagy and oxidative stress responses to promote survival during extracellular matrix detachment.
(17) Blais, J. D.; Addison, C. L.; Edge, R.; Falls, T.; Zhao, H.; Kishore, W.; Koumenis, C.; Harding, H. P.; Ron, D.; Holcik, M.; Bell, J. C. Mol. Cell. Biol. 2006, 26, 9517-9532.PERK-dependent translational regulation promotes tumor cell adaptation and angiogenesis in response to hypoxic stress.
(18) Taalab Y M, Ibrahim N, Maher A, Hassan M, Mohamed W, Moustafa A A, Salama M, Johar D, Bernstein L. Rev Neurosci. 2018 Jun. 27; 29(4):387-415. Mechanisms of disordered neurodegenerative function: concepts and facts about the different roles of the protein kinase RNA-like endoplasmic reticulum kinase (PERK).
(19) Remondelli P, Renna M. Front Mol Neurosci. 2017 Jun. 16; 10:187. The Endoplasmic Reticulum Unfolded Protein Response in Neurodegenerative Disorders and Its Potential Therapeutic Significance.
(20) Halliday M, Mallucci G R. Neuropathol Appl Neurobiol. 2015 June; 41(4):414-27.Review: Modulating the unfolded protein response to prevent neurodegeneration and enhance memory.
(21) Halliday M, Radford H, Sekine Y, Moreno J, Verity N, le Quesne J, Ortori C A, Barrett D A, Fromont C, Fischer P M, Harding H P, Ron D, Mallucci G R. Cell Death Dis. 2015 Mar. 5; 6:e1672.Partial restoration of protein synthesis rates by the small molecule ISRIB prevents neurodegeneration without pancreatic toxicity.
(22) Moreno J A, Radford H, Peretti D, Steinert J R, Verity N, Martin M G, Halliday M, Morgan J, Dinsdale D, Ortori C A, Barrett D A, Tsaytler P, Bertolotti A, Willis A E, Bushell M, Mallucci G R. Nature 2012; 485: 507-11. Sustained translational repression by eIF2alpha-P mediates prion neurodegeneration.
(23) Skopkova M, Hennig F, Shin B S, Turner C E, Stanikova D, Brennerova K, Stanik J, Fischer U, Henden L, Müller U, Steinberger D, Leshinsky-Silver E, Bottani A, Kurdiova T, Ukropec J, Nyitrayova O, Kolnikova M, Klimes I, Borck G, Bahlo M, Haas S A, Kim J R, Lotspeich-Cole L E, Gasperikova D, Dever T E, Kalscheuer V M. Hum Mutat. 2017 April; 38(4):409-425. EIF2S3 Mutations Associated with Severe X-Linked Intellectual Disability Syndrome MEHMO.
(24) Hamilton E M C, van der Lei H D W, Vermeulen G, Gerver J A M, Lourenço C M, Naidu S, Mierzewska H, Gemke RJBJ, de Vet H C W, Uitdehaag B M J, Lissenberg-Witte B I; VWM Research Group, van der Knaap M S. Ann Neurol. 2018 August; 84(2):274-288. Natural History of Vanishing White Matter.
(25) Bugiani M, Vuong C, Breur M, van der Knaap M S. Brain Pathol. 2018 May; 28(3):408-421. Vanishing white matter: a leukodystrophy due to astrocytic dysfunction.
(26) Wong Y L, LeBon L, Edalji R, Lim H B, Sun C, Sidrauski C. Elife. 2018 Feb. 28; 7. The small molecule ISRIB rescues the stability and activity of Vanishing White Matter Disease eIF2B mutant complexes.
(27) Wong Y L, LeBon L, Basso A M, Kohlhaas K L, Nikkel A L, Robb H M, Donnelly-Roberts D L, Prakash J, Swensen A M, Rubinstein N D, Krishnan S, McAllister F E, Haste N V, O'Brien J J, Roy M, Ireland A, Frost J M, Shi L, Riedmaier S, Martin K, Dart M J, Sidrauski C. Elife. 2019 Jan. 9; 8. eIF2B activator prevents neurological defects caused by a chronic integrated stress response.
(28) Nguyen H G, Conn C S, Kye Y, Xue L, Forester C M, Cowan J E, Hsieh A C, Cunningham J T, Truillet C, Tameire F, Evans M J, Evans C P, Yang J C, Hann B, Koumenis C, Walter P, Carroll P R, Ruggero D. Sci Transl Med. 2018 May 2; 10(439). Development of a stress response therapy targeting aggressive prostate cancer.
(29) Waring M, Expert Opinion on Drug Discovery Volume 5, 2010—Issue 3, 235-248. Lipophilicity in Drug Discovery.
(30) Alelyunas Y W, et. al. Bioorg. Med. Chem. Lett., 20(24) 2010, 7312-7316. Experimental solubility profiling of marketed CNS drugs, exploring solubility limit of CNS discovery candidate.
(31) Redfern W S, et. al., Cardiovascular Research 58(2003), 32-45. Relationships between preclinical cardiac electrophysiology, clinical QT interval prolongation and torsade de pointes for a broad range of drugs.

The invention claimed is:
1. A compound of formula (I)

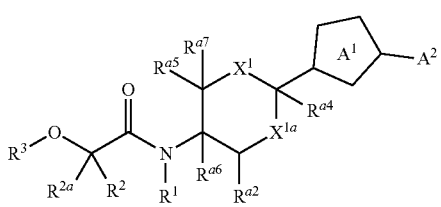

or a pharmaceutically acceptable salt, solvate, hydrate, tautomer or stereoisomer thereof, wherein $X^1$ is $N(R^{a1})$;

$X^{1a}$ is a covalent single bond or $CH(R^{a3})$;

$R^{a1}$ is H, $C(O)OC_{1-4}$ alkyl, or $C_{1-4}$ alkyl, wherein $C(O)OC_{1-4}$ alkyl and $C_{1-4}$ alkyl are optionally substituted with one or more substituents selected from the group consisting of halogen, OH, and O—$C_{1-3}$ alkyl, wherein the substituents are the same or different;

$R^{a2}$ and $R^{a3}$ are independently selected from the group consisting of H, OH, $OC_{1-4}$ alkyl, halogen, $C_{1-4}$ alkyl, and $A^{2a}$; and $R^{a4}$, $R^{a5}$, $R^{a6}$, and $R^{a7}$ are independently selected from the group consisting of H, halogen, $C_{1-4}$ alkyl, and $A^{2a}$, provided that only one of $R^{a2}$, $R^{a3}$, $R^{a4}$, $R^{a5}$, $R^{a6}$, and $R^{a7}$ is $A^{2a}$;

or $R^{a1}$ and one of $R^{a2}$ and $R^{a3}$ form a methylene or ethylene group;

or $R^{a1}$ and $R^{a6}$ form an ethylene group;

or $R^{a2}$ and $R^{a5}$ form a covalent single bond;

or $R^{a5}$, $R^{a7}$ are joined to form an oxo group;

$A^1$ is $C_5$ cycloalkylene, $C_5$ cycloalkenylene, or a nitrogen ring atom containing 5-membered heterocyclene, wherein $A^1$ is optionally substituted with one or more $R^4$, which are the same or different;

each $R^4$ is independently oxo (=O) where the ring is at least partially saturated, thiooxo (=S) where the ring is at least partially saturated, halogen, CN, $OR^5$, or $C_{1-6}$ alkyl, wherein $C_{1-6}$ alkyl is optionally substituted with one or more halogen, which are the same or different;

$R^5$ is H or $C_{1-6}$ alkyl, wherein $C_{1-6}$ alkyl is optionally substituted with one or more halogen, which are the same or different;

$A^2$ is $R^{6a}$ or $A^{2a}$;

$R^{6a}$ is $OR^{6a1}$, $SR^{6a1}$, $N(R^{6a1}R^{6a2})$, $C_{1-6}$ alkyl, $C_{2-6}$ alkenyl or $C_{2-6}$ alkynyl, wherein $C_{1-6}$ alkyl, $C_{2-6}$ alkenyl, and $C_{2-6}$ alkynyl are optionally substituted with one or more substituents selected from the group consisting of halogen, $OR^{6a3}$, CN, and $A^{2a}$, wherein the substituents are the same or different;

$R^{6a1}$ and $R^{6a2}$ are independently selected from the group consisting of H, $C_{1-6}$ alkyl, $C_{2-6}$ alkenyl, $C_{2-6}$ alkynyl, and $A^{2a}$, wherein $C_{1-6}$ alkyl, $C_{2-6}$ alkenyl, and $C_{2-6}$ alkynyl are optionally substituted with one or more substituents selected from the group consisting of halogen, CN, $OR^{6a3}$, $OA^{2a}$ and $A^{2a}$, wherein the substituents are the same or different;

$R^{6a3}$ is H, or $C_{1-4}$ alkyl, wherein $C_{1-4}$ alkyl is optionally substituted with one or more halogen, which are the same or different;

$A^{2a}$ is phenyl, $C_{3-7}$ cycloalkyl, $C_{4-12}$ bicycloalkyl, or 3- to 7-membered heterocyclyl, wherein $A^{2a}$ is optionally substituted with one or more $R^6$, which are the same or different;

each $R^6$ is independently $R^{6b}$, OH, $OR^{6b}$, halogen, or CN, wherein $R^{6b}$ is cyclopropyl, $C_{1-6}$ alkyl, $C_{2-6}$ alkenyl, or $C_{2-6}$ alkynyl, wherein $R^{6b}$ is optionally substituted with one or more halogen, which are the same or different; or two $R^6$ are joined to form together with the atoms to which they are attached a ring $A^{2b}$;

$A^{2b}$ is phenyl, $C_{3-7}$ cycloalkyl; or 3 to 7 membered heterocyclyl, wherein $A^{2b}$ is optionally substituted with one or more $R^7$, which are the same or different;

each $R^7$ is independently $C_{1-6}$ alkyl, $C_{2-6}$ alkenyl or $C_{2-6}$ alkynyl, wherein $C_{1-6}$ alkyl, $C_{2-6}$ alkenyl, and $C_{2-6}$ alkynyl are optionally substituted with one or more halogen, which are the same or different;

$R^1$ is H or $C_{1-4}$ alkyl, preferably H, wherein $C_{1-4}$ alkyl is optionally substituted with one or more halogen, which are the same or different;

$R^2$ is H, F, or $C_{1-4}$ alkyl, wherein $C_{1-4}$ alkyl is optionally substituted with one or more halogen, which are the same or different; and $R^3$ is $A^3$, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more $R^8$, which are the same or different; or $R^2$ and $R^3$ are joined to form together with the oxygen atom and carbon atom to which they are attached a ring $A^3a$, wherein $A^3a$ is a 7 to 12 membered heterobicyclyl, wherein 7 to 12 membered heterobicyclyl is optionally substituted with one or more $R^{10}$, which are the same or different;

$R^{2a}$ is H or F;

each $R^8$ is independently halogen; CN, $C(O)OR^9$, $OR^9$, $C(O)R^9$, $C(O)N(R^9R^{9a})$ $S(O)_2N(R^9R^{9a})$, $S(O)N(R^9R^{9a})$, $S(O)_2R^9$, $S(O)R^9$, $N(R^9)S(O)_2N(R^{9a}R^{9b})$, $SR^9$, $N(R^9R^{9a})$, $NO_2$, $OC(O)R^9$, $N(R^9)C(O)R^{9a}$, $N(R^9)SO_2R^{9a}$, $N(R^9)S(O)R^{9a}$, $N(R^9)C(O)N(R^{9a}R^{9b})$, $N(R^9)C(O)OR^{9a}$, $OC(O)N(R^9R^{9a})$, or $A^3$;

$R^9$, $R^{9a}$, and $R^{9b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different, or one OH, or one $OC_{1-4}$ alkyl, or one $A^3$;

each $A^3$ is independently phenyl, naphthyl, $C_{3-7}$ cycloalkyl, 3 to 7 membered heterocyclyl, or 7 to 12 membered heterobicyclyl, wherein $A^3$ is optionally substituted with one or more $R^{10}$, which are the same or different;

each $R^{10}$ is independently halogen, CN, $C(O)OR^{11}$, $OR^{11}$, $C(O)R^{11}$, $C(O)N(R^{11}R^{11a})$ $S(O)_2N(R^{11}R^{11a})$, $S(O)N(R^{11}R^{11a})$, $S(O)_2R^{11}$, $S(O)R^{11}$, $N(R^{11})S(O)_2N(R^{11a}R^{11b})$, $SR^{11}$, $N(R^{11}R^{11a})$, $NO_2$, $OC(O)R^{11}$, $N(R^{11})C(O)R^{11a}$, $N(R^{11})S(O)_2R^{11a}$, $N(R^{11})S(O)R^{11a}$, $N(R^{11})C(O)OR^{11a}$, $N(R^{11})C(O)N(R^{11a}R^{11b})$ $OC(O)N(R^{11}R^{11a})$, oxo (=O) where the ring is at least partially saturated, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more $R^{12}$, which are the same or different;

$R^{11}$, $R^{11a}$, and $R^{11b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different;

each $R^{12}$ is independently halogen, CN, $C(O)OR^{13}$, $OR^{13}$, $C(O)R^{13}$, $C(O)N(R^{13}R^{13a})$, $S(O)_2N(R^{13}R^{13a})$, $S(O)N(R^{13}R^{13a})$, $S(O)_2R^{13}$, $S(O)R^{13}$, $N(R^{13})S(O)_2N$ ($R^{13a}R^{13b}$), $SR^{13}$, $N(R^{13}R^{13a})$, $NO_2$, $OC(O)R^{13}$, $N(R^{13})C(O)R^{13a}$, $N(R^{13})SO_2R^{13a}$, $N(R^{13})S(O)R^{13a}$, $N(R^{13})C(O)N(R^{13a}R^{13b})$, $N(R^{13})C(O)OR^{13a}$, or $OC(O)N(R^{13}R^{13a})$;

$R^{13}$, $R^{13a}$, and $R^{13b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different, provided that the following compounds or a pharmaceutically acceptable salt, solvate, hydrate, tautomer, or stereoisomer thereof are excluded:

CAS 1396491-78-3

CAS 1212733-42-0

CAS 1212728-70-5

CAS 1212723-70-0

CAS 1212688-74-8

CAS 1212685-85-2

CAS 1212683-11-8

CAS 1212664-04-4

CAS 1212658-99-5

CAS 1212634-69-9

-continued

CAS 1212633-89-0
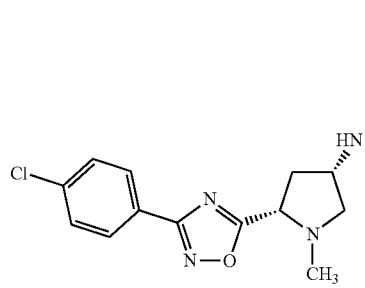

CAS 1212628-07-3
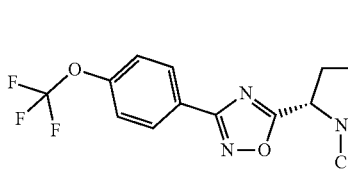

CAS 1212619-73-2
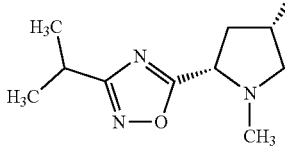

CAS 1212618-04-6
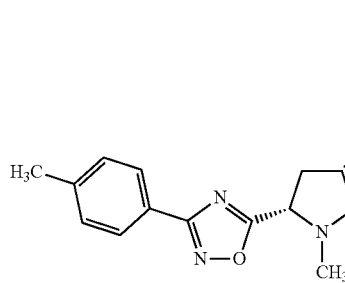

CAS 1212567-76-4
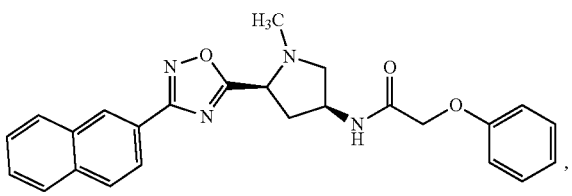

-continued

CAS 1212561-17-5
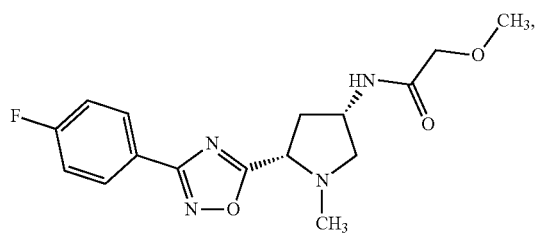

CAS 1212554-50-1
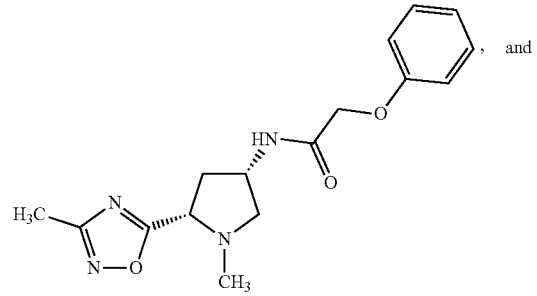

, and

CAS 1212507-42-0
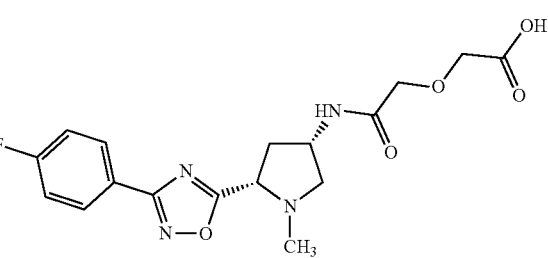

2. The compound of claim 1 or a pharmaceutically acceptable salt, solvate, hydrate, tautomer or stereoisomer thereof, wherein $X^1$ is NH or N—$C_{1-4}$ alkyl, wherein $C_{1-4}$ alkyl is optionally substituted with one or more substituents selected from the group consisting of halogen, OH, and O—$C_{1-3}$ alkyl, wherein the substituents are the same or different.

3. The compound of claim 1 or a pharmaceutically acceptable salt, solvate, hydrate, tautomer or stereoisomer thereof, wherein $X^{1a}$ is $CH(R^{a3})$.

4. The compound of claim 1 or a pharmaceutically acceptable salt, solvate, hydrate, tautomer or stereoisomer thereof, wherein
$R^{a2}$ and $R^{a3}$ are independently selected from the group consisting of H, OH, $OC_{1-4}$ alkyl, halogen, $C_{1-4}$ alkyl, and $A^{2a}$; and
$R^{a4}$, $R^{a5}$, $R^{a6}$, and $R^{a7}$ are independently selected from the group consisting of H, halogen, $C_{1-4}$ alkyl, and $A^{2a}$, provided that only one of $R^{a2}$, $R^{a3}$, $R^{a4}$, $R^{a5}$, $R^{a6}$, and $R^{a7}$ is $A^{2a}$;
or $R^{a5}$ and $R^{a7}$ are joined to form an oxo group.

5. The compound of claim 1 or a pharmaceutically acceptable salt, solvate, hydrate, tautomer or stereoisomer thereof, wherein $R^{a2}$, $R^{a3}$, $R^{a4}$, $R^{a5}$, $R^{a6}$, and $R^{a7}$ are H.

6. The compound of claim 1 or a pharmaceutically acceptable salt, solvate, hydrate, tautomer or stereoisomer thereof, wherein $A^1$ is a nitrogen ring atom containing 5-membered heterocyclene and wherein $A^1$ is optionally substituted with one or more $R^4$, which are the same or different.

7. The compound of claim 1 or a pharmaceutically acceptable salt, solvate, hydrate, tautomer or stereoisomer thereof, wherein $A^1$ is a nitrogen ring atom containing 5-membered heterocyclene selected from the group of bivalent heterocycles consisting of oxadiazole, imidazole, imidazolidine, pyrazole and triazole, and wherein $A^1$ is optionally substituted with one or more $R^4$, which are the same or different.

8. The compound of claim 1 or a pharmaceutically acceptable salt, solvate, hydrate, tautomer or stereoisomer thereof, wherein A1 is unsubstituted or substituted with one or two $R^4$, which are the same or different, preferably $A^1$ is unsubstituted.

9. The compound of claim 1 or a pharmaceutically acceptable salt, solvate, hydrate, tautomer or stereoisomer thereof, wherein $R^4$ is oxo, where the ring is at least partly saturated.

10. The compound of claim 1 or a pharmaceutically acceptable salt, solvate, hydrate, tautomer or stereoisomer thereof, wherein $A^1$ is

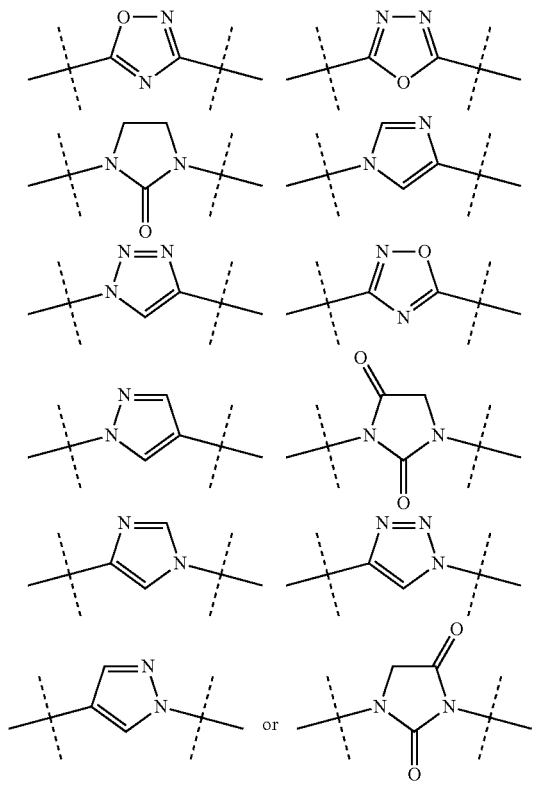

11. The compound of claim 1 or a pharmaceutically acceptable salt, solvate, hydrate, tautomer or stereoisomer thereof, wherein $A^2$ is $R^{6a}$.

12. The compound of claim 11 or a pharmaceutically acceptable salt, solvate, hydrate, tautomer or stereoisomer thereof, wherein $R^{6a}$ is $OR^{6a1}$ and $R^{6a1}$ is $A^{2a}$ or $C_{1-6}$ alkyl, optionally substituted with one or more halogen and/or one $A^{2a}$ and/or one $OR^{6a3}$; or $R^{6a}$ is $C_{1-6}$ alkyl, optionally substituted with one or more halogen and/or one Aa and/or one $OR^{6a3}$.

13. The compound of claim 1 or a pharmaceutically acceptable salt, solvate, hydrate, tautomer or stereoisomer thereof, wherein $R^{6a1}$ and $R^{6a2}$ are independently selected from the group consisting of H, $C_{1-6}$ alkyl, $C_{2-6}$ alkenyl, $C_{2-6}$ alkynyl, and $A^{2a}$, wherein $C_{1-6}$ alkyl, $C_{2-6}$ alkenyl, and $C_{2-6}$ alkynyl are optionally substituted with one or more substituents selected from the group consisting of halogen; CN, $OR^{6a3}$, and $A^{2a}$, wherein the substituents are the same or different.

14. The compound of claim 11 or a pharmaceutically acceptable salt, solvate, hydrate, tautomer or stereoisomer thereof, wherein $R^{6a}$ is $C_{1-6}$ alkyl, optionally substituted with one or more halogen and/or one $OR^{6a3}$ or $R^{6a}$ is $OR^{6a1}$ and $R^{6a1}$ is preferably $C_{1-6}$ alkyl, optionally substituted with one or more F and/or one $OR^{6a3}$.

15. The compound of claim 1 or a pharmaceutically acceptable salt, solvate, hydrate, tautomer or stereoisomer thereof, wherein $A^2$ is $A^{2a}$.

16. The compound of claim 1 or a pharmaceutically acceptable salt, solvate, hydrate, tautomer or stereoisomer thereof, wherein $A^{2a}$ is phenyl, cyclobutyl, azetidinyl, pyrrolidinyl, or 5- to 6-membered aromatic heterocyclyl, and wherein $A^{2a}$ is optionally substituted with one or more $R^6$, which are the same or different.

17. The compound of claim 1 or a pharmaceutically acceptable salt, solvate, hydrate, tautomer or stereoisomer thereof, wherein $A^{2a}$ is substituted with one or two $R^6$, which are the same or different.

18. The compound of claim 1 or a pharmaceutically acceptable salt, solvate, hydrate, tautomer or stereoisomer thereof, wherein each $R^6$ is independently F, Cl, $CF_3$, $OCH_3$, $OCHF_2$, $OCF_3$, $CH_3$, $CH_2CH_3$, $CH_2CF_3$, O-cyclopropyl, or cyclopropyl.

19. The compound of claim 1 or a pharmaceutically acceptable salt, solvate, hydrate, tautomer or stereoisomer thereof, wherein $R^2$ is $CH_3$, F, or H.

20. The compound of claim 1 or a pharmaceutically acceptable salt, solvate, hydrate, tautomer or stereoisomer thereof, wherein $R^3$ is $A^3$.

21. The compound of claim 1 or a pharmaceutically acceptable salt, solvate, hydrate, tautomer or stereoisomer thereof, wherein $A^3$ is phenyl, pyridyl, pyrazinyl, pyrimidazyl, cyclopropyl, cyclobutyl or cyclohexyl, and wherein $A^3$ is optionally substituted with one or more $R^{10}$, which are the same or different.

22. The compound of claim 1 or a pharmaceutically acceptable salt, solvate, hydrate, tautomer or stereoisomer thereof, wherein $A^3$ is substituted with one, two, or three $R^{10}$, which are the same or different.

23. The compound of claim 1 or a pharmaceutically acceptable salt, solvate, hydrate, tautomer or stereoisomer thereof, wherein $R^2$ and $R^3$ are joined together with the oxygen and carbon atom to which they are attached to form a dihydrobenzopyran ring, wherein the ring is optionally substituted with one or more $R^{10}$, which are the same or different.

24. The compound of claim 1 or a pharmaceutically acceptable salt, solvate, hydrate, tautomer or stereoisomer thereof, wherein $R^{10}$ is independently F, Cl, Br, CN, $CHF_2$, $CF_3$, $OCH_3$, $OCF_3$, CH=O, $CH_2OH$ or $CH_3$.

25. The compound of claim 1 or a pharmaceutically acceptable salt, solvate, hydrate, tautomer or stereoisomer thereof, wherein $R^{a1}$ is H, or $C_{1-4}$ alkyl, wherein $C_{1-4}$ alkyl is optionally substituted with one or more substituents selected from the group consisting of halogen, OH, and O—$C_{1-3}$ alkyl, wherein the substituents are the same or different.

26. The compound of claim 1 or a pharmaceutically acceptable salt, solvate, hydrate, tautomer or stereoisomer thereof for use as a medicament, wherein the compound is tert-butyl (2R,5S)-5-[2-(4-chloro-3-fluorophenoxy)acetamido]-2-{5-[4-(trifluoromethyl)phenyl]-1,3,4-oxadiazol-2-yl}piperidine-1-carboxylate;

2-(4-chloro-3-fluorophenoxy)-N-[(3S,6R)-6-{5-[4-(trifluoromethyl)phenyl]-1,3,4-oxadiazol-2-yl}piperidin-3-yl]acetamide;

tert-butyl (2R,5S)-5-[2-(4-chlorophenoxy)propanamido]-2-{5-[4-(trifluoromethyl)phenyl]-1,3,4-oxadiazol-2-yl}piperidine-1-carboxylate;

2-(4-chlorophenoxy)-N-[(3S,6R)-6-{5-[4-(trifluoromethyl)phenyl]-1,3,4-oxadiazol-2-yl}piperidin-3-yl]propenamide;

N-[(3R,6S)-6-[5-(4-chlorophenyl)-1,3,4-oxadiazol-2-yl]piperidin-3-yl]-2-[(1s,3s)-3-(trifluoromethoxy)cyclobutoxy]acetamide;

tert-butyl (2R,5S)-5-{2-[(6-chloro-5-fluoropyridin-3-yl)oxy]acetamido}-2-[5-(4-chlorophenyl)-1,3,4-oxadiazol-2-yl]piperidine-1-carboxylate;

2-[(6-chloro-5-fluoropyridin-3-yl)oxy]-N-[(3S,6R)-6-[5-(4-chlorophenyl)-1,3,4-oxadiazol-2-yl]piperidin-3-yl]acetamide;

tert-butyl (2R,5S)-5-[2-(3,4-dichlorophenoxy)acetamido]-2-{5-[(1s,3s)-3-(trifluoromethoxy)cyclobutyl]-1,3,4-oxadiazol-2-yl}piperidine-1-carboxylate;

2-(3,4-dichlorophenoxy)-N-[(3S,6R)-6-{5-[(1s,3s)-3-(trifluoromethoxy)cyclobutyl]-1,3,4-oxadiazol-2-yl}piperidin-3-yl]acetamide;

2-[3-chloro-4-(trifluoromethyl)phenoxy]-N-[(3S,6R)-6-{5-[(1s,3s)-3-(trifluoromethoxy)cyclobutyl]-1,3,4-oxadiazol-2-yl}piperidin-3-yl]acetamide;

2-[4-chloro-3-(difluoromethyl)phenoxy]-N-[(3S,6R)-6-{5-[2-(trifluoromethoxy)ethoxy]-1,3,4-oxadiazol-2-yl}piperidin-3-yl]acetamide;

2-(4-chloro-3-methylphenoxy)-N-[(3S,6R)-6-{5-[2-(trifluoromethoxy)ethoxy]-1,3,4-oxadiazol-2-yl}piperidin-3-yl]acetamide;

2-(3,4-dimethylphenoxy)-N-[(3S,6R)-6-{5-[2-(trifluoromethoxy)ethoxy]-1,3,4-oxadiazol-2-yl}piperidin-3-yl]acetamide;

N-[(3S,6R)-6-{5-[2-(trifluoromethoxy)ethoxy]-1,3,4-oxadiazol-2-yl}piperidin-3-yl]-2-{[6-(trifluoromethyl)pyridin-3-yl]oxy}acetamide;

2-[3-methoxy-4-(trifluoromethyl)phenoxy]-N-[(3S,6R)-6-{5-[2-(trifluoromethoxy)ethoxy]-1,3,4-oxadiazol-2-yl}piperidin-3-yl]acetamide;

tert-butyl (2R,5S)-5-[2-(4-chloro-2-fluorophenoxy)acetamido]-2-[5-(3,3,3-trifluoropropoxy)-1,3,4-oxadiazol-2-yl]piperidine-1-carboxylate;

2-(4-chloro-2-fluorophenoxy)-N-[(3S,6R)-6-[5-(3,3,3-trifluoropropoxy)-1,3,4-oxadiazol-2-yl]piperidin-3-yl]acetamide;

2-(3-chloro-4-fluorophenoxy)-N-[(3S,6R)-6-[5-(3,3,3-trifluoropropoxy)-1,3,4-oxadiazol-2-yl]piperidin-3-yl]acetamide;

2-[4-(trifluoromethyl)phenoxy]-N-[(3S,6R)-6-[5-(3,3,3-trifluoropropoxy)-1,3,4-oxadiazol-2-yl]piperidin-3-yl]acetamide;

2-(3,4-dichlorophenoxy)-N-[(3S,6R)-6-[5-(3,3,3-trifluoropropoxy)-1,3,4-oxadiazol-2-yl]piperidin-3-yl]acetamide;

2-(4-chloro-2,3-difluorophenoxy)-N-[(3S,6R)-6-[5-(3,3,3-trifluoropropoxy)-1,3,4-oxadiazol-2-yl]piperidin-3-yl]acetamide;

2-(4-chloro-3,5-difluorophenoxy)-N-[(3S,6R)-6-[5-(3,3,3-trifluoropropoxy)-1,3,4-oxadiazol-2-yl]piperidin-3-yl]acetamide;

2-[3-fluoro-4-(trifluoromethyl)phenoxy]-N-[(3S,6R)-6-[5-(3,3,3-trifluoropropoxy)-1,3,4-oxadiazol-2-yl]piperidin-3-yl]acetamide;

2-(4-chloro-3-fluorophenoxy)-2,2-difluoro-N-[(3S,6R)-6-[5-(3,3,3-trifluoropropoxy)-1,3,4-oxadiazol-2-yl]piperidin-3-yl]acetamide;

2-[3-chloro-4-(trifluoromethyl)phenoxy]-N-[(3S,6R)-6-[5-(3,3,3-trifluoropropoxy)-1,3,4-oxadiazol-2-yl]piperidin-3-yl]acetamide;

2-(3,4,5-trichlorophenoxy)-N-[(3S,6R)-6-[5-(3,3,3-trifluoropropoxy)-1,3,4-oxadiazol-2-yl]piperidin-3-yl]acetamide;

2-(4-bromophenoxy)-N-[(3S,6R)-6-[5-(3,3,3-trifluoropropoxy)-1,3,4-oxadiazol-2-yl]piperidin-3-yl]acetamide;

2-[3-(trifluoromethyl)phenoxy]-N-[(3S,6R)-6-[5-(3,3,3-trifluoropropoxy)-1,3,4-oxadiazol-2-yl]piperidin-3-yl]acetamide;

2-(4-chloro-3-cyanophenoxy)-N-[(3S,6R)-6-{5-[2-(trifluoromethoxy)ethoxy]-1,3,4-oxadiazol-2-yl}piperidin-3-yl]acetamide;

tert-butyl (2R,4S)-4-[2-(4-chloro-3-fluorophenoxy)acetamido]-2-[5-(4-chlorophenyl)-1,3,4-oxadiazol-2-yl]pyrrolidine-1-carboxylate;

2-(4-chloro-3-fluorophenoxy)-N-[(3S,5R)-5-[5-(4-chlorophenyl)-1,3,4-oxadiazol-2-yl]pyrrolidin-3-yl]acetamide;

tert-butyl (2R,5S)-5-[2-(4-chloro-3-fluorophenoxy)acetamido]-2-[5-(3,3,3-trifluoropropoxy)-1,3,4-oxadiazol-2-yl]piperidine-1-carboxylate;

2-(4-chloro-3-fluorophenoxy)-N-[(3S,6R)-6-[5-(3,3,3-trifluoropropoxy)-1,3,4-oxadiazol-2-yl]piperidin-3-yl]acetamide;

2-(4-chloro-3-fluorophenoxy)-N-[(3S,6R)-6-[5-(6-methylpyridin-3-yl)-1,3,4-oxadiazol-2-yl]piperidin-3-yl]acetamide;

2-(4-chloro-3-fluorophenoxy)-N-[(3R,6S)-6-[5-(4-chlorophenyl)-1,3,4-oxadiazol-2-yl]piperidin-3-yl]acetamide;

2-(4-chloro-3-fluorophenoxy)-N-[(3R,6R)-6-[5-(4-chlorophenyl)-1,3,4-oxadiazol-2-yl]piperidin-3-yl]acetamide;

rac-2-(4-chloro-3-fluorophenoxy)-N-[(3R,6S)-6-[5-(4-chlorophenyl)-1,3,4-oxadiazol-2-yl]-2-oxopiperidin-3-yl]acetamide;

rac-2-(4-chloro-3-fluorophenoxy)-N-[(3R,6R)-2-oxo-6-{5-[(1s,3s)-3-(trifluoromethoxy)cyclobutyl]-1,3,4-oxadiazol-2-yl}piperidin-3-yl]acetamide;

tert-butyl (2R,5S)-5-[2-(4-chloro-3-fluorophenoxy)acetamido]-2-[5-(4-chlorophenyl)-1,3,4-oxadiazol-2-yl]piperidine-1-carboxylate;

2-(4-chloro-3-fluorophenoxy)-N-[(3S,6R)-6-[5-(4-chlorophenyl)-1,3,4-oxadiazol-2-yl]piperidin-3-yl]acetamide;

tert-butyl (2S,5R)-5-[2-(4-chloro-3-fluorophenoxy)acetamido]-2-[5-(3,3,3-trifluoropropoxy)-1,3,4-oxadiazol-2-yl]piperidine-1-carboxylate;

2-(4-chloro-3-fluorophenoxy)-N-[(3R,6S)-6-[5-(3,3,3-trifluoropropoxy)-1,3,4-oxadiazol-2-yl]piperidin-3-yl]acetamide;

2-(4-chloro-3-fluorophenoxy)-N-[(3R,6S)-6-{5-[3-(trifluoromethoxy)azetidin-1-yl]-1,3,4-oxadiazol-2-yl}piperidin-3-yl]acetamide;

2-(4-chloro-3-fluorophenoxy)-N-[(3R,6S)-6-[5-(4-chlorophenyl)-1,3,4-oxadiazol-2-yl]-1-methylpiperidin-3-yl]acetamide;

2-(4-chloro-3-fluorophenoxy)-N-[(3S,6R)-6-[5-(4-chlorophenyl)-1,3,4-oxadiazol-2-yl]-1-methylpiperidin-3-yl]acetamide;

2-(4-chloro-3-fluorophenoxy)-N-[(3S,6R)-6-[5-(4-chlorophenyl)-1,3,4-oxadiazol-2-yl]-1-ethylpiperidin-3-yl]acetamide;

2-(4-chloro-3-fluorophenoxy)-N-[(3R,6S)-6-[5-(4-chlorophenyl)-1,3,4-oxadiazol-2-yl]-1-ethylpiperidin-3-yl]acetamide;

2-(4-chloro-3-fluorophenoxy)-N-[(3R,6S)-6-[5-(4-chlorophenyl)-1,3,4-oxadiazol-2-yl]-1-(2-methoxyethyl)piperidin-3-yl]acetamide;

tert-butyl (2R,5S)-5-[2-(4-chloro-3-fluorophenoxy)acetamido]-2-{5-[(1s,3s)-3-(trifluoromethoxy)cyclobutyl]-1,3,4-oxadiazol-2-yl}piperidine-1-carboxylate;

2-(4-chloro-3-fluorophenoxy)-N-[(3S,6R)-6-{5-[(1s,3s)-3-(trifluoromethoxy)cyclobutyl]-1,3,4-oxadiazol-2-yl}piperidin-3-yl]acetamide;

N-[(3S,6R)-6-[5-(5-chloro-1-methyl-1H-pyrazol-3-yl)-1,3,4-oxadiazol-2-yl]piperidin-3-yl]-2-(4-chloro-3-fluorophenoxy)acetamide;

2-(4-chloro-3-fluorophenoxy)-N-[(3S,6R)-6-{5-[6-(trifluoromethyl)pyridin-3-yl]-1,3,4-oxadiazol-2-yl}piperidin-3-yl]acetamide;

2-(4-chloro-3-fluorophenoxy)-N-[(3S,6R)-6-[5-(5-chloropyridin-2-yl)-1,3,4-oxadiazol-2-yl]piperidin-3-yl]acetamide;

2-(4-chloro-3-fluorophenoxy)-N-[(3S,6R)-6-[5-(4-chloro-3-fluorophenyl)-1,3,4-oxadiazol-2-yl]piperidin-3-yl]acetamide;

2-(4-chloro-3-fluorophenoxy)-N-[(3S,6R)-6-{5-[3-(trifluoromethoxy)propyl]-1,3,4-oxadiazol-2-yl}piperidin-3-yl]acetamide;

tert-butyl (2R,5S)-5-[2-(4-chloro-3-fluorophenoxy)acetamido]-2-{5-[1-(2,2,2-trifluoroethyl)azetidin-3-yl]-1,3,4-oxadiazol-2-yl}piperidine-1-carboxylate;

2-(4-chloro-3-fluorophenoxy)-N-[(3S,6R)-6-{5-[1-(2,2,2-trifluoroethyl)azetidin-3-yl]-1,3,4-oxadiazol-2-yl}piperidin-3-yl]acetamide;

tert-butyl (2R,5S)-5-[2-(4-chloro-3-fluorophenoxy)acetamido]-2-[5-(3-cyclopropoxycyclobutyl)-1,3,4-oxadiazol-2-yl]piperidine-1-carboxylate;

2-(4-chloro-3-fluorophenoxy)-N-[(3S,6R)-6-[5-(3-cyclopropoxycyclobutyl)-1,3,4-oxadiazol-2-yl]piperidin-3-yl]acetamide;

2-(3,4-dichlorophenoxy)-N-[(3S,6R)-6-{5-[(1s,3s)-3-(difluoromethoxy)cyclobutyl]-1,3,4-oxadiazol-2-yl}piperidin-3-yl]acetamide;

2-(4-chloro-3-fluorophenoxy)-N-[(3S,6R)-6-{5-[(trifluoromethoxy)methyl]-1,3,4-oxadiazol-2-yl}piperidin-3-yl]acetamide;

tert-butyl (2R,5S)-5-[2-(4-chloro-3-fluorophenoxy)acetamido]-2-[5-(3,3,3-trifluoro-2-methylpropoxy)-1,3,4-oxadiazol-2-yl]piperidine-1-carboxylate;

2-(4-chloro-3-fluorophenoxy)-N-[(3S,6R)-6-[5-(3,3,3-trifluoro-2-methylpropoxy)-1,3,4-oxadiazol-2-yl]piperidin-3-yl]acetamide;

2-(4-chloro-3-fluorophenoxy)-N-[(3S,6R)-6-{5-[(4,4,4-trifluorobutan-2-yl)oxy]-1,3,4-oxadiazol-2-yl}piperidin-3-yl]acetamide;

2-(4-chloro-3-fluorophenoxy)-N-[(3S,6R)-6-[5-(3,3-difluorobutoxy)-1,3,4-oxadiazol-2-yl]piperidin-3-yl]acetamide;

2-(4-chloro-3-fluorophenoxy)-N-[(3S,6R)-6-{5-[(2,2-difluorocyclopropyl)methoxy]-1,3,4-oxadiazol-2-yl}piperidin-3-yl]acetamide;

N-[(3S,6R)-6-(5-butoxy-1,3,4-oxadiazol-2-yl)piperidin-3-yl]-2-(4-chloro-3-fluorophenoxy)acetamide;

2-(4-chloro-3-fluorophenoxy)-N-[(3S,6R)-6-{5-[(3,3-difluorocyclopentyl)oxy]-1,3,4-oxadiazol-2-yl}piperidin-3-yl]acetamide;

2-(4-chloro-3-fluorophenoxy)-N-[(3S,6R)-6-[5-(2-cyclopropylethoxy)-1,3,4-oxadiazol-2-yl]piperidin-3-yl]acetamide;

2-(4-chloro-3-fluorophenoxy)-N-[(3S,6R)-6-[5-(3-methylbutoxy)-1,3,4-oxadiazol-2-yl]piperidin-3-yl]acetamide;

2-(4-chloro-3-fluorophenoxy)-N-[(3S,6R)-6-{5-[(2,2-difluorocyclobutyl)methoxy]-1,3,4-oxadiazol-2-yl}piperidin-3-yl]acetamide;

2-(4-chloro-3-fluorophenoxy)-N-[(3S,6R)-6-[5-(3,3-difluorocyclobutoxy)-1,3,4-oxadiazol-2-yl]piperidin-3-yl]acetamide;

2-(4-chloro-3-fluorophenoxy)-N-[(3S,6R)-6-[5-(2,2,3,3,3-pentafluoropropoxy)-1,3,4-oxadiazol-2-yl]piperidin-3-yl]acetamide;

2-(4-chloro-3-fluorophenoxy)-N-[(3S,6R)-6-[5-(4,4,4-trifluorobutoxy)-1,3,4-oxadiazol-2-yl]piperidin-3-yl]acetamide;

2-(4-chloro-3-fluorophenoxy)-N-[(3S,6R)-6-{5-[2-(difluoromethoxy)ethoxy]-1,3,4-oxadiazol-2-yl}piperidin-3-yl]acetamide;

tert-butyl (2R,5S)-5-[2-(4-chloro-3-fluorophenoxy)acetamido]-2-{5-[2-(trifluoromethoxy)ethoxy]-1,3,4-oxadiazol-2-yl}piperidine-1-carboxylate;

2-(4-chloro-3-fluorophenoxy)-N-[(3S,6R)-6-{5-[2-(trifluoromethoxy)ethoxy]-1,3,4-oxadiazol-2-yl}piperidin-3-yl]acetamide;

2-(4-chloro-3-fluorophenoxy)-N-[(3S,6R)-6-[5-(pentyloxy)-1,3,4-oxadiazol-2-yl]piperidin-3-yl]acetamide;

2-(4-chloro-3-fluorophenoxy)-N-[(3S,6R)-6-[5-(3-methoxypropoxy)-1,3,4-oxadiazol-2-yl]piperidin-3-yl]acetamide;

2-(4-chloro-3-fluorophenoxy)-N-[(3S,6R)-6-[5-(2-cyclopropoxyethoxy)-1,3,4-oxadiazol-2-yl]piperidin-3-yl]acetamide;

2-(4-chloro-3-fluorophenoxy)-N-[(3S,6R)-6-[5-(2-ethoxyethoxy)-1,3,4-oxadiazol-2-yl]piperidin-3-yl]acetamide;

2-(4-chloro-3-fluorophenoxy)-N-[(3S,6R)-6-[5-(2-cyclobutoxyethoxy)-1,3,4-oxadiazol-2-yl]piperidin-3-yl]acetamide;

2-(4-chloro-3-fluorophenoxy)-N-[(3R,6S)-6-{5-[2-(trifluoromethoxy)ethoxy]-1,3,4-oxadiazol-2-yl}piperidin-3-yl]acetamide;

2-(4-chloro-3-fluorophenoxy)-N-[(3S,6R)-6-{5-[(4,4-difluoropentyl)oxy]-1,3,4-oxadiazol-2-yl}piperidin-3-yl]acetamide;

2-(3,4-dichlorophenoxy)-N-[(3S,6R)-6-{5-[2-(trifluoromethoxy)ethoxy]-1,3,4-oxadiazol-2-yl}piperidin-3-yl]acetamide;

N-[(3S,6R)-6-[5-(2-cyclopropoxyethoxy)-1,3,4-oxadiazol-2-yl]piperidin-3-yl]-2-(3,4-dichlorophenoxy)acetamide;

2-(4-chloro-3-fluorophenoxy)-N-[(3S,6R)-6-{5-[2-(2,2-difluorocyclopropoxy)ethoxy]-1,3,4-oxadiazol-2-yl}piperidin-3-yl]acetamide;

2-(4-chloro-3-fluorophenoxy)-N-[(3S,6R)-6-(5-{[2-(trifluoromethyl)cyclopropyl]methoxy}-1,3,4-oxadiazol-2-yl)piperidin-3-yl]acetamide;

tert-butyl (2R,5S)-5-[2-(4-chloro-3-fluorophenoxy)acetamido]-2-{5-[3-(trifluoromethyl)azetidin-1-yl]-1,3,4-oxadiazol-2-yl}piperidine-1-carboxylate;

2-(4-chloro-3-fluorophenoxy)-N-[(3S,6R)-6-{5-[3-(trifluoromethyl)azetidin-1-yl]-1,3,4-oxadiazol-2-yl}piperidin-3-yl]acetamide;
2-(4-chloro-3-fluorophenoxy)-N-[(3S,6R)-6-{5-[3-(trifluoromethoxy)azetidin-1-yl]-1,3,4-oxadiazol-2-yl}piperidin-3-yl]acetamide;
2-(4-chloro-3-fluorophenoxy)-N-[(3S,6R)-6-{5-[3-(2,2,2-trifluoroethyl)azetidin-1-yl]-1,3,4-oxadiazol-2-yl}piperidin-3-yl]acetamide;
2-(4-chloro-3-fluorophenoxy)-N-[(3S,6R)-6-{5-[3-methyl-3-(trifluoromethoxy)azetidin-1-yl]-1,3,4-oxadiazol-2-yl}piperidin-3-yl]acetamide;
2-(4-chloro-3-fluorophenoxy)-N-[(3S,6R)-6-(5-{methyl[2-(trifluoromethoxy)ethyl]amino}-1,3,4-oxadiazol-2-yl)piperidin-3-yl]acetamide;
2-(4-chloro-3-fluorophenoxy)-N-[(3S,6R)-6-[5-(3-cyclopropoxyazetidin-1-yl)-1,3,4-oxadiazol-2-yl]piperidin-3-yl]acetamide;
2-(4-chloro-3-fluorophenoxy)-N-[(3S,6R)-6-{5-[3-(trifluoromethoxy)pyrrolidin-1-yl]-1,3,4-oxadiazol-2-yl}piperidin-3-yl]acetamide;
tert-butyl (2R,5S)-5-[2-(4-chloro-3-fluorophenoxy)acetamido]-2-{5-[(1s,3s)-3-(trifluoromethoxy)cyclobutyl]-1,2,4-oxadiazol-3-yl}piperidine-1-carboxylate;
2-(4-chloro-3-fluorophenoxy)-N-[(3S,6R)-6-{5-[(1s,3s)-3-(trifluoromethoxy)cyclobutyl]-1,2,4-oxadiazol-3-yl}piperidin-3-yl]acetamide;
tert-butyl (2R,5S)-5-{2-[(6-chloro-5-fluoropyridin-3-yl)oxy]acetamido}-2-[5-(3,4-dichlorophenyl)-1,3,4-oxadiazol-2-yl]piperidine-1-carboxylate;
2-[(6-chloro-5-fluoropyridin-3-yl)oxy]-N-[(3S,6R)-6-[5-(3,4-dichlorophenyl)-1,3,4-oxadiazol-2-yl]piperidin-3-yl]acetamide;
2-(4-chloro-3-fluorophenoxy)-N-[(3S,6R)-1-methyl-6-{5-[2-(trifluoromethoxy)ethoxy]-1,3,4-oxadiazol-2-yl}piperidin-3-yl]acetamide;
2-(4-chloro-3-fluorophenoxy)-N-[(3S,6R)-6-(5-{2-[(1R)-2,2-difluorocyclopropoxy]ethoxy}-1,3,4-oxadiazol-2-yl)piperidin-3-yl]acetamide;
2-(4-chloro-3-fluorophenoxy)-N-[(3S,6R)-6-(5-{2-[(1S)-2,2-difluorocyclopropoxy]ethoxy}-1,3,4-oxadiazol-2-yl)piperidin-3-yl]acetamide;
2-(4-chloro-3-fluorophenoxy)-N-[(3S,6R)-6-{5-[(1r,3r)-3-cyclopropoxycyclobutyl]-1,3,4-oxadiazol-2-yl}piperidin-3-yl]acetamide;
2-(4-chloro-3-fluorophenoxy)-N-[(3S,6R)-6-{5-[(1s,3s)-3-cyclopropoxycyclobutyl]-1,3,4-oxadiazol-2-yl}piperidin-3-yl]acetamide;
(2R)-2-(4-chlorophenoxy)-N-[(3S,6R)-6-{5-[4-(trifluoromethyl)phenyl]-1,3,4-oxadiazol-2-yl}piperidin-3-yl]propenamide;
(2S)-2-(4-chlorophenoxy)-N-[(3S,6R)-6-{5-[4-(trifluoromethyl)phenyl]-1,3,4-oxadiazol-2-yl}piperidin-3-yl]propenamide;
2-(4-chloro-3-fluorophenoxy)-N-[(3S,6R)-6-[5-(4-chlorophenyl)-1,3,4-oxadiazol-2-yl]-2-oxopiperidin-3-yl]acetamide;
2-(4-chloro-3-fluorophenoxy)-N-[(3R,6S)-6-[5-(4-chlorophenyl)-1,3,4-oxadiazol-2-yl]-2-oxopiperidin-3-yl]acetamide;
2-(4-chloro-3-fluorophenoxy)-N-[(3S,6R)-6-{5-[(3 S)-3-(trifluoromethoxy)pyrrolidin-1-yl]-1,3,4-oxadiazol-2-yl}piperidin-3-yl]acetamide;
2-(4-chloro-3-fluorophenoxy)-N-[(3S,6R)-6-{5-[(3R)-3-(trifluoromethoxy)pyrrolidin-1-yl]-1,3,4-oxadiazol-2-yl}piperidin-3-yl]acetamide;
N-[(3S,6R)-6-{5-[2-(trifluoromethoxy)ethoxy]-1,3,4-oxadiazol-2-yl}piperidin-3-yl]-2-[4-(trifluoromethyl)phenoxy]acetamide;
2-[3-chloro-4-(difluoromethyl)phenoxy]-N-[(3S,6R)-6-{5-[2-(trifluoromethoxy)ethoxy]-1,3,4-oxadiazol-2-yl}piperidin-3-yl]acetamide; or
2-[3-fluoro-4-(trifluoromethyl)phenoxy]-N-[(3S,6R)-6-{5-[2-(trifluoromethoxy)ethoxy]-1,3,4-oxadiazol-2-yl}piperidin-3-yl]acetamide.

27. The compound of claim 1 or a pharmaceutically acceptable salt, solvate, hydrate, tautomer, or stereoisomer thereof, wherein the compound is 2-(4-chloro-3-fluorophenoxy)-N-[(3S,6R)-6-{5-[2-(trifluoromethyl)ethoxy]-1,3,4-oxadiazol-2-yl}piperidin-3-yl]acetamide; or 2-(4-chloro-3-fluorophenoxy)-N-[(3S,6R)-6-{5-[2-(trifluoromethyl)ethoxy]-1,3,4-oxadiazol-2-yl}piperidin-3-yl]acetamide.

28. The compound of claim 1 or a pharmaceutically acceptable salt, solvate, hydrate, tautomer or stereoisomer thereof, wherein the compound is of formula (Ia)

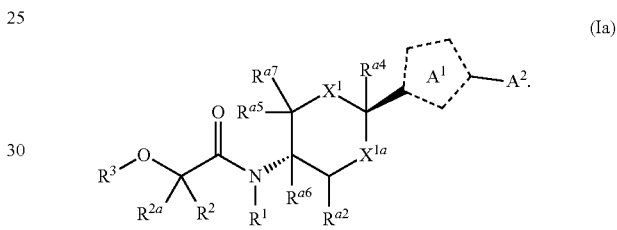

(Ia)

29. A pharmaceutical composition comprising at least one compound or a pharmaceutically acceptable salt, solvate, hydrate, tautomer or stereoisomer thereof of claim 1 together with a pharmaceutically acceptable carrier, optionally in combination with one or more other bioactive compounds or pharmaceutical compositions.

30. A method of treating, controlling, or delaying in a mammalian patient in need of the treatment of one or more diseases or disorders associated with integrated stress response selected from the group consisting of leukodystrophies, intellectual disability syndrome, neoplastic diseases, infectious diseases, musculoskeletal diseases, metabolic diseases, ocular diseases, organ fibrosis, chronic and acute diseases of the liver, chronic and acute diseases of the lung, chronic and acute diseases of the kidney, myocardial infarction, cardiovascular disease, arrhythmias, atherosclerosis, spinal cord injury, ischemic stroke, and neuropathic pain, wherein the method comprises administering to the patient a therapeutically effective amount of a compound of formula (I):

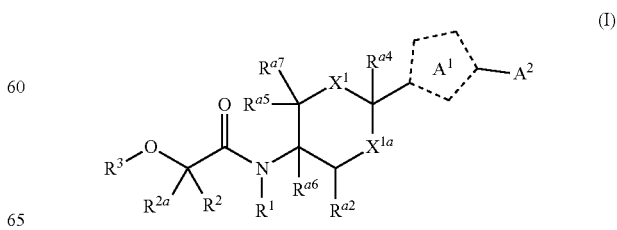

(I)

or a pharmaceutically acceptable salt, solvate, hydrate, tautomer or stereoisomer thereof, wherein $X^1$ is $N(R^{a1})$;

$X^{1a}$ is a covalent single bond or $CH(R^{a3})$;

$R^{a1}$ is H, $C(O)OC_{1-4}$ alkyl, or $C_{1-4}$ alkyl, wherein $C(O)OC_{1-4}$ alkyl and $C_{1-4}$ alkyl are optionally substituted with one or more substituents selected from the group consisting of halogen, OH, and $O-C_{1-3}$ alkyl, wherein the substituents are the same or different;

$R^{a2}$ and $R^{a3}$ are independently selected from the group consisting of H, OH, $OC_{1-4}$ alkyl, halogen, $C_{1-4}$ alkyl, and $A^{2a}$; and $R^{a4}$, $R^{a5}$, $R^{a6}$, and $R^{a7}$ are independently selected from the group consisting of H, halogen, $C_{1-4}$ alkyl, and $A^{2a}$, provided that only one of $R^{a2}$, $R^{a3}$, $R^{a4}$, $R^{a5}$, $R^{a6}$, and $R^{a7}$ is $A^{2a}$;

or $R^{a1}$ and one of $R^{a2}$ and $R^{a3}$ form a methylene or ethylene group;

or $R^{a1}$ and $R^{a6}$ form an ethylene group;

or $R^{a2}$ and $R^{a5}$ form a covalent single bond;

or $R^{a5}$, $R^{a7}$ are joined to form an oxo group;

$A^1$ is $C_5$ cycloalkylene, $C_5$ cycloalkenylene, or a nitrogen ring atom containing 5-membered heterocyclene, wherein $A^1$ is optionally substituted with one or more $R^4$, which are the same or different;

each $R^4$ is independently oxo (=O) where the ring is at least partially saturated, thiooxo (=S) where the ring is at least partially saturated, halogen, CN, $OR^5$, or $C_{1-6}$ alkyl, wherein $C_{1-6}$ alkyl is optionally substituted with one or more halogen, which are the same or different;

$R^5$ is H or $C_{1-6}$ alkyl, wherein $C_{1-6}$ alkyl is optionally substituted with one or more halogen, which are the same or different;

$A^2$ is $R^{6a}$ or $A^{2a}$;

$R^{6a}$ is $OR^{6a1}$, $SR^{6a1}$, $N(R^{6a1}R^{6a2})$, $C_{1-6}$ alkyl, $C_{2-6}$ alkenyl or $C_{2-6}$ alkynyl, wherein $C_{1-6}$ alkyl, $C_{2-6}$ alkenyl, and $C_{2-6}$ alkynyl are optionally substituted with one or more substituents selected from the group consisting of halogen, $OR^{6a3}$, CN, and $A^{2a}$, wherein the substituents are the same or different;

$R^{6a1}$ and $R^{6a2}$ are independently selected from the group consisting of H, $C_{1-6}$ alkyl, $C_{2-6}$ alkenyl, $C_{2-6}$ alkynyl, and $A^{2a}$, wherein $C_{1-6}$ alkyl, $C_{2-6}$ alkenyl, and $C_{2-6}$ alkynyl are optionally substituted with one or more substituents selected from the group consisting of halogen, CN, $OR^{6a3}$, $OA^{2a}$ and $A^{2a}$, wherein the substituents are the same or different;

$R^{6a3}$ is H, or $C_{1-4}$ alkyl, wherein $C_{1-4}$ alkyl is optionally substituted with one or more halogen, which are the same or different;

$A^{2a}$ is phenyl, $C_{3-7}$ cycloalkyl, $C_{4-12}$ bicycloalkyl, or 3- to 7-membered heterocyclyl, wherein $A^{2a}$ is optionally substituted with one or more $R^6$, which are the same or different;

each $R^6$ is independently $R^{6b}$, OH, $OR^{6b}$, halogen, or CN, wherein $R^{6b}$ is cyclopropyl, $C_{1-6}$ alkyl, $C_{2-6}$ alkenyl, or $C_{2-6}$ alkynyl, wherein $R^{6b}$ is optionally substituted with one or more halogen, which are the same or different; or two $R^6$ are joined to form together with the atoms to which they are attached a ring $A^{2b}$;

$A^{2b}$ is phenyl, $C_{3-7}$ cycloalkyl; or 3 to 7 membered heterocyclyl, wherein $A^{2b}$ is optionally substituted with one or more $R^7$, which are the same or different;

each $R^7$ is independently $C_{1-6}$ alkyl, $C_{2-6}$ alkenyl or $C_{2-6}$ alkynyl, wherein $C_{1-6}$ alkyl, $C_{2-6}$ alkenyl, and $C_{2-6}$ alkynyl are optionally substituted with one or more halogen, which are the same or different;

$R^1$ is H or $C_{1-4}$ alkyl, preferably H, wherein $C_{1-4}$ alkyl is optionally substituted with one or more halogen, which are the same or different;

$R^2$ is H, F, or $C_{1-4}$ alkyl, wherein $C_{1-4}$ alkyl is optionally substituted with one or more halogen, which are the same or different; and $R^3$ is $A^3$, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more $R^8$, which are the same or different; or $R^2$ and $R^3$ are joined to form together with the oxygen atom and carbon atom to which they are attached a ring $A^3a$, wherein $A^3a$ is a 7 to 12 membered heterobicyclyl, wherein 7 to 12 membered heterobicyclyl is optionally substituted with one or more $R^{10}$, which are the same or different;

$R^{2a}$ is H or F;

each $R^8$ is independently halogen; CN, $C(O)OR^9$, $OR^9$, $C(O)R^9$, $C(O)N(R^9R^{9a})$, $S(O)_2N(R^9R^{9a})$, $S(O)N(R^9R^{9a})$, $S(O)_2R^9$, $S(O)R^9$, $N(R^9)S(O)_2N(R^{9a}R^{9b})$, $SR^9$, $N(R^9R^{9a})$, $NO_2$, $OC(O)R^9$, $N(R^9)C(O)R^{9a}$, $N(R^9)SO_2R^{9a}$, $N(R^9)S(O)R^{9a}$, $N(R^9)C(O)N(R^{9a}R^{9b})$, $N(R^9)C(O)OR^{9a}$, $OC(O)N(R^9R^{9a})$, or $A^3$;

$R^9$, $R^{9a}$, and $R^{9b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different, or one OH, or one $OC_{1-4}$ alkyl, or one $A^3$;

each $A^3$ is independently phenyl, naphthyl, $C_{3-7}$ cycloalkyl, 3 to 7 membered heterocyclyl, or 7 to 12 membered heterobicyclyl, wherein $A^3$ is optionally substituted with one or more $R^{10}$, which are the same or different;

each $R^{10}$ is independently halogen, CN, $C(O)OR^{11}$, $OR^{11}$, $C(O)R^{11}$, $C(O)N(R^{11}R^{11a})$, $S(O)_2N(R^{11}R^{11a})$, $S(O)N(R^{11}R^{11a})$, $S(O)_2R^{11}$, $S(O)R^{11}$, $N(R^{11})S(O)_2N(R^{11a}R^{11b})$, $SR^{11}$, $N(R^{11}R^{11a})$, $NO_2$, $OC(O)R^{11}$, $N(R^{11})C(O)R^{11a}$, $N(R^{11})S(O)_2R^{11a}$, $N(R^{11})S(O)R^{11a}$, $N(R^{11})C(O)OR^{11a}$, $N(R^{11})C(O)N(R^{11a}R^{11b})$, $OC(O)N(R^{11}R^{11a})$, oxo (=O) where the ring is at least partially saturated, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more $R^{12}$, which are the same or different;

$R^{11}$, $R^{11a}$, and $R^{11b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different;

each $R^{12}$ is independently halogen, CN, $C(O)OR^{13}$, $OR^{13}$, $C(O)R^{13}$, $C(O)N(R^{13}R^{13a})$, $S(O)_2N(R^{13}R^{13a})$, $S(O)N(R^{13}R^{13a})$, $S(O)_2R^{13}$, $S(O)R^{13}$, $N(R^{13})S(O)_2N(R^{13a}R^{13b})$, $SR^{13}$, $N(R^{13}R^{13a})$, $NO_2$, $OC(O)R^{13}$, $N(R^{13})C(O)R^{13a}$, $N(R^{13})SO_2R^{13a}$, $N(R^{13})S(O)R^{13a}$, $N(R^{13})C(O)N(R^{13a}R^{13b})$, $N(R^{13})C(O)OR^{13a}$, or $OC(O)N(R^{13}R^{13a})$;

$R^{13}$, $R^{13a}$, and $R^{13b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different.

31. The compound of claim 2 or a pharmaceutically acceptable salt, solvate, hydrate, tautomer or stereoisomer thereof, wherein $X^1$ is NH, $N(CH_3)$, $N(CH_2CH_3)$, or $N(CH_2CH_2OCH_3)$.

\* \* \* \* \*